US008476072B2

(12) United States Patent
Cabaniols et al.

(10) Patent No.: US 8,476,072 B2
(45) Date of Patent: Jul. 2, 2013

(54) MEGANUCLEASE RECOMBINATION SYSTEM

(75) Inventors: Jean-Pierre Cabaniols, Saint Leu la Foret (FR); Andre Choulika, Paris (FR); Christophe Delenda, Paris (FR)

(73) Assignee: Cellectis, Romainville (FR)

( * ) Notice: Subject to any disclaimer, the term of this patent is extended or adjusted under 35 U.S.C. 154(b) by 0 days.

(21) Appl. No.: 13/125,193

(22) PCT Filed: Oct. 23, 2009

(86) PCT No.: PCT/IB2009/007526
§ 371 (c)(1), (2), (4) Date: Jul. 11, 2011

(87) PCT Pub. No.: WO2010/046786
PCT Pub. Date: Apr. 29, 2010

(65) Prior Publication Data

US 2011/0263028 A1 Oct. 27, 2011

(30) Foreign Application Priority Data

Oct. 23, 2008 (EP) .................................... 08291002

(51) Int. Cl.
*C12N 15/87* (2006.01)
*C12N 15/00* (2006.01)
*C12N 15/10* (2006.01)

(52) U.S. Cl.
USPC ........ 435/463; 435/320.1; 435/325; 435/357; 435/358; 435/366; 435/369; 435/477

(58) Field of Classification Search
None
See application file for complete search history.

(56) References Cited

U.S. PATENT DOCUMENTS

2006/0068395 A1* 3/2006 Wood et al. ....................... 435/6
2006/0153826 A1 7/2006 Arnould et al.
2006/0206949 A1 9/2006 Arnould et al.
2009/0222937 A1 9/2009 Arnould et al.

FOREIGN PATENT DOCUMENTS

WO 2004 067753 8/2004
WO 2007 093836 8/2007
WO WO 2009118192 A1 * 10/2009

OTHER PUBLICATIONS

Noveen et al. Design of compact multiple cloning sites. Biotechniques, vol. 15, No. 2, pp. 210-212 and 214, 1993.*

Ahern. Biochemical, reagents kits offer scientists good return on investment. The Scientist, vol. 9, No. 15, p. 20, Jul. 1995, printed as pp. 1/7 to 7/7.*

Cabaniols Jean-Pierre et al. "Robust Cell Line Development Using Meganucleases." Methods in Molecular Biology, vol. 435. Pages 31-45, XP-002514259 (2008).

Khanamad H. et al. "A novel single step double positive double negative selection strategy for beta-globin gene replacement." Biochemical and Biophysical Research Communications, vol. 345, No. 1. pp. 14-20, XP 24925048 (Jun. 23, 2006).

Huang Ying et al. "An efficient and targeted gene integration system for high-level antibody expression." Journal of Immunological Methods, vol. 322, No. 1-2. pp. 28-39, XP 22040562 (Apr. 14, 2007).

Perez Christophe et al. "Factors affecting double-strand break-induced homologous recombination in mammalian cells." Biotechniques, vol. 39, No. 1. pp. 109-115, XP 8065842 (Jul. 1, 2005).

Gouble Agnes et al. "Efficient in toto targeted recombination in mouse liver by meganuclease-induced double-strand break." Journal of Gene Medicine, vol. 8, No. 5. pp. 616-622, XP 2427714 (May 1, 2006).

Anonymous. "Cellectis BioResearch, a subsidiary of Cellectis S. A., announces the market launch of a first revolutionary research kit Considerable time savings in the development of stable cell clones." Cellectis News. XP 2514260 (Dec. 1, 2008).

Cabaniols Jean-Pierre et al. "Targeted gene modification in drug discovery and development." Current Opinion in Pharmacology, vol. 9, No. 5. pp. 657-663, XP 26665562 (Oct. 1, 2009).

International Search Report issued Mar. 4, 2010 in PCT/IB09/07526 filed Oct. 23, 2009.

* cited by examiner

*Primary Examiner* — Jennifer Dunston

(74) *Attorney, Agent, or Firm* — Oblon, Spivak, McClelland, Maier & Neustadt, L.L.P.

(57) ABSTRACT

The invention relates to a set of genetic constructs which allow the efficient and reproducible introduction of a specific nucleotide sequence at a fixed position in the genome by generating a double strand break at a specific position in the genome using a meganuclease and so stimulating a homologous recombination event at this locus between the genomic site and a transfected donor sequence. The present invention also relates to methods using these constructs and to these materials in the form of a kit.

12 Claims, 34 Drawing Sheets cGPS chromosomal locus of insertion [construct (i)]

Western Blot (Ac anti-ATX)

SEQUENCE LISTING

```
<160> NUMBER OF SEQ ID NOS: 70

<210> SEQ ID NO 1
<211> LENGTH: 883
<212> TYPE: DNA
<213> ORGANISM: Homo sapiens

<400> SEQUENCE: 1

gatctaaagc taactgtagg actgagtcta ttctaaactg aaagcctgga catctggagt      60

accaggggga gatgacgtgt tacgggcttc cataaaagca gctggctttg aatggaagga     120

gccaagaggc cagcacagga gcggattcgt cgctttcacg gccatcgagc cgaacctctc     180

gcaagtccgt gagccgttaa ggaggccccc agtcccgacc cttcgcccca agcccctcgg     240

ggtccccggg cctggtactc cttgccacac gggaggggcg cggaagccgg ggcggaggag     300

gagccaaccc cgggctgggc tgagacccgc agaggaagac gctctaggga tttgtcccgg     360

actagcgaga tggcaaggct gaggacggga ggctgattga gaggcgaagg tacaccctaa     420

tctcaataca acctttggag ctaagccagc aatggtagag ggaagattct gcacgtccct     480

tccaggcggc ctccccgtca ccaccccccc caacccgccc cgaccggagc tgagagtaat     540

tcatacaaaa ggactcgccc ctgccttggg gaatcccagg gaccgtcgtt aaactcccac     600

taacgtagaa cccagagatc gctgcgttcc cgccccctca cccgcccgct ctcgtcatca     660

ctgaggtgga gaagagcatg cgtgaggctc cggtgcccgt cagtgggcag agcgcacatc     720

gcccacagtc cccgagaagt tggggggagg ggtcggcaat tgaaccggtg cctagagaag     780

gtggcgcggg gtaaactggg aaagtgatgt cgtgtactgg ctccgccttt ttcccgaggg     840

tgggggagaa ccgtatataa gtgcagtagt cgccgtgaac gtt                       883


<210> SEQ ID NO 2
<211> LENGTH: 1026
<212> TYPE: DNA
<213> ORGANISM: Artificial Sequence
<220> FEATURE:
<223> OTHER INFORMATION: Description of Artificial Sequence: Synthetic
      Hygromycin resistance gene

<400> SEQUENCE: 2

atgaaaaagc ctgaactcac cgcgacgtct gtcgagaagt ttctgatcga aaagttcgac      60

agcgtctccg acctgatgca gctctcggag ggcgaagaat ctcgtgcttt cagcttcgat     120

gtaggagggc gtggatatgt cctgcgggta aatagctgcg ccgatggttt ctacaaagat     180

cgttatgttt atcggcactt tgcatcggcc gcgctcccga ttccggaagt gcttgacatt     240

ggggaattca gcgagagcct gacctattgc atctcccgcc gtgcacaggg tgtcacgttg     300

caagacctgc ctgaaaccga actgcccgct gttctgcagc cggtcgcgga ggccatggat     360

gcgatcgctg cggccgatct tagccagacg agcgggttcg gcccattcgg accgcaagga     420

atcggtcaat acactacatg gcgtgatttc atatgcgcga ttgctgatcc ccatgtgtat     480

cactggcaaa ctgtgatgga cgacaccgtc agtgcgtccg tcgcgcaggc tctcgatgag     540

ctgatgcttt gggccgagga ctgccccgaa gtccggcacc tcgtgcacgc ggatttcggc     600

tccaacaatg tcctgacgga caatggccgc ataacagcgg tcattgactg gagcgaggcg     660

atgttcgggg attcccaata cgaggtcgcc aacatcttct tctggaggcc gtggttggct     720
```

```
tgtatggagc agcagacgcg ctacttcgag cggaggcatc cggagcttgc aggatcgccg    780

cggctccggg cgtatatgct ccgcattggt cttgaccaac tctatcagag cttggttgac    840

ggcaatttcg atgatgcagc ttgggcgcag ggtcgatgcg acgcaatcgt ccgatccgga    900

gccgggactg tcgggcgtac acaaatcgcc cgcagaagcg cggccgtctg gaccgatggc    960

tgtgtagaag tactcgccga tagtggaaac cgacgcccca gcactcgtcc gagggcaaag   1020

gaatag                                                              1026
```

<210> SEQ ID NO 3
<211> LENGTH: 946
<212> TYPE: DNA
<213> ORGANISM: Artificial Sequence
<220> FEATURE:
<223> OTHER INFORMATION: Description of Artificial Sequence: Synthetic first homologous portion

<400> SEQUENCE: 3

```
taagtgccgt gtgtggttcc cgcgggcctg gcctctttac gggttatggc ccttgcgtgc     60

cttgaattac ttccacgccc ctggctgcag tacgtgattc ttgatcccga gcttcgggtt    120

ggaagtgggt gggagagttc gaggccttgc gcttaaggag ccccttcgcc tcgtgcttga    180

gttgaggcct ggcttgggcg ctggggccgc cgcgtgcgaa tctggtggca ccttcgcgcc    240

tgtctcgctg ctttcgataa gtctctagcc atttaaaatt tttgatgacc tgctgcgacg    300

ctttttttct ggcaagatag tcttgtaaat gcgggccaag atcgatctgc acactggtat    360

ttcggttttt ggggccgcgg gcggcgacgg ggcccgtgcg tcccagcgca catgttcggc    420

gaggcggggc ctgcgagcgc ggccaccgag aatcggacgg gggtagtctc aagctggccg    480

gcctgctctg gtgcctggcc tcgcgccgcc gtgtatcgcc ccgccctggg cggcaaggct    540

ggcccggtcg gcaccagttg cgtgagcgga aagatggccg cttcccggcc ctgctgcagg    600

gagctcaaaa tggaggacgc ggcgctcggg agagcgggcg ggtgagtcac ccacacaaag    660

gaaaagggcc tttccgtcct cagccgtcgc ttcatgtgac tccacggagt accgggcgcc    720

gtccaggcac ctcgattagt tctcgagctt ttggagtacg tcgtctttag gttgggggga    780

ggggttttat gcgatggagt ttccccacac tgagtgggtg gagactgaag ttaggccagc    840

ttggcacttg atgtaattct ccttggaatt tgcccttttt gagtttggat cttggttcat    900

tctcaagcct cagacagtgg ttcaaagttt ttttcttcca tttcag                   946
```

<210> SEQ ID NO 4
<211> LENGTH: 265
<212> TYPE: DNA
<213> ORGANISM: Artificial Sequence
<220> FEATURE:
<223> OTHER INFORMATION: Description of Artificial Sequence: Synthetic SV40 polyA (for hygro) polynucleotide

<400> SEQUENCE: 4

```
gagatttcga ttccaccgcc gccttctatg aaaggttggg cttcggaatc gttttccggg     60

acgccggctg gatgatcctc cagcgcgggg atctcatgct ggagttcttc gcccacccca    120

acttgtttat tgcagcttat aatggttaca aataaagcaa tagcatcaca aatttcacaa    180

ataaagcatt tttttcactg cattctagtt gtggtttgtc caaactcatc aatgtatctt    240

atcatgtctg tataccgtcg acctc                                          265
```

<210> SEQ ID NO 5
<211> LENGTH: 250
<212> TYPE: DNA

<213> ORGANISM: Artificial Sequence
<220> FEATURE:
<223> OTHER INFORMATION: Description of Artificial Sequence: Synthetic
SV40 polyA (for Neo) polynucleotide

<400> SEQUENCE: 5

```
gagatttcga ttccaccgcc gccttctatg aaaggttggg cttcggaatc gttttccggg     60

acgccggctg gatgatcctc cagcgcgggg atctcatgct ggagttcttc gcccacccca    120

acttgtttat tgcagcttat aatggttaca aataaagcaa tagcatcaca aatttcacaa    180

ataaagcatt tttttcactg cattctagtt gtggtttgtc caaactcatc aatgtatctt    240

atcatgtctg                                                           250
```

<210> SEQ ID NO 6
<211> LENGTH: 4424
<212> TYPE: DNA
<213> ORGANISM: Artificial Sequence
<220> FEATURE:
<223> OTHER INFORMATION: Description of Artificial Sequence: Synthetic
cGPS insert

<400> SEQUENCE: 6

```
cgacggatcg ggagatctaa agctaactgt aggactgagt ctattctaaa ctgaaagcct     60

ggacatctgg agtaccaggg ggagatgacg tgttacgggc ttccataaaa gcagctggct    120

ttgaatggaa ggagccaaga ggccagcaca ggagcggatt cgtcgctttc acggccatcg    180

agccgaacct ctcgcaagtc cgtgagccgt taaggaggcc cccagtcccg acccttcgcc    240

ccaagcccct cggggtcccc gggcctggta ctccttgcca cacgggaggg gcgcggaagc    300

cggggcggag gaggagccaa ccccgggctg ggctgagacc cgcagaggaa gacgctctag    360

ggatttgtcc cggactagcg agatggcaag gctgaggacg ggaggctgat tgagaggcga    420

aggtacaccc taatctcaat acaacctttg gagctaagcc agcaatggta gagggaagat    480

tctgcacgtc ccttccaggc ggcctccccg tcaccacccc ccccaacccg ccccgaccgg    540

agctgagagt aattcataca aaaggactcg cccctgcctt ggggaatccc agggaccgtc    600

gttaaactcc cactaacgta gaacccagag atcgctgcgt tcccgccccc tcacccgccc    660

gctctcgtca tcactgaggt ggagaagagc atgcgtgagg ctccggtgcc cgtcagtggg    720

cagagcgcac atcgcccaca gtccccgaga agttgggggg aggggtcggc aattgaaccg    780

gtgcctagag aaggtggcgc ggggtaaact gggaaagtga tgtcgtgtac tggctccgcc    840

tttttcccga gggtggggga gaaccgtata taagtgcagt agtcgccgtg aacgttcttt    900

ttcgcaacgg gtttgccgcc agaacacagg taagtgccgt gtgtggttcc cgcgggcctg    960

gcctctttac gggttatggc ccttgcgtgc cttgaattac ttccacgccc ctggctgcag   1020

tacgtgattc ttgatcccga gcttcgggtt ggaagtgggt gggagagttc gaggccttgc   1080

gcttaaggag ccccttcgcc tcgtgcttga gttgaggcct ggcttgggcg ctggggccgc   1140

cgcgtgcgaa tctggtggca ccttcgcgcc tgtctcgctg ctttcgataa gtctctagcc   1200

atttaaaatt tttgatgacc tgctgcgacg ctttttttct ggcaagatag tcttgtaaat   1260

gcgggccaag atcgatctgc acactggtat ttcggttttt ggggccgcgg gcggcgacgg   1320

ggcccgtgcg tcccagcgca catgttcggc gaggcggggc ctgcgagcgc ggccaccgag   1380

aatcggacgg gggtagtctc aagctggccg gcctgctctg gtgcctggcc tcgcgccgcc   1440

gtgtatcgcc ccgccctggg cggcaaggct ggcccggtcg gcaccagttg cgtgagcgga   1500

aagatggccg cttcccggcc ctgctgcagg gagctcaaaa tggaggacgc ggcgctcggg   1560
```

-continued

```
agagcgggcg ggtgagtcac ccacacaaag gaaaagggcc tttccgtcct cagccgtcgc   1620
ttcatgtgac tccacggagt accgggcgcc gtccaggcac ctcgattagt tctcgagctt   1680
ttggagtacg tcgtctttag gttgggggga ggggttttat gcgatggagt ttccccacac   1740
tgagtgggtg gagactgaag ttaggccagc ttggcacttg atgtaattct ccttggaatt   1800
tgcccttttt gagtttggat cttggttcat tctcaagcct cagacagtgg ttcaaagttt   1860
ttttcttcca tttcaggtgt cgtggaatca aaacgtcgta cgacgttttg agggatccag   1920
cgccaccatg aaaaagcctg aactcaccgc gacgtctgtc gagaagtttc tgatcgaaaa   1980
gttcgacagc gtctccgacc tgatgcagct ctcggagggc gaagaatctc gtgctttcag   2040
cttcgatgta ggagggcgtg gatatgtcct gcgggtaaat agctgcgccg atggtttcta   2100
caaagatcgt tatgtttatc ggcactttgc atcggccgcg ctcccgattc cggaagtgct   2160
tgacattggg gaattcagcg agagcctgac ctattgcatc tcccgccgtg cacagggtgt   2220
cacgttgcaa gacctgcctg aaaccgaact gcccgctgtt ctgcagccgg tcgcggaggc   2280
catggatgcg atcgctgcgg ccgatcttag ccagacgagc gggttcggcc cattcggacc   2340
gcaaggaatc ggtcaataca ctacatggcg tgatttcata tgcgcgattg ctgatcccca   2400
tgtgtatcac tggcaaactg tgatggacga caccgtcagt gcgtccgtcg cgcaggctct   2460
cgatgagctg atgctttggg ccgaggactg ccccgaagtc cggcacctcg tgcacgcgga   2520
tttcggctcc aacaatgtcc tgacggacaa tggccgcata acagcggtca ttgactggag   2580
cgaggcgatg ttcggggatt cccaatacga ggtcgccaac atcttcttct ggaggccgtg   2640
gttggcttgt atggagcagc agacgcgcta cttcgagcgg aggcatccgg agcttgcagg   2700
atcgccgcgg ctccgggcgt atatgctccg cattggtctt gaccaactct atcagagctt   2760
ggttgacggc aatttcgatg atgcagcttg ggcgcagggt cgatgcgacg caatcgtccg   2820
atccggagcc gggactgtcg ggcgtacaca aatcgcccgc agaagcgcgg ccgtctggac   2880
cgatggctgt gtagaagtac tcgccgatag tggaaaccga cgccccagca ctcgtccgag   2940
ggcaaaggaa tagcacgtgc tacgagattt cgattccacc gccgccttct atgaaaggtt   3000
gggcttcgga atcgttttcc gggacgccgg ctggatgatc ctccagcgcg gggatctcat   3060
gctggagttc ttcgcccacc ccaacttgtt tattgcagct tataatggtt acaaataaag   3120
caatagcatc acaaatttca caaataaagc atttttttca ctgcattcta gttgtggttt   3180
gtccaaactc atcaatgtat cttatcatgt ctgtataccg tcgacctcta gctagagctt   3240
ggctaggctt ttgcaaaaag ctcccgggag cttgtatatc cattttcgga tctgatcaag   3300
agacaggatg aggatcgttt cgcatgattg aacaagatgg attgcacgca ggttctccgg   3360
ccgcttgggt ggagaggcta ttcggctatg actgggcaca acagacaatc ggctgctctg   3420
atgccgccgt gttccggctg tcagcgcagg ggcgcccggt tctttttgtc aagaccgacc   3480
tgtccggtgc cctgaatgaa ctgcaggacg aggcagcgcg gctatcgtgg ctggccacga   3540
cgggcgttcc ttgcgcagct gtgctcgacg ttgtcactga agcgggaagg gactggctgc   3600
tattgggcga agtgccgggg caggatctcc tgtcatctca ccttgctcct gccgagaaag   3660
tatccatcat ggctgatgca atgcggcggc tgcatacgct tgatccggct acctgcccat   3720
tcgaccacca agcgaaacat cgcatcgagc gagcacgtac tcggatggaa gccggtcttg   3780
tcgatcagga tgatctggac gaagagcatc aggggctcgc gccagccgaa ctgttcgcca   3840
ggctcaaggc gcgcatgccc gacggcgagg atctcgtcgt gacccatggc gatgcctgct   3900
tgccgaatat catggtggaa aatggccgct tttctggatt catcgactgt ggccggctgg   3960
```

gtgtggcgga ccgctatcag gacatagcgt tggctacccg tgatattgct gaagagcttg 4020
gcggcgaatg ggctgaccgc ttcctcgtgc tttacggtat cgccgctccc gattcgcagc 4080
gcatcgcctt ctatcgcctt cttgacgagt tcttctgagc gggactctgg ggttcgaaat 4140
gaccgaccaa gcgacgccca acctgccatc acgagatttc gattccaccg ccgccttcta 4200
tgaaaggttg ggcttcggaa tcgttttccg ggacgccggc tggatgatcc tccagcgcgg 4260
ggatctcatg ctggagttct tcgcccaccc caacttgttt attgcagctt ataatggtta 4320
caaataaagc aatagcatca caaatttcac aaataaagca tttttttcac tgcattctag 4380
ttgtggtttg tccaaactca tcaatgtatc ttatcatgtc tgta 4424

<210> SEQ ID NO 7
<211> LENGTH: 795
<212> TYPE: DNA
<213> ORGANISM: Artificial Sequence
<220> FEATURE:
<223> OTHER INFORMATION: Description of Artificial Sequence: Synthetic Neomycin polynucleotide w/o promoter

<400> SEQUENCE: 7
atgattgaac aagatggatt gcacgcaggt tctccggccg cttgggtgga gaggctattc 60
ggctatgact gggcacaaca gacaatcggc tgctctgatg ccgccgtgtt ccggctgtca 120
gcgcaggggc gcccggttct ttttgtcaag accgacctgt ccggtgccct gaatgaactg 180
caggacgagg cagcgcggct atcgtggctg gccacgacgg gcgttccttg cgcagctgtg 240
ctcgacgttg tcactgaagc gggaagggac tggctgctat tgggcgaagt gccggggcag 300
gatctcctgt catctcacct tgctcctgcc gagaaagtat ccatcatggc tgatgcaatg 360
cggcggctgc atacgcttga tccggctacc tgcccattcg accaccaagc gaaacatcgc 420
atcgagcgag cacgtactcg gatggaagcc ggtcttgtcg atcaggatga tctggacgaa 480
gagcatcagg ggctcgcgcc agccgaactg ttcgccaggc tcaaggcgcg catgcccgac 540
ggcgaggatc tcgtcgtgac ccatggcgat gcctgcttgc cgaatatcat ggtggaaaat 600
ggccgctttt ctggattcat cgactgtggc cggctgggtg tggcggaccg ctatcaggac 660
atagcgttgg ctacccgtga tattgctgaa gagcttggcg gcgaatgggc tgaccgcttc 720
ctcgtgcttt acggtatcgc cgctcccgat tcgcagcgca tcgccttcta tcgccttctt 780
gacgagttct tctga 795

<210> SEQ ID NO 8
<211> LENGTH: 24
<212> TYPE: DNA
<213> ORGANISM: Chlamydomonas reinhardtii

<400> SEQUENCE: 8
tcaaaacgtc gtacgacgtt ttga 24

<210> SEQ ID NO 9
<211> LENGTH: 1872
<212> TYPE: DNA
<213> ORGANISM: Homo sapiens

<400> SEQUENCE: 9
gatctaaagc taactgtagg actgagtcta ttctaaactg aaagcctgga catctggagt 60
accaggggga gatgacgtgt tacgggcttc cataaaagca gctggctttg aatggaagga 120
gccaagaggc cagcacagga gcggattcgt cgctttcacg gccatcgagc cgaacctctc 180
gcaagtccgt gagccgttaa ggaggccccc agtcccgacc cttcgcccca agcccctcgg 240

```
ggtccccggg cctggtactc cttgccacac gggaggggcg cggaagccgg ggcggaggag    300

gagccaaccc cgggctgggc tgagacccgc agaggaagac gctctaggga tttgtcccgg    360

actagcgaga tggcaaggct gaggacggga ggctgattga gaggcgaagg tacaccctaa    420

tctcaataca acctttggag ctaagccagc aatggtagag ggaagattct gcacgtccct    480

tccaggcggc ctccccgtca ccaccccccc caacccgccc cgaccggagc tgagagtaat    540

tcatacaaaa ggactcgccc ctgccttggg gaatcccagg gaccgtcgtt aaactcccac    600

taacgtagaa cccagagatc gctgcgttcc cgccccctca cccgcccgct ctcgtcatca    660

ctgaggtgga gaagagcatg cgtgaggctc cggtgcccgt cagtgggcag agcgcacatc    720

gcccacagtc cccgagaagt tggggggagg ggtcggcaat tgaaccggtg cctagagaag    780

gtggcgcggg gtaaactggg aaagtgatgt cgtgtactgg ctccgccttt ttcccgaggg    840

tgggggagaa ccgtatataa gtgcagtagt cgccgtgaac gttctttttc gcaacgggtt    900

tgccgccaga acacaggtaa gtgccgtgtg tggttcccgc gggcctggcc tctttacggg    960

ttatggccct tgcgtgcctt gaattacttc cacgcccctg gctgcagtac gtgattcttg   1020

atcccgagct tcgggttgga agtgggtggg agagttcgag gccttgcgct taaggagccc   1080

cttcgcctcg tgcttgagtt gaggcctggc ttgggcgctg gggccgccgc gtgcgaatct   1140

ggtggcacct tcgcgcctgt ctcgctgctt tcgataagtc tctagccatt taaaattttt   1200

gatgacctgc tgcgacgctt tttttctggc aagatagtct tgtaaatgcg ggccaagatc   1260

gatctgcaca ctggtatttc ggtttttggg gccgcgggcg gcgacggggc ccgtgcgtcc   1320

cagcgcacat gttcggcgag gcggggcctg cgagcgcggc caccgagaat cggacggggg   1380

tagtctcaag ctggccggcc tgctctggtg cctggcctcg cgccgccgtg tatcgccccg   1440

ccctgggcgg caaggctggc ccggtcggca ccagttgcgt gagcggaaag atggccgctt   1500

cccggccctg ctgcagggag ctcaaaatgg aggacgcggc gctcgggaga gcgggcgggt   1560

gagtcaccca cacaaaggaa aagggccttt ccgtcctcag ccgtcgcttc atgtgactcc   1620

acggagtacc gggcgccgtc caggcacctc gattagttct cgagcttttg gagtacgtcg   1680

tctttaggtt ggggggaggg gttttatgcg atggagtttc cccacactga gtgggtggag   1740

actgaagtta ggccagcttg gcacttgatg taattctcct tggaatttgc cctttttgag   1800

tttggatctt ggttcattct caagcctcag acagtggttc aaagtttttt tcttccattt   1860

caggtgtcgt gg                                                      1872
```

<210> SEQ ID NO 10
<211> LENGTH: 946
<212> TYPE: DNA
<213> ORGANISM: Homo sapiens

<400> SEQUENCE: 10

```
taagtgccgt gtgtggttcc cgcgggcctg gcctctttac gggttatggc ccttgcgtgc     60

cttgaattac ttccacgccc ctggctgcag tacgtgattc ttgatcccga gcttcgggtt    120

ggaagtgggt gggagagttc gaggccttgc gcttaaggag ccccttcgcc tcgtgcttga    180

gttgaggcct ggcttgggcg ctggggccgc cgcgtgcgaa tctggtggca ccttcgcgcc    240

tgtctcgctg ctttcgataa gtctctagcc atttaaaatt tttgatgacc tgctgcgacg    300

ctttttttct ggcaagatag tcttgtaaat gcgggccaag atcgatctgc acactggtat    360

ttcggttttt ggggccgcgg gcggcgacgg ggcccgtgcg tcccagcgca catgttcggc    420

gaggcggggc ctgcgagcgc ggccaccgag aatcggacgg gggtagtctc aagctggccg    480
```

gcctgctctg gtgcctggcc tcgcgccgcc gtgtatcgcc ccgccctggg cggcaaggct 540
ggcccggtcg gcaccagttg cgtgagcgga aagatggccg cttcccggcc ctgctgcagg 600
gagctcaaaa tggaggacgc ggcgctcggg agagcgggcg ggtgagtcac ccacacaaag 660
gaaaagggcc tttccgtcct cagccgtcgc ttcatgtgac tccacggagt accgggcgcc 720
gtccaggcac ctcgattagt tctcgagctt ttggagtacg tcgtctttag gttgggggga 780
ggggttttat gcgatggagt ttccccacac tgagtgggtg gagactgaag ttaggccagc 840
ttggcacttg atgtaattct ccttggaatt tgcccttttt gagtttggat cttggttcat 900
tctcaagcct cagacagtgg ttcaaagttt ttttcttcca tttcag 946

<210> SEQ ID NO 11
<211> LENGTH: 34
<212> TYPE: DNA
<213> ORGANISM: Homo sapiens

<400> SEQUENCE: 11
ctttttcgca acgggtttgc cgccagaaca cagg 34

<210> SEQ ID NO 12
<211> LENGTH: 9
<212> TYPE: DNA
<213> ORGANISM: Homo sapiens

<400> SEQUENCE: 12 gtgtcgtgg 9

<210> SEQ ID NO 13
<211> LENGTH: 530
<212> TYPE: DNA
<213> ORGANISM: Artificial Sequence
<220> FEATURE:
<223> OTHER INFORMATION: Description of Artificial Sequence: Synthetic
5' homology region/2nd homologous portion

<400> SEQUENCE: 13
atgattgaac aagatggatt gcacgcaggt tctccggccg cttgggtgga gaggctattc 60
ggctatgact gggcacaaca gacaatcggc tgctctgatg ccgccgtgtt ccggctgtca 120
gcgcaggggc gcccggttct ttttgtcaag accgacctgt ccggtgccct gaatgaactg 180
caggacgagg cagcgcggct atcgtggctg gccacgacgg gcgttccttg cgcagctgtg 240
ctcgacgttg tcactgaagc gggaagggac tggctgctat tgggcgaagt gccggggcag 300
gatctcctgt catctcacct tgctcctgcc gagaaagtat ccatcatggc tgatgcaatg 360
cggcggctgc atacgcttga tccggctacc tgcccattcg accaccaagc gaaacatcgc 420
atcgagcgag cacgtactcg gatggaagcc ggtcttgtcg atcaggatga tctggacgaa 480
gagcatcagg ggctcgcgcc agccgaactg ttcgccaggc tcaaggcgcg 530

<210> SEQ ID NO 14
<211> LENGTH: 504
<212> TYPE: DNA
<213> ORGANISM: Artificial Sequence
<220> FEATURE:
<223> OTHER INFORMATION: Description of Artificial Sequence: Synthetic
I-CreI N75 polynucleotide

<400> SEQUENCE: 14
atggccaata ccaaatataa caaagagttc ctgctgtacc tggccggctt tgtggacggt 60
gacggtagca tcatcgctca gattaaacca aaccagtctt ataagtttaa acatcagcta 120

```
agcttgacct ttcaggtgac tcaaaagacc cagcgccgtt ggtttctgga caaactagtg    180

gatgaaattg gcgttggtta cgtacgtgat cgcggatccg tttccaacta catcttaagc    240

gaaatcaagc cgctgcacaa cttcctgact caactgcagc cgtttctgaa actgaaacag    300

aaacaggcaa acctggttct gaaaattatc gaacagctgc cgtctgcaaa agaatccccg    360

gacaaattcc tggaagtttg tacctgggtg gatcagattg cagctctgaa cgattctaag    420

acgcgtaaaa ccacttctga aaccgttcgt gctgtgctgg acagcctgag cgagaagaag    480

aaatcctccc cggcggccga ctaa                                           504
```

<210> SEQ ID NO 15
<211> LENGTH: 504
<212> TYPE: DNA
<213> ORGANISM: Artificial Sequence
<220> FEATURE:
<223> OTHER INFORMATION: Description of Artificial Sequence: Synthetic I-CreI 75N 105A 132V polynucleotide

<400> SEQUENCE: 15

```
atggccaata ccaaatataa caaagagttc ctgctgtacc tggccggctt tgtggacggt     60

gacggtagca tcatcgctca gattaaacca aaccagtctt ataagtttaa acatcagcta    120

agcttgacct ttcaggtgac tcaaaagacc cagcgccgtt ggtttctgga caaactagtg    180

gatgaaattg gcgttggtta cgtacgtgat cgcggatccg tttccaacta catcttaagc    240

gaaatcaagc cgctgcacaa cttcctgact caactgcagc cgtttctgaa actgaaacag    300

aaacaggcaa acctggctct gaaaattatc gaacagctgc cgtctgcaaa agaatccccg    360

gacaaattcc tggaagtttg tacctgggtg gatcaggttg cagctctgaa cgattctaag    420

acgcgtaaaa ccacttctga aaccgttcgt gctgtgctgg acagcctgag cgagaagaag    480

aaatcctccc cggcggccga ctaa                                           504
```

<210> SEQ ID NO 16
<211> LENGTH: 3075
<212> TYPE: DNA
<213> ORGANISM: Artificial Sequence
<220> FEATURE:
<223> OTHER INFORMATION: Description of Artificial Sequence: Synthetic LacZ gene

<400> SEQUENCE: 16

```
atgatagatc ccgtcgtttt acaacgtcgt gactgggaaa accctggcgt tacccaactt     60

aatcgccttg cagcacatcc ccctttcgcc agctggcgta atagcgaaga ggcccgcacc    120

gatcgccctt cccaacagtt gcgcagcctg aatggcgaat ggcgctttgc ctggtttccg    180

gtaccagaag cggtgccgga aagctggctg gagtgcgatc ttcctgaggc cgatactgtc    240

gtcgtcccct caaactggca gatgcacggt tacgatgcgc ccatctacac caacgtaacc    300

tatcccatta cggtcaatcc gccgtttgtt cccacggaga atccgacggg ttgttactcg    360

ctcacattta atgttgatga aagctggcta caggaaggcc agacgcgaat tatttttgat    420

ggcgttaact cggcgtttca tctgtggtgc aacgggcgct gggtcggtta cggccaggac    480

agtcgtttgc cgtctgaatt tgacctgagc gcatttttac gcgccggaga aaaccgcctc    540

gcggtgatgg tgctgcgttg gagtgacggc agttatctgg aagatcagga tatgtggcgg    600

atgagcggca ttttccgtga cgtctcgttg ctgcataaac cgactacaca aatcagcgat    660

ttccatgttg ccactcgctt taatgatgat ttcagccgcg ctgtactgga ggctgaagtt    720

cagatgtgcg gcgagttgcg tgactaccta cgggtaacag tttctttatg gcagggtgaa    780
```

```
acgcaggtcg ccagcggcac cgcgcctttc ggcggtgaaa ttatcgatga gcgtggtggt    840
tatgccgatc gcgtcacact acgtctgaac gtcgaaaacc cgaaactgtg gagcgccgaa    900
atcccgaatc tctatcgtgc ggtggttgaa ctgcacaccg ccgacggcac gctgattgaa    960
gcagaagcct gcgatgtcgg tttccgcgag gtgcggattg aaaatggtct gctgctgctg   1020
aacggcaagc cgttgctgat tcgaggcgtt aaccgtcacg agcatcatcc tctgcatggt   1080
caggtcatgg atgagcagac gatggtgcag gatatcctgc tgatgaagca gaacaacttt   1140
aacgccgtgc gctgttcgca ttatccgaac catccgctgt ggtacacgct gtgcgaccgc   1200
tacggcctgt atgtggtgga tgaagccaat attgaaaccc acggcatggt gccaatgaat   1260
cgtctgaccg atgatccgcg ctggctaccg gcgatgagcg aacgcgtaac gcgaatggtg   1320
cagcgcgatc gtaatcaccc gagtgtgatc atctggtcgc tggggaatga atcaggccac   1380
ggcgctaatc acgacgcgct gtatcgctgg atcaaatctg tcgatccttc ccgcccggtg   1440
cagtatgaag gcggcggagc cgacaccacg gccaccgata ttatttgccc gatgtacgcg   1500
cgcgtggatg aagaccagcc cttcccggct gtgccgaaat ggtccatcaa aaaatggctt   1560
tcgctacctg gagagacgcg cccgctgatc ctttgcgaat acgcccacgc gatgggtaac   1620
agtcttggcg gtttcgctaa atactggcag gcgtttcgtc agtatccccg tttacagggc   1680
ggcttcgtct gggactgggt ggatcagtcg ctgattaaat atgatgaaaa cggcaacccg   1740
tggtcggctt acggcggtga ttttggcgat acgccgaacg atcgccagtt ctgtatgaac   1800
ggtctggtct ttgccgaccg cacgccgcat ccagcgctga cggaagcaaa acaccagcag   1860
cagtttttcc agttccgttt atccgggcaa accatcgaag tgaccagcga atacctgttc   1920
cgtcatagcg ataacgagct cctgcactgg atggtggcgc tggatggtaa gccgctggca   1980
agcggtgaag tgcctctgga tgtcgctcca caaggtaaac agttgattga actgcctgaa   2040
ctaccgcagc cggagagcgc cgggcaactc tggctcacag tacgcgtagt gcaaccgaac   2100
gcgaccgcat ggtcagaagc cgggcacatc agcgcctggc agcagtggcg tctggcggaa   2160
aacctcagtg tgacgctccc cgccgcgtcc cacgccatcc cgcatctgac caccagcgaa   2220
atggattttt gcatcgagct gggtaataag cgttggcaat ttaaccgcca gtcaggcttt   2280
ctttcacaga tgtggattgg cgataaaaaa caactgctga cgccgctgcg cgatcagttc   2340
acccgtgcac cgctggataa cgacattggc gtaagtgaag cgacccgcat tgaccctaac   2400
gcctgggtcg aacgctggaa ggcggcgggc cattaccagg ccgaagcagc gttgttgcag   2460
tgcacggcag atacacttgc tgatgcggtg ctgattacga ccgctcacgc gtggcagcat   2520
caggggaaaa ccttatttat cagccggaaa acctaccgga ttgatggtag tggtcaaatg   2580
gcgattaccg ttgatgttga agtggcgagc gatacaccgc atccggcgcg gattggcctg   2640
aactgccagc tggcgcaggt agcagagcgg gtaaactggc tcggattagg gccgcaagaa   2700
aactatcccg accgccttac tgccgcctgt tttgaccgct gggatctgcc attgtcagac   2760
atgtataccc cgtacgtctt cccgagcgaa aacggtctgc gctgcgggac gcgcgaattg   2820
aattatggcc cacaccagtg gcgcggcgac ttccagttca acatcagccg ctacagtcaa   2880
cagcaactga tggaaaccag ccatcgccat ctgctgcacg cggaagaagg cacatggctg   2940
aatatcgacg gtttccatat ggggattggt ggcgacgact cctggagccc gtcagtatcg   3000
gcggaattcc agctgagcgc cggtcgctac cattaccagt tggtctggtg tcaaaaagcg   3060
gccgctcgag tctag                                                     3075
```

```
<210> SEQ ID NO 17
<211> LENGTH: 9981
<212> TYPE: DNA
<213> ORGANISM: Artificial Sequence
<220> FEATURE:
<223> OTHER INFORMATION: Description of Artificial Sequence: Synthetic
      pTV_DS_LacZ polynucleotide

<400> SEQUENCE: 17

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accatatgcg gtgtgaaata ccgcacagat gcgtaaggag aaaataccgc atcaggcgcc     240

attcgccatt caggctgcgc aactgttggg aagggcgatc ggtgcgggcc tcttcgctat     300

tacgccagct ggcgaaaggg ggatgtgctg caaggcgatt aagttgggta acgccagggt     360

tttcccagtc acgacgttgt aaaacgacgg ccagtgaatt ttaaggagcc ccttcgcctc     420

gtgcttgagt tgaggcctgg cttgggcgct ggggccgccg cgtgcgaatc tggtggcacc     480

ttcgcgcctg tctcgctgct ttcgataagt ctctagccat ttaaaatttt tgatgacctg     540

ctgcgacgct ttttttctgg caagatagtc ttgtaaatgc gggccaagat cgatctgcac     600

actggtattt cggtttttgg ggccgcgggc ggcgacgggg cccgtgcgtc ccagcgcaca     660

tgttcggcga ggcggggcct gcgagcgcgg ccaccgagaa tcggacgggg gtagtctcaa     720

gctggccggc ctgctctggt gcctggcctc gcgccgccgt gtatcgcccc gccctgggcg     780

gcaaggctgg cccggtcggc accagttgcg tgagcggaaa gatggccgct tcccggccct     840

gctgcaggga gctcaaaatg gaggacgcgg cgctcgggag agcgggcggg tgagtcaccc     900

acacaaagga aaagggcctt tccgtcctca gccgtcgctt catgtgactc cacggagtac     960

cgggcgccgt ccaggcacct cgattagttc tcgagctttt ggagtacgtc gtctttaggt    1020

tggggggagg ggttttatgc gatggagttt ccccacactg agtgggtgga gactgaagtt    1080

aggccagctt ggcacttgat gtaattctcc ttggaatttg ccctttttga gtttggatct    1140

tggttcattc tcaagcctca gacagtggtt caaagttttt ttcttccatt tcaggtgtcg    1200

tggaattggc tagagcttgc atgcctgcag gtcggccgcc acgaccggtg ccgccaccat    1260

cccctgaccc acgcccctga cccctcacaa ggagacgacc ttccatgacc gagtacaagc    1320

ccacggtgcg cctcgccacc cgcgacgacg tcccccgggc cgtacgcacc ctcgccgccg    1380

cgttcgccga ctaccccgcc acgcgccaca ccgtcgaccc ggaccgccac atcgagcggg    1440

tcaccgagct gcaagaactc ttcctcacgc gcgtcgggct cgacatcggc aaggtgtggg    1500

tcgcggacga cggcgccgcg gtggcggtct ggaccacgcc ggagagcgtc gaagcggggg    1560

cggtgttcgc cgagatcggc ccgcgcatgg ccgagttgag cggttcccgg ctggccgcgc    1620

agcaacagat ggaaggcctc ctggcgccgc accggcccaa ggagcccgcg tggttcctgg    1680

ccaccgtcgg cgtctcgccc gaccaccagg gcaagggtct gggcagcgcc gtcgtgctcc    1740

ccggagtgga ggcggccgag cgcgccgggg tgcccgcctt cctggagacc tccgcgcccc    1800

gcaacctccc cttctacgag cggctcggct tcaccgtcac cgccgacgtc gaggtgcccg    1860

aaggaccgcg cacctggtgc atgacccgca agcccggtgc ctgacgcccg ccccacgacc    1920

cgcagcgccc gaccgaaagg agcgcacgac cccatggctc cgaccgaagc cgacccgggc    1980

ggccccgccg accccgcacc cgcccccgag gcccaccgac tctagaggat cataatcagc    2040

cataccacat ttgtagaggt tttacttgct ttaaaaaacc tcccacacct ccccctgaac    2100
```

```
ctgaaacata aaatgaatgc aattgttgtt gttaacttgt ttattgcagc ttataatggt   2160

tacaaataaa gcaatagcat cacaaatttc acaaataaag cattttttc actgcattct   2220

agttgtggtt tgtccaaact catcaatgta tcttatcatg tctggatcct agcgtttaaa   2280

cttaagcttg gtaccgagct cggatccact agtaatggtt acaaataaag caatagcatc   2340

acaaatttca caaataaagc atttttttca ctgcattcta gttgtggttt gtccaaactc   2400

atcaatgtat cttatcatgt ctgtacgatg tacgggccag atatacgcgt tgacattgat   2460

tattgactag ttattaatag taatcaatta cggggtcatt agttcatagc ccatatatgg   2520

agttccgcgt tacataactt acggtaaatg gcccgcctgg ctgaccgccc aacgaccccc   2580

gcccattgac gtcaataatg acgtatgttc ccatagtaac gccaataggg actttccatt   2640

gacgtcaatg ggtggagtat ttacggtaaa ctgcccactt ggcagtacat caagtgtatc   2700

atatgccaag tacgccccct attgacgtca atgacggtaa atggcccgcc tggcattatg   2760

cccagtacat gaccttatgg gactttccta cttggcagta catctacgta ttagtcatcg   2820

ctattaccat ggtgatgcgg ttttggcagt acatcaatgg gcgtggatag cggtttgact   2880

cacggggatt tccaagtctc caccccattg acgtcaatgg gagtttgttt tggcaccaaa   2940

atcaacggga ctttccaaaa tgtcgtaaca actccgcccc attgacgcaa atgggcggta   3000

ggcgtgtacg gtgggaggtc tatataagca gagctctctg gctaactaga gaacccactg   3060

cttactggct tatcgaaatt aatacgactc actataggga gacccaagct ggctagctag   3120

tccagtgtgg tggaattctg cagatcgaaa cgatgataga tcccgtcgtt ttacaacgtc   3180

gtgactggga aaaccctggc gttacccaac ttaatcgcct tgcagcacat ccccctttcg   3240

ccagctggcg taatagcgaa gaggcccgca ccgatcgccc ttcccaacag ttgcgcagcc   3300

tgaatggcga atggcgcttt gcctggtttc cggtaccaga agcggtgccg gaaagctggc   3360

tggagtgcga tcttcctgag gccgatactg tcgtcgtccc ctcaaactgg cagatgcacg   3420

gttacgatgc gcccatctac accaacgtaa cctatcccat tacggtcaat ccgccgtttg   3480

ttcccacgga gaatccgacg ggttgttact cgctcacatt taatgttgat gaaagctggc   3540

tacaggaagg ccagacgcga attatttttg atggcgttaa ctcggcgttt catctgtggt   3600

gcaacgggcg ctgggtcggt tacggccagg acagtcgttt gccgtctgaa tttgacctga   3660

gcgcattttt acgcgccgga gaaaaccgcc tcgcggtgat ggtgctgcgt tggagtgacg   3720

gcagttatct ggaagatcag gatatgtggc ggatgagcgg cattttccgt gacgtctcgt   3780

tgctgcataa accgactaca caaatcagcg atttccatgt tgccactcgc tttaatgatg   3840

atttcagccg cgctgtactg gaggctgaag ttcagatgtg cggcgagttg cgtgactacc   3900

tacgggtaac agtttcttta tggcagggtg aaacgcaggt cgccagcggc accgcgcctt   3960

tcggcggtga aattatcgat gagcgtggtg gttatgccga tcgcgtcaca ctacgtctga   4020

acgtcgaaaa cccgaaactg tggagcgccg aaatcccgaa tctctatcgt gcggtggttg   4080

aactgcacac cgccgacggc acgctgattg aagcagaagc ctgcgatgtc ggtttccgcg   4140

aggtgcggat tgaaaatggt ctgctgctgc tgaacggcaa gccgttgctg attcgaggcg   4200

ttaaccgtca cgagcatcat cctctgcatg gtcaggtcat ggatgagcag acgatggtgc   4260

aggatatcct gctgatgaag cagaacaact ttaacgccgt gcgctgttcg cattatccga   4320

accatccgct gtggtacacg ctgtgcgacc gctacggcct gtatgtggtg gatgaagcca   4380

atattgaaac ccacggcatg gtgccaatga atcgtctgac cgatgatccg cgctggctac   4440

cggcgatgag cgaacgcgta acgcgaatgg tgcagcgcga tcgtaatcac ccgagtgtga   4500
```

-continued

```
tcatctggtc gctggggaat gaatcaggcc acggcgctaa tcacgacgcg ctgtatcgct   4560
ggatcaaatc tgtcgatcct tcccgcccgg tgcagtatga aggcggcgga gccgacacca   4620
cggccaccga tattatttgc ccgatgtacg cgcgcgtgga tgaagaccag cccttcccgg   4680
ctgtgccgaa atggtccatc aaaaaatggc tttcgctacc tggagagacg cgcccgctga   4740
tcctttgcga atacgcccac gcgatgggta acagtcttgg cggtttcgct aaatactggc   4800
aggcgtttcg tcagtatccc cgtttacagg gcggcttcgt ctgggactgg gtggatcagt   4860
cgctgattaa atatgatgaa aacggcaacc cgtggtcggc ttacggcggt gattttggcg   4920
atacgccgaa cgatcgccag ttctgtatga acggtctggt ctttgccgac cgcacgccgc   4980
atccagcgct gacggaagca aaacaccagc agcagttttt ccagttccgt ttatccgggc   5040
aaaccatcga agtgaccagc gaatacctgt tccgtcatag cgataacgag ctcctgcact   5100
ggatggtggc gctggatggt aagccgctgg caagcggtga agtgcctctg gatgtcgctc   5160
cacaaggtaa acagttgatt gaactgcctg aactaccgca gccggagagc gccgggcaac   5220
tctggctcac agtacgcgta gtgcaaccga acgcgaccgc atggtcagaa gccgggcaca   5280
tcagcgcctg gcagcagtgg cgtctggcgg aaaacctcag tgtgacgctc cccgccgcgt   5340
cccacgccat cccgcatctg accaccagcg aaatggattt ttgcatcgag ctgggtaata   5400
agcgttggca atttaaccgc cagtcaggct ttctttcaca gatgtggatt ggcgataaaa   5460
aacaactgct gacgccgctg cgcgatcagt tcacccgtgc accgctggat aacgacattg   5520
gcgtaagtga agcgacccgc attgacccta acgcctgggt cgaacgctgg aaggcggcgg   5580
gccattacca ggccgaagca gcgttgttgc agtgcacggc agatacactt gctgatgcgg   5640
tgctgattac gaccgctcac gcgtggcagc atcaggggaa aaccttattt atcagccgga   5700
aaacctaccg gattgatggt agtggtcaaa tggcgattac cgttgatgtt gaagtggcga   5760
gcgatacacc gcatccggcg cggattggcc tgaactgcca gctggcgcag gtagcagagc   5820
gggtaaactg gctcggatta gggccgcaag aaaactatcc cgaccgcctt actgccgcct   5880
gttttgaccg ctgggatctg ccattgtcag acatgtatac cccgtacgtc ttcccgagcg   5940
aaaacggtct gcgctgcggg acgcgcgaat tgaattatgg cccacaccag tggcgcggcg   6000
acttccagtt caacatcagc cgctacagtc aacagcaact gatggaaacc agccatcgcc   6060
atctgctgca cgcggaagaa ggcacatggc tgaatatcga cggtttccat atggggattg   6120
gtggcgacga ctcctggagc ccgtcagtat cggcggaatt ccagctgagc gccggtcgct   6180
accattacca gttggtctgg tgtcaaaaag cggccgctcg agtctagagg gcccgtttaa   6240
acccgctgat cagcctcgac tgtgccttct agttgccagc catctgttgt ttgcccctcc   6300
cccgtgcctt ccttgaccct ggaaggtgcc actcccactg tcctttccta ataaaatgag   6360
gaaattgcat cgcattgtct gagtaggtgt cattctattc tggggggtgg ggtggggcag   6420
gacagcaagg gggaggattg ggaagacaat agcaggcatg ctggggatgc ggtgggctct   6480
atggcttctg aggcggaaag aaccagctgg ggctctaggg ggtatcccca cgcgccctgt   6540
agcggcgcat taagcgcggc gggtgtggtg gttacgcgca gcgtgaccgc tacacttgcc   6600
agcgccctag cgcccgctcc tttcgctttc ttcccttcct ttctcgccac gttcgcctac   6660
cgtcgaatca ccggtaacct tataagggat tttgccgatt tcggcctatt ggttaaaaaa   6720
tgagctgatt taacaaaaat ttaacgcgaa ttaattctgt ggaatgtgtg tcagttaggg   6780
tgtggaaagt ccccaggctc cccagcaggc agaagtatgc aaagcatgca tctcaattag   6840
tcagcaacca ggtgtggaaa gtccccaggc tccccagcag gcagaagtat gcaaagcatg   6900
```

```
catctcaatt agtcagcaac catagtcccg cccctaactc cgcccatccc gcccctaact   6960
ccgcccagtt ccgcccattc tccgccccat ggctgactaa ttttttttat ttatgcagag   7020
gccgaggccg cctctgcctc tgagctattc cagaagtagt gaggaggctt ttttggaggc   7080
ctaggctttt gcaaaaagct cccgggagct tgtatatcca ttttcggatc tgatcaagag   7140
acaggatgag gatcgtttcg catgattgaa caagatggat tgcacgcagg ttctccggcc   7200
gcttgggtgg agaggctatt cggctatgac tgggcacaac agacaatcgg ctgctctgat   7260
gccgccgtgt tccggctgtc agcgcagggg cgcccggttc tttttgtcaa gaccgacctg   7320
tccggtgccc tgaatgaact gcaggacgag gcagcgcggc tatcgtggct ggccacgacg   7380
ggcgttcctt gcgcagctgt gctcgacgtt gtcactgaag cgggaaggga ctggctgcta   7440
ttgggcgaag tgccggggca ggatctcctg tcatctcacc ttgctcctgc cgagaaagta   7500
tccatcatgg ctgatgcaat gcggcggctg catacgcttg atccggctac ctgcccattc   7560
gaccaccaag cgaaacatcg catcgagcga gcacgtactc ggatggaagc cggtcttgtc   7620
gatcaggatg atctggacga agagcatcag gggctcgcgc cagccgaact gttcgccagg   7680
ctcaaggcgc gaattcgagc tcggtacccg gggatcctct agagtcgacc tgcaggcatg   7740
caagcttggc gtaatcatgg tcatagctgt ttcctgtgtg aaattgttat ccgctcacaa   7800
ttccacacaa catacgagcc ggaagcataa agtgtaaagc ctggggtgcc taatgagtga   7860
gctaactcac attaattgcg ttgcgctcac tgcccgcttt ccagtcggga aacctgtcgt   7920
gccagctgca ttaatgaatc ggccaacgcg cggggagagg cggtttgcgt attgggcgct   7980
cttccgcttc ctcgctcact gactcgctgc gctcggtcgt tcggctgcgg cgagcggtat   8040
cagctcactc aaaggcggta atacggttat ccacagaatc aggggataac gcaggaaaga   8100
acatgtgagc aaaaggccag caaaaggcca ggaaccgtaa aaaggccgcg ttgctggcgt   8160
ttttccatag gctccgcccc cctgacgagc atcacaaaaa tcgacgctca agtcagaggt   8220
ggcgaaaccc gacaggacta taaagatacc aggcgtttcc ccctggaagc tccctcgtgc   8280
gctctcctgt tccgaccctg ccgcttaccg gatacctgtc cgcctttctc ccttcgggaa   8340
gcgtggcgct ttctcatagc tcacgctgta ggtatctcag ttcggtgtag gtcgttcgct   8400
ccaagctggg ctgtgtgcac gaaccccccg ttcagcccga ccgctgcgcc ttatccggta   8460
actatcgtct tgagtccaac ccggtaagac acgacttatc gccactggca gcagccactg   8520
gtaacaggat tagcagagcg aggtatgtag gcggtgctac agagttcttg aagtggtggc   8580
ctaactacgg ctacactaga aggacagtat ttggtatctg cgctctgctg aagccagtta   8640
ccttcggaaa aagagttggt agctcttgat ccggcaaaca aaccaccgct ggtagcggtg   8700
gtttttttgt ttgcaagcag cagattacgc gcagaaaaaa aggatctcaa gaagatcctt   8760
tgatcttttc tacggggtct gacgctcagt ggaacgaaaa ctcacgttaa gggattttgg   8820
tcatgagatt atcaaaaagg atcttcacct agatcctttt aaattaaaaa tgaagtttta   8880
aatcaatcta aagtatatat gagtaaactt ggtctgacag ttaccaatgc ttaatcagtg   8940
aggcacctat ctcagcgatc tgtctatttc gttcatccat agttgcctga ctccccgtcg   9000
tgtagataac tacgatacgg gagggcttac catctggccc cagtgctgca atgataccgc   9060
gagacccacg ctcaccggct ccagatttat cagcaataaa ccagccagcc ggaagggccg   9120
agcgcagaag tggtcctgca actttatccg cctccatcca gtctattaat tgttgccggg   9180
aagctagagt aagtagttcg ccagttaata gtttgcgcaa cgttgttgcc attgctacag   9240
gcatcgtggt gtcacgctcg tcgtttggta tggcttcatt cagctccggt tcccaacgat   9300
```

```
caaggcgagt tacatgatcc cccatgttgt gcaaaaaagc ggttagctcc ttcggtcctc   9360

cgatcgttgt cagaagtaag ttggccgcag tgttatcact catggttatg gcagcactgc   9420

ataattctct tactgtcatg ccatccgtaa gatgcttttc tgtgactggt gagtactcaa   9480

ccaagtcatt ctgagaatag tgtatgcggc gaccgagttg ctcttgcccg gcgtcaatac   9540

gggataatac cgcgccacat agcagaactt taaaagtgct catcattgga aaacgttctt   9600

cggggcgaaa actctcaagg atcttaccgc tgttgagatc cagttcgatg taacccactc   9660

gtgcacccaa ctgatcttca gcatctttta ctttcaccag cgtttctggg tgagcaaaaa   9720

caggaaggca aaatgccgca aaaaagggaa taagggcgac acggaaatgt tgaatactca   9780

tactcttcct ttttcaatat tattgaagca tttatcaggg ttattgtctc atgagcggat   9840

acatatttga atgtatttag aaaaataaac aaataggggt tccgcgcaca tttccccgaa   9900

aagtgccacc tgacgtctaa gaaaccatta ttatcatgac attaacctat aaaaataggc   9960

gtatcacgag gccctttcgt c                                             9981
```

<210> SEQ ID NO 18
<211> LENGTH: 7291
<212> TYPE: DNA
<213> ORGANISM: Artificial Sequence
<220> FEATURE:
<223> OTHER INFORMATION: Description of Artificial Sequence: Synthetic KI-construct-LacZ control polynucleotide

<400> SEQUENCE: 18

```
ttaaggagcc ccttcgcctc gtgcttgagt tgaggcctgg cttgggcgct ggggccgccg     60

cgtgcgaatc tggtggcacc ttcgcgcctg tctcgctgct ttcgataagt ctctagccat    120

ttaaaatttt tgatgacctg ctgcgacgct ttttttctgg caagatagtc ttgtaaatgc    180

gggccaagat cgatctgcac actggtattt cggtttttgg ggccgcgggc ggcgacgggg    240

cccgtgcgtc ccagcgcaca tgttcggcga ggcggggcct gcgagcgcgg ccaccgagaa    300

tcggacgggg gtagtctcaa gctggccggc ctgctctggt gcctggcctc gcgccgccgt    360

gtatcgcccc gccctgggcg gcaaggctgg cccggtcggc accagttgcg tgagcggaaa    420

gatggccgct tcccggccct gctgcaggga gctcaaaatg gaggacgcgg cgctcgggag    480

agcgggcggg tgagtcaccc acacaaagga aaagggcctt tccgtcctca gccgtcgctt    540

catgtgactc cacggagtac cgggcgccgt ccaggcacct cgattagttc tcgagctttt    600

ggagtacgtc gtctttaggt tgggggggagg ggttttatgc gatggagttt ccccacactg    660

agtgggtgga gactgaagtt aggccagctt ggcacttgat gtaattctcc ttggaatttg    720

ccctttttga gtttggatct tggttcattc tcaagcctca gacagtggtt caaagttttt    780

ttcttccatt tcaggtgtcg tggaattggc tagagcttgc atgcctgcag gtcggccgcc    840

acgaccggtg ccgccaccat cccctgaccc acgcccctga cccctcacaa ggagacgacc    900

ttccatgacc gagtacaagc ccacggtgcg cctcgccacc cgcgacgacg tcccccgggc    960

cgtacgcacc ctcgccgccg cgttcgccga ctaccccgcc acgcgccaca ccgtcgaccc   1020

ggaccgccac atcgagcggg tcaccgagct gcaagaactc ttcctcacgc gcgtcgggct   1080

cgacatcggc aaggtgtggg tcgcggacga cggcgccgcg gtggcggtct ggaccacgcc   1140

ggagagcgtc gaagcggggg cggtgttcgc cgagatcggc ccgcgcatgg ccgagttgag   1200

cggttcccgg ctggccgcgc agcaacagat ggaaggcctc ctggcgccgc accggcccaa   1260

ggagcccgcg tggttcctgg ccaccgtcgg cgtctcgccc gaccaccagg gcaagggtct   1320

gggcagcgcc gtcgtgctcc ccggagtgga ggcggccgag cgcgccgggg tgcccgcctt   1380
```

```
cctggagacc tccgcgcccc gcaacctccc cttctacgag cggctcggct tcaccgtcac   1440
cgccgacgtc gaggtgcccg aaggaccgcg cacctggtgc atgacccgca agcccggtgc   1500
ctgacgcccg ccccacgacc cgcagcgccc gaccgaaagg agcgcacgac cccatggctc   1560
cgaccgaagc cgacccgggc ggccccgccg accccgcacc cgcccccgag gcccaccgac   1620
tctagaggat cataatcagc cataccacat ttgtagaggt tttacttgct ttaaaaaacc   1680
tcccacacct ccccctgaac ctgaaacata aaatgaatgc aattgttgtt gttaacttgt   1740
ttattgcagc ttataatggt tacaaataaa gcaatagcat cacaaatttc acaaataaag   1800
catttttttc actgcattct agttgtggtt tgtccaaact catcaatgta tcttatcatg   1860
tctggatcct agcgtttaaa cttaagcttg gtaccgagct cggatccact agtaatggtt   1920
acaaataaag caatagcatc acaaatttca caaataaagc atttttttca ctgcattcta   1980
gttgtggttt gtccaaactc atcaatgtat cttatcatgt ctgtacgatg tacgggccag   2040
atatacgcgt tgacattgat tattgactag ttattaatag taatcaatta cggggtcatt   2100
agttcatagc ccatatatgg agttccgcgt tacataactt acggtaaatg gcccgcctgg   2160
ctgaccgccc aacgaccccc gcccattgac gtcaataatg acgtatgttc ccatagtaac   2220
gccaataggg actttccatt gacgtcaatg ggtggagtat ttacggtaaa ctgcccactt   2280
ggcagtacat caagtgtatc atatgccaag tacgccccct attgacgtca atgacggtaa   2340
atggcccgcc tggcattatg cccagtacat gaccttatgg gactttccta cttggcagta   2400
catctacgta ttagtcatcg ctattaccat ggtgatgcgg ttttggcagt acatcaatgg   2460
gcgtggatag cggtttgact cacggggatt tccaagtctc caccccattg acgtcaatgg   2520
gagtttgttt tggcaccaaa atcaacggga ctttccaaaa tgtcgtaaca actccgcccc   2580
attgacgcaa atgggcggta ggcgtgtacg gtgggaggtc tatataagca gagctctctg   2640
gctaactaga gaacccactg cttactggct tatcgaaatt aatacgactc actataggga   2700
gacccaagct ggctagctag tccagtgtgg tggaattctg cagatcgaaa cgatgataga   2760
tcccgtcgtt ttacaacgtc gtgactggga aaaccctggc gttacccaac ttaatcgcct   2820
tgcagcacat ccccctttcg ccagctggcg taatagcgaa gaggcccgca ccgatcgccc   2880
ttcccaacag ttgcgcagcc tgaatggcga atggcgcttt gcctggtttc cggtaccaga   2940
agcggtgccg gaaagctggc tggagtgcga tcttcctgag gccgatactg tcgtcgtccc   3000
ctcaaactgg cagatgcacg gttacgatgc gcccatctac accaacgtaa cctatcccat   3060
tacggtcaat ccgccgtttg ttcccacgga gaatccgacg ggttgttact cgctcacatt   3120
taatgttgat gaaagctggc tacaggaagg ccagacgcga attatttttg atggcgttaa   3180
ctcggcgttt catctgtggt gcaacgggcg ctgggtcggt tacggccagg acagtcgttt   3240
gccgtctgaa tttgacctga gcgcattttt acgcgccgga gaaaaccgcc tcgcggtgat   3300
ggtgctgcgt tggagtgacg gcagttatct ggaagatcag gatatgtggc ggatgagcgg   3360
cattttccgt gacgtctcgt tgctgcataa accgactaca caaatcagcg atttccatgt   3420
tgccactcgc tttaatgatg atttcagccg cgctgtactg gaggctgaag ttcagatgtg   3480
cggcgagttg cgtgactacc tacgggtaac agtttcttta tggcagggtg aaacgcaggt   3540
cgccagcggc accgcgcctt tcggcggtga aattatcgat gagcgtggtg gttatgccga   3600
tcgcgtcaca ctacgtctga acgtcgaaaa cccgaaactg tggagcgccg aaatcccgaa   3660
tctctatcgt gcggtggttg aactgcacac cgccgacggc acgctgattg aagcagaagc   3720
ctgcgatgtc ggtttccgcg aggtgcggat tgaaaatggt ctgctgctgc tgaacggcaa   3780
```

```
gccgttgctg attcgaggcg ttaaccgtca cgagcatcat cctctgcatg gtcaggtcat   3840
ggatgagcag acgatggtgc aggatatcct gctgatgaag cagaacaact ttaacgccgt   3900
gcgctgttcg cattatccga accatccgct gtggtacacg ctgtgcgacc gctacggcct   3960
gtatgtggtg gatgaagcca atattgaaac ccacggcatg gtgccaatga atcgtctgac   4020
cgatgatccg cgctggctac cggcgatgag cgaacgcgta acgcgaatgg tgcagcgcga   4080
tcgtaatcac ccgagtgtga tcatctggtc gctggggaat gaatcaggcc acggcgctaa   4140
tcacgacgcg ctgtatcgct ggatcaaatc tgtcgatcct tcccgcccgg tgcagtatga   4200
aggcggcgga gccgacacca cggccaccga tattatttgc ccgatgtacg cgcgcgtgga   4260
tgaagaccag cccttcccgg ctgtgccgaa atggtccatc aaaaaatggc tttcgctacc   4320
tggagagacg cgcccgctga tcctttgcga atacgcccac gcgatgggta acagtcttgg   4380
cggtttcgct aaatactggc aggcgtttcg tcagtatccc cgtttacagg gcggcttcgt   4440
ctgggactgg gtggatcagt cgctgattaa atatgatgaa aacggcaacc cgtggtcggc   4500
ttacggcggt gattttggcg atacgccgaa cgatcgccag ttctgtatga acggtctggt   4560
ctttgccgac cgcacgccgc atccagcgct gacggaagca aaacaccagc agcagttttt   4620
ccagttccgt ttatccgggc aaaccatcga agtgaccagc gaatacctgt tccgtcatag   4680
cgataacgag ctcctgcact ggatggtggc gctggatggt aagccgctgg caagcggtga   4740
agtgcctctg gatgtcgctc cacaaggtaa acagttgatt gaactgcctg aactaccgca   4800
gccggagagc gccgggcaac tctggctcac agtacgcgta gtgcaaccga acgcgaccgc   4860
atggtcagaa gccgggcaca tcagcgcctg gcagcagtgg cgtctggcgg aaaacctcag   4920
tgtgacgctc cccgccgcgt cccacgccat cccgcatctg accaccagcg aaatggattt   4980
ttgcatcgag ctgggtaata agcgttggca atttaaccgc cagtcaggct ttctttcaca   5040
gatgtggatt ggcgataaaa aacaactgct gacgccgctg cgcgatcagt tcacccgtgc   5100
accgctggat aacgacattg gcgtaagtga agcgacccgc attgacccta acgcctgggt   5160
cgaacgctgg aaggcggcgg gccattacca ggccgaagca gcgttgttgc agtgcacggc   5220
agatacactt gctgatgcgg tgctgattac gaccgctcac gcgtggcagc atcaggggaa   5280
aaccttattt atcagccgga aaacctaccg gattgatggt agtggtcaaa tggcgattac   5340
cgttgatgtt gaagtggcga gcgatacacc gcatccggcg cggattggcc tgaactgcca   5400
gctggcgcag gtagcagagc gggtaaactg gctcggatta gggccgcaag aaaactatcc   5460
cgaccgcctt actgccgcct gttttgaccg ctgggatctg ccattgtcag acatgtatac   5520
cccgtacgtc ttcccgagcg aaaacggtct gcgctgcggg acgcgcgaat tgaattatgg   5580
cccacaccag tggcgcggcg acttccagtt caacatcagc cgctacagtc aacagcaact   5640
gatggaaacc agccatcgcc atctgctgca cgcggaagaa ggcacatggc tgaatatcga   5700
cggtttccat atggggattg gtggcgacga ctcctggagc ccgtcagtat cggcggaatt   5760
ccagctgagc gccggtcgct accattacca gttggtctgg tgtcaaaaag cggccgctcg   5820
agtctagagg gcccgtttaa acccgctgat cagcctcgac tgtgccttct agttgccagc   5880
catctgttgt ttgcccctcc cccgtgcctt ccttgaccct ggaaggtgcc actcccactg   5940
tcctttccta ataaaatgag gaaattgcat cgcattgtct gagtaggtgt cattctattc   6000
tggggggtgg ggtggggcag gacagcaagg gggaggattg ggaagacaat agcaggcatg   6060
ctggggatgc ggtgggctct atggcttctg aggcggaaag aaccagctgg ggctctaggg   6120
ggtatcccca cgcgccctgt agcggcgcat taagcgcggc gggtgtggtg gttacgcgca   6180
```

```
gcgtgaccgc tacacttgcc agcgccctag cgcccgctcc tttcgctttc ttcccttcct   6240

ttctcgccac gttcgcctac cgtcgaatca ccggtaacct tataagggat tttgccgatt   6300

tcggcctatt ggttaaaaaa tgagctgatt taacaaaaat ttaacgcgaa ttaattctgt   6360

ggaatgtgtg tcagttaggg tgtggaaagt ccccaggctc cccagcaggc agaagtatgc   6420

aaagcatgca tctcaattag tcagcaacca ggtgtggaaa gtccccaggc tccccagcag   6480

gcagaagtat gcaaagcatg catctcaatt agtcagcaac catagtcccg cccctaactc   6540

cgcccatccc gcccctaact ccgcccagtt ccgcccattc tccgccccat ggctgactaa   6600

ttttttttat ttatgcagag gccgaggccg cctctgcctc tgagctattc cagaagtagt   6660

gaggaggctt ttttggaggc ctaggctttt gcaaaaagct cccgggagct tgtatatcca   6720

ttttcggatc tgatcaagag acaggatgag gatcgtttcg catgattgaa caagatggat   6780

tgcacgcagg ttctccggcc gcttgggtgg agaggctatt cggctatgac tgggcacaac   6840

agacaatcgg ctgctctgat gccgccgtgt tccggctgtc agcgcagggg cgcccggttc   6900

tttttgtcaa gaccgacctg tccggtgccc tgaatgaact gcaggacgag gcagcgcggc   6960

tatcgtggct ggccacgacg ggcgttcctt gcgcagctgt gctcgacgtt gtcactgaag   7020

cgggaaggga ctggctgcta ttgggcgaag tgccggggca ggatctcctg tcatctcacc   7080

ttgctcctgc cgagaaagta tccatcatgg ctgatgcaat gcggcggctg catacgcttg   7140

atccggctac ctgcccattc gaccaccaag cgaaacatcg catcgagcga gcacgtactc   7200

ggatggaagc cggtcttgtc gatcaggatg atctggacga agagcatcag gggctcgcgc   7260

cagccgaact gttcgccagg ctcaaggcgc g                                  7291
```

<210> SEQ ID NO 19
<211> LENGTH: 131
<212> TYPE: DNA
<213> ORGANISM: Artificial Sequence
<220> FEATURE:
<223> OTHER INFORMATION: Description of Artificial Sequence: Synthetic SV40pA (for puro) polynucleotide

<400> SEQUENCE: 19

```
aacttgttta ttgcagctta taatggttac aaataaagca atagcatcac aaatttcaca     60

aataaagcat ttttttcact gcattctagt tgtggtttgt ccaaactcat caatgtatct    120

tatcatgtct g                                                         131
```

<210> SEQ ID NO 20
<211> LENGTH: 344
<212> TYPE: DNA
<213> ORGANISM: Artificial Sequence
<220> FEATURE:
<223> OTHER INFORMATION: Description of Artificial Sequence: Synthetic SV40 promoter polynucleotide

<400> SEQUENCE: 20

```
ctgtggaatg tgtgtcagtt agggtgtgga aagtccccag gctccccagc aggcagaagt     60

atgcaaagca tgcatctcaa ttagtcagca accaggtgtg gaaagtcccc aggctcccca    120

gcaggcagaa gtatgcaaag catgcatctc aattagtcag caaccatagt cccgccccta    180

actccgccca tcccgcccct aactccgccc agttccgccc attctccgcc ccatggctga    240

ctaatttttt ttatttatgc agaggccgag gccgcctctg cctctgagct attccagaag    300

tagtgaggag gcttttttgg aggcctaggc ttttgcaaaa agct                     344
```

<210> SEQ ID NO 21
<211> LENGTH: 600
<212> TYPE: DNA
<213> ORGANISM: Artificial Sequence
<220> FEATURE:
<223> OTHER INFORMATION: Description of Artificial Sequence: Synthetic puromycin resistance gene

<400> SEQUENCE: 21
atgaccgagt acaagcccac ggtgcgcctc gccacccgcg acgacgtccc ccgggccgta 60
cgcaccctcg ccgccgcgtt cgccgactac cccgccacgc gccacaccgt cgacccggac 120
cgccacatcg agcgggtcac cgagctgcaa gaactcttcc tcacgcgcgt cgggctcgac 180
atcggcaagg tgtgggtcgc ggacgacggc gccgcggtgg cggtctggac cacgccggag 240
agcgtcgaag cgggggcggt gttcgccgag atcggcccgc gcatggccga gttgagcggt 300
tcccggctgg ccgcgcagca acagatggaa ggcctcctgg cgccgcaccg gcccaaggag 360
cccgcgtggt tcctggccac cgtcggcgtc tcgcccgacc accagggcaa gggtctgggc 420
agcgccgtcg tgctccccgg agtggaggcg gccgagcgcg ccggggtgcc cgccttcctg 480
gagacctccg cgccccgcaa cctccccttc tacgagcggc tcggcttcac cgtcaccgcc 540
gacgtcgagg tgcccgaagg accgcgcacc tggtgcatga cccgcaagcc cggtgcctga 600

<210> SEQ ID NO 22
<211> LENGTH: 6932
<212> TYPE: DNA
<213> ORGANISM: Artificial Sequence
<220> FEATURE:
<223> OTHER INFORMATION: Description of Artificial Sequence: Synthetic pTV_DS_MCS polynucleotide

<400> SEQUENCE: 22
ctagccttag gcgcgccaga tctgtacatt cgaagatatc ttaattaagc ggccgctcga 60
gtctagaggg cccgtttaaa cccgctgatc agcctcgact gtgccttcta gttgccagcc 120
atctgttgtt tgcccctccc ccgtgccttc cttgaccctg gaaggtgcca ctcccactgt 180
cctttcctaa taaaatgagg aaattgcatc gcattgtctg agtaggtgtc attctattct 240
ggggggtggg gtggggcagg acagcaaggg ggaggattgg gaagacaata gcaggcatgc 300
tggggatgcg gtgggctcta tggcttctga ggcggaaaga accagctggg gctctagggg 360
gtatccccac gcgccctgta gcggcgcatt aagcgcggcg ggtgtggtgg ttacgcgcag 420
cgtgaccgct acacttgcca gcgccctagc gcccgctcct ttcgctttct tcccttcctt 480
tctcgccacg ttcgcctacc gtcgaatcac cggtaacctt ataagggatt ttgccgattt 540
cggcctattg gttaaaaaat gagctgattt aacaaaaatt taacgcgaat taattctgtg 600
gaatgtgtgt cagttagggt gtggaaagtc cccaggctcc ccagcaggca gaagtatgca 660
aagcatgcat ctcaattagt cagcaaccag gtgtggaaag tccccaggct ccccagcagg 720
cagaagtatg caaagcatgc atctcaatta gtcagcaacc atagtcccgc ccctaactcc 780
gcccatcccg cccctaactc cgcccagttc cgcccattct ccgccccatg gctgactaat 840
ttttttattt tatgcagagg ccgaggccgc ctctgcctct gagctattcc agaagtagtg 900
aggaggcttt tttggaggcc taggcttttg caaaaagctc ccgggagctt gtatatccat 960
tttcggatct gatcaagaga caggatgagg atcgtttcgc atgattgaac aagatggatt 1020
gcacgcaggt tctccggccg cttgggtgga gaggctattc ggctatgact gggcacaaca 1080
gacaatcggc tgctctgatg ccgccgtgtt ccggctgtca gcgcaggggc gcccggttct 1140
ttttgtcaag accgacctgt ccggtgccct gaatgaactg caggacgagg cagcgcggct 1200

```
atcgtggctg gccacgacgg gcgttccttg cgcagctgtg ctcgacgttg tcactgaagc   1260
gggaagggac tggctgctat tgggcgaagt gccggggcag gatctcctgt catctcacct   1320
tgctcctgcc gagaaagtat ccatcatggc tgatgcaatg cggcggctgc atacgcttga   1380
tccggctacc tgcccattcg accaccaagc gaaacatcgc atcgagcgag cacgtactcg   1440
gatggaagcc ggtcttgtcg atcaggatga tctggacgaa gagcatcagg ggctcgcgcc   1500
agccgaactg ttcgccaggc tcaaggcgcg aattcgagct cggtacccgg ggatcctcta   1560
gagtcgacct gcaggcatgc aagcttggcg taatcatggt catagctgtt tcctgtgtga   1620
aattgttatc cgctcacaat tccacacaac atacgagccg gaagcataaa gtgtaaagcc   1680
tggggtgcct aatgagtgag ctaactcaca ttaattgcgt tgcgctcact gcccgctttc   1740
cagtcgggaa acctgtcgtg ccagctgcat taatgaatcg gccaacgcgc ggggagaggc   1800
ggtttgcgta ttgggcgctc ttccgcttcc tcgctcactg actcgctgcg ctcggtcgtt   1860
cggctgcggc gagcggtatc agctcactca aaggcggtaa tacggttatc cacagaatca   1920
ggggataacg caggaaagaa catgtgagca aaaggccagc aaaaggccag gaaccgtaaa   1980
aaggccgcgt tgctggcgtt tttccatagg ctccgccccc ctgacgagca tcacaaaaat   2040
cgacgctcaa gtcagaggtg gcgaaacccg acaggactat aaagatacca ggcgtttccc   2100
cctggaagct ccctcgtgcg ctctcctgtt ccgaccctgc cgcttaccgg atacctgtcc   2160
gcctttctcc cttcgggaag cgtggcgctt tctcatagct cacgctgtag gtatctcagt   2220
tcggtgtagg tcgttcgctc caagctgggc tgtgtgcacg aaccccccgt tcagcccgac   2280
cgctgcgcct tatccggtaa ctatcgtctt gagtccaacc cggtaagaca cgacttatcg   2340
ccactggcag cagccactgg taacaggatt agcagagcga ggtatgtagg cggtgctaca   2400
gagttcttga agtggtggcc taactacggc tacactagaa ggacagtatt tggtatctgc   2460
gctctgctga agccagttac cttcggaaaa agagttggta gctcttgatc cggcaaacaa   2520
accaccgctg gtagcggtgg tttttttgtt tgcaagcagc agattacgcg cagaaaaaaa   2580
ggatctcaag aagatccttt gatcttttct acggggtctg acgctcagtg gaacgaaaac   2640
tcacgttaag ggattttggt catgagatta tcaaaaagga tcttcaccta gatcctttta   2700
aattaaaaat gaagttttaa atcaatctaa agtatatatg agtaaacttg gtctgacagt   2760
taccaatgct taatcagtga ggcacctatc tcagcgatct gtctatttcg ttcatccata   2820
gttgcctgac tccccgtcgt gtagataact acgatacggg agggcttacc atctggcccc   2880
agtgctgcaa tgataccgcg agacccacgc tcaccggctc cagatttatc agcaataaac   2940
cagccagccg gaagggccga gcgcagaagt ggtcctgcaa ctttatccgc ctccatccag   3000
tctattaatt gttgccggga agctagagta agtagttcgc cagttaatag tttgcgcaac   3060
gttgttgcca ttgctacagg catcgtggtg tcacgctcgt cgtttggtat ggcttcattc   3120
agctccggtt cccaacgatc aaggcgagtt acatgatccc ccatgttgtg caaaaaagcg   3180
gttagctcct tcggtcctcc gatcgttgtc agaagtaagt tggccgcagt gttatcactc   3240
atggttatgg cagcactgca taattctctt actgtcatgc catccgtaag atgcttttct   3300
gtgactggtg agtactcaac caagtcattc tgagaatagt gtatgcggcg accgagttgc   3360
tcttgcccgg cgtcaatacg ggataatacc gcgccacata gcagaacttt aaaagtgctc   3420
atcattggaa aacgttcttc ggggcgaaaa ctctcaagga tcttaccgct gttgagatcc   3480
agttcgatgt aacccactcg tgcacccaac tgatcttcag catcttttac tttcaccagc   3540
gtttctgggt gagcaaaaac aggaaggcaa aatgccgcaa aaaagggaat aagggcgaca   3600
```

```
cggaaatgtt gaatactcat actcttcctt tttcaatatt attgaagcat ttatcagggt   3660
tattgtctca tgagcggata catatttgaa tgtatttaga aaaataaaca aataggggtt   3720
ccgcgcacat ttccccgaaa agtgccacct gacgtctaag aaaccattat tatcatgaca   3780
ttaacctata aaaataggcg tatcacgagg ccctttcgtc tcgcgcgttt cggtgatgac   3840
ggtgaaaacc tctgacacat gcagctcccg gagacggtca cagcttgtct gtaagcggat   3900
gccgggagca gacaagcccg tcagggcgcg tcagcgggtg ttggcgggtg tcggggctgg   3960
cttaactatg cggcatcaga gcagattgta ctgagagtgc accatatgcg gtgtgaaata   4020
ccgcacagat gcgtaaggag aaaataccgc atcaggcgcc attcgccatt caggctgcgc   4080
aactgttggg aagggcgatc ggtgcgggcc tcttcgctat tacgccagct ggcgaaaggg   4140
ggatgtgctg caaggcgatt aagttgggta acgccagggt tttcccagtc acgacgttgt   4200
aaaacgacgg ccagtgaatt ttaaggagcc ccttcgcctc gtgcttgagt tgaggcctgg   4260
cttgggcgct ggggccgccg cgtgcgaatc tggtggcacc ttcgcgcctg tctcgctgct   4320
ttcgataagt ctctagccat ttaaaatttt tgatgacctg ctgcgacgct ttttttctgg   4380
caagatagtc ttgtaaatgc gggccaagat cgatctgcac actggtattt cggtttttgg   4440
ggccgcgggc ggcgacgggg cccgtgcgtc ccagcgcaca tgttcggcga ggcggggcct   4500
gcgagcgcgg ccaccgagaa tcggacgggg gtagtctcaa gctggccggc ctgctctggt   4560
gcctggcctc gcgccgccgt gtatcgcccc gccctgggcg gcaaggctgg cccggtcggc   4620
accagttgcg tgagcggaaa gatggccgct tcccggccct gctgcaggga gctcaaaatg   4680
gaggacgcgg cgctcgggag agcgggcggg tgagtcaccc acacaaagga aaagggcctt   4740
tccgtcctca gccgtcgctt catgtgactc cacggagtac cgggcgccgt ccaggcacct   4800
cgattagttc tcgagctttt ggagtacgtc gtctttaggt tgggggggagg ggttttatgc   4860
gatggagttt ccccacactg agtgggtgga gactgaagtt aggccagctt ggcacttgat   4920
gtaattctcc ttggaatttg ccctttttga gtttggatct tggttcattc tcaagcctca   4980
gacagtggtt caaagttttt ttcttccatt tcaggtgtcg tggaattggc tagagcttgc   5040
atgcctgcag gtcggccgcc acgaccggtg ccgccaccat cccctgaccc acgcccctga   5100
cccctcacaa ggagacgacc ttccatgacc gagtacaagc ccacggtgcg cctcgccacc   5160
cgcgacgacg tcccccgggc cgtacgcacc ctcgccgccg cgttcgccga ctaccccgcc   5220
acgcgccaca ccgtcgaccc ggaccgccac atcgagcggg tcaccgagct gcaagaactc   5280
ttcctcacgc gcgtcgggct cgacatcggc aaggtgtggg tcgcggacga cggcgccgcg   5340
gtggcggtct ggaccacgcc ggagagcgtc gaagcggggg cggtgttcgc cgagatcggc   5400
ccgcgcatgg ccgagttgag cggttcccgg ctggccgcgc agcaacagat ggaaggcctc   5460
ctggcgccgc accggcccaa ggagcccgcg tggttcctgg ccaccgtcgg cgtctcgccc   5520
gaccaccagg gcaagggtct gggcagcgcc gtcgtgctcc ccggagtgga ggcggccgag   5580
cgcgccgggg tgcccgcctt cctggagacc tccgcgcccc gcaacctccc cttctacgag   5640
cggctcggct tcaccgtcac cgccgacgtc gaggtgcccg aaggaccgcg cacctggtgc   5700
atgacccgca agcccggtgc ctgacgcccg ccccacgacc cgcagcgccc gaccgaaagg   5760
agcgcacgac cccatggctc cgaccgaagc cgacccgggc ggccccgccg accccgcacc   5820
cgcccccgag gcccaccgac tctagaggat cataatcagc cataccacat ttgtagaggt   5880
tttacttgct ttaaaaaacc tcccacacct ccccctgaac ctgaaacata aaatgaatgc   5940
aattgttgtt gttaacttgt ttattgcagc ttataatggt tacaaataaa gcaatagcat   6000
```

```
cacaaatttc acaaataaag cattttttc actgcattct agttgtggtt tgtccaaact   6060

catcaatgta tcttatcatg tctggatcct agcgtttaaa cttaagcttg gtaccgagct   6120

cggatccact agtaatggtt acaaataaag caatagcatc acaaatttca caaataaagc   6180

atttttttca ctgcattcta gttgtggttt gtccaaactc atcaatgtat cttatcatgt   6240

ctgtacgatg tacgggccag atatacgcgt tgacattgat tattgactag ttattaatag   6300

taatcaatta cggggtcatt agttcatagc ccatatatgg agttccgcgt tacataactt   6360

acggtaaatg gcccgcctgg ctgaccgccc aacgaccccc gcccattgac gtcaataatg   6420

acgtatgttc ccatagtaac gccaataggg actttccatt gacgtcaatg ggtggagtat   6480

ttacggtaaa ctgcccactt ggcagtacat caagtgtatc atatgccaag tacgccccct   6540

attgacgtca atgacggtaa atggcccgcc tggcattatg cccagtacat gaccttatgg   6600

gactttccta cttggcagta catctacgta ttagtcatcg ctattaccat ggtgatgcgg   6660

ttttggcagt acatcaatgg gcgtggatag cggtttgact cacggggatt tccaagtctc   6720

caccccattg acgtcaatgg gagtttgttt tggcaccaaa atcaacggga ctttccaaaa   6780

tgtcgtaaca actccgcccc attgacgcaa atgggcggta ggcgtgtacg gtgggaggtc   6840

tatataagca gagctctctg gctaactaga gaacccactg cttactggct tatcgaaatt   6900

aatacgactc actataggga gacccaagct gg                                 6932
```

```
<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      MCS/Multiple Cloning Site oligonucleotide

<400> SEQUENCE: 23

ctagccttag gcgcgccaga tctgtacatt cgaagatatc ttaattaagc g              51
```

```
<210> SEQ ID NO 24
<211> LENGTH: 4216
<212> TYPE: DNA
<213> ORGANISM: Artificial Sequence
<220> FEATURE:
<223> OTHER INFORMATION: Description of Artificial Sequence: Synthetic
      KI-construct

<400> SEQUENCE: 24

ttaaggagcc ccttcgcctc gtgcttgagt tgaggcctgg cttgggcgct ggggccgccg     60

cgtgcgaatc tggtggcacc ttcgcgcctg tctcgctgct ttcgataagt ctctagccat    120

ttaaaatttt tgatgacctg ctgcgacgct ttttttctgg caagatagtc ttgtaaatgc    180

gggccaagat cgatctgcac actggtattt cggtttttgg ggccgcgggc ggcgacgggg    240

cccgtgcgtc ccagcgcaca tgttcggcga ggcggggcct gcgagcgcgg ccaccgagaa    300

tcggacgggg gtagtctcaa gctggccggc ctgctctggt gcctggcctc gcgccgccgt    360

gtatcgcccc gccctgggcg gcaaggctgg cccggtcggc accagttgcg tgagcggaaa    420

gatggccgct tcccggccct gctgcaggga gctcaaaatg gaggacgcgg cgctcgggag    480

agcgggcggg tgagtcaccc acacaaagga aaagggcctt tccgtcctca gccgtcgctt    540

catgtgactc cacggagtac cgggcgccgt ccaggcacct cgattagttc tcgagctttt    600

ggagtacgtc gtctttaggt tgggggggagg ggttttatgc gatggagttt ccccacactg    660

agtgggtgga gactgaagtt aggccagctt ggcacttgat gtaattctcc ttggaatttg    720
```

```
ccctttttga gtttggatct tggttcattc tcaagcctca gacagtggtt caaagttttt    780
ttcttccatt tcaggtgtcg tggaattggc tagagcttgc atgcctgcag gtcggccgcc    840
acgaccggtg ccgccaccat cccctgaccc acgcccctga cccctcacaa ggagacgacc    900
ttccatgacc gagtacaagc ccacggtgcg cctcgccacc cgcgacgacg tcccccgggc    960
cgtacgcacc ctcgccgccg cgttcgccga ctaccccgcc acgcgccaca ccgtcgaccc   1020
ggaccgccac atcgagcggg tcaccgagct gcaagaactc ttcctcacgc gcgtcgggct   1080
cgacatcggc aaggtgtggg tcgcggacga cggcgccgcg gtggcggtct ggaccacgcc   1140
ggagagcgtc gaagcggggg cggtgttcgc cgagatcggc ccgcgcatgg ccgagttgag   1200
cggttcccgg ctggccgcgc agcaacagat ggaaggcctc ctggcgccgc accggcccaa   1260
ggagcccgcg tggttcctgg ccaccgtcgg cgtctcgccc gaccaccagg gcaagggtct   1320
gggcagcgcc gtcgtgctcc ccggagtgga ggcggccgag cgcgccgggg tgcccgcctt   1380
cctggagacc tccgcgcccc gcaacctccc cttctacgag cggctcggct tcaccgtcac   1440
cgccgacgtc gaggtgcccg aaggaccgcg cacctggtgc atgacccgca agcccggtgc   1500
ctgacgcccg ccccacgacc cgcagcgccc gaccgaaagg agcgcacgac cccatggctc   1560
cgaccgaagc cgacccgggc ggccccgccg accccgcacc cgcccccgag gcccaccgac   1620
tctagaggat cataatcagc cataccacat ttgtagaggt tttacttgct ttaaaaaacc   1680
tcccacacct ccccctgaac ctgaaacata aaatgaatgc aattgttgtt gttaacttgt   1740
ttattgcagc ttataatggt tacaaataaa gcaatagcat cacaaatttc acaaataaag   1800
catttttttc actgcattct agttgtggtt tgtccaaact catcaatgta tcttatcatg   1860
tctggatcct agcgtttaaa cttaagcttg gtaccgagct cggatccact agtaatggtt   1920
acaaataaag caatagcatc acaaatttca caaataaagc atttttttca ctgcattcta   1980
gttgtggttt gtccaaactc atcaatgtat cttatcatgt ctgtacgatg tacgggccag   2040
atatacgcgt tgacattgat tattgactag ttattaatag taatcaatta cggggtcatt   2100
agttcatagc ccatatatgg agttccgcgt tacataactt acggtaaatg gcccgcctgg   2160
ctgaccgccc aacgaccccc gcccattgac gtcaataatg acgtatgttc ccatagtaac   2220
gccaataggg actttccatt gacgtcaatg ggtggagtat ttacggtaaa ctgcccactt   2280
ggcagtacat caagtgtatc atatgccaag tacgccccct attgacgtca atgacggtaa   2340
atggcccgcc tggcattatg cccagtacat gaccttatgg gactttccta cttggcagta   2400
catctacgta ttagtcatcg ctattaccat ggtgatgcgg ttttggcagt acatcaatgg   2460
gcgtggatag cggtttgact cacggggatt tccaagtctc caccccattg acgtcaatgg   2520
gagtttgttt tggcaccaaa atcaacggga ctttccaaaa tgtcgtaaca actccgcccc   2580
attgacgcaa atgggcggta ggcgtgtacg gtgggaggtc tatataagca gagctctctg   2640
gctaactaga gaacccactg cttactggct tatcgaaatt aatacgactc actataggga   2700
gacccaagct ggctagcgct gatatcgatc gcgagcggcc gctcgagtct agagggcccg   2760
tttaaacccg ctgatcagcc tcgactgtgc cttctagttg ccagccatct gttgtttgcc   2820
cctcccccgt gccttccttg accctggaag gtgccactcc cactgtcctt tcctaataaa   2880
atgaggaaat tgcatcgcat tgtctgagta ggtgtcattc tattctgggg ggtggggtgg   2940
ggcaggacag caagggggag gattgggaag acaatagcag gcatgctggg gatgcggtgg   3000
gctctatggc ttctgaggcg gaaagaacca gctggggctc tagggggtat ccccacgcgc   3060
cctgtagcgg cgcattaagc gcggcgggtg tggtggttac gcgcagcgtg accgctacac   3120
```

ttgccagcgc cctagcgccc gctcctttcg ctttcttccc ttcctttctc gccacgttcg 3180
cctaccgtcg aatcaccggt aaccttataa gggattttgc cgatttcggc ctattggtta 3240
aaaaatgagc tgatttaaca aaaatttaac gcgaattaat tctgtggaat gtgtgtcagt 3300
tagggtgtgg aaagtcccca ggctccccag caggcagaag tatgcaaagc atgcatctca 3360
attagtcagc aaccaggtgt ggaaagtccc caggctcccc agcaggcaga agtatgcaaa 3420
gcatgcatct caattagtca gcaaccatag tcccgcccct aactccgccc atcccgcccc 3480
taactccgcc cagttccgcc cattctccgc cccatggctg actaattttt tttatttatg 3540
cagaggccga ggccgcctct gcctctgagc tattccagaa gtagtgagga ggcttttttg 3600
gaggcctagg cttttgcaaa aagctcccgg gagcttgtat atccattttc ggatctgatc 3660
aagagacagg atgaggatcg tttcgcatga ttgaacaaga tggattgcac gcaggttctc 3720
cggccgcttg ggtggagagg ctattcggct atgactgggc acaacagaca atcggctgct 3780
ctgatgccgc cgtgttccgg ctgtcagcgc aggggcgccc ggttcttttt gtcaagaccg 3840
acctgtccgg tgccctgaat gaactgcagg acgaggcagc gcggctatcg tggctggcca 3900
cgacgggcgt tccttgcgca gctgtgctcg acgttgtcac tgaagcggga agggactggc 3960
tgctattggg cgaagtgccg gggcaggatc tcctgtcatc tcaccttgct cctgccgaga 4020
aagtatccat catggctgat gcaatgcggc ggctgcatac gcttgatccg gctacctgcc 4080
cattcgacca ccaagcgaaa catcgcatcg agcgagcacg tactcggatg gaagccggtc 4140
ttgtcgatca ggatgatctg gacgaagagc atcaggggct cgcgccagcc gaactgttcg 4200
ccaggctcaa ggcgcg 4216

<210> SEQ ID NO 25
<211> LENGTH: 655
<212> TYPE: DNA
<213> ORGANISM: Artificial Sequence
<220> FEATURE:
<223> OTHER INFORMATION: Description of Artificial Sequence: Synthetic hCMV promoter polynucleotide

<400> SEQUENCE: 25
cgatgtacgg gccagatata cgcgttgaca ttgattattg actagttatt aatagtaatc 60
aattacgggg tcattagttc atagcccata tatggagttc cgcgttacat aacttacggt 120
aaatggcccg cctggctgac cgcccaacga cccccgccca ttgacgtcaa taatgacgta 180
tgttcccata gtaacgccaa tagggacttt ccattgacgt caatgggtgg agtatttacg 240
gtaaactgcc cacttggcag tacatcaagt gtatcatatg ccaagtacgc cccctattga 300
cgtcaatgac ggtaaatggc ccgcctggca ttatgcccag tacatgacct tatgggactt 360
tcctacttgg cagtacatct acgtattagt catcgctatt accatggtga tgcggttttg 420
gcagtacatc aatgggcgtg gatagcggtt tgactcacgg ggatttccaa gtctccaccc 480
cattgacgtc aatgggagtt tgttttggca ccaaaatcaa cgggactttc caaaatgtcg 540
taacaactcc gccccattga cgcaaatggg cggtaggcgt gtacggtggg aggtctatat 600
aagcagagct ctctggctaa ctagagaacc cactgcttac tggcttatcg aaatt 655

<210> SEQ ID NO 26
<211> LENGTH: 530
<212> TYPE: DNA
<213> ORGANISM: Artificial Sequence
<220> FEATURE:
<223> OTHER INFORMATION: Description of Artificial Sequence: Synthetic delta Neomycin gene

<400> SEQUENCE: 26
atgattgaac aagatggatt gcacgcaggt tctccggccg cttgggtgga gaggctattc 60
ggctatgact gggcacaaca gacaatcggc tgctctgatg ccgccgtgtt ccggctgtca 120
gcgcaggggc gcccggttct ttttgtcaag accgacctgt ccggtgccct gaatgaactg 180
caggacgagg cagcgcggct atcgtggctg gccacgacgg gcgttccttg cgcagctgtg 240
ctcgacgttg tcactgaagc gggaagggac tggctgctat tgggcgaagt gccggggcag 300
gatctcctgt catctcacct tgctcctgcc gagaaagtat ccatcatggc tgatgcaatg 360
cggcggctgc atacgcttga tccggctacc tgcccattcg accaccaagc gaaacatcgc 420
atcgagcgag cacgtactcg gatggaagcc ggtcttgtcg atcaggatga tctggacgaa 480
gagcatcagg ggctcgcgcc agccgaactg ttcgccaggc tcaaggcgcg 530

<210> SEQ ID NO 27
<211> LENGTH: 215
<212> TYPE: DNA
<213> ORGANISM: Artificial Sequence
<220> FEATURE:
<223> OTHER INFORMATION: Description of Artificial Sequence: Synthetic bovine growth hormone polyA polynucleotide

<400> SEQUENCE: 27
gcctcgactg tgccttctag ttgccagcca tctgttgttt gcccctcccc cgtgccttcc 60
ttgaccctgg aaggtgccac tcccactgtc ctttcctaat aaaatgagga aattgcatcg 120
cattgtctga gtaggtgtca ttctattctg gggggtgggg tggggcagga cagcaagggg 180
gaggattggg aagacaatag caggcatgct gggga 215

<210> SEQ ID NO 28
<211> LENGTH: 806
<212> TYPE: DNA
<213> ORGANISM: Artificial Sequence
<220> FEATURE:
<223> OTHER INFORMATION: Description of Artificial Sequence: Synthetic 5' homologous portion in vector

<400> SEQUENCE: 28
ttaaggagcc ccttcgcctc gtgcttgagt tgaggcctgg cttgggcgct ggggccgccg 60
cgtgcgaatc tggtggcacc ttcgcgcctg tctcgctgct ttcgataagt ctctagccat 120
ttaaaatttt tgatgacctg ctgcgacgct ttttttctgg caagatagtc ttgtaaatgc 180
gggccaagat cgatctgcac actggtattt cggtttttgg ggccgcgggc ggcgacgggg 240
cccgtgcgtc ccagcgcaca tgttcggcga ggcggggcct gcgagcgcgg ccaccgagaa 300
tcggacgggg gtagtctcaa gctggccggc ctgctctggt gcctggcctc gcgccgccgt 360
gtatcgcccc gccctgggcg gcaaggctgg cccggtcggc accagttgcg tgagcggaaa 420
gatggccgct tcccggccct gctgcaggga gctcaaaatg gaggacgcgg cgctcgggag 480
agcgggcggg tgagtcaccc acacaaagga aaagggcctt tccgtcctca gccgtcgctt 540
catgtgactc cacggagtac cgggcgccgt ccaggcacct cgattagttc tcgagctttt 600
ggagtacgtc gtctttaggt tggggggagg ggttttatgc gatggagttt ccccacactg 660
agtgggtgga gactgaagtt aggccagctt ggcacttgat gtaattctcc ttggaatttg 720
ccctttttga gtttggatct tggttcattc tcaagcctca gacagtggtt caaagttttt 780
ttcttccatt tcaggtgtcg tggaat 806

<210> SEQ ID NO 29
<211> LENGTH: 801
<212> TYPE: DNA
<213> ORGANISM: Artificial Sequence
<220> FEATURE:
<223> OTHER INFORMATION: Description of Artificial Sequence: Synthetic 3' homologous portion in vector

<400> SEQUENCE: 29
agccccttcg cctcgtgctt gagttgaggc ctggcttggg cgctggggcc gccgcgtgcg 60
aatctggtgg caccttcgcg cctgtctcgc tgctttcgat aagtctctag ccatttaaaa 120
tttttgatga cctgctgcga cgcttttttt ctggcaagat agtcttgtaa atgcgggcca 180
agatcgatct gcacactggt atttcggttt ttggggccgc gggcggcgac ggggcccgtg 240
cgtcccagcg cacatgttcg gcgaggcggg gcctgcgagc gcggccaccg agaatcggac 300
gggggtagtc tcaagctggc cggcctgctc tggtgcctgg cctcgcgccg ccgtgtatcg 360
ccccgccctg ggcggcaagg ctggcccggt cggcaccagt tgcgtgagcg gaaagatggc 420
cgcttcccgg ccctgctgca gggagctcaa aatggaggac gcggcgctcg ggagagcggg 480
cgggtgagtc acccacacaa aggaaaaggg cctttccgtc ctcagccgtc gcttcatgtg 540
actccacgga gtaccgggcg ccgtccaggc acctcgatta gttctcgagc ttttggagta 600
cgtcgtcttt aggttggggg gaggggtttt atgcgatgga gtttccccac actgagtggg 660
tggagactga agttaggcca gcttggcact tgatgtaatt ctccttggaa tttgcccttt 720
ttgagtttgg atcttggttc attctcaagc ctcagacagt ggttcaaagt ttttttcttc 780
catttcaggt gtcgtggaat t 801

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic F1_Prom oligonucleotide

<400> SEQUENCE: 30
ccccgaccgg agctgagagt aatt 24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic B1_Pur oligonucleotide

<400> SEQUENCE: 31
caggaggcct tccatctgtt g 21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic CLS_P4_Fwd2 oligonucleotide

<400> SEQUENCE: 32
ctgtggaatg tgtgtcagt 19

<210> SEQ ID NO 33
<211> LENGTH: 24

<212> TYPE: DNA
<213> ORGANISM: Artificial Sequence
<220> FEATURE:
<223> OTHER INFORMATION: Description of Artificial Sequence: Synthetic CLS_P4_Rev1 oligonucleotide

<400> SEQUENCE: 33

```
caacgctatg tcctgatagc ggtc                                         24
```

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic Capped polyA oligonucleotide

<400> SEQUENCE: 34

```
aaaaaaaaaa aaaaaaaaaa aaaaaaaaaa                                   30
```

<210> SEQ ID NO 35
<211> LENGTH: 642
<212> TYPE: DNA
<213> ORGANISM: Artificial Sequence
<220> FEATURE:
<223> OTHER INFORMATION: Description of Artificial Sequence: Synthetic Capped polyA meganuclease polynucleotide

<400> SEQUENCE: 35

```
aaaaaaaaaa aaaaaaaaaa aaaaaaaaaa tggctaatac taaatataat aaagaatttc     60

ttctttatct tgctggtttt gttgatggtg atggttctat tattgctcaa attaaaccta    120

atcaatctta taaatttaaa catcaacttt ctcttacttt tcaagttact caaaaaactc    180

aacgtcgttg gtttcttgat aaacttgttg atgaaattgg tgttggttat gttcgtgatc    240

gtggttctgt ttctaattat attctttctg aaattaaacc tcttcataat tttcttactc    300

aacttcaacc ttttcttaaa cttaaacaaa aacaagctaa tcttgttctt aaaattattg    360

aacaacttcc ttctgctaaa gaatctcctg ataaatttct tgaagtttgt acttgggttg    420

atcaaattgc tgctcttaat gattctaaaa ctcgtaaaac tacttctgaa actgttcgtg    480

ctgttcttga ttctctttct gaaaaaaaaa aatcttctcc tgctgctgat aaaaaaaaaa    540

aaaaaaaaaa aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aa                        642
```

<210> SEQ ID NO 36
<211> LENGTH: 163
<212> TYPE: PRT
<213> ORGANISM: Chlamydomonas reinhardtii

<400> SEQUENCE: 36

```
Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
```

```
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro


<210> SEQ ID NO 37
<211> LENGTH: 194
<212> TYPE: PRT
<213> ORGANISM: Desulfurococcus mobilis

<400> SEQUENCE: 37

Met His Asn Asn Glu Asn Val Ser Gly Ile Ser Ala Tyr Leu Leu Gly
1               5                   10                  15

Leu Ile Ile Gly Asp Gly Gly Leu Tyr Lys Leu Lys Tyr Lys Gly Asn
            20                  25                  30

Arg Ser Glu Tyr Arg Val Val Ile Thr Gln Lys Ser Glu Asn Leu Ile
        35                  40                  45

Lys Gln His Ile Ala Pro Leu Met Gln Phe Leu Ile Asp Glu Leu Asn
    50                  55                  60

Val Lys Ser Lys Ile Gln Ile Val Lys Gly Asp Thr Arg Tyr Glu Leu
65                  70                  75                  80

Arg Val Ser Ser Lys Lys Leu Tyr Tyr Tyr Phe Ala Asn Met Leu Glu
                85                  90                  95

Arg Ile Arg Leu Phe Asn Met Arg Glu Gln Ile Ala Phe Ile Lys Gly
            100                 105                 110

Leu Tyr Val Ala Glu Gly Asp Lys Thr Leu Lys Arg Leu Arg Ile Trp
        115                 120                 125

Asn Lys Asn Lys Ala Leu Leu Glu Ile Val Ser Arg Trp Leu Asn Asn
    130                 135                 140

Leu Gly Val Arg Asn Thr Ile His Leu Asp Asp His Arg His Gly Val
145                 150                 155                 160

Tyr Val Leu Asn Ile Ser Leu Arg Asp Arg Ile Lys Phe Val His Thr
                165                 170                 175

Ile Leu Ser Ser His Leu Asn Pro Leu Pro Pro Glu Arg Ala Gly Gly
            180                 185                 190

Tyr Thr


<210> SEQ ID NO 38
<211> LENGTH: 5647
<212> TYPE: DNA
<213> ORGANISM: Artificial Sequence
<220> FEATURE:
<223> OTHER INFORMATION: Description of Artificial Sequence: Synthetic
      pCLS1088 polynucleotide

<400> SEQUENCE: 38

cttgtacaaa gtggttgatc tagagggccc gcggttcgaa ggtaagccta tccctaaccc     60

tctcctcggt ctcgattcta cgcgtaccgg ttagtaatga gtttaaacgg gggaggctaa    120

ctgaaacacg gaaggagaca ataccggaag gaacccgcgc tatgacggca ataaaaagac    180

agaataaaac gcacgggtgt tgggtcgttt gttcataaac gcggggttcg gtcccagggc    240
```

```
tggcactctg tcgatacccc accgagaccc cattggggcc aatacgcccg cgtttcttcc    300
ttttccccac cccacccccc aagttcgggt gaaggcccag ggctcgcagc caacgtcggg    360
gcggcaggcc ctgccatagc agatctgcgc agctggggct ctagggggta tccccacgcg    420
ccctgtagcg gcgcattaag cgcggcgggt gtggtggtta cgcgcagcgt gaccgctaca    480
cttgccagcg ccctagcgcc cgctcctttc gctttcttcc cttcctttct cgccacgttc    540
gccggctttc cccgtcaagc tctaaatcgg ggcatccctt tagggttccg atttagtgct    600
ttacggcacc tcgaccccaa aaaacttgat tagggtgatg gttcacgtag tgggccatcg    660
ccctgataga cggtttttcg ccctttgacg ttggagtcca cgttctttaa tagtggactc    720
ttgttccaaa ctggaacaac actcaaccct atctcggtct attcttttga tttataaggg    780
attttgggga tttcggccta ttggttaaaa aatgagctga tttaacaaaa atttaacgcg    840
aattaattct gtggaatgtg tgtcagttag ggtgtggaaa gtccccaggc tccccagcag    900
gcagaagtat gcaaagcatg catctcaatt agtcagcaac caggtgtgga aagtccccag    960
gctccccagc aggcagaagt atgcaaagca tgcatctcaa ttagtcagca accatagtcc   1020
cgcccctaac tccgcccatc ccgcccctaa ctccgcccag ttccgcccat tctccgcccc   1080
atggctgact aatttttttt atttatgcag aggccgaggc cgcctctgcc tctgagctat   1140
tccagaagta gtgaggaggc ttttttggag gcctaggctt ttgcaaaaag ctcccgggag   1200
cttgtatatc cattttcgga tctgatcagc acgtgttgac aattaatcat cggcatagta   1260
tatcggcata gtataatacg acaaggtgag gaactaaacc atggccaagc ctttgtctca   1320
agaagaatcc accctcattg aaagagcaac ggctacaatc aacagcatcc ccatctctga   1380
agactacagc gtcgccagcg cagctctctc tagcgacggc cgcatcttca ctggtgtcaa   1440
tgtatatcat tttactgggg gaccttgtgc agaactcgtg gtgctgggca ctgctgctgc   1500
tgcggcagct ggcaacctga cttgtatcgt cgcgatcgga aatgagaaca ggggcatctt   1560
gagcccctgc ggacggtgcc gacaggtgct tctcgatctg catcctggga tcaaagccat   1620
agtgaaggac agtgatggac agccgacggc agttgggatt cgtgaattgc tgccctctgg   1680
ttatgtgtgg gagggctaag cacttcgtgg ccgaggagca ggactgacac gtgctacgag   1740
atttcgattc caccgccgcc ttctatgaaa ggttgggctt cggaatcgtt ttccgggacg   1800
ccggctggat gatcctccag cgcggggatc tcatgctgga gttcttcgcc caccccaact   1860
tgtttattgc agcttataat ggttacaaat aaagcaatag catcacaaat ttcacaaata   1920
aagcattttt ttcactgcat tctagttgtg gtttgtccaa actcatcaat gtatcttatc   1980
atgtctgtat accgtcgacc tctagctaga gcttggcgta atcatggtca tagctgtttc   2040
ctgtgtgaaa ttgttatccg ctcacaattc cacacaacat acgagccgga agcataaagt   2100
gtaaagcctg gggtgcctaa tgagtgagct aactcacatt aattgcgttg cgctcactgc   2160
ccgctttcca gtcgggaaac ctgtcgtgcc agctgcatta atgaatcggc caacgcgcgg   2220
ggagaggcgg tttgcgtatt gggcgctctt ccgcttcctc gctcactgac tcgctgcgct   2280
cggtcgttcg gctgcggcga gcggtatcag ctcactcaaa ggcggtaata cggttatcca   2340
cagaatcagg ggataacgca ggaaagaaca tgtgagcaaa aggccagcaa aaggccagga   2400
accgtaaaaa ggccgcgttg ctggcgtttt tccataggct ccgcccccct gacgagcatc   2460
acaaaaatcg acgctcaagt cagaggtggc gaaacccgac aggactataa agataccagg   2520
cgtttccccc tggaagctcc ctcgtgcgct ctcctgttcc gaccctgccg cttaccggat   2580
acctgtccgc ctttctccct tcgggaagcg tggcgctttc tcatagctca cgctgtaggt   2640
```

```
atctcagttc ggtgtaggtc gttcgctcca agctgggctg tgtgcacgaa ccccccgttc   2700
agcccgaccg ctgcgcctta tccggtaact atcgtcttga gtccaacccg gtaagacacg   2760
acttatcgcc actggcagca gccactggta acaggattag cagagcgagg tatgtaggcg   2820
gtgctacaga gttcttgaag tggtggccta actacggcta cactagaaga acagtatttg   2880
gtatctgcgc tctgctgaag ccagttacct tcggaaaaag agttggtagc tcttgatccg   2940
gcaaacaaac caccgctggt agcggttttt ttgtttgcaa gcagcagatt acgcgcagaa   3000
aaaaaggatc tcaagaagat cctttgatct tttctacggg gtctgacgct cagtggaacg   3060
aaaactcacg ttaagggatt ttggtcatga gattatcaaa aaggatcttc acctagatcc   3120
ttttaaatta aaaatgaagt tttaaatcaa tctaaagtat atatgagtaa acttggtctg   3180
acagttacca atgcttaatc agtgaggcac ctatctcagc gatctgtcta tttcgttcat   3240
ccatagttgc ctgactcccc gtcgtgtaga taactacgat acgggagggc ttaccatctg   3300
gccccagtgc tgcaatgata ccgcgagacc cacgctcacc ggctccagat ttatcagcaa   3360
taaaccagcc agccggaagg gccgagcgca gaagtggtcc tgcaacttta tccgcctcca   3420
tccagtctat taattgttgc cgggaagcta gagtaagtag ttcgccagtt aatagtttgc   3480
gcaacgttgt tgccattgct acaggcatcg tggtgtcacg ctcgtcgttt ggtatggctt   3540
cattcagctc cggttcccaa cgatcaaggc gagttacatg atcccccatg ttgtgcaaaa   3600
aagcggttag ctccttcggt cctccgatcg ttgtcagaag taagttggcc gcagtgttat   3660
cactcatggt tatggcagca ctgcataatt ctcttactgt catgccatcc gtaagatgct   3720
tttctgtgac tggtgagtac tcaaccaagt cattctgaga atagtgtatg cggcgaccga   3780
gttgctcttg cccggcgtca atacgggata ataccgcgcc acatagcaga actttaaaag   3840
tgctcatcat tggaaaacgt tcttcggggc gaaaactctc aaggatctta ccgctgttga   3900
gatccagttc gatgtaaccc actcgtgcac ccaactgatc ttcagcatct tttactttca   3960
ccagcgtttc tgggtgagca aaaacaggaa ggcaaaatgc cgcaaaaaag ggaataaggg   4020
cgacacggaa atgttgaata ctcatactct tcctttttca atattattga agcatttatc   4080
agggttattg tctcatgagc ggatacatat ttgaatgtat ttagaaaaat aaacaaatag   4140
gggttccgcg cacatttccc cgaaaagtgc cacctgacgt cgacggatcg ggagatctcc   4200
cgatccccta tggtgcactc tcagtacaat ctgctctgat gccgcatagt taagccagta   4260
tctgctccct gcttgtgtgt tggaggtcgc tgagtagtgc gcgagcaaaa tttaagctac   4320
aacaaggcaa ggcttgaccg acaattgcat gaagaatctg cttagggtta ggcgttttgc   4380
gctgcttcgc gatgtacggg ccagatatac gcgttgacat tgattattga ctagttatta   4440
atagtaatca attacggggt cattagttca tagcccatat atggagttcc gcgttacata   4500
acttacggta aatggcccgc ctggctgacc gcccaacgac ccccgcccat tgacgtcaat   4560
aatgacgtat gttcccatag taacgccaat agggactttc cattgacgtc aatgggtgga   4620
gtatttacgg taaactgccc acttggcagt acatcaagtg tatcatatgc caagtacgcc   4680
ccctattgac gtcaatgacg gtaaatggcc cgcctggcat tatgcccagt acatgacctt   4740
atgggacttt cctacttggc agtacatcta cgtattagtc atcgctatta ccatggtgat   4800
gcggttttgg cagtacatca atgggcgtgg atagcggttt gactcacggg gatttccaag   4860
tctccacccc attgacgtca atgggagttt gttttggcac caaaatcaac gggactttcc   4920
aaaatgtcgt aacaactccg ccccattgac gcaaatgggc ggtaggcgtg tacggtggga   4980
ggtctatata agcagagctc tctggctaac tagagaaccc actgcttact ggcttatcga   5040
```

```
aattaatacg actcactata gggagaccca agctggctag ttaagctatc aacaagtttg   5100

tacaaaaaag caggcttcga aggagataga accatggcca ataccaaata taacaaagag   5160

ttcctgctgt acctggccgg ctttgtggac ggtgacggta gcatcatcgc tcagattaaa   5220

ccaaaccagt cttataagtt taaacatcag ctaagcttga cctttcaggt gactcaaaag   5280

acccagcgcc gttggtttct ggacaaacta gtggatgaaa ttggcgttgg ttacgtacgt   5340

gatcgcggat ccgtttccaa ctacatctta agcgaaatca agccgctgca caacttcctg   5400

actcaactgc agccgtttct gaaactgaaa cagaaacagg caaacctggt tctgaaaatt   5460

atcgaacagc tgccgtctgc aaaagaatcc ccggacaaat tcctggaagt ttgtacctgg   5520

gtggatcaga ttgcagctct gaacgattct aagacgcgta aaaccacttc tgaaaccgtt   5580

cgtgctgtgc tggacagcct gagcgagaag aagaaatcct ccccggcggc cgactaaacc   5640

cagcttt                                                             5647
```

```
<210> SEQ ID NO 39
<211> LENGTH: 5647
<212> TYPE: DNA
<213> ORGANISM: Artificial Sequence
<220> FEATURE:
<223> OTHER INFORMATION: Description of Artificial Sequence: Synthetic
      pCLS2147 polynucleotide

<400> SEQUENCE: 39
```

```
cttgtacaaa gtggttgatc tagagggccc gcggttcgaa ggtaagccta tccctaaccc     60

tctcctcggt ctcgattcta cgcgtaccgg ttagtaatga gtttaaacgg gggaggctaa    120

ctgaaacacg gaaggagaca ataccggaag gaacccgcgc tatgacggca ataaaaagac    180

agaataaaac gcacgggtgt tgggtcgttt gttcataaac gcggggttcg gtcccagggc    240

tggcactctg tcgatacccc accgagaccc cattggggcc aatacgcccg cgtttcttcc    300

ttttccccac cccacccccc aagttcgggt gaaggcccag ggctcgcagc caacgtcggg    360

gcggcaggcc ctgccatagc agatctgcgc agctggggct ctaggggggta tccccacgcg    420

ccctgtagcg gcgcattaag cgcggcgggt gtggtggtta cgcgcagcgt gaccgctaca    480

cttgccagcg ccctagcgcc cgctcctttc gctttcttcc cttcctttct cgccacgttc    540

gccggctttc cccgtcaagc tctaaatcgg ggcatccctt tagggttccg atttagtgct    600

ttacggcacc tcgaccccaa aaaacttgat tagggtgatg gttcacgtag tgggccatcg    660

ccctgataga cggtttttcg ccctttgacg ttggagtcca cgttctttaa tagtggactc    720

ttgttccaaa ctggaacaac actcaaccct atctcggtct attcttttga tttataaggg    780

attttgggga tttcggccta ttggttaaaa aatgagctga tttaacaaaa atttaacgcg    840

aattaattct gtggaatgtg tgtcagttag ggtgtggaaa gtccccaggc tccccagcag    900

gcagaagtat gcaaagcatg catctcaatt agtcagcaac caggtgtgga aagtccccag    960

gctccccagc aggcagaagt atgcaaagca tgcatctcaa ttagtcagca accatagtcc   1020

cgcccctaac tccgcccatc ccgcccctaa ctccgcccag ttccgcccat tctccgcccc   1080

atggctgact aatttttttt atttatgcag aggccgaggc cgcctctgcc tctgagctat   1140

tccagaagta gtgaggaggc ttttttggag gcctaggctt ttgcaaaaag ctcccgggag   1200

cttgtatatc cattttcgga tctgatcagc acgtgttgac aattaatcat cggcatagta   1260

tatcggcata gtataatacg acaaggtgag gaactaaacc atggccaagc ctttgtctca   1320

agaagaatcc accctcattg aaagagcaac ggctacaatc aacagcatcc ccatctctga   1380
```

-continued

```
agactacagc gtcgccagcg cagctctctc tagcgacggc cgcatcttca ctggtgtcaa   1440
tgtatatcat tttactgggg gaccttgtgc agaactcgtg gtgctgggca ctgctgctgc   1500
tgcggcagct ggcaacctga cttgtatcgt cgcgatcgga aatgagaaca ggggcatctt   1560
gagcccctgc ggacggtgcc gacaggtgct tctcgatctg catcctggga tcaaagccat   1620
agtgaaggac agtgatggac agccgacggc agttgggatt cgtgaattgc tgccctctgg   1680
ttatgtgtgg gagggctaag cacttcgtgg ccgaggagca ggactgacac gtgctacgag   1740
atttcgattc caccgccgcc ttctatgaaa ggttgggctt cggaatcgtt ttccgggacg   1800
ccggctggat gatcctccag cgcggggatc tcatgctgga gttcttcgcc caccccaact   1860
tgtttattgc agcttataat ggttacaaat aaagcaatag catcacaaat ttcacaaata   1920
aagcattttt ttcactgcat tctagttgtg gtttgtccaa actcatcaat gtatcttatc   1980
atgtctgtat accgtcgacc tctagctaga gcttggcgta atcatggtca tagctgtttc   2040
ctgtgtgaaa ttgttatccg ctcacaattc cacacaacat acgagccgga agcataaagt   2100
gtaaagcctg gggtgcctaa tgagtgagct aactcacatt aattgcgttg cgctcactgc   2160
ccgctttcca gtcgggaaac ctgtcgtgcc agctgcatta atgaatcggc caacgcgcgg   2220
ggagaggcgg tttgcgtatt gggcgctctt ccgcttcctc gctcactgac tcgctgcgct   2280
cggtcgttcg gctgcggcga gcggtatcag ctcactcaaa ggcggtaata cggttatcca   2340
cagaatcagg ggataacgca ggaaagaaca tgtgagcaaa aggccagcaa aaggccagga   2400
accgtaaaaa ggccgcgttg ctggcgtttt tccataggct ccgcccccct gacgagcatc   2460
acaaaaatcg acgctcaagt cagaggtggc gaaacccgac aggactataa agataccagg   2520
cgtttccccc tggaagctcc ctcgtgcgct ctcctgttcc gaccctgccg cttaccggat   2580
acctgtccgc ctttctccct tcgggaagcg tggcgctttc tcatagctca cgctgtaggt   2640
atctcagttc ggtgtaggtc gttcgctcca agctgggctg tgtgcacgaa ccccccgttc   2700
agcccgaccg ctgcgcctta tccggtaact atcgtcttga gtccaacccg gtaagacacg   2760
acttatcgcc actggcagca gccactggta acaggattag cagagcgagg tatgtaggcg   2820
gtgctacaga gttcttgaag tggtggccta actacggcta cactagaaga acagtatttg   2880
gtatctgcgc tctgctgaag ccagttacct tcggaaaaag agttggtagc tcttgatccg   2940
gcaaacaaac caccgctggt agcggttttt ttgtttgcaa gcagcagatt acgcgcagaa   3000
aaaaaggatc tcaagaagat cctttgatct tttctacggg gtctgacgct cagtggaacg   3060
aaaactcacg ttaagggatt ttggtcatga gattatcaaa aaggatcttc acctagatcc   3120
ttttaaatta aaaatgaagt tttaaatcaa tctaaagtat atatgagtaa acttggtctg   3180
acagttacca atgcttaatc agtgaggcac ctatctcagc gatctgtcta tttcgttcat   3240
ccatagttgc ctgactcccc gtcgtgtaga taactacgat acgggagggc ttaccatctg   3300
gccccagtgc tgcaatgata ccgcgagacc cacgctcacc ggctccagat ttatcagcaa   3360
taaaccagcc agccggaagg gccgagcgca gaagtggtcc tgcaacttta tccgcctcca   3420
tccagtctat taattgttgc cgggaagcta gagtaagtag ttcgccagtt aatagtttgc   3480
gcaacgttgt tgccattgct acaggcatcg tggtgtcacg ctcgtcgttt ggtatggctt   3540
cattcagctc cggttcccaa cgatcaaggc gagttacatg atcccccatg ttgtgcaaaa   3600
aagcggttag ctccttcggt cctccgatcg ttgtcagaag taagttggcc gcagtgttat   3660
cactcatggt tatggcagca ctgcataatt ctcttactgt catgccatcc gtaagatgct   3720
tttctgtgac tggtgagtac tcaaccaagt cattctgaga atagtgtatg cggcgaccga   3780
```

```
gttgctcttg cccggcgtca atacgggata ataccgcgcc acatagcaga actttaaaag   3840

tgctcatcat tggaaaacgt tcttcggggc gaaaactctc aaggatctta ccgctgttga   3900

gatccagttc gatgtaaccc actcgtgcac ccaactgatc ttcagcatct tttactttca   3960

ccagcgtttc tgggtgagca aaaacaggaa ggcaaaatgc cgcaaaaaag ggaataaggg   4020

cgacacggaa atgttgaata ctcatactct tcctttttca atattattga agcatttatc   4080

agggttattg tctcatgagc ggatacatat ttgaatgtat ttagaaaaat aaacaaatag   4140

gggttccgcg cacatttccc cgaaaagtgc cacctgacgt cgacggatcg ggagatctcc   4200

cgatccccta tggtgcactc tcagtacaat ctgctctgat gccgcatagt taagccagta   4260

tctgctccct gcttgtgtgt tggaggtcgc tgagtagtgc gcgagcaaaa tttaagctac   4320

aacaaggcaa ggcttgaccg acaattgcat gaagaatctg cttagggtta ggcgttttgc   4380

gctgcttcgc gatgtacggg ccagatatac gcgttgacat tgattattga ctagttatta   4440

atagtaatca attacggggt cattagttca tagcccatat atggagttcc gcgttacata   4500

acttacggta aatggcccgc ctggctgacc gcccaacgac ccccgcccat tgacgtcaat   4560

aatgacgtat gttcccatag taacgccaat agggactttc cattgacgtc aatgggtgga   4620

gtatttacgg taaactgccc acttggcagt acatcaagtg tatcatatgc caagtacgcc   4680

ccctattgac gtcaatgacg gtaaatggcc cgcctggcat tatgcccagt acatgacctt   4740

atgggacttt cctacttggc agtacatcta cgtattagtc atcgctatta ccatggtgat   4800

gcggttttgg cagtacatca atgggcgtgg atagcggttt gactcacggg gatttccaag   4860

tctccacccc attgacgtca atgggagttt gttttggcac caaaatcaac gggactttcc   4920

aaaatgtcgt aacaactccg ccccattgac gcaaatgggc ggtaggcgtg tacggtggga   4980

ggtctatata agcagagctc tctggctaac tagagaaccc actgcttact ggcttatcga   5040

aattaatacg actcactata gggagaccca agctggctag ttaagctatc aacaagtttg   5100

tacaaaaaag caggcttcga aggagataga accatggcca ataccaaata taacaaagag   5160

ttcctgctgt acctggccgg ctttgtggac ggtgacggta gcatcatcgc tcagattaaa   5220

ccaaaccagt cttataagtt taaacatcag ctaagcttga cctttcaggt gactcaaaag   5280

acccagcgcc gttggtttct ggacaaacta gtggatgaaa ttggcgttgg ttacgtacgt   5340

gatcgcggat ccgtttccaa ctacatctta agcgaaatca agccgctgca caacttcctg   5400

actcaactgc agccgtttct gaaactgaaa cagaaacagg caaacctggc tctgaaaatt   5460

atcgaacagc tgccgtctgc aaaagaatcc ccggacaaat tcctggaagt ttgtacctgg   5520

gtggatcagg ttgcagctct gaacgattct aagacgcgta aaaccacttc tgaaaccgtt   5580

cgtgctgtgc tggacagcct gagcgagaag aagaaatcct ccccggcggc cgactaaacc   5640

cagcttt                                                             5647
```

<210> SEQ ID NO 40
<211> LENGTH: 1428
<212> TYPE: DNA
<213> ORGANISM: Homo sapiens

<400> SEQUENCE: 40

```
atggcgtact accatcacca tcaccatcac tctagatcag aaggagttcg aaccaaccgg     60

ggagtccctt ttaggcactt gcttctggtg ctgcaactgg cgctcctccc agcagccact    120

cagggaaaga aagtggtgct gggcaaaaaa ggggatacag tggaactgac ctgtacagct    180

tcccagaaga agagcataca attccactgg aaaaactcca accagataaa gattctggga    240
```

```
aatcagggct ccttcttaac taaaggtcca tccaagctga atgatcgcgc tgactcaaga    300

agaagccttt gggaccaagg aaacttcccc ctgatcatca agaatcttaa gatagaagac    360

tcagatactt acatctgtga agtggaggac cagaaggagg aggtgcaatt gctagtgttc    420

ggattgactg ccaactctga cacccacctg cttcaggggc agagcctgac cctgaccttg    480

gagagccccc ctggtagtag cccctcagtg caatgtagga gtccaagggg taaaaacata    540

caggggggga agaccctctc cgtgtctcag ctggagctcc aggatagtgg cacctggaca    600

tgcactgtct tgcagaacca gaagaaggtg gagttcaaaa tagacatcgt ggtgctagct    660

ttccagaagg cctccagcat agtctataag aaagaggggg aacaggtgga gttctccttc    720

ccactcgcct ttacagttga aaagctgacg ggcagtggcg agctgtggtg gcaggcggag    780

agggcttcct cctccaagtc ttggatcacc tttgacctga agaacaagga agtgtctgta    840

aaacgggtta cccaggaccc taagctccag atgggcaaga agctcccgct ccacctcacc    900

ctgccccagg ccttgcctca gtatgctggc tctggaaacc tcaccctggc ccttgaagcg    960

aaaacaggaa agttgcatca ggaagtgaac ctggtggtga tgagagccac tcagctccag   1020

aaaaatttga cctgtgaggt gtggggaccc acctccccta agctgatgct gagcttgaaa   1080

ctggagaaca aggaggcaaa ggtctcgaag cgggagaagg cggtgtgggt gctgaaccct   1140

gaggcgggga tgtggcagtg tctgctgagt gactcgggac aggtcctgct ggaatccaac   1200

atcaaggttc tgcccacatg gtccaccccg gtgcagccaa tggccctgat tgtgctgggg   1260

ggcgtcgccg gcctcctgct tttcattggg ctaggcatct tcttctgtgt caggtgccgg   1320

caccgaaggc gccaagcaga gcggatgtct cagatcaaga gactcctcag tgagaagaag   1380

acctgccagt gccctcaccg gtttcagaag acatgtagcc ccatttag                1428
```

<210> SEQ ID NO 41
<211> LENGTH: 8211
<212> TYPE: DNA
<213> ORGANISM: Artificial Sequence
<220> FEATURE:
<223> OTHER INFORMATION: Description of Artificial Sequence: Synthetic pTV-DS-CD4 polynucleotide

<400> SEQUENCE: 41

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ttaaggagcc ccttcgcctc    420

gtgcttgagt tgaggcctgg cttgggcgct ggggccgccg cgtgcgaatc tggtggcacc    480

ttcgcgcctg tctcgctgct ttcgataagt ctctagccat ttaaaatttt tgatgacctg    540

ctgcgacgct ttttttctgg caagatagtc ttgtaaatgc gggccaagat cgatctgcac    600

actggtattt cggtttttgg ggccgcgggc ggcgacgggg cccgtgcgtc ccagcgcaca    660

tgttcggcga ggcggggcct gcgagcgcgg ccaccgagaa tcggacgggg gtagtctcaa    720

gctggccggc ctgctctggt gcctggcctc gcgccgccgt gtatcgcccc gccctgggcg    780

gcaaggctgg cccggtcggc accagttgcg tgagcggaaa gatggccgct tcccggccct    840

gctgcaggga gctcaaaatg gaggacgcgg cgctcgggag agcgggcggg tgagtcaccc    900
```

```
acacaaagga aaagggcctt tccgtcctca gccgtcgctt catgtgactc cacggagtac    960
cgggcgccgt ccaggcacct cgattagttc tcgagctttt ggagtacgtc gtctttaggt   1020
tggggggagg ggttttatgc gatggagttt ccccacactg agtgggtgga gactgaagtt   1080
aggccagctt ggcacttgat gtaattctcc ttggaatttg ccctttttga gtttggatct   1140
tggttcattc tcaagcctca gacagtggtt caaagttttt ttcttccatt tcaggtgtcg   1200
tggaattggc tagagcttgc atgcctgcag gtcggccgcc acgaccggtg ccgccaccat   1260
cccctgaccc acgcccctga cccctcacaa ggagacgacc ttccatgacc gagtacaagc   1320
ccacggtgcg cctcgccacc cgcgacgacg tcccccgggc cgtacgcacc ctcgccgccg   1380
cgttcgccga ctaccccgcc acgcgccaca ccgtcgaccc ggaccgccac atcgagcggg   1440
tcaccgagct gcaagaactc ttcctcacgc gcgtcgggct cgacatcggc aaggtgtggg   1500
tcgcggacga cggcgccgcg gtggcggtct ggaccacgcc ggagagcgtc gaagcggggg   1560
cggtgttcgc cgagatcggc ccgcgcatgg ccgagttgag cggttcccgg ctggccgcgc   1620
agcaacagat ggaaggcctc ctggcgccgc accggcccaa ggagcccgcg tggttcctgg   1680
ccaccgtcgg cgtctcgccc gaccaccagg gcaagggtct gggcagcgcc gtcgtgctcc   1740
ccggagtgga ggcggccgag cgcgccgggg tgcccgcctt cctggagacc tccgcgcccc   1800
gcaacctccc cttctacgag cggctcggct tcaccgtcac cgccgacgtc gaggtgcccg   1860
aaggaccgcg cacctggtgc atgacccgca agcccggtgc ctgacgcccg ccccacgacc   1920
cgcagcgccc gaccgaaagg agcgcacgac cccatggctc cgaccgaagc cgacccgggc   1980
ggccccgccg accccgcacc cgcccccgag gcccaccgac tctagaggat cataatcagc   2040
cataccacat ttgtagaggt tttacttgct ttaaaaaacc tcccacacct ccccctgaac   2100
ctgaaacata aaatgaatgc aattgttgtt gttaacttgt ttattgcagc ttataatggt   2160
tacaaataaa gcaatagcat cacaaatttc acaaataaag cattttttc actgcattct    2220
agttgtggtt tgtccaaact catcaatgta tcttatcatg tctggatcct agcgtttaaa   2280
cttaagcttg gtaccgagct cggatccact agcgatgtac gggccagata tacgcgttga   2340
cattgattat tgactagtta ttaatagtaa tcaattacgg ggtcattagt tcatagccca   2400
tatatggagt tccgcgttac ataacttacg gtaaatggcc cgcctggctg accgcccaac   2460
gacccccgcc cattgacgtc aataatgacg tatgttccca tagtaacgcc aatagggact   2520
ttccattgac gtcaatgggt ggagtattta cggtaaactg cccacttggc agtacatcaa   2580
gtgtatcata tgccaagtac gccccctatt gacgtcaatg acggtaaatg gcccgcctgg   2640
cattatgccc agtacatgac cttatgggac tttcctactt ggcagtacat ctacgtatta   2700
gtcatcgcta ttaccatggt gatgcggttt tggcagtaca tcaatgggcg tggatagcgg   2760
tttgactcac ggggatttcc aagtctccac cccattgacg tcaatgggag tttgttttgg   2820
caccaaaatc aacgggactt tccaaaatgt cgtaacaact ccgccccatt gacgcaaatg   2880
ggcggtaggc gtgtacggtg ggaggtctat ataagcagag ctctctggct aactagagaa   2940
cccactgctt actggcttat cgaaattaat acgactcact atagggagac ccaagctggc   3000
tagcgctgat atggcgtact accatcacca tcaccatcac tctagatcag aaggagttcg   3060
aaccaaccgg ggagtccctt ttaggcactt gcttctggtg ctgcaactgg cgctcctccc   3120
agcagccact cagggaaaga aagtggtgct gggcaaaaaa ggggatacag tggaactgac   3180
ctgtacagct tcccagaaga agagcataca attccactgg aaaaactcca accagataaa   3240
gattctggga aatcagggct ccttcttaac taaaggtcca tccaagctga atgatcgcgc   3300
```

```
tgactcaaga agaagccttt gggaccaagg aaacttcccc ctgatcatca agaatcttaa   3360
gatagaagac tcagatactt acatctgtga agtggaggac cagaaggagg aggtgcaatt   3420
gctagtgttc ggattgactg ccaactctga cacccacctg cttcaggggc agagcctgac   3480
cctgaccttg gagagccccc ctggtagtag cccctcagtg caatgtagga gtccaagggg   3540
taaaaacata caggggggga agaccctctc cgtgtctcag ctggagctcc aggatagtgg   3600
cacctggaca tgcactgtct tgcagaacca gaagaaggtg gagttcaaaa tagacatcgt   3660
ggtgctagct ttccagaagg cctccagcat agtctataag aaagaggggg aacaggtgga   3720
gttctccttc ccactcgcct ttacagttga aaagctgacg ggcagtggcg agctgtggtg   3780
gcaggcggag agggcttcct cctccaagtc ttggatcacc tttgacctga agaacaagga   3840
agtgtctgta aaacgggtta cccaggaccc taagctccag atgggcaaga agctcccgct   3900
ccacctcacc ctgccccagg ccttgcctca gtatgctggc tctggaaacc tcaccctggc   3960
ccttgaagcg aaaacaggaa agttgcatca ggaagtgaac ctggtggtga tgagagccac   4020
tcagctccag aaaaatttga cctgtgaggt gtggggaccc acctccccta agctgatgct   4080
gagcttgaaa ctggagaaca aggaggcaaa ggtctcgaag cgggagaagg cggtgtgggt   4140
gctgaaccct gaggcgggga tgtggcagtg tctgctgagt gactcgggac aggtcctgct   4200
ggaatccaac atcaaggttc tgcccacatg gtccaccccg gtgcagccaa tggccctgat   4260
tgtgctgggg ggcgtcgccg gcctcctgct tttcattggg ctaggcatct tcttctgtgt   4320
caggtgccgg caccgaaggc gccaagcaga gcggatgtct cagatcaaga gactcctcag   4380
tgagaagaag acctgccagt gccctcaccg gtttcagaag acatgtagat cgatcgcgag   4440
cggccgctcg agtctagagg gcccgtttaa acccgctgat cagcctcgac tgtgccttct   4500
agttgccagc catctgttgt ttgcccctcc cccgtgcctt ccttgaccct ggaaggtgcc   4560
actcccactg tcctttccta ataaaatgag gaaattgcat cgcattgtct gagtaggtgt   4620
cattctattc tggggggtgg ggtggggcag gacagcaagg gggaggattg ggaagacaat   4680
agcaggcatg ctggggatgc ggtgggctct atggcttctg aggcggaaag aaccagctgg   4740
ggctctaggg ggtatcccca cgcgccctgt agcggcgcat taagcgcggc gggtgtggtg   4800
gttacgcgca gcgtgaccgc tacacttgcc agcgccctag cgcccgctcc tttcgctttc   4860
ttcccttcct ttctcgccac gttcgcctac cgtcgaatca ccggtaacct tataagggat   4920
tttgccgatt tcggcctatt ggttaaaaaa tgagctgatt taacaaaaat ttaacgcgaa   4980
ttaattctgt ggaatgtgtg tcagttaggg tgtggaaagt ccccaggctc cccagcaggc   5040
agaagtatgc aaagcatgca tctcaattag tcagcaacca ggtgtggaaa gtccccaggc   5100
tccccagcag gcagaagtat gcaaagcatg catctcaatt agtcagcaac catagtcccg   5160
cccctaactc cgcccatccc gcccctaact ccgcccagtt ccgcccattc tccgccccat   5220
ggctgactaa ttttttttat ttatgcagag gccgaggccg cctctgcctc tgagctattc   5280
cagaagtagt gaggaggctt ttttggaggc ctaggctttt gcaaaaagct cccgggagct   5340
tgtatatcca ttttcggatc tgatcaagag acaggatgag gatcgtttcg catgattgaa   5400
caagatggat tgcacgcagg ttctccggcc gcttgggtgg agaggctatt cggctatgac   5460
tgggcacaac agacaatcgg ctgctctgat gccgccgtgt tccggctgtc agcgcagggg   5520
cgcccggttc tttttgtcaa gaccgacctg tccggtgccc tgaatgaact gcaggacgag   5580
gcagcgcggc tatcgtggct ggccacgacg ggcgttcctt gcgcagctgt gctcgacgtt   5640
gtcactgaag cgggaaggga ctggctgcta ttgggcgaag tgccggggca ggatctcctg   5700
```

```
tcatctcacc ttgctcctgc cgagaaagta tccatcatgg ctgatgcaat gcggcggctg   5760
catacgcttg atccggctac ctgcccattc gaccaccaag cgaaacatcg catcgagcga   5820
gcacgtactc ggatggaagc cggtcttgtc gatcaggatg atctggacga agagcatcag   5880
gggctcgcgc cagccgaact gttcgccagg ctcaaggcgc gaattcgagc tcggtacccg   5940
gggatcctct agagtcgacc tgcaggcatg caagcttggc gtaatcatgg tcatagctgt   6000
ttcctgtgtg aaattgttat ccgctcacaa ttccacacaa catacgagcc ggaagcataa   6060
agtgtaaagc ctggggtgcc taatgagtga gctaactcac attaattgcg ttgcgctcac   6120
tgcccgcttt ccagtcggga aacctgtcgt gccagctgca ttaatgaatc ggccaacgcg   6180
cggggagagg cggtttgcgt attgggcgct cttccgcttc ctcgctcact gactcgctgc   6240
gctcggtcgt tcggctgcgg cgagcggtat cagctcactc aaaggcggta atacggttat   6300
ccacagaatc aggggataac gcaggaaaga acatgtgagc aaaaggccag caaaaggcca   6360
ggaaccgtaa aaaggccgcg ttgctggcgt ttttccatag gctccgcccc cctgacgagc   6420
atcacaaaaa tcgacgctca agtcagaggt ggcgaaaccc gacaggacta taaagatacc   6480
aggcgtttcc ccctggaagc tccctcgtgc gctctcctgt tccgaccctg ccgcttaccg   6540
gatacctgtc cgcctttctc ccttcgggaa gcgtggcgct ttctcatagc tcacgctgta   6600
ggtatctcag ttcggtgtag gtcgttcgct ccaagctggg ctgtgtgcac gaaccccccg   6660
ttcagcccga ccgctgcgcc ttatccggta actatcgtct tgagtccaac ccggtaagac   6720
acgacttatc gccactggca gcagccactg gtaacaggat tagcagagcg aggtatgtag   6780
gcggtgctac agagttcttg aagtggtggc ctaactacgg ctacactaga aggacagtat   6840
ttggtatctg cgctctgctg aagccagtta ccttcggaaa aagagttggt agctcttgat   6900
ccggcaaaca aaccaccgct ggtagcggtg gtttttttgt ttgcaagcag cagattacgc   6960
gcagaaaaaa aggatctcaa gaagatcctt tgatcttttc tacggggtct gacgctcagt   7020
ggaacgaaaa ctcacgttaa gggattttgg tcatgagatt atcaaaaagg atcttcacct   7080
agatcctttt aaattaaaaa tgaagtttta aatcaatcta aagtatatat gagtaaactt   7140
ggtctgacag ttaccaatgc ttaatcagtg aggcacctat ctcagcgatc tgtctatttc   7200
gttcatccat agttgcctga ctccccgtcg tgtagataac tacgatacgg gagggcttac   7260
catctggccc cagtgctgca atgataccgc gagacccacg ctcaccggct ccagatttat   7320
cagcaataaa ccagccagcc ggaagggccg agcgcagaag tggtcctgca actttatccg   7380
cctccatcca gtctattaat tgttgccggg aagctagagt aagtagttcg ccagttaata   7440
gtttgcgcaa cgttgttgcc attgctacag gcatcgtggt gtcacgctcg tcgtttggta   7500
tggcttcatt cagctccggt tcccaacgat caaggcgagt tacatgatcc cccatgttgt   7560
gcaaaaaagc ggttagctcc ttcggtcctc cgatcgttgt cagaagtaag ttggccgcag   7620
tgttatcact catggttatg gcagcactgc ataattctct tactgtcatg ccatccgtaa   7680
gatgcttttc tgtgactggt gagtactcaa ccaagtcatt ctgagaatag tgtatgcggc   7740
gaccgagttg ctcttgcccg gcgtcaatac gggataatac cgcgccacat agcagaactt   7800
taaaagtgct catcattgga aaacgttctt cggggcgaaa actctcaagg atcttaccgc   7860
tgttgagatc cagttcgatg taacccactc gtgcacccaa ctgatcttca gcatctttta   7920
ctttcaccag cgtttctggg tgagcaaaaa caggaaggca aaatgccgca aaaaagggaa   7980
taagggcgac acggaaatgt tgaatactca tactcttcct ttttcaatat tattgaagca   8040
tttatcaggg ttattgtctc atgagcggat acatatttga atgtatttag aaaaataaac   8100
```

```
aaataggggt tccgcgcaca tttccccgaa aagtgccacc tgacgtctaa gaaaccatta   8160

ttatcatgac attaacctat aaaaataggc gtatcacgag gccctttcgt c            8211
```

<210> SEQ ID NO 42
<211> LENGTH: 1109
<212> TYPE: DNA
<213> ORGANISM: Homo sapiens

<400> SEQUENCE: 42

```
atggacatgg cggatgagcc actcaatgga agccacacat ggctatccat tccatttgac     60

ctcaatggct ctgtggtgtc aaccaacacc tcaaaccaga cagagccgta ctatgacctg    120

acaagcaatg cagtcctcac attcatctat tttgtggtct gcatcattgg gttgtgtggc    180

aacacacttg tcatttatgt catcctccgc tatgccaaga tgaagaccat caccaacatt    240

tacatcctca acctggccat cgcagatgag ctcttcatgc tgggtctgcc tttcttggct    300

atgcaggtgg ctctggtcca ctggcccttt ggcaaggcca tttgccgggt ggtcatgact    360

gtggatggca tcaatcagtt caccagcatc ttctgcctga cagtcatgag catcgaccga    420

tacctggctg tggtccaccc catcaagtcg gccaagtgga ggagaccccg gacggccaag    480

atgatcacca tggctgtgtg gggagtctct ctgctggtca tcttgcccat catgatatat    540

gctgggctcc ggagcaacca gtgggggaga agcagctgca ccatcaactg gccaggtgaa    600

tctggggctt ggtacacagg gttcatcatc tacactttca ttctggggtt cctggtaccc    660

ctcaccatca tctgtctttg ctacctgttc attatcatca aggtgaagtc ctctggaatc    720

cgagtgggct cctctaagag gaagaagtct gagaagaagg tcacccgaat ggtgtccatc    780

gtggtggctg tcttcatctt ctgctggctt cccttctaca tattcaacgt ttcttccgtc    840

tccatggcca tcagccccac cccagccctt aaaggcatgt ttgactttgt ggtggtcctc    900

acctatgcta acagctgtgc caaccctatc ctatatgcct tcttgtctga caacttcaag    960

aagagcttcc agaatgtcct ctgcttggtc aaggtgagcg gcacagatga tggggagcgg   1020

agtgacagta agcaggacaa atcccggctg aatgagacca cggagaccca gaggaccctc   1080

ctcaatggag acctccaaac cagtatctc                                     1109
```

<210> SEQ ID NO 43
<211> LENGTH: 8065
<212> TYPE: DNA
<213> ORGANISM: Artificial Sequence
<220> FEATURE:
<223> OTHER INFORMATION: Description of Artificial Sequence: Synthetic pTV-DS-SSTR2 polynucleotide

<400> SEQUENCE: 43

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt taaggagccc cttcgcctcg    420

tgcttgagtt gaggcctggc ctgggcgctg gggccgccgc gtgcgaatct ggtggcacct    480

tcgcgcctgt ctcgctgctt tcgataagtc tctagccatt taaaattttt gatgacctgc    540
```

-continued

```
tgcgacgctt tttttctggc aagatagtct tgtaaatgcg ggccaagatc gatctgcaca    600
ctggtatttc ggtttttggg gccgcgggcg gcgacggggc ccgtgcgtcc cagcgcacat    660
gttcggcgag gcggggcctg cgagcgcggc caccgagaat cggacggggg tagtctcaag    720
ctggccggcc tgctctggtg cctggcctcg cgccgccgtg tatcgccccg ccctgggcgg    780
caaggctggc ccggtcggca ccagttgcgt gagcggaaag atggccgctt cccggccctg    840
ctgcagggag ctcaaaatgg aggacgcggc gctcgggaga gcgggcgggt gagtcaccca    900
cacaaaggaa aagggccttt ccgtcctcag ccgtcgcttc atgtgactcc acggagtacc    960
gggcgccgtc caggcacctc gattagttct cgagcttttg gagtacgtcg tctttaggtt   1020
ggggggaggg gttttatgcg atggagtttc cccacactga gtgggtggag actgaagtta   1080
ggccagcttg gcacttgatg taattctcct tggaatttgc cctttttgag tttggatctt   1140
ggttcattct caagcctcag acagtggttc aaagtttttt tcttccattt caggtgtcgt   1200
gaggaattgg ctaagcttgc atgcctgcag gtcggccgcc acgaccggtg ccgccaccat   1260
cccctgaccc acgcccctga cccctcacaa ggagacgacc ttccatgacc gagtacaagc   1320
ccacggtgcg cctcgccacc cgcgacgacg tcccccgggc cgtacgcacc ctcgccgccg   1380
cgttcgccga ctaccccgcc acgcgccaca ccgtcgaccc ggaccgccac atcgagcggg   1440
tcaccgagct gcaagaactc ttcctcacgc gcgtcgggct cgacatcggc aaggtgtggg   1500
tcgcggacga cggcgccgcg gtggcggtct ggaccacgcc ggagagcgtc gaagcggggg   1560
cggtgttcgc cgagatcggc ccgcgcatgg ccgagttgag cggttcccgg ctggccgcgc   1620
agcaacagat ggaaggcctc ctggcgccgc accggcccaa ggagcccgcg tggttcctgg   1680
ccaccgtcgg cgtctcgccc gaccaccagg gcaagggtct gggcagcgcc gtcgtgctcc   1740
ccggagtgga ggcggccgag cgcgccgggg tgcccgcctt cctggagacc tccgcgcccc   1800
gcaacctccc cttctacgag cggctcggct tcaccgtcac cgccgacgtc gaggtgcccg   1860
aaggaccgcg cacctggtgc atgacccgca agcccggtgc ctgacgcccg ccccacgacc   1920
cgcagcgccc gaccgaaagg agcgcacgac cccatggctc cgaccgaagc cacccggggc   1980
ggccccgccg accccgcacc cgcccccgag gcccaccgac tctagaggat cataatcagc   2040
cataccacat ttgtagaggt tttacttgct ttaaaaaacc tcccacacct ccccctgaac   2100
ctgaaacata aaatgaatgc aattgttgtt gttaacttgt ttattgcagc ttataatggt   2160
tacaaataaa gcaatagcat cacaaatttc acaaataaag cattttttcc actgcattct   2220
agttgtggtt tgtccaaact catcaatgta tcttatcatg tctggatcta gcgtttaaac   2280
ttaagcttgg taccgagctc ggatccacta gcgatgtacg ggccagatat acgcgttgac   2340
attgattatt gactagttat taatagtaat caattacggg gtcattagtt catagcccat   2400
atatggagtt ccgcgttaca taacttacgg taaatggccc gcctggctga ccgcccaacg   2460
acccccgccc attgacgtca ataatgacgt atgttcccat agtaacgcca atagggactt   2520
tccattgacg tcaatgggtg gagtatttac ggtaaactgc ccacttggca gtacatcaag   2580
tgtatcatat gccaagtacg ccccctattg acgtcaatga cggtaaatgg cccgcctggc   2640
attatgccca gtacatgacc ttatgggact ttcctacttg gcagtacatc tacgtattag   2700
tcatcgctat taccatggtg atgcggtttt ggcagtacat caatgggcgt ggatagcggt   2760
ttgactcacg gggatttcca agtctccacc ccattgacgt caatgggagt ttgttttggc   2820
accaaaatca acgggacttt ccaaaatgtc gtaacaactc cgccccattg acgcaaatgg   2880
gcggtaggcg tgtacggtgg gaggtctata taagcagagc tctctggcta actagagaac   2940
```

-continued

```
ccactgctta ctggcttatc gaaattaata cgactcacta tagggagacc caagctggct   3000

agcaccatgg acatggcgga tgagccactc aatggaagcc acacatggct atccattcca   3060

tttgacctca atggctctgt ggtgtcaacc aacacctcaa accagacaga gccgtactat   3120

gacctgacaa gcaatgcagt cctcacattc atctattttg tggtctgcat cattgggttg   3180

tgtggcaaca cacttgtcat ttatgtcatc ctccgctatg ccaagatgaa gaccatcacc   3240

aacatttaca tcctcaacct ggccatcgca gatgagctct tcatgctggg tctgcctttc   3300

ttggctatgc aggtggctct ggtccactgg ccctttggca aggccatttg ccgggtggtc   3360

atgactgtgg atggcatcaa tcagttcacc agcatcttct gcctgacagt catgagcatc   3420

gaccgatacc tggctgtggt ccaccccatc aagtcggcca agtggaggag accccggacg   3480

gccaagatga tcaccatggc tgtgtgggga gtctctctgc tggtcatctt gcccatcatg   3540

atatatgctg ggctccggag caaccagtgg gggagaagca gctgcaccat caactggcca   3600

ggtgaatctg gggcttggta cacagggttc atcatctaca ctttcattct ggggttcctg   3660

gtacccctca ccatcatctg tctttgctac ctgttcatta tcatcaaggt gaagtcctct   3720

ggaatccgag tgggctcctc taagaggaag aagtctgaga agaaggtcac ccgaatggtg   3780

tccatcgtgg tggctgtctt catcttctgc tggcttccct tctacatatt caacgtttct   3840

tccgtctcca tggccatcag ccccacccca gcccttaaag gcatgtttga ctttgtggtg   3900

gtcctcacct atgctaacag ctgtgccaac cctatcctat atgccttctt gtctgacaac   3960

ttcaagaaga gcttccagaa tgtcctctgc ttggtcaagg tgagcggcac agatgatggg   4020

gagcggagtg acagtaagca ggacaaatcc cggctgaatg agaccacgga gacccagagg   4080

accctcctca atggagacct ccaaaccagt atctcaagct tcgaattggg aggtggcggt   4140

agcggaggtg gcggtagcct cgaggattca ctggccgtcg ttttacaacg tcgtgactgg   4200

gaaaaccctg gcgttaccca acttaatcgc cttgcagcac gtcccccttt cgccagctgg   4260

cgtaatagcg aagaggcccg caccgatcgc tgagcggccg ctcgagtcta gagggcccgt   4320

ttaaacccgc tgatcagcct cgactgtgcc ttctagttgc cagccatctg ttgtttgccc   4380

ctcccccgtg ccttccttga ccctggaagg tgccactccc actgtccttt cctaataaaa   4440

tgaggaaatt gcatcgcatt gtctgagtag gtgtcattct attctggggg gtggggtggg   4500

gcaggacagc aagggggagg attgggaaga caatagcagg catgctgggg atgcggtggg   4560

ctctatggct tctgaggcgg aaagaaccag ctggggctct agggggtatc cccacgcgcc   4620

ctgtagcggc gcattaagcg cggcgggtgt ggtggttacg cgcagcgtga ccgctacact   4680

tgccagcgcc ctagcgcccg ctcctttcgc tttcttccct tcctttctcg ccacgttcgc   4740

ctaccgtcga atcaccggta accttataag ggattttgcc gatttcggcc tattggttaa   4800

aaaatgagct gatttaacaa aaatttaacg cgaattaatt ctgtggaatg tgtgtcagtt   4860

agggtgtgga aagtccccag gctccccagc aggcagaagt atgcaaagca tgcatctcaa   4920

ttagtcagca accaggtgtg gaaagtcccc aggctcccca gcaggcagaa gtatgcaaag   4980

catgcatctc aattagtcag caaccatagt cccgccccta actccgccca tcccgcccct   5040

aactccgccc agttccgccc attctccgcc ccatggctga ctaatttttt ttatttatgc   5100

agaggccgag gccgcctctg cctctgagct attccagaag tagtgaggag gcttttttgg   5160

aggcctaggc ttttgcaaaa agctcccggg agcttgtata tccattttcg gatctgatca   5220

agagacagga tgaggatcgt ttcgcatgat tgaacaagat ggattgcacg caggttctcc   5280

ggccgcttgg gtggagaggc tattcggcta tgactgggca caacagacaa tcggctgctc   5340
```

```
tgatgccgcc gtgttccggc tgtcagcgca ggggcgcccg gttctttttg tcaagaccga   5400
cctgtccggt gccctgaatg aactgcagga cgaggcagcg cggctatcgt ggctggccac   5460
gacgggcgtt ccttgcgcag ctgtgctcga cgttgtcact gaagcgggaa gggactggct   5520
gctattgggc gaagtgccgg ggcaggatct cctgtcatct caccttgctc ctgccgagaa   5580
agtatccatc atggctgatg caatgcggcg gctgcatacg cttgatccgg ctacctgccc   5640
attcgaccac caagcgaaac atcgcatcga gcgagcacgt actcggatgg aagccggtct   5700
tgtcgatcag gatgatctgg acgaagagca tcaggggctc gcgccagccg aactgttcgc   5760
caggctcaag gcgcgaattc gagctcggta cccggggatc ctctagagtc gacctgcagg   5820
catgcaagct tggcgtaatc atggtcatag ctgtttcctg tgtgaaattg ttatccgctc   5880
acaattccac acaacatacg agccggaagc ataaagtgta aagcctgggg tgcctaatga   5940
gtgagctaac tcacattaat tgcgttgcgc tcactgcccg ctttccagtc gggaaacctg   6000
tcgtgccagc tgcattaatg aatcggccaa cgcgcgggga gaggcggttt gcgtattggg   6060
cgctcttccg cttcctcgct cactgactcg ctgcgctcgg tcgttcggct gcggcgagcg   6120
gtatcagctc actcaaaggc ggtaatacgg ttatccacag aatcagggga taacgcagga   6180
aagaacatgt gagcaaaagg ccagcaaaag gccaggaacc gtaaaaaggc cgcgttgctg   6240
gcgtttttcc ataggctccg cccccctgac gagcatcaca aaaatcgacg ctcaagtcag   6300
aggtggcgaa acccgacagg actataaaga taccaggcgt ttccccctgg aagctccctc   6360
gtgcgctctc ctgttccgac cctgccgctt accggatacc tgtccgcctt tctcccttcg   6420
ggaagcgtgg cgctttctca tagctcacgc tgtaggtatc tcagttcggt gtaggtcgtt   6480
cgctccaagc tgggctgtgt gcacgaaccc cccgttcagc ccgaccgctg cgccttatcc   6540
ggtaactatc gtcttgagtc caacccggta agacacgact tatcgccact ggcagcagcc   6600
actggtaaca ggattagcag agcgaggtat gtaggcggtg ctacagagtt cttgaagtgg   6660
tggcctaact acggctacac tagaagaaca gtatttggta tctgcgctct gctgaagcca   6720
gttaccttcg gaaaaagagt tggtagctct tgatccggca aacaaaccac cgctggtagc   6780
ggtggttttt ttgtttgcaa gcagcagatt acgcgcagaa aaaaaggatc tcaagaagat   6840
cctttgatct tttctacggg gtctgacgct cagtggaacg aaaactcacg ttaagggatt   6900
ttggtcatga gattatcaaa aaggatcttc acctagatcc ttttaaatta aaaatgaagt   6960
tttaaatcaa tctaaagtat atatgagtaa acttggtctg acagttacca atgcttaatc   7020
agtgaggcac ctatctcagc gatctgtcta tttcgttcat ccatagttgc ctgactcccc   7080
gtcgtgtaga taactacgat acgggagggc ttaccatctg gccccagtgc tgcaatgata   7140
ccgcgagacc cacgctcacc ggctccagat ttatcagcaa taaaccagcc agccggaagg   7200
gccgagcgca gaagtggtcc tgcaacttta tccgcctcca tccagtctat taattgttgc   7260
cgggaagcta gagtaagtag ttcgccagtt aatagtttgc gcaacgttgt tgccattgct   7320
acaggcatcg tggtgtcacg ctcgtcgttt ggtatggctt cattcagctc cggttcccaa   7380
cgatcaaggc gagttacatg atcccccatg ttgtgcaaaa aagcggttag ctccttcggt   7440
cctccgatcg ttgtcagaag taagttggcc gcagtgttat cactcatggt tatggcagca   7500
ctgcataatt ctcttactgt catgccatcc gtaagatgct tttctgtgac tggtgagtac   7560
tcaaccaagt cattctgaga atagtgtatg cggcgaccga gttgctcttg cccggcgtca   7620
atacgggata ataccgcgcc acatagcaga actttaaaag tgctcatcat tggaaaacgt   7680
tcttcggggc gaaaactctc aaggatctta ccgctgttga gatccagttc gatgtaaccc   7740
```

```
actcgtgcac ccaactgatc ttcagcatct tttactttca ccagcgtttc tgggtgagca   7800

aaaacaggaa ggcaaaatgc cgcaaaaaag ggaataaggg cgacacggaa atgttgaata   7860

ctcatactct tcctttttca atattattga agcatttatc agggttattg tctcatgagc   7920

ggatacatat ttgaatgtat ttagaaaaat aaacaaatag gggttccgcg cacatttccc   7980

cgaaaagtgc cacctgacgt ctaagaaacc attattatca tgacattaac ctataaaaat   8040

aggcgtatca cgaggccctt tcgtc                                         8065
```

<210> SEQ ID NO 44
<211> LENGTH: 2589
<212> TYPE: DNA
<213> ORGANISM: Homo sapiens

<400> SEQUENCE: 44

```
atggcaagga ggagctcgtt ccagtcgtgt cagataaatat ccctgttcac ttttgccgtt     60

ggagtcaata tctgcttagg attcactgca catcgaatta agagagcaga aggatgggag    120

gaaggtcctc ctacagtgct atcagactcc ccctggacca acatctccgg atcttgcaag    180

ggcaggtgct ttgaacttca agaggctgga cctcctgatt gtcgctgtga caacttgtgt    240

aagagctata ccagttgctg ccatgacttt gatgagctgt gtttgaagac agcccgtggc    300

tgggagtgta ctaaggacag atgtggagaa gtcagaaatg aagaaaatgc ctgtcactgc    360

tcagaggact gcttggccag ggagagactgc tgtaccaatt accaagtggt ttgcaaagga   420

gagtcgcatt gggttgatga tgactgtgag gaaataaagg ccgcagaatg ccctgcaggg    480

tttgttcgcc ctccattaat catcttctcc gtggatggct tccgtgcatc atacatgaag    540

aaaggcagca aagtcatgcc taatattgaa aaactaaggt cttgtggcac acactctccc    600

tacatgaggc cggtgtaccc aactaaaacc tttcctaact tatacacttt ggccactggg    660

ctatatccag aatcacatgg aattgttggc aattcaatgt atgatcctgt atttgatgcc    720

acttttcatc tgcgagggcg agagaaattt aatcatagat ggtggggagg tcaaccgcta    780

tggattacag ccaccaagca aggggtgaaa gctggaacat tcttttggtc tgttgtcatc    840

cctcacgagc ggagaatatt aaccatattg cagtggctca ccctgccaga tcatgagagg    900

ccttcggtct atgccttcta ttctgagcaa cctgatttct ctggacacaa atatggccct    960

ttcggccctg agatgacaaa tcctctgagg gaaatcgaca aaattgtggg gcaattaatg   1020

gatggactga aacaactaaa actgcatcgg tgtgtcaacg tcatctttgt cggagaccat   1080

ggaatggaag atgtcacatg tgatagaact gagttcttga gtaattacct aactaatgtg   1140

gatgatatta ctttagtgcc tggaactcta ggaagaattc gatccaaatt tagcaacaat   1200

gctaaatatg accccaaagc cattattgcc aatctcacgt gtaaaaaacc agatcagcac   1260

tttaagcctt acttgaaaca gcaccttccc aaacgtttgc actatgccaa caacagaaga   1320

attgaggata tccatttatt ggtggaacgc agatggcatg ttgcaaggaa acctttggat   1380

gtttataaga aaccatcagg aaaatgcttt ttccagggag accacggatt tgataacaag   1440

gtcaacagca tgcagactgt ttttgtaggt tatggcccaa catttaagta caagactaaa   1500

gtgcctccat ttgaaaacat tgaactttac aatgttatgt gtgatctcct gggattgaag   1560

ccagctccta ataatgggac ccatggaagt ttgaatcatc tcctgcgcac taataccttc   1620

aggccaacca tgccagagga agttaccaga cccaattatc cagggattat gtaccttcag   1680

tctgattttg acctgggctg cacttgtgat gataaggtag agccaaagaa caagttggat   1740

gaactcaaca aacggcttca tacaaaaggg tctacagaag agagacacct cctctatggg   1800
```

-continued cgacctgcag tgctttatcg gactagatat gatatcttat atcacactga ctttgaaagt 1860
ggttatagtg aaatattcct aatgccactc tggacatcat atactgtttc caaacaggct 1920
gaggtttcca gcgttcctga ccatctgacc agttgcgtcc ggcctgatgt ccgtgtttct 1980
ccgagtttca gtcagaactg tttggcctac aaaaatgata agcagatgtc ctacggattc 2040
ctctttcctc cttatctgag ctcttcacca gaggctaaat atgatgcatt ccttgtaacc 2100
aatatggttc caatgtatcc tgctttcaaa cgggtctgga attatttcca aagggtattg 2160
gtgaagaaat atgcttcgga aagaaatgga gttaacgtga taagtggacc aatcttcgac 2220
tatgactatg atggcttaca tgacacagaa gacaaaataa aacagtacgt ggaaggcagt 2280
tccattcctg ttccaactca ctactacagc atcatcacca gctgtctgga tttcactcag 2340
cctgccgaca agtgtgacgg ccctctctct gtgtcctcct tcatcctgcc tcaccggcct 2400
gacaacgagg agagctgcaa tagctcagag gacgaatcaa aatgggtaga agaactcatg 2460
aagatgcaca cagctagggt gcgtgacatt gaacatctca ccagcctgga cttcttccga 2520
aagaccagcc gcagctaccc agaaatcctg acactcaaga catacctgca tacatatgag 2580
agcgagatt 2589

<210> SEQ ID NO 45
<211> LENGTH: 9485
<212> TYPE: DNA
<213> ORGANISM: Artificial Sequence
<220> FEATURE:
<223> OTHER INFORMATION: Description of Artificial Sequence: Synthetic
pTV-DS-hATX polynucleotide

<400> SEQUENCE: 45
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt ttaaggagcc ccttcgcctc 420
gtgcttgagt tgaggcctgg cttgggcgct ggggccgccg cgtgcgaatc tggtggcacc 480
ttcgcgcctg tctcgctgct ttcgataagt ctctagccat ttaaaatttt tgatgacctg 540
ctgcgacgct ttttttctgg caagatagtc ttgtaaatgc gggccaagat cgatctgcac 600
actggtattt cggtttttgg ggccgcgggc ggcgacgggg cccgtgcgtc ccagcgcaca 660
tgttcggcga ggcggggcct gcgagcgcgg ccaccgagaa tcggacgggg gtagtctcaa 720
gctggccggc ctgctctggt gcctggcctc gcgccgccgt gtatcgcccc gccctgggcg 780
gcaaggctgg cccggtcggc accagttgcg tgagcggaaa gatggccgct tcccggccct 840
gctgcaggga gctcaaaatg gaggacgcgg cgctcgggag agcgggcggg tgagtcaccc 900
acacaaagga aaagggcctt tccgtcctca gccgtcgctt catgtgactc cacggagtac 960
cgggcgccgt ccaggcacct cgattagttc tcgagctttt ggagtacgtc gtctttaggt 1020
tggggggagg ggttttatgc gatggagttt ccccacactg agtgggtgga gactgaagtt 1080
aggccagctt ggcacttgat gtaattctcc ttggaatttg ccctttttga gtttggatct 1140
tggttcattc tcaagcctca gacagtggtt caaagttttt ttcttccatt tcaggtgtcg 1200
tggaattggc tagagcttgc atgcctgcag gtcggccgcc acgaccggtg ccgccaccat 1260

```
cccctgaccc acgcccctga cccctcacaa ggagacgacc ttccatgacc gagtacaagc 1320
ccacggtgcg cctcgccacc cgcgacgacg tcccccgggc cgtacgcacc ctcgccgccg 1380
cgttcgccga ctaccccgcc acgcgccaca ccgtcgaccc ggaccgccac atcgagcggg 1440
tcaccgagct gcaagaactc ttcctcacgc gcgtcgggct cgacatcggc aaggtgtggg 1500
tcgcggacga cggcgccgcg gtggcggtct ggaccacgcc ggagagcgtc gaagcggggg 1560
cggtgttcgc cgagatcggc ccgcgcatgg ccgagttgag cggttcccgg ctggccgcgc 1620
agcaacagat ggaaggcctc ctggcgccgc accggcccaa ggagcccgcg tggttcctgg 1680
ccaccgtcgg cgtctcgccc gaccaccagg gcaagggtct gggcagcgcc gtcgtgctcc 1740
ccggagtgga ggcggccgag cgcgccgggg tgcccgcctt cctggagacc tccgcgcccc 1800
gcaacctccc cttctacgag cggctcggct tcaccgtcac cgccgacgtc gaggtgcccg 1860
aaggaccgcg cacctggtgc atgacccgca agcccggtgc ctgacgcccg ccccacgacc 1920
cgcagcgccc gaccgaaagg agcgcacgac cccatggctc cgaccgaagc cgacccgggc 1980
ggccccgccg accccgcacc cgcccccgag gcccaccgac tctagaggat cataatcagc 2040
cataccacat ttgtagaggt tttacttgct ttaaaaaacc tcccacacct ccccctgaac 2100
ctgaaacata aaatgaatgc aattgttgtt gttaacttgt ttattgcagc ttataatggt 2160
tacaaataaa gcaatagcat cacaaatttc acaaataaag cattttttc actgcattct 2220
agttgtggtt tgtccaaact catcaatgta tcttatcatg tctggatcct agcgtttaaa 2280
cttaagcttg gtaccgagct cggatccact agtaatggtt acaaataaag caatagcatc 2340
acaaatttca caaataaagc atttttttca ctgcattcta gttgtggttt gtccaaactc 2400
atcaatgtat cttatcatgt ctgtacgatg tacgggccag atatacgcgt tgacattgat 2460
tattgactag ttattaatag taatcaatta cggggtcatt agttcatagc ccatatatgg 2520
agttccgcgt tacataactt acggtaaatg gcccgcctgg ctgaccgccc aacgaccccc 2580
gcccattgac gtcaataatg acgtatgttc ccatagtaac gccaataggg actttccatt 2640
gacgtcaatg ggtggagtat ttacggtaaa ctgcccactt ggcagtacat caagtgtatc 2700
atatgccaag tacgccccct attgacgtca atgacggtaa atggcccgcc tggcattatg 2760
cccagtacat gaccttatgg gactttccta cttggcagta catctacgta ttagtcatcg 2820
ctattaccat ggtgatgcgg ttttggcagt acatcaatgg gcgtggatag cggtttgact 2880
cacggggatt tccaagtctc caccccattg acgtcaatgg gagtttgttt tggcaccaaa 2940
atcaacggga ctttccaaaa tgtcgtaaca actccgcccc attgacgcaa atgggcggta 3000
ggcgtgtacg gtgggaggtc tatataagca gagctctctg gctaactaga gaacccactg 3060
cttactggct tatcgaaatt aatacgactc actataggga gacccaagct ggctagccac 3120
catggcaagg aggagctcgt tccagtcgtg tcagataata tccctgttca cttttgccgt 3180
tggagtcaat atctgcttag gattcactgc acatcgaatt aagagagcag aaggatggga 3240
ggaaggtcct cctacagtgc tatcagactc cccctggacc aacatctccg gatcttgcaa 3300
gggcaggtgc tttgaacttc aagaggctgg acctcctgat tgtcgctgtg acaacttgtg 3360
taagagctat accagttgct gccatgactt tgatgagctg tgtttgaaga cagcccgtgg 3420
ctgggagtgt actaaggaca gatgtggaga agtcagaaat gaagaaaatg cctgtcactg 3480
ctcagaggac tgcttggcca ggggagactg ctgtaccaat taccaagtgg tttgcaaagg 3540
agagtcgcat tgggttgatg atgactgtga ggaaataaag gccgcagaat gccctgcagg 3600
gtttgttcgc cctccattaa tcatcttctc cgtggatggc ttccgtgcat catacatgaa 3660
```

```
gaaaggcagc aaagtcatgc ctaatattga aaaactaagg tcttgtggca cacactctcc   3720
ctacatgagg ccggtgtacc caactaaaac ctttcctaac ttatacactt tggccactgg   3780
gctatatcca gaatcacatg gaattgttgg caattcaatg tatgatcctg tatttgatgc   3840
cacttttcat ctgcgagggc gagagaaatt taatcataga tggtggggag gtcaaccgct   3900
atggattaca gccaccaagc aaggggtgaa agctggaaca ttcttttggt ctgttgtcat   3960
ccctcacgag cggagaatat taaccatatt gcagtggctc accctgccag atcatgagag   4020
gccttcggtc tatgccttct attctgagca acctgatttc tctggacaca aatatggccc   4080
tttcggccct gagatgacaa atcctctgag ggaaatcgac aaaattgtgg ggcaattaat   4140
ggatggactg aaacaactaa aactgcatcg gtgtgtcaac gtcatctttg tcggagacca   4200
tggaatggaa gatgtcacat gtgatagaac tgagttcttg agtaattacc taactaatgt   4260
ggatgatatt actttagtgc ctggaactct aggaagaatt cgatccaaat ttagcaacaa   4320
tgctaaatat gaccccaaag ccattattgc caatctcacg tgtaaaaaac cagatcagca   4380
ctttaagcct tacttgaaac agcaccttcc caaacgtttg cactatgcca acaacagaag   4440
aattgaggat atccatttat tggtggaacg cagatggcat gttgcaagga aacctttgga   4500
tgtttataag aaaccatcag gaaaatgctt tttccaggga gaccacggat ttgataacaa   4560
ggtcaacagc atgcagactg tttttgtagg ttatggccca acatttaagt acaagactaa   4620
agtgcctcca tttgaaaaca ttgaacttta caatgttatg tgtgatctcc tgggattgaa   4680
gccagctcct aataatggga cccatggaag tttgaatcat ctcctgcgca ctaatacctt   4740
caggccaacc atgccagagg aagttaccag acccaattat ccagggatta tgtaccttca   4800
gtctgatttt gacctgggct gcacttgtga tgataaggta gagccaaaga acaagttgga   4860
tgaactcaac aaacggcttc atacaaaagg gtctacagaa gagagacacc tcctctatgg   4920
gcgacctgca gtgctttatc ggactagata tgatatctta tatcacactg actttgaaag   4980
tggttatagt gaaatattcc taatgccact ctggacatca tatactgttt ccaaacaggc   5040
tgaggtttcc agcgttcctg accatctgac cagttgcgtc cggcctgatg tccgtgtttc   5100
tccgagtttc agtcagaact gtttggccta caaaaatgat aagcagatgt cctacggatt   5160
cctctttcct ccttatctga gctcttcacc agaggctaaa tatgatgcat tccttgtaac   5220
caatatggtt ccaatgtatc ctgctttcaa acgggtctgg aattatttcc aaagggtatt   5280
ggtgaagaaa tatgcttcgg aaagaaatgg agttaacgtg ataagtggac caatcttcga   5340
ctatgactat gatggcttac atgacacaga agacaaaata aaacagtacg tggaaggcag   5400
ttccattcct gttccaactc actactacag catcatcacc agctgtctgg atttcactca   5460
gcctgccgac aagtgtgacg gccctctctc tgtgtcctcc ttcatcctgc ctcaccggcc   5520
tgacaacgag gagagctgca atagctcaga ggacgaatca aaatgggtag aagaactcat   5580
gaagatgcac acagctaggg tgcgtgacat tgaacatctc accagcctgg acttcttccg   5640
aaagaccagc cgcagctacc cagaaatcct gacactcaag acatacctgc atacatatga   5700
gagcgagatt taagcggccg ctcgagtcta gagggcccgt ttaaacccgc tgatcagcct   5760
cgactgtgcc ttctagttgc cagccatctg ttgtttgccc ctcccccgtg ccttccttga   5820
ccctggaagg tgccactccc actgtccttt cctaataaaa tgaggaaatt gcatcgcatt   5880
gtctgagtag gtgtcattct attctggggg gtggggtggg gcaggacagc aagggggagg   5940
attgggaaga caatagcagg catgctgggg atgcggtggg ctctatggct tctgaggcgg   6000
aaagaaccag ctggggctct agggggtatc cccacgcgcc ctgtagcggc gcattaagcg   6060
```

```
cggcgggtgt ggtggttacg cgcagcgtga ccgctacact tgccagcgcc ctagcgcccg   6120
ctcctttcgc tttcttccct tcctttctcg ccacgttcgc ctaccgtcga atcaccggta   6180
accttataag ggattttgcc gatttcggcc tattggttaa aaaatgagct gatttaacaa   6240
aaatttaacg cgaattaatt ctgtggaatg tgtgtcagtt agggtgtgga aagtccccag   6300
gctccccagc aggcagaagt atgcaaagca tgcatctcaa ttagtcagca accaggtgtg   6360
gaaagtcccc aggctcccca gcaggcagaa gtatgcaaag catgcatctc aattagtcag   6420
caaccatagt cccgccccta actccgccca tcccgcccct aactccgccc agttccgccc   6480
attctccgcc ccatggctga ctaatttttt ttatttatgc agaggccgag gccgcctctg   6540
cctctgagct attccagaag tagtgaggag gcttttttgg aggcctaggc ttttgcaaaa   6600
agctcccggg agcttgtata tccattttcg gatctgatca agagacagga tgaggatcgt   6660
ttcgcatgat tgaacaagat ggattgcacg caggttctcc ggccgcttgg gtggagaggc   6720
tattcggcta tgactgggca caacagacaa tcggctgctc tgatgccgcc gtgttccggc   6780
tgtcagcgca ggggcgcccg gttctttttg tcaagaccga cctgtccggt gccctgaatg   6840
aactgcagga cgaggcagcg cggctatcgt ggctggccac gacgggcgtt ccttgcgcag   6900
ctgtgctcga cgttgtcact gaagcgggaa gggactggct gctattgggc gaagtgccgg   6960
ggcaggatct cctgtcatct caccttgctc ctgccgagaa agtatccatc atggctgatg   7020
caatgcggcg gctgcatacg cttgatccgg ctacctgccc attcgaccac caagcgaaac   7080
atcgcatcga gcgagcacgt actcggatgg aagccggtct tgtcgatcag gatgatctgg   7140
acgaagagca tcaggggctc gcgccagccg aactgttcgc caggctcaag gcgcgaattc   7200
gagctcggta cccggggatc ctctagagtc gacctgcagg catgcaagct tggcgtaatc   7260
atggtcatag ctgtttcctg tgtgaaattg ttatccgctc acaattccac acaacatacg   7320
agccggaagc ataaagtgta aagcctgggg tgcctaatga gtgagctaac tcacattaat   7380
tgcgttgcgc tcactgcccg ctttccagtc gggaaacctg tcgtgccagc tgcattaatg   7440
aatcggccaa cgcgcgggga gaggcggttt gcgtattggg cgctcttccg cttcctcgct   7500
cactgactcg ctgcgctcgg tcgttcggct gcggcgagcg gtatcagctc actcaaaggc   7560
ggtaatacgg ttatccacag aatcagggga taacgcagga aagaacatgt gagcaaaagg   7620
ccagcaaaag gccaggaacc gtaaaaaggc cgcgttgctg gcgtttttcc ataggctccg   7680
cccccctgac gagcatcaca aaaatcgacg ctcaagtcag aggtggcgaa acccgacagg   7740
actataaaga taccaggcgt ttccccctgg aagctccctc gtgcgctctc ctgttccgac   7800
cctgccgctt accggatacc tgtccgcctt tctcccttcg ggaagcgtgg cgctttctca   7860
tagctcacgc tgtaggtatc tcagttcggt gtaggtcgtt cgctccaagc tgggctgtgt   7920
gcacgaaccc cccgttcagc ccgaccgctg cgccttatcc ggtaactatc gtcttgagtc   7980
caacccggta agacacgact tatcgccact ggcagcagcc actggtaaca ggattagcag   8040
agcgaggtat gtaggcggtg ctacagagtt cttgaagtgg tggcctaact acggctacac   8100
tagaaggaca gtatttggta tctgcgctct gctgaagcca gttaccttcg gaaaaagagt   8160
tggtagctct tgatccggca aacaaaccac cgctggtagc ggtggttttt ttgtttgcaa   8220
gcagcagatt acgcgcagaa aaaaaggatc tcaagaagat cctttgatct tttctacggg   8280
gtctgacgct cagtggaacg aaaactcacg ttaagggatt ttggtcatga gattatcaaa   8340
aaggatcttc acctagatcc ttttaaatta aaaatgaagt tttaaatcaa tctaaagtat   8400
atatgagtaa acttggtctg acagttacca atgcttaatc agtgaggcac ctatctcagc   8460
```

```
gatctgtcta tttcgttcat ccatagttgc ctgactcccc gtcgtgtaga taactacgat   8520
acgggagggc ttaccatctg gccccagtgc tgcaatgata ccgcgagacc cacgctcacc   8580
ggctccagat ttatcagcaa taaaccagcc agccggaagg gccgagcgca gaagtggtcc   8640
tgcaacttta tccgcctcca tccagtctat taattgttgc cgggaagcta gagtaagtag   8700
ttcgccagtt aatagtttgc gcaacgttgt tgccattgct acaggcatcg tggtgtcacg   8760
ctcgtcgttt ggtatggctt cattcagctc cggttcccaa cgatcaaggc gagttacatg   8820
atcccccatg ttgtgcaaaa aagcggttag ctccttcggt cctccgatcg ttgtcagaag   8880
taagttggcc gcagtgttat cactcatggt tatggcagca ctgcataatt ctcttactgt   8940
catgccatcc gtaagatgct tttctgtgac tggtgagtac tcaaccaagt cattctgaga   9000
atagtgtatg cggcgaccga gttgctcttg cccggcgtca atacgggata ataccgcgcc   9060
acatagcaga actttaaaag tgctcatcat tggaaaacgt tcttcggggc gaaaactctc   9120
aaggatctta ccgctgttga gatccagttc gatgtaaccc actcgtgcac ccaactgatc   9180
ttcagcatct tttactttca ccagcgtttc tgggtgagca aaaacaggaa ggcaaaatgc   9240
cgcaaaaaag ggaataaggg cgacacggaa atgttgaata ctcatactct tcctttttca   9300
atattattga agcatttatc agggttattg tctcatgagc ggatacatat ttgaatgtat   9360
ttagaaaaat aaacaaatag gggttccgcg cacatttccc cgaaaagtgc cacctgacgt   9420
ctaagaaacc attattatca tgacattaac ctataaaaat aggcgtatca cgaggccctt   9480
tcgtc                                                               9485
```

<210> SEQ ID NO 46
<211> LENGTH: 1053
<212> TYPE: DNA
<213> ORGANISM: Homo sapiens

<400> SEQUENCE: 46

```
atgcagggca acggcagcgc gctgcccaac gcctcccagc ccgtgctccg cggggacggc     60
gcgcggccct cgtggctggc gtccgccctg gcctgcgtcc tcatcttcac catcgtggtg    120
gacatcctgg gcaacctcct ggtcatcctg tcggtgtatc ggaacaagaa gctcaggaac    180
gccggcaaca tctttgtggt gagcttagcg gtggcagacc tggtggtggc catttatccg    240
tacccgttgg tgctgatgtc gatatttaac aacgggtgga acctgggcta tctgcactgc    300
caagtcagtg ggttcctgat gggcctgagc gtcatcggct ccatattcaa catcaccggc    360
atcgccatca accgctactg ctacatctgc cacagtctca agtacgacaa actgtacagc    420
agcaagaact ccctctgcta cgtgctcctc atatggctcc tgacgctggc ggccgtcctg    480
cccaacctcc gtgcagggac tctccagtac gacccgagga tctactcgtg caccttcgcc    540
cagtccgtca gctccgccta caccatcgcc gtggtggttt tccacttcct cgtccccatg    600
atcatagtca tcttctgtta cctgagaata tggatcctgg ttctccaggt cagacagagg    660
gtgaaacctg accgcaaacc caaactgaaa ccacaggact tcaggaattt tgtcaccatg    720
tttgtggttt ttgtcctttt tgccatttgc tgggctcctc tgaacttcat tggcctggcc    780
gtggcctctg accccgccag catggtgcct aggatcccag agtggctgtt tgtggccagt    840
tactacatgg cgtatttcaa cagctgcctc aatgccatta tatacgggct actgaaccaa    900
aatttcagga aggaatacag gagaattata gtctcgctct gtacagccag ggtgttcttt    960
gtggacagct ctaacgacgt ggccgatagg gttaaatgga aaccgtctcc actgatgacc   1020
aacaataatg tagtaaaggt ggactccgtt taa                               1053
```

<210> SEQ ID NO 47
<211> LENGTH: 7946
<212> TYPE: DNA
<213> ORGANISM: Artificial Sequence
<220> FEATURE:
<223> OTHER INFORMATION: Description of Artificial Sequence: Synthetic
pTV-DS-hMT1 polynucleotide

<400> SEQUENCE: 47

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ttaaggagcc ccttcgcctc    420

gtgcttgagt tgaggcctgg cttgggcgct ggggccgccg cgtgcgaatc tggtggcacc    480

ttcgcgcctg tctcgctgct ttcgataagt ctctagccat ttaaaatttt tgatgacctg    540

ctgcgacgct ttttttctgg caagatagtc ttgtaaatgc gggccaagat cgatctgcac    600

actggtattt cggtttttgg ggccgcgggc ggcgacgggg cccgtgcgtc ccagcgcaca    660

tgttcggcga ggcggggcct gcgagcgcgg ccaccgagaa tcggacgggg gtagtctcaa    720

gctggccggc ctgctctggt gcctggcctc gcgccgccgt gtatcgcccc gccctgggcg    780

gcaaggctgg cccggtcggc accagttgcg tgagcggaaa gatggccgct tcccggccct    840

gctgcaggga gctcaaaatg gaggacgcgg cgctcgggag agcgggcggg tgagtcaccc    900

acacaaagga aaagggcctt tccgtcctca gccgtcgctt catgtgactc cacggagtac    960

cgggcgccgt ccaggcacct cgattagttc tcgagctttt ggagtacgtc gtctttaggt   1020

tgggggggagg ggttttatgc gatggagttt ccccacactg agtgggtgga gactgaagtt  1080

aggccagctt ggcacttgat gtaattctcc ttggaatttg ccctttttga gtttggatct   1140

tggttcattc tcaagcctca gacagtggtt caaagttttt ttcttccatt tcaggtgtcg   1200

tggaattggc tagagcttgc atgcctgcag gtcggccgcc acgaccggtg ccgccaccat   1260

cccctgaccc acgcccctga cccctcacaa ggagacgacc ttccatgacc gagtacaagc   1320

ccacggtgcg cctcgccacc cgcgacgacg tcccccgggc cgtacgcacc ctcgccgccg   1380

cgttcgccga ctaccccgcc acgcgccaca ccgtcgaccc ggaccgccac atcgagcggg   1440

tcaccgagct gcaagaactc ttcctcacgc gcgtcgggct cgacatcggc aaggtgtggg   1500

tcgcggacga cggcgccgcg gtggcggtct ggaccacgcc ggagagcgtc gaagcggggg   1560

cggtgttcgc cgagatcggc ccgcgcatgg ccgagttgag cggttcccgg ctggccgcgc   1620

agcaacagat ggaaggcctc ctggcgccgc accggcccaa ggagcccgcg tggttcctgg   1680

ccaccgtcgg cgtctcgccc gaccaccagg gcaagggtct gggcagcgcc gtcgtgctcc   1740

ccggagtgga ggcggccgag cgcgccgggg tgcccgcctt cctggagacc tccgcgcccc   1800

gcaacctccc cttctacgag cggctcggct tcaccgtcac cgccgacgtc gaggtgcccg   1860

aaggaccgcg cacctggtgc atgacccgca agcccggtgc ctgacgcccg ccccacgacc   1920

cgcagcgccc gaccgaaagg agcgcacgac cccatggctc cgaccgaagc cgacccgggc   1980

ggccccgccg accccgcacc cgcccccgag gcccaccgac tctagaggat cataatcagc   2040
```

```
cataccacat ttgtagaggt tttacttgct ttaaaaaacc tcccacacct cccctgaac   2100
ctgaaacata aaatgaatgc aattgttgtt gttaacttgt ttattgcagc ttataatggt   2160
tacaaataaa gcaatagcat cacaaatttc acaaataaag catttttttc actgcattct   2220
agttgtggtt tgtccaaact catcaatgta tcttatcatg tctggatcct agcgtttaaa   2280
cttaagcttg gtaccgagct cggatccact agtaatggtt acaaataaag caatagcatc   2340
acaaatttca caaataaagc atttttttca ctgcattcta gttgtggttt gtccaaactc   2400
atcaatgtat cttatcatgt ctgtacgatg tacgggccag atatacgcgt tgacattgat   2460
tattgactag ttattaatag taatcaatta cggggtcatt agttcatagc ccatatatgg   2520
agttccgcgt tacataactt acggtaaatg gcccgcctgg ctgaccgccc aacgaccccc   2580
gcccattgac gtcaataatg acgtatgttc ccatagtaac gccaataggg actttccatt   2640
gacgtcaatg ggtggagtat ttacggtaaa ctgcccactt ggcagtacat caagtgtatc   2700
atatgccaag tacgccccct attgacgtca atgacggtaa atggcccgcc tggcattatg   2760
cccagtacat gaccttatgg gactttccta cttggcagta catctacgta ttagtcatcg   2820
ctattaccat ggtgatgcgg ttttggcagt acatcaatgg gcgtggatag cggtttgact   2880
cacggggatt tccaagtctc caccccattg acgtcaatgg gagtttgttt tggcaccaaa   2940
atcaacggga ctttccaaaa tgtcgtaaca actccgcccc attgacgcaa atgggcggta   3000
ggcgtgtacg gtgggaggtc tatataagca gagctctctg gctaactaga gaacccactg   3060
cttactggct tatcgaaatt aatacgactc actataggga gacccaagct ggctagccac   3120
catgcagggc aacggcagcg cgctgcccaa cgcctcccag cccgtgctcc gcggggacgg   3180
cgcgcggccc tcgtggctgg cgtccgccct ggcctgcgtc ctcatcttca ccatcgtggt   3240
ggacatcctg ggcaacctcc tggtcatcct gtcggtgtat cggaacaaga agctcaggaa   3300
cgccggcaac atctttgtgg tgagcttagc ggtggcagac ctggtggtgg ccatttatcc   3360
gtacccgttg gtgctgatgt cgatatttaa caacgggtgg aacctgggct atctgcactg   3420
ccaagtcagt gggttcctga tgggcctgag cgtcatcggc tccatattca acatcaccgg   3480
catcgccatc aaccgctact gctacatctg ccacagtctc aagtacgaca aactgtacag   3540
cagcaagaac tccctctgct acgtgctcct catatggctc ctgacgctgg cggccgtcct   3600
gcccaacctc cgtgcaggga ctctccagta cgacccgagg atctactcgt gcaccttcgc   3660
ccagtccgtc agctccgcct acaccatcgc cgtggtggtt ttccacttcc tcgtccccat   3720
gatcatagtc atcttctgtt acctgagaat atggatcctg gttctccagg tcagacagag   3780
ggtgaaacct gaccgcaaac ccaaactgaa accacaggac ttcaggaatt ttgtcaccat   3840
gtttgtggtt tttgtccttt ttgccatttg ctgggctcct ctgaacttca ttggcctggc   3900
cgtggcctct gaccccgcca gcatggtgcc taggatccca gagtggctgt ttgtggccag   3960
ttactacatg gcgtatttca acagctgcct caatgccatt atatacgggc tactgaacca   4020
aaatttcagg aaggaataca ggagaattat agtctcgctc tgtacagcca gggtgttctt   4080
tgtggacagc tctaacgacg tggccgatag ggttaaatgg aaaccgtctc cactgatgac   4140
caacaataat gtagtaaagg tggactccgt ttaagcggcc gctcgagtct agagggcccg   4200
tttaaacccg ctgatcagcc tcgactgtgc cttctagttg ccagccatct gttgtttgcc   4260
cctcccccgt gccttccttg accctggaag gtgccactcc cactgtcctt tcctaataaa   4320
atgaggaaat tgcatcgcat tgtctgagta ggtgtcattc tattctgggg ggtggggtgg   4380
ggcaggacag caagggggag gattgggaag acaatagcag gcatgctggg gatgcggtgg   4440
```

-continued

```
gctctatggc ttctgaggcg gaaagaacca gctggggctc tagggggtat ccccacgcgc   4500
cctgtagcgg cgcattaagc gcggcgggtg tggtggttac gcgcagcgtg accgctacac   4560
ttgccagcgc cctagcgccc gctcctttcg ctttcttccc ttcctttctc gccacgttcg   4620
cctaccgtcg aatcaccggt aaccttataa gggattttgc cgatttcggc ctattggtta   4680
aaaaatgagc tgatttaaca aaaatttaac gcgaattaat tctgtggaat gtgtgtcagt   4740
tagggtgtgg aaagtcccca ggctccccag caggcagaag tatgcaaagc atgcatctca   4800
attagtcagc aaccaggtgt ggaaagtccc caggctcccc agcaggcaga agtatgcaaa   4860
gcatgcatct caattagtca gcaaccatag tcccgcccct aactccgccc atcccgcccc   4920
taactccgcc cagttccgcc cattctccgc cccatggctg actaattttt tttatttatg   4980
cagaggccga ggccgcctct gcctctgagc tattccagaa gtagtgagga ggcttttttg   5040
gaggcctagg cttttgcaaa aagctcccgg gagcttgtat atccattttc ggatctgatc   5100
aagagacagg atgaggatcg tttcgcatga ttgaacaaga tggattgcac gcaggttctc   5160
cggccgcttg ggtggagagg ctattcggct atgactgggc acaacagaca atcggctgct   5220
ctgatgccgc cgtgttccgg ctgtcagcgc aggggcgccc ggttcttttt gtcaagaccg   5280
acctgtccgg tgccctgaat gaactgcagg acgaggcagc gcggctatcg tggctggcca   5340
cgacgggcgt tccttgcgca gctgtgctcg acgttgtcac tgaagcggga agggactggc   5400
tgctattggg cgaagtgccg gggcaggatc tcctgtcatc tcaccttgct cctgccgaga   5460
aagtatccat catggctgat gcaatgcggc ggctgcatac gcttgatccg gctacctgcc   5520
cattcgacca ccaagcgaaa catcgcatcg agcgagcacg tactcggatg gaagccggtc   5580
ttgtcgatca ggatgatctg gacgaagagc atcaggggct cgcgccagcc gaactgttcg   5640
ccaggctcaa ggcgcgaatt cgagctcggt acccggggat cctctagagt cgacctgcag   5700
gcatgcaagc ttggcgtaat catggtcata gctgtttcct gtgtgaaatt gttatccgct   5760
cacaattcca cacaacatac gagccggaag cataaagtgt aaagcctggg gtgcctaatg   5820
agtgagctaa ctcacattaa ttgcgttgcg ctcactgccc gctttccagt cgggaaacct   5880
gtcgtgccag ctgcattaat gaatcggcca acgcgcgggg agaggcggtt tgcgtattgg   5940
gcgctcttcc gcttcctcgc tcactgactc gctgcgctcg gtcgttcggc tgcggcgagc   6000
ggtatcagct cactcaaagg cggtaatacg gttatccaca gaatcagggg ataacgcagg   6060
aaagaacatg tgagcaaaag gccagcaaaa ggccaggaac cgtaaaaagg ccgcgttgct   6120
ggcgtttttc cataggctcc gcccccctga cgagcatcac aaaaatcgac gctcaagtca   6180
gaggtggcga aacccgacag gactataaag ataccaggcg tttccccctg gaagctccct   6240
cgtgcgctct cctgttccga ccctgccgct taccggatac ctgtccgcct ttctcccttc   6300
gggaagcgtg gcgctttctc atagctcacg ctgtaggtat ctcagttcgg tgtaggtcgt   6360
tcgctccaag ctgggctgtg tgcacgaacc ccccgttcag cccgaccgct gcgccttatc   6420
cggtaactat cgtcttgagt ccaacccggt aagacacgac ttatcgccac tggcagcagc   6480
cactggtaac aggattagca gagcgaggta tgtaggcggt gctacagagt tcttgaagtg   6540
gtggcctaac tacggctaca ctagaaggac agtatttggt atctgcgctc tgctgaagcc   6600
agttaccttc ggaaaaagag ttggtagctc ttgatccggc aaacaaacca ccgctggtag   6660
cggtggtttt tttgtttgca agcagcagat tacgcgcaga aaaaaaggat ctcaagaaga   6720
tcctttgatc ttttctacgg ggtctgacgc tcagtggaac gaaaactcac gttaagggat   6780
tttggtcatg agattatcaa aaaggatctt cacctagatc cttttaaatt aaaaatgaag   6840
```

```
ttttaaatca atctaaagta tatatgagta aacttggtct gacagttacc aatgcttaat   6900

cagtgaggca cctatctcag cgatctgtct atttcgttca tccatagttg cctgactccc   6960

cgtcgtgtag ataactacga tacgggaggg cttaccatct ggccccagtg ctgcaatgat   7020

accgcgagac ccacgctcac cggctccaga tttatcagca ataaaccagc cagccggaag   7080

ggccgagcgc agaagtggtc ctgcaacttt atccgcctcc atccagtcta ttaattgttg   7140

ccgggaagct agagtaagta gttcgccagt taatagtttg cgcaacgttg ttgccattgc   7200

tacaggcatc gtggtgtcac gctcgtcgtt tggtatggct tcattcagct ccggttccca   7260

acgatcaagg cgagttacat gatcccccat gttgtgcaaa aaagcggtta gctccttcgg   7320

tcctccgatc gttgtcagaa gtaagttggc cgcagtgtta tcactcatgg ttatggcagc   7380

actgcataat tctcttactg tcatgccatc cgtaagatgc ttttctgtga ctggtgagta   7440

ctcaaccaag tcattctgag aatagtgtat gcggcgaccg agttgctctt gcccggcgtc   7500

aatacgggat aataccgcgc cacatagcag aactttaaaa gtgctcatca ttggaaaacg   7560

ttcttcgggg cgaaaactct caaggatctt accgctgttg agatccagtt cgatgtaacc   7620

cactcgtgca cccaactgat cttcagcatc ttttactttc accagcgttt ctgggtgagc   7680

aaaaacagga aggcaaaatg ccgcaaaaaa gggaataagg gcgacacgga aatgttgaat   7740

actcatactc ttcctttttc aatattattg aagcatttat cagggttatt gtctcatgag   7800

cggatacata tttgaatgta tttagaaaaa taaacaaata ggggttccgc gcacatttcc   7860

ccgaaaagtg ccacctgacg tctaagaaac cattattatc atgacattaa cctataaaaa   7920

taggcgtatc acgaggccct ttcgtc                                        7946
```

<210> SEQ ID NO 48
<211> LENGTH: 1089
<212> TYPE: DNA
<213> ORGANISM: Homo sapiens

<400> SEQUENCE: 48

```
atgtcagaga acggctcctt cgccaactgc tgcgaggcgg gcgggtgggc agtgcgcccg     60

ggctggtcgg gggctggcag cgcgcggccc tccaggaccc ctcgacctcc ctgggtggct    120

ccagcgctgt ccgcggtgct catcgtcacc accgccgtgg acgtcgtggg caacctcctg    180

gtgatcctct ccgtgctcag gaaccgcaag ctccggaacg caggtaattt gttcttggtg    240

agtctggcat tggctgacct ggtggtggcc ttctacccct acccgctaat cctcgtggcc    300

atcttctatg acggctgggc cctgggggag gagcactgca aggccagcgc ctttgtgatg    360

ggcctgagcg tcatcggctc tgtcttcaat atcactgcca tcgccattaa ccgctactgc    420

tacatctgcc acagcatggc ctaccaccga atctaccggc gctggcacac ccctctgcac    480

atctgcctca tctggctcct caccgtggtg gccttgctgc ccaacttctt tgtggggtcc    540

ctggagtacg acccacgcat ctattcctgc accttcatcc agaccgccag cacccagtac    600

acggcggcag tggtggtcat ccacttcctc ctccctatcg ctgtcgtgtc cttctgctac    660

ctgcgcatct gggtgctggt gcttcaggcc cgcaggaaag ccaagccaga gagcaggctg    720

tgcctgaagc ccagcgactt gcggagcttt ctaaccatgt ttgtggtgtt tgtgatcttt    780

gccatctgct gggctccact taactgcatc ggcctcgctg tggccatcaa cccccaagaa    840

atggctcccc agatccctga ggggctattt gtcactagct acttactggc ttatttcaac    900

agctgcctga atgccattgt ctatgggctc ttgaaccaaa acttccgcag ggaatacaag    960

aggatcctct tggccctttg gaacccacgg cactgcattc aagatgcttc caagggcagc   1020
```

```
cacgcggagg ggctgcagag cccagctcca cccatcattg gtgtgcagca ccaggcagat   1080

gctctctag                                                           1089
```

```
<210> SEQ ID NO 49
<211> LENGTH: 7982
<212> TYPE: DNA
<213> ORGANISM: Artificial Sequence
<220> FEATURE:
<223> OTHER INFORMATION: Description of Artificial Sequence: Synthetic
      pTV-DS-hMT2 polynucleotide

<400> SEQUENCE: 49

tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ttaaggagcc ccttcgcctc    420

gtgcttgagt tgaggcctgg cttgggcgct ggggccgccg cgtgcgaatc tggtggcacc    480

ttcgcgcctg tctcgctgct ttcgataagt ctctagccat ttaaaatttt tgatgacctg    540

ctgcgacgct ttttttctgg caagatagtc ttgtaaatgc gggccaagat cgatctgcac    600

actggtattt cggtttttgg ggccgcgggc ggcgacgggg cccgtgcgtc ccagcgcaca    660

tgttcggcga ggcggggcct gcgagcgcgg ccaccgagaa tcggacgggg gtagtctcaa    720

gctggccggc ctgctctggt gcctggcctc gcgccgccgt gtatcgcccc gccctgggcg    780

gcaaggctgg cccggtcggc accagttgcg tgagcggaaa gatggccgct tcccggccct    840

gctgcaggga gctcaaaatg gaggacgcgg cgctcgggag agcgggcggg tgagtcaccc    900

acacaaagga aaagggcctt tccgtcctca gccgtcgctt catgtgactc cacggagtac    960

cgggcgccgt ccaggcacct cgattagttc tcgagctttt ggagtacgtc gtctttaggt   1020

tggggggagg ggttttatgc gatggagttt ccccacactg agtgggtgga gactgaagtt   1080

aggccagctt ggcacttgat gtaattctcc ttggaatttg ccctttttga gtttggatct   1140

tggttcattc tcaagcctca gacagtggtt caaagttttt ttcttccatt tcaggtgtcg   1200

tggaattggc tagagcttgc atgcctgcag gtcggccgcc acgaccggtg ccgccaccat   1260

cccctgaccc acgcccctga cccctcacaa ggagacgacc ttccatgacc gagtacaagc   1320

ccacggtgcg cctcgccacc cgcgacgacg tcccccgggc cgtacgcacc ctcgccgccg   1380

cgttcgccga ctaccccgcc acgcgccaca ccgtcgaccc ggaccgccac atcgagcggg   1440

tcaccgagct gcaagaactc ttcctcacgc gcgtcgggct cgacatcggc aaggtgtggg   1500

tcgcggacga cggcgccgcg gtggcggtct ggaccacgcc ggagagcgtc gaagcggggg   1560

cggtgttcgc cgagatcggc ccgcgcatgg ccgagttgag cggttcccgg ctggccgcgc   1620

agcaacagat ggaaggcctc ctggcgccgc accggcccaa ggagcccgcg tggttcctgg   1680

ccaccgtcgg cgtctcgccc gaccaccagg gcaagggtct gggcagcgcc gtcgtgctcc   1740

ccggagtgga ggcggccgag cgcgccgggg tgcccgcctt cctggagacc tccgcgcccc   1800

gcaacctccc cttctacgag cggctcggct tcaccgtcac cgccgacgtc gaggtgcccg   1860

aaggaccgcg cacctggtgc atgacccgca agcccggtgc ctgacgcccg ccccacgacc   1920

cgcagcgccc gaccgaaagg agcgcacgac cccatggctc cgaccgaagc cgacccgggc   1980
```

```
ggccccgccg accccgcacc cgcccccgag gcccaccgac tctagaggat cataatcagc   2040
cataccacat ttgtagaggt tttacttgct ttaaaaaacc tcccacacct ccccctgaac   2100
ctgaaacata aaatgaatgc aattgttgtt gttaacttgt ttattgcagc ttataatggt   2160
tacaaataaa gcaatagcat cacaaatttc acaaataaag catttttttc actgcattct   2220
agttgtggtt tgtccaaact catcaatgta tcttatcatg tctggatcct agcgtttaaa   2280
cttaagcttg gtaccgagct cggatccact agtaatggtt acaaataaag caatagcatc   2340
acaaatttca caaataaagc atttttttca ctgcattcta gttgtggttt gtccaaactc   2400
atcaatgtat cttatcatgt ctgtacgatg tacgggccag atatacgcgt tgacattgat   2460
tattgactag ttattaatag taatcaatta cggggtcatt agttcatagc ccatatatgg   2520
agttccgcgt tacataactt acggtaaatg gcccgcctgg ctgaccgccc aacgaccccc   2580
gcccattgac gtcaataatg acgtatgttc ccatagtaac gccaataggg actttccatt   2640
gacgtcaatg ggtggagtat ttacggtaaa ctgcccactt ggcagtacat caagtgtatc   2700
atatgccaag tacgccccct attgacgtca atgacggtaa atggcccgcc tggcattatg   2760
cccagtacat gaccttatgg gactttccta cttggcagta catctacgta ttagtcatcg   2820
ctattaccat ggtgatgcgg ttttggcagt acatcaatgg gcgtggatag cggtttgact   2880
cacggggatt tccaagtctc caccccattg acgtcaatgg gagtttgttt tggcaccaaa   2940
atcaacggga ctttccaaaa tgtcgtaaca actccgcccc attgacgcaa atgggcggta   3000
ggcgtgtacg gtgggaggtc tatataagca gagctctctg gctaactaga gaacccactg   3060
cttactggct tatcgaaatt aatacgactc actataggga gacccaagct ggctagccac   3120
catgtcagag aacggctcct tcgccaactg ctgcgaggcg ggcgggtggg cagtgcgccc   3180
gggctggtcg gggctggca gcgcgcggcc ctccaggacc cctcgacctc cctgggtggc   3240
tccagcgctg tccgcggtgc tcatcgtcac caccgccgtg gacgtcgtgg gcaacctcct   3300
ggtgatcctc tccgtgctca ggaaccgcaa gctccggaac gcaggtaatt tgttcttggt   3360
gagtctggca ttggctgacc tggtggtggc cttctacccc tacccgctaa tcctcgtggc   3420
catcttctat gacggctggg ccctgggga ggagcactgc aaggccagcg cctttgtgat   3480
gggcctgagc gtcatcggct ctgtcttcaa tatcactgcc atcgccatta accgctactg   3540
ctacatctgc cacagcatgg cctaccaccg aatctaccgg cgctggcaca cccctctgca   3600
catctgcctc atctggctcc tcaccgtggt ggccttgctg cccaacttct ttgtggggtc   3660
cctggagtac gacccacgca tctattcctg caccttcatc cagaccgcca gcacccagta   3720
cacggcggca gtggtggtca tccacttcct cctccctatc gctgtcgtgt ccttctgcta   3780
cctgcgcatc tgggtgctgg tgcttcaggc ccgcaggaaa gccaagccag agagcaggct   3840
gtgcctgaag cccagcgact tgcggagctt tctaaccatg tttgtggtgt ttgtgatctt   3900
tgccatctgc tgggctccac ttaactgcat cggcctcgct gtggccatca acccccaaga   3960
aatggctccc cagatccctg aggggctatt tgtcactagc tacttactgg cttatttcaa   4020
cagctgcctg aatgccattg tctatgggct cttgaaccaa aacttccgca gggaatacaa   4080
gaggatcctc ttggcccttt ggaacccacg gcactgcatt caagatgctt ccaagggcag   4140
ccacgcggag ggctgcaga gcccagctcc acccatcatt ggtgtgcagc accaggcaga   4200
tgctctctag gcggccgctc gagtctagag ggcccgttta aacccgctga tcagcctcga   4260
ctgtgccttc tagttgccag ccatctgttg tttgcccctc ccccgtgcct tccttgaccc   4320
tggaaggtgc cactcccact gtcctttcct aataaaatga ggaaattgca tcgcattgtc   4380
```

-continued

```
tgagtaggtg tcattctatt ctggggggtg gggtggggca ggacagcaag ggggaggatt   4440
gggaagacaa tagcaggcat gctggggatg cggtgggctc tatggcttct gaggcggaaa   4500
gaaccagctg gggctctagg gggtatcccc acgcgccctg tagcggcgca ttaagcgcgg   4560
cgggtgtggt ggttacgcgc agcgtgaccg ctacacttgc cagcgcccta gcgcccgctc   4620
ctttcgcttt cttcccttcc tttctcgcca cgttcgccta ccgtcgaatc accggtaacc   4680
ttataaggga ttttgccgat ttcggcctat tggttaaaaa atgagctgat ttaacaaaaa   4740
tttaacgcga attaattctg tggaatgtgt gtcagttagg gtgtggaaag tccccaggct   4800
ccccagcagg cagaagtatg caaagcatgc atctcaatta gtcagcaacc aggtgtggaa   4860
agtccccagg ctccccagca ggcagaagta tgcaaagcat gcatctcaat tagtcagcaa   4920
ccatagtccc gcccctaact ccgcccatcc cgcccctaac tccgcccagt tccgcccatt   4980
ctccgcccca tggctgacta attttttta tttatgcaga ggccgaggcc gcctctgcct   5040
ctgagctatt ccagaagtag tgaggaggct tttttggagg cctaggcttt tgcaaaaagc   5100
tcccgggagc ttgtatatcc attttcggat ctgatcaaga gacaggatga ggatcgtttc   5160
gcatgattga acaagatgga ttgcacgcag gttctccggc cgcttgggtg gagaggctat   5220
tcggctatga ctgggcacaa cagacaatcg gctgctctga tgccgccgtg ttccggctgt   5280
cagcgcaggg gcgcccggtt ctttttgtca agaccgacct gtccggtgcc ctgaatgaac   5340
tgcaggacga ggcagcgcgg ctatcgtggc tggccacgac gggcgttcct tgcgcagctg   5400
tgctcgacgt tgtcactgaa gcgggaaggg actggctgct attgggcgaa gtgccggggc   5460
aggatctcct gtcatctcac cttgctcctg ccgagaaagt atccatcatg gctgatgcaa   5520
tgcggcggct gcatacgctt gatccggcta cctgcccatt cgaccaccaa gcgaaacatc   5580
gcatcgagcg agcacgtact cggatggaag ccggtcttgt cgatcaggat gatctggacg   5640
aagagcatca ggggctcgcg ccagccgaac tgttcgccag gctcaaggcg cgaattcgag   5700
ctcggtaccc ggggatcctc tagagtcgac ctgcaggcat gcaagcttgg cgtaatcatg   5760
gtcatagctg tttcctgtgt gaaattgtta tccgctcaca attccacaca acatacgagc   5820
cggaagcata aagtgtaaag cctggggtgc ctaatgagtg agctaactca cattaattgc   5880
gttgcgctca ctgcccgctt tccagtcggg aaacctgtcg tgccagctgc attaatgaat   5940
cggccaacgc gcggggagag gcggtttgcg tattgggcgc tcttccgctt cctcgctcac   6000
tgactcgctg cgctcggtcg ttcggctgcg gcgagcggta tcagctcact caaaggcggt   6060
aatacggtta tccacagaat caggggataa cgcaggaaag aacatgtgag caaaaggcca   6120
gcaaaaggcc aggaaccgta aaaaggccgc gttgctggcg tttttccata ggctccgccc   6180
ccctgacgag catcacaaaa atcgacgctc aagtcagagg tggcgaaacc cgacaggact   6240
ataaagatac caggcgtttc cccctggaag ctccctcgtg cgctctcctg ttccgaccct   6300
gccgcttacc ggatacctgt ccgcctttct cccttcggga agcgtggcgc tttctcatag   6360
ctcacgctgt aggtatctca gttcggtgta ggtcgttcgc tccaagctgg gctgtgtgca   6420
cgaacccccc gttcagcccg accgctgcgc cttatccggt aactatcgtc ttgagtccaa   6480
cccggtaaga cacgacttat cgccactggc agcagccact ggtaacagga ttagcagagc   6540
gaggtatgta ggcggtgcta cagagttctt gaagtggtgg cctaactacg gctacactag   6600
aaggacagta tttggtatct gcgctctgct gaagccagtt accttcggaa aaagagttgg   6660
tagctcttga tccggcaaac aaaccaccgc tggtagcggt ggtttttttg tttgcaagca   6720
gcagattacg cgcagaaaaa aaggatctca agaagatcct ttgatctttt ctacggggtc   6780
```

```
tgacgctcag tggaacgaaa actcacgtta agggattttg gtcatgagat tatcaaaaag   6840

gatcttcacc tagatccttt taaattaaaa atgaagtttt aaatcaatct aaagtatata   6900

tgagtaaact tggtctgaca gttaccaatg cttaatcagt gaggcaccta tctcagcgat   6960

ctgtctattt cgttcatcca tagttgcctg actccccgtc gtgtagataa ctacgatacg   7020

ggagggctta ccatctggcc ccagtgctgc aatgataccg cgagacccac gctcaccggc   7080

tccagattta tcagcaataa accagccagc cggaagggcc gagcgcagaa gtggtcctgc   7140

aactttatcc gcctccatcc agtctattaa ttgttgccgg gaagctagag taagtagttc   7200

gccagttaat agtttgcgca acgttgttgc cattgctaca ggcatcgtgg tgtcacgctc   7260

gtcgtttggt atggcttcat tcagctccgg ttcccaacga tcaaggcgag ttacatgatc   7320

ccccatgttg tgcaaaaaag cggttagctc cttcggtcct ccgatcgttg tcagaagtaa   7380

gttggccgca gtgttatcac tcatggttat ggcagcactg cataattctc ttactgtcat   7440

gccatccgta agatgctttt ctgtgactgg tgagtactca accaagtcat tctgagaata   7500

gtgtatgcgg cgaccgagtt gctcttgccc ggcgtcaata cgggataata ccgcgccaca   7560

tagcagaact ttaaaagtgc tcatcattgg aaaacgttct tcggggcgaa aactctcaag   7620

gatcttaccg ctgttgagat ccagttcgat gtaacccact cgtgcaccca actgatcttc   7680

agcatctttt actttcacca gcgtttctgg gtgagcaaaa acaggaaggc aaaatgccgc   7740

aaaaaaggga ataagggcga cacggaaatg ttgaatactc atactcttcc tttttcaata   7800

ttattgaagc atttatcagg gttattgtct catgagcgga tacatatttg aatgtattta   7860

gaaaaataaa caaatagggg ttccgcgcac atttccccga aaagtgccac ctgacgtcta   7920

agaaaccatt attatcatga cattaaccta taaaaatagg cgtatcacga ggccctttcg   7980

tc                                                                  7982
```

<210> SEQ ID NO 50
<211> LENGTH: 1386
<212> TYPE: DNA
<213> ORGANISM: Homo sapiens

<400> SEQUENCE: 50

```
atgggatgga gctgtatcat cctgttcctc gtggccacag caaccggtgt ccacagccag     60

gtgcagctac agcagtgggg cgcaggactg ttgaagcctt cggagaccct gtccctcacc    120

tgcgctgtct atggtgggtc cttcagtgct tactactgga gctggatccg ccagccccca    180

gggaaggggc tggagtggat tggggacatc aatcatggtg gaggcaccaa ctacaacccg    240

tccctcaaga gtcgagtcac catatcagta gacacgtcca agaaccagtt ctccctgaag    300

ctgaactctg taaccgccgc ggacacggct gtgtattact gtgcgagcct aactgcctac    360

tggggccagg gaagcctggt caccgtctcc tcagctagca ccaagggccc atcggtcttc    420

cccctggcac cctcctccaa gagcacctct gggggcacag cggccctggg ctgcctggtc    480

aaggactact tccccgaacc ggtgacggtg tcgtggaact caggcgccct gaccagcggc    540

gtgcacacct tcccggccgt cctacagtcc tcaggactct actccctcag cagcgtggtg    600

accgtgccct ccagcagctt gggcacccag acctacatct gcaacgtgaa tcacaagccc    660

agcaacacca aggtggacaa gagagttgag cccaaatctt gtgacaaaac tcacacatgc    720

ccaccgtgcc cagcacctga actcctgggg ggaccgtcag tcttcctctt ccccccaaaa    780

cccaaggaca ccctcatgat ctcccggacc cctgaggtca catgcgtggt ggtggacgtg    840

agccacgaag accctgaggt caagttcaac tggtacgtgg acggcgtgga ggtgcataat    900
```

```
gccaagacaa agccgcggga ggagcagtac aacagcacgt accgtgtggt cagcgtcctc    960

accgtcctgc accaggactg gctgaatggc aaggagtaca agtgcaaggt ctccaacaaa   1020

gccctcccag cccccatcga gaaaaccatc tccaaagcca aagggcagcc ccgagaacca   1080

caggtgtaca ccctgccccc atcccgggat gagctgacca agaaccaggt cagcctgacc   1140

tgcctggtca aaggcttcta tcccagcgac atcgccgtgg agtgggagag caatgggcag   1200

ccggagaaca actacaagac cacgcctccc gtgctggact ccgacggctc cttcttcctc   1260

tacagcaagc tcaccgtgga caagagcagg tggcagcagg ggaacgtctt ctcatgctcc   1320

gtgatgcatg aggctctgca caaccactac acgcagaaga gcctctccct gtctccgggt   1380

aaatga                                                              1386
```

<210> SEQ ID NO 51
<211> LENGTH: 702
<212> TYPE: DNA
<213> ORGANISM: Homo sapiens

<400> SEQUENCE: 51

```
atgggatgga gctgtatcat cctgttcctc gtggccacag caaccggtgt ccacagcgac     60

atccagatga cccagtctcc aacctcactg tctgcatctg taggagacag agtcaccatc    120

acttgtcggg cgagtcaggg tattagcagc tggttaacct ggtatcagca gaaaccagag    180

aaagccccta agtccctgat ctatgctgca tccagtttgc aaagtggggt cccatcaagg    240

ttcagcggca gtggatctgg gacagatttc actctcacca tcagcagcct gcagcctgaa    300

gattttgcaa cttattactg ccaacagtat gatagttacc ctatcacctt cggccaaggg    360

acacgactgg agattaaacg tacggtggcg gcgccatctg tcttcatctt cccgccatct    420

gatgagcagt tgaaatctgg aactgcctct gttgtgtgcc tgctgaataa cttctatccc    480

agagaggcca aagtacagtg gaaggtggat aacgccctcc aatcgggtaa ctcccaggag    540

agtgtcacag agcaggacag caaggacagc acctacagcc tcagcagcac cctgacgctg    600

agcaaagcag actacgagaa acacaaagtc tacgcctgcg aagtcaccca tcagggcctg    660

agctcgcccg tcacaaagag cttcaacagg ggagagtgtt ag                       702
```

<210> SEQ ID NO 52
<211> LENGTH: 1212
<212> TYPE: DNA
<213> ORGANISM: Homo sapiens

<400> SEQUENCE: 52

```
ggcctccgcg ccgggttttg gcgcctcccg cgggcgcccc cctcctcacg gcgagcgctg     60

ccacgtcaga cgaagggcgc agcgagcgtc ctgatccttc cgcccggacg ctcaggacag    120

cggcccgctg ctcataagac tcggccttag aaccccagta tcagcagaag gacattttag    180

gacgggactt gggtgactct agggcactgg ttttctttcc agagagcgga acaggcgagg    240

aaaagtagtc ccttctcggc gattctgcgg agggatctcc gtggggcggt gaacgccgat    300

gattatataa ggacgcgccg ggtgtggcac agctagttcc gtcgcagccg ggatttgggt    360

cgcggttctt gtttgtggat cgctgtgatc gtcacttggt gagtagcggg ctgctgggct    420

ggccggggct ttcgtggccg ccgggccgct cggtgggacg gaagcgtgtg gagagaccgc    480

caagggctgt agtctgggtc cgcgagcaag gttgccctga actgggggtt ggggggagcg    540

cagcaaaatg gcggctgttc ccgagtcttg aatggaagac gcttgtgagg cgggctgtga    600

ggtcgttgaa acaaggtggg ggcatggtgg ggcggcaaga acccaaggtc ttgaggcctt    660
```

```
cgctaatgcg ggaaagctct tattcgggtg agatgggctg gggcaccatc tggggaccct    720

gacgtgaagt ttgtcactga ctggagaact cggtttgtcg tctgttgcgg gggcggcagt    780

tatggcggtg ccgttgggca gtgcacccgt acctttggga gcgcgcgccc tcgtcgtgtc    840

gtgacgtcac ccgttctgtt ggcttataat gcagggtggg gccacctgcc ggtaggtgtg    900

cggtaggctt ttctccgtcg caggacgcag ggttcgggcc tagggtaggc tctcctgaat    960

cgacaggcgc cggacctctg gtgaggggag ggataagtga ggcgtcagtt tctttggtcg   1020

gttttatgta cctatcttct taagtagctg aagctccggt tttgaactat gcgctcgggg   1080

ttggcgagtg tgttttgtga agttttttag gcaccttttg aaatgtaatc atttgggtca   1140

atatgtaatt ttcagtgtta gactagtaaa ttgtccgcta aattctggcc gtttttggct   1200

tttttgttag ac                                                        1212
```

<210> SEQ ID NO 53
<211> LENGTH: 12640
<212> TYPE: DNA
<213> ORGANISM: Artificial Sequence
<220> FEATURE:
<223> OTHER INFORMATION: Description of Artificial Sequence: Synthetic pTV-DS-5F11 polynucleotide

<400> SEQUENCE: 53

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ttaaggagcc ccttcgcctc    420

gtgcttgagt tgaggcctgg cttgggcgct ggggccgccg cgtgcgaatc tggtggcacc    480

ttcgcgcctg tctcgctgct ttcgataagt ctctagccat ttaaaatttt tgatgacctg    540

ctgcgacgct ttttttctgg caagatagtc ttgtaaatgc gggccaagat cgatctgcac    600

actggtattt cggtttttgg ggccgcgggc ggcgacgggg cccgtgcgtc ccagcgcaca    660

tgttcggcga ggcggggcct gcgagcgcgg ccaccgagaa tcggacgggg gtagtctcaa    720

gctggccggc ctgctctggt gcctggcctc gcgccgccgt gtatcgcccc gccctgggcg    780

gcaaggctgg cccggtcggc accagttgcg tgagcggaaa gatggccgct tcccggccct    840

gctgcaggga gctcaaaatg gaggacgcgg cgctcgggag agcgggcggg tgagtcaccc    900

acacaaagga aaagggcctt tccgtcctca gccgtcgctt catgtgactc cacggagtac    960

cgggcgccgt ccaggcacct cgattagttc tcgagctttt ggagtacgtc gtctttaggt   1020

tggggggagg ggttttatgc gatggagttt ccccacactg agtgggtgga gactgaagtt   1080

aggccagctt ggcacttgat gtaattctcc ttggaatttg ccctttttga gtttggatct   1140

tggttcattc tcaagcctca gacagtggtt caaagttttt ttcttccatt tcaggtgtcg   1200

tggaattggc tagagcttgc atgcctgcag gtcggccgcc acgaccggtg ccgccaccat   1260

cccctgaccc acgcccctga cccctcacaa ggagacgacc ttccatgacc gagtacaagc   1320

ccacggtgcg cctcgccacc cgcgacgacg tcccccgggc cgtacgcacc ctcgccgccg   1380

cgttcgccga ctaccccgcc acgcgccaca ccgtcgaccc ggaccgccac atcgagcggg   1440
```

-continued

```
tcaccgagct gcaagaactc ttcctcacgc gcgtcgggct cgacatcggc aaggtgtggg   1500

tcgcggacga cggcgccgcg gtggcggtct ggaccacgcc ggagagcgtc gaagcggggg   1560

cggtgttcgc cgagatcggc ccgcgcatgg ccgagttgag cggttcccgg ctggccgcgc   1620

agcaacagat ggaaggcctc ctggcgccgc accggcccaa ggagcccgcg tggttcctgg   1680

ccaccgtcgg cgtctcgccc gaccaccagg gcaagggtct gggcagcgcc gtcgtgctcc   1740

ccggagtgga ggcggccgag cgcgccgggg tgcccgcctt cctggagacc tccgcgcccc   1800

gcaacctccc cttctacgag cggctcggct tcaccgtcac cgccgacgtc gaggtgcccg   1860

aaggaccgcg cacctggtgc atgacccgca agcccggtgc ctgacgcccg ccccacgacc   1920

cgcagcgccc gaccgaaagg agcgcacgac cccatggctc cgaccgaagc cgacccgggc   1980

ggccccgccg accccgcacc cgccccccgag gcccaccgac tctagaggat cataatcagc   2040

cataccacat ttgtagaggt tttacttgct ttaaaaaacc tcccacacct ccccctgaac   2100

ctgaaacata aaatgaatgc aattgttgtt gttaacttgt ttattgcagc ttataatggt   2160

tacaaataaa gcaatagcat cacaaatttc acaaataaag catttttttc actgcattct   2220

agttgtggtt tgtccaaact catcaatgta tcttatcatg tctggatcct agcgtttaaa   2280

cttaagcttg gtaccgagct cggatccact agtaatggtt acaaataaag caatagcatc   2340

acaaatttca caaataaagc atttttttca ctgcattcta gttgtggttt gtccaaactc   2400

atcaatgtat cttatcatgt ctgtacgatg tacgggccag atatacgcgc gaggcctccg   2460

cgccgggttt tggcgcctcc cgcgggcgcc cccctcctca cggcgagcgc tgccacgtca   2520

gacgaagggc gcagcgagcg tcctgatcct tccgcccgga cgctcaggac agcggcccgc   2580

tgctcataag actcggcctt agaaccccag tatcagcaga aggacatttt aggacgggac   2640

ttgggtgact ctagggcact ggttttcttt ccagagagcg gaacaggcga ggaaaagtag   2700

tcccttctcg gcgattctgc ggagggatct ccgtggggcg gtgaacgccg atgattatat   2760

aaggacgcgc cgggtgtggc acagctagtt ccgtcgcagc cgggatttgg gtcgcggttc   2820

ttgtttgtgg atcgctgtga tcgtcacttg gtgagtagcg ggctgctggg ctggccgggg   2880

ctttcgtggc cgccgggccg ctcggtggga cggaagcgtg tggagagacc gccaagggct   2940

gtagtctggg tccgcgagca aggttgccct gaactggggg ttggggggag cgcagcaaaa   3000

tggcggctgt tcccgagtct tgaatggaag acgcttgtga ggcgggctgt gaggtcgttg   3060

aaacaaggtg gggggcatgg tgggcggcaa gaacccaagg tcttgaggcc ttcgctaatg   3120

cgggaaagct cttattcggg tgagatgggc tggggcacca tctggggacc ctgacgtgaa   3180

gtttgtcact gactggagaa ctcggtttgt cgtctgttgc gggggcggca gttatggcgg   3240

tgccgttggg cagtgcaccc gtacctttgg gagcgcgcgc cctcgtcgtg tcgtgacgtc   3300

acccgttctg ttggcttata atgcagggtg gggccacctg ccggtaggtg tgcggtaggc   3360

ttttctccgt cgcaggacgc aggttcgggc cctagggtag gctctcctga atcgacaggc   3420

gccggacctc tggtgagggg agggataagt gaggcgtcag tttctttggt cggttttatg   3480

tacctatctt cttaagtagc tgaagctccg gttttgaact atgcgctcgg ggttggcgag   3540

tgtgttttgt gaagtttttt aggcaccttt tgaaatgtaa tcatttgggt caatatgtaa   3600

ttttcagtgt tagactagta aattgtccgc taaattctgg ccgtttttgg ctttttttgtt   3660

agacagatct gtttaaactt aagcttgccg ccaccatggg atggagctgt atcatcctgt   3720

tcctcgtggc cacagcaacc ggtgtccaca gcgacatcca gatgacccag tctccaacct   3780

cactgtctgc atctgtagga gacagagtca ccatcacttg tcgggcgagt cagggtatta   3840
```

-continued

```
gcagctggtt aacctggtat cagcagaaac cagagaaagc ccctaagtcc ctgatctatg   3900
ctgcatccag tttgcaaagt ggggtcccat caaggttcag cggcagtgga tctgggacag   3960
atttcactct caccatcagc agcctgcagc ctgaagattt tgcaacttat tactgccaac   4020
agtatgatag ttaccctatc accttcggcc aagggacacg actggagatt aaacgtacgg   4080
tggcggcgcc atctgtcttc atcttcccgc catctgatga gcagttgaaa tctggaactg   4140
cctctgttgt gtgcctgctg aataacttct atcccagaga ggccaaagta cagtggaagg   4200
tggataacgc cctccaatcg ggtaactccc aggagagtgt cacagagcag gacagcaagg   4260
acagcaccta cagcctcagc agcaccctga cgctgagcaa agcagactac gagaaacaca   4320
aagtctacgc ctgcgaagtc acccatcagg gcctgagctc gcccgtcaca aagagcttca   4380
acaggggaga gtgttaggga tccatctaga agggagaagt gcccccacct gctcctcagt   4440
tccagcctga ccccctccca tcctttggcc tctgaccctt tttccacagg ggacctaccc   4500
ctattgcggt cctccagctc atctttcacc tcaccccccct cctcctcctt ggctttaatt   4560
atgctaatgt tggaggagaa tgaataaata aagtgaatct ttgcacctgt ggtttctctc   4620
tttcctcatt taataattat tatctgttgt tttaccaact actcaatttc tcttataagg   4680
gactaaatat gtagtcatcc taaggcgcat aaccatttat aaaaatcatc cttcattcta   4740
ttttacccta tcatcctctg caagacagtc ctccctcaaa cccacaagcc ttctgtcctc   4800
acagtcccct gggccatcgg accgctatca ggacatagcg ttggctaccc gtgatattgc   4860
tgaagagctt ggcggcgaat gggctgaccg cttcctcgtg ctttacggta tcgccgctcc   4920
cgattcgcag cgcatcgcct tctatcgcct tcttgacgag ttcttctgag cgggactctg   4980
gggttcgaaa tgaccgacca agcgacgccc aacctgccat cacgagattt cgattccacc   5040
gccgccttct atgaaaggtt gggcttcgga atcgttttcc gggacgccgg ctggatgatc   5100
ctccagcgcg gggatctcat gctggagttc ttcgcccacc ccaacttgtt tattgcagct   5160
tataatggtt acaaataaag caatagcatc acaaatttca caaataaagc atttttttca   5220
ctgcattcta gttgtggttt gtccaaactc atcaatgtat cttatcatgt ctgtataccg   5280
tcgacctcta gctagagctt ggcgtaatca tggtcatagc tgtttcctgt gtgaaattgt   5340
tatccgctca caattccaca caacatacga gccggaagca taaagtgtaa agcctggggt   5400
gcctaatgag tgagctaact cacattaatt gcgttgcgct cactgcccgc tttccagtcg   5460
ggaaacctgt cgtgccagct gcattaatga atcggccaac gcgcggggag aggcggtttg   5520
cgtattgggc gctcttccgc ttcctcgctc actgactcgc tgcgctcggt cgttcggctg   5580
cggcgagcgg tatcagctca ctcaaaggcg gtaatacggt tatccacaga atcaggggat   5640
aacgcaggaa agaacatgcg aggcctccgc gccgggtttt ggcgcctccc gcgggcgccc   5700
ccctcctcac ggcgagcgct gccacgtcag acgaagggcg cagcgagcgt cctgatcctt   5760
ccgcccggac gctcaggaca gcggcccgct gctcataaga ctcggcctta gaaccccagt   5820
atcagcagaa ggacatttta ggacgggact tgggtgactc tagggcactg gttttctttc   5880
cagagagcgg aacaggcgag gaaaagtagt cccttctcgg cgattctgcg gagggatctc   5940
cgtggggcgg tgaacgccga tgattatata aggacgcgcc gggtgtggca cagctagttc   6000
cgtcgcagcc gggatttggg tcgcggttct tgtttgtgga tcgctgtgat cgtcacttgg   6060
tgagtagcgg gctgctgggc tggccggggc tttcgtggcc gccgggccgc tcggtgggac   6120
ggaagcgtgt ggagagaccg ccaagggctg tagtctgggt ccgcgagcaa ggttgccctg   6180
aactgggggt tgggggggagc gcagcaaaat ggcggctgtt cccgagtctt gaatggaaga   6240
```

-continued

```
cgcttgtgag gcgggctgtg aggtcgttga aacaaggtgg ggggcatggt gggcggcaag   6300
aacccaaggt cttgaggcct tcgctaatgc gggaaagctc ttattcgggt gagatgggct   6360
ggggcaccat ctggggaccc tgacgtgaag tttgtcactg actggagaac tcggtttgtc   6420
gtctgttgcg ggggcggcag ttatggcggt gccgttgggc agtgcacccg tacctttggg   6480
agcgcgcgcc ctcgtcgtgt cgtgacgtca cccgttctgt tggcttataa tgcagggtgg   6540
ggccacctgc cggtaggtgt gcggtaggct tttctccgtc gcaggacgca gggttcgggc   6600
ctagggtagg ctctcctgaa tcgacaggcg ccggacctct ggtgagggga gggataagtg   6660
aggcgtcagt ttctttggtc ggttttatgt acctatcttc ttaagtagct gaagctccgg   6720
ttttgaacta tgcgctcggg gttggcgagt gtgttttgtg aagtttttta ggcacctttt   6780
gaaatgtaat catttgggtc aatatgtaat tttcagtgtt agactagtaa attgtccgct   6840
aaattctggc cgtttttggc tttttttgtta gacagatctg tttaaactta agcttgccgc   6900
caccatggga tggagctgta tcatcctgtt cctcgtggcc acagcaaccg gtgtccacag   6960
ccaggtgcag ctacagcagt ggggcgcagg actgttgaag ccttcggaga ccctgtccct   7020
cacctgcgct gtctatggtg ggtccttcag tgcttactac tggagctgga tccgccagcc   7080
cccagggaag gggctggagt ggattgggga catcaatcat ggtggaggca ccaactacaa   7140
cccgtccctc aagagtcgag tcaccatatc agtagacacg tccaagaacc agttctccct   7200
gaagctgaac tctgtaaccg ccgcggacac ggctgtgtat tactgtgcga gcctaactgc   7260
ctactggggc cagggaagcc tggtcaccgt ctcctcagct agcaccaagg gcccatcggt   7320
cttccccctg gcaccctcct ccaagagcac ctctgggggc acagcggccc tgggctgcct   7380
ggtcaaggac tacttccccg aaccggtgac ggtgtcgtgg aactcaggcg ccctgaccag   7440
cggcgtgcac accttcccgg ccgtcctaca gtcctcagga ctctactccc tcagcagcgt   7500
ggtgaccgtg ccctccagca gcttgggcac ccagacctac atctgcaacg tgaatcacaa   7560
gcccagcaac accaaggtgg acaagagagt tgagcccaaa tcttgtgaca aaactcacac   7620
atgcccaccg tgcccagcac ctgaactcct ggggggaccg tcagtcttcc tcttcccccc   7680
aaaacccaag gacaccctca tgatctcccg gacccctgag gtcacatgcg tggtggtgga   7740
cgtgagccac gaagaccctg aggtcaagtt caactggtac gtggacggcg tggaggtgca   7800
taatgccaag acaaagccgc gggaggagca gtacaacagc acgtaccgtg tggtcagcgt   7860
cctcaccgtc ctgcaccagg actggctgaa tggcaaggag tacaagtgca aggtctccaa   7920
caaagccctc ccagccccca tcgagaaaac catctccaaa gccaaagggc agccccgaga   7980
accacaggtg tacaccctgc ccccatcccg ggatgagctg accaagaacc aggtcagcct   8040
gacctgcctg gtcaaaggct tctatcccag cgacatcgcc gtggagtggg agagcaatgg   8100
gcagccggag aacaactaca agaccacgcc tcccgtgctg gactccgacg gctccttctt   8160
cctctacagc aagctcaccg tggacaagag caggtggcag caggggaacg tcttctcatg   8220
ctccgtgatg catgaggctc tgcacaacca ctacacgcag aagagcctct ccctgtctcc   8280
gggtaaatga gtgcgacggc cggcaaggga tccaggggag agtgttagag ggagaagtgc   8340
ccccacctgc tcctcagttc cagcctgacc ccctcccatc ctttggcctc tgaccctttt   8400
tccacagggg acctacccct attgcggtcc tccagctcat ctttcacctc acccccctcc   8460
tcctccttgg ctttaattat gctaatgttg gaggagaatg aataaataaa gtgaatcttt   8520
gcacctgtgg tttctctctt tcctcattta ataattatta tctgttgttt taccaactac   8580
tcaatttctc ttataaggga ctaaatatgt agtcatccta aggcgcataa ccatttataa   8640
```

```
aaatcatcct tcattctatt ttaccctatc atcctctgca agacagtcct ccctcaaacc   8700
cacaagcctt ctgtcctcac agtcccctgg gccatgtgag caaaaggcca gcaaaaggcc   8760
aggaaccgta aaaaggccgc gttgctggcg tttttccata ggctccgccc ccctgacgag   8820
catcacaaaa atcgacgctc aagtcagagg tggcgaaacc cgatagttgc ggccgctcga   8880
gtctagaggg cccgtttaaa cccgctgatc agcctcgact gtgccttcta gttgccagcc   8940
atctgttgtt tgcccctccc ccgtgccttc cttgaccctg gaaggtgcca ctcccactgt   9000
cctttcctaa taaaatgagg aaattgcatc gcattgtctg agtaggtgtc attctattct   9060
ggggggtggg gtggggcagg acagcaaggg ggaggattgg gaagacaata gcaggcatgc   9120
tggggatgcg gtgggctcta tggcttctga ggcggaaaga accagctggg gctctagggg   9180
gtatccccac gcgccctgta gcggcgcatt aagcgcggcg ggtgtggtgg ttacgcgcag   9240
cgtgaccgct acacttgcca gcgccctagc gcccgctcct ttcgctttct tcccttcctt   9300
tctcgccacg ttcgcctacc gtcgaatcac cggtaacctt ataagggatt ttgccgattt   9360
cggcctattg gttaaaaaat gagctgattt aacaaaaatt taacgcgaat taattctgtg   9420
gaatgtgtgt cagttagggt gtggaaagtc cccaggctcc ccagcaggca gaagtatgca   9480
aagcatgcat ctcaattagt cagcaaccag gtgtggaaag tccccaggct ccccagcagg   9540
cagaagtatg caaagcatgc atctcaatta gtcagcaacc atagtcccgc ccctaactcc   9600
gcccatcccg cccctaactc cgcccagttc cgcccattct ccgccccatg gctgactaat   9660
ttttttattt tatgcagagg ccgaggccgc ctctgcctct gagctattcc agaagtagtg   9720
aggaggcttt tttggaggcc taggcttttg caaaaagctc ccgggagctt gtatatccat   9780
tttcggatct gatcaagaga caggatgagg atcgtttcgc atgattgaac aagatggatt   9840
gcacgcaggt tctccggccg cttgggtgga gaggctattc ggctatgact gggcacaaca   9900
gacaatcggc tgctctgatg ccgccgtgtt ccggctgtca gcgcaggggc gcccggttct   9960
ttttgtcaag accgacctgt ccggtgccct gaatgaactg caggacgagg cagcgcggct  10020
atcgtggctg gccacgacgg gcgttccttg cgcagctgtg ctcgacgttg tcactgaagc  10080
gggaagggac tggctgctat tgggcgaagt gccggggcag gatctcctgt catctcacct  10140
tgctcctgcc gagaaagtat ccatcatggc tgatgcaatg cggcggctgc atacgcttga  10200
tccggctacc tgcccattcg accaccaagc gaaacatcgc atcgagcgag cacgtactcg  10260
gatggaagcc ggtcttgtcg atcaggatga tctggacgaa gagcatcagg ggctcgcgcc  10320
agccgaactg ttcgccaggc tcaaggcgcg aattcgagct cggtacccgg ggatcctcta  10380
gagtcgacct gcaggcatgc aagcttggcg taatcatggt catagctgtt tcctgtgtga  10440
aattgttatc cgctcacaat tccacacaac atacgagccg gaagcataaa gtgtaaagcc  10500
tggggtgcct aatgagtgag ctaactcaca ttaattgcgt tgcgctcact gcccgctttc  10560
cagtcgggaa acctgtcgtg ccagctgcat taatgaatcg gccaacgcgc ggggagaggc  10620
ggtttgcgta ttgggcgctc ttccgcttcc tcgctcactg actcgctgcg ctcggtcgtt  10680
cggctgcggc gagcggtatc agctcactca aaggcggtaa tacggttatc cacagaatca  10740
ggggataacg caggaaagaa catgtgagca aaaggccagc aaaaggccag gaaccgtaaa  10800
aaggccgcgt tgctggcgtt tttccatagg ctccgccccc ctgacgagca tcacaaaaat  10860
cgacgctcaa gtcagaggtg gcgaaacccg acaggactat aaagatacca ggcgtttccc  10920
cctggaagct ccctcgtgcg ctctcctgtt ccgaccctgc cgcttaccgg atacctgtcc  10980
gcctttctcc cttcgggaag cgtggcgctt tctcatagct cacgctgtag gtatctcagt  11040
```

```
tcggtgtagg tcgttcgctc caagctgggc tgtgtgcacg aaccccccgt tcagcccgac  11100

cgctgcgcct tatccggtaa ctatcgtctt gagtccaacc cggtaagaca cgacttatcg  11160

ccactggcag cagccactgg taacaggatt agcagagcga ggtatgtagg cggtgctaca  11220

gagttcttga agtggtggcc taactacggc tacactagaa ggacagtatt tggtatctgc  11280

gctctgctga agccagttac cttcggaaaa agagttggta gctcttgatc cggcaaacaa  11340

accaccgctg gtagcggtgg tttttttgtt tgcaagcagc agattacgcg cagaaaaaaa  11400

ggatctcaag aagatccttt gatcttttct acggggtctg acgctcagtg gaacgaaaac  11460

tcacgttaag ggattttggt catgagatta tcaaaaagga tcttcaccta gatcctttta  11520

aattaaaaat gaagttttaa atcaatctaa agtatatatg agtaaacttg gtctgacagt  11580

taccaatgct taatcagtga ggcacctatc tcagcgatct gtctatttcg ttcatccata  11640

gttgcctgac tccccgtcgt gtagataact acgatacggg agggcttacc atctggcccc  11700

agtgctgcaa tgataccgcg agacccacgc tcaccggctc cagatttatc agcaataaac  11760

cagccagccg gaagggccga gcgcagaagt ggtcctgcaa ctttatccgc ctccatccag  11820

tctattaatt gttgccggga agctagagta agtagttcgc cagttaatag tttgcgcaac  11880

gttgttgcca ttgctacagg catcgtggtg tcacgctcgt cgtttggtat ggcttcattc  11940

agctccggtt cccaacgatc aaggcgagtt acatgatccc ccatgttgtg caaaaaagcg  12000

gttagctcct tcggtcctcc gatcgttgtc agaagtaagt tggccgcagt gttatcactc  12060

atggttatgg cagcactgca taattctctt actgtcatgc catccgtaag atgcttttct  12120

gtgactggtg agtactcaac caagtcattc tgagaatagt gtatgcggcg accgagttgc  12180

tcttgcccgg cgtcaatacg ggataatacc gcgccacata gcagaacttt aaaagtgctc  12240

atcattggaa aacgttcttc ggggcgaaaa ctctcaagga tcttaccgct gttgagatcc  12300

agttcgatgt aacccactcg tgcacccaac tgatcttcag catcttttac tttcaccagc  12360

gtttctgggt gagcaaaaac aggaaggcaa aatgccgcaa aaaagggaat aagggcgaca  12420

cggaaatgtt gaatactcat actcttcctt tttcaatatt attgaagcat ttatcagggt  12480

tattgtctca tgagcggata catatttgaa tgtatttaga aaaataaaca aataggggtt  12540

ccgcgcacat ttccccgaaa agtgccacct gacgtctaag aaaccattat tatcatgaca  12600

ttaacctata aaaataggcg tatcacgagg ccctttcgtc                        12640
```

```
<210> SEQ ID NO 54
<211> LENGTH: 1653
<212> TYPE: DNA
<213> ORGANISM: Artificial Sequence
<220> FEATURE:
<223> OTHER INFORMATION: Description of Artificial Sequence: Synthetic
      Luciferase ORF polynucleotide

<400> SEQUENCE: 54

atggaagatg ccaaaaacat taagaagggc ccagcgccat tctacccact cgaagacggg     60

accgccggcg agcagctgca caaagccatg aagcgctacg ccctggtgcc cggcaccatc    120

gcctttaccg acgcacatat cgaggtggac attacctacg ccgagtactt cgagatgagc    180

gttcggctgg cagaagctat gaagcgctat gggctgaata caaaccatcg gatcgtggtg    240

tgcagcgaga atagcttgca gttcttcatg cccgtgttgg gtgccctgtt catcggtgtg    300

gctgtggccc cagctaacga catctacaac gagcgcgagc tgctgaacag catgggcatc    360

agccagccca ccgtcgtatt cgtgagcaag aaagggctgc aaaagatcct caacgtgcaa    420

aagaagctac cgatcataca aaagatcatc atcatggata gcaagaccga ctaccagggc    480
```

```
ttccaaagca tgtacacctt cgtgacttcc catttgccac ccggcttcaa cgagtacgac    540

ttcgtgcccg agagcttcga ccgggacaaa accatcgccc tgatcatgaa cagtagtggc    600

agtaccggat tgcccaaggg cgtagcccta ccgcaccgca ccgcttgtgt ccgattcagt    660

catgcccgcg accccatctt cggcaaccag atcatccccg acaccgctat cctcagcgtg    720

gtgccatttc accacggctt cggcatgttc accacgctgg gctacttgat ctgcggcttt    780

cgggtcgtgc tcatgtaccg cttcgaggag gagctattct tgcgcagctt gcaagactat    840

aagattcaat ctgccctgct ggtgcccaca ctatttagct tcttcgctaa gagcactctc    900

atcgacaagt acgacctaag caacttgcac gagatcgcca gcggcggggc gccgctcagc    960

aaggaggtag gtgaggccgt ggccaaacgc ttccacctac caggcatccg ccagggctac   1020

ggcctgacag aaacaaccag cgccattctg atcacccccg aaggggacga caagcctggc   1080

gcagtaggca aggtggtgcc cttcttcgag gctaaggtgg tggacttgga caccggtaag   1140

acactgggtg tgaaccagcg cggcgagctg tgcgtccgtg gccccatgat catgagcggc   1200

tacgttaaca accccgaggc tacaaacgct ctcatcgaca aggacggctg gctgcacagc   1260

ggcgacatcg cctactggga cgaggacgag cacttcttca tcgtggaccg gctgaagagc   1320

ctgatcaaat acaagggcta ccaggtagcc ccagccgaac tggagagcat cctgctgcaa   1380

caccccaaca tcttcgacgc cggggtcgcc ggcctgcccg acgacgatgc cggcgagctg   1440

cccgccgcag tcgtcgtgct ggaacacggt aaaaccatga ccgagaagga gatcgtggac   1500

tatgtggcca gccaggttac aaccgccaag aagctgcgcg gtggtgttgt gttcgtggac   1560

gaggtgccta aggactgac cggcaagttg gacgcccgca agatccgcga gattctcatt    1620

aaggccaaga agggcggcaa gatcgccgtg taa                                 1653
```

<210> SEQ ID NO 55
<211> LENGTH: 8708
<212> TYPE: DNA
<213> ORGANISM: Artificial Sequence
<220> FEATURE:
<223> OTHER INFORMATION: Description of Artificial Sequence: Synthetic pTV-DS-luciferase polynucleotide

<400> SEQUENCE: 55

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgaatt ttaaggagcc ccttcgcctc    420

gtgcttgagt tgaggcctgg cttgggcgct ggggccgccg cgtgcgaatc tggtggcacc    480

ttcgcgcctg tctcgctgct ttcgataagt ctctagccat ttaaaatttt tgatgacctg    540

ctgcgacgct ttttttctgg caagatagtc ttgtaaatgc gggccaagat cgatctgcac    600

actggtattt cggtttttgg ggccgcgggc ggcgacgggg cccgtgcgtc ccagcgcaca    660

tgttcggcga ggcggggcct gcgagcgcgg ccaccgagaa tcggacgggg gtagtctcaa    720

gctggccggc ctgctctggt gcctggcctc gcgccgccgt gtatcgcccc gccctgggcg    780

gcaaggctgg cccggtcggc accagttgcg tgagcggaaa gatggccgct tcccggccct    840
```

```
gctgcaggga gctcaaaatg gaggacgcgg cgctcgggag agcgggcggg tgagtcaccc    900
acacaaagga aaagggcctt tccgtcctca gccgtcgctt catgtgactc cacggagtac    960
cgggcgccgt ccaggcacct cgattagttc tcgagctttt ggagtacgtc gtctttaggt   1020
tggggggagg ggttttatgc gatggagttt ccccacactg agtgggtgga gactgaagtt   1080
aggccagctt ggcacttgat gtaattctcc ttggaatttg ccctttttga gtttggatct   1140
tggttcattc tcaagcctca gacagtggtt caaagttttt ttcttccatt tcaggtgtcg   1200
tggaattggc tagagcttgc atgcctgcag gtcggccgcc acgaccggtg ccgccaccat   1260
cccctgaccc acgcccctga cccctcacaa ggagacgacc ttccatgacc gagtacaagc   1320
ccacggtgcg cctcgccacc cgcgacgacg tcccccgggc cgtacgcacc ctcgccgccg   1380
cgttcgccga ctaccccgcc acgcgccaca ccgtcgaccc ggaccgccac atcgagcggg   1440
tcaccgagct gcaagaactc ttcctcacgc gcgtcgggct cgacatcggc aaggtgtggg   1500
tcgcggacga cggcgccgcg gtggcggtct ggaccacgcc ggagagcgtc gaagcggggg   1560
cggtgttcgc cgagatcggc ccgcgcatgg ccgagttgag cggttcccgg ctggccgcgc   1620
agcaacagat ggaaggcctc ctggcgccgc accggcccaa ggagcccgcg tggttcctgg   1680
ccaccgtcgg cgtctcgccc gaccaccagg gcaagggtct gggcagcgcc gtcgtgctcc   1740
ccggagtgga ggcggccgag cgcgccgggg tgcccgcctt cctggagacc tccgcgcccc   1800
gcaacctccc cttctacgag cggctcggct tcaccgtcac cgccgacgtc gaggtgcccg   1860
aaggaccgcg cacctggtgc atgacccgca agcccggtgc ctgacgcccg ccccacgacc   1920
cgcagcgccc gaccgaaagg agcgcacgac cccatggctc cgaccgaagc cgacccgggc   1980
ggccccgccg accccgcacc cgcccccgag gcccaccgac tctagaggat cataatcagc   2040
cataccacat ttgtagaggt tttacttgct ttaaaaaacc tcccacacct ccccctgaac   2100
ctgaaacata aaatgaatgc aattgttgtt gttaacttgt ttattgcagc ttataatggt   2160
tacaaataaa gcaatagcat cacaaatttc acaaataaag catttttttc actgcattct   2220
agttgtggtt tgtccaaact catcaatgta tcttatcatg tctggatcct agcgtttaaa   2280
cttaagcttg gtaccgagct cggatccact agcgatgtac gggccagata tacgcgttga   2340
cattgattat tgactagtta ttaatagtaa tcaattacgg ggtcattagt tcatagccca   2400
tatatggagt tccgcgttac ataacttacg gtaaatggcc cgcctggctg accgcccaac   2460
gacccccgcc cattgacgtc aataatgacg tatgttccca tagtaacgcc aatagggact   2520
ttccattgac gtcaatgggt ggagtattta cggtaaactg cccacttggc agtacatcaa   2580
gtgtatcata tgccaagtac gccccctatt gacgtcaatg acggtaaatg gcccgcctgg   2640
cattatgccc agtacatgac cttatgggac tttcctactt ggcagtacat ctacgtatta   2700
gtcatcgcta ttaccatggt gatgcggttt tggcagtaca tcaatgggcg tggatagcgg   2760
tttgactcac ggggatttcc aagtctccac cccattgacg tcaatgggag tttgttttgg   2820
caccaaaatc aacgggactt tccaaaatgt cgtaacaact ccgccccatt gacgcaaatg   2880
ggcggtaggc gtgtacggtg ggaggtctat ataagcagag ctctctggct aactagagaa   2940
cccactgctt actggcttat cgaaattaat acgactcact atagggagac ccaagctggc   3000
tagcgctgat atcgatcgcg agcggccgcg aattcactag tgattgcaga attcatggaa   3060
gatgccaaaa acattaagaa gggcccagcg ccattctacc cactcgaaga cgggaccgcc   3120
ggcgagcagc tgcacaaagc catgaagcgc tacgccctgg tgcccggcac catcgccttt   3180
accgacgcac atatcgaggt ggacattacc tacgccgagt acttcgagat gagcgttcgg   3240
```

-continued

```
ctggcagaag ctatgaagcg ctatgggctg aatacaaacc atcggatcgt ggtgtgcagc   3300

gagaatagct tgcagttctt catgcccgtg ttgggtgccc tgttcatcgg tgtggctgtg   3360

gccccagcta acgacatcta caacgagcgc gagctgctga acagcatggg catcagccag   3420

cccaccgtcg tattcgtgag caagaaaggg ctgcaaaaga tcctcaacgt gcaaaagaag   3480

ctaccgatca tacaaaagat catcatcatg gatagcaaga ccgactacca gggcttccaa   3540

agcatgtaca ccttcgtgac ttcccatttg ccacccggct tcaacgagta cgacttcgtg   3600

cccgagagct tcgaccggga caaaaccatc gccctgatca tgaacagtag tggcagtacc   3660

ggattgccca agggcgtagc cctaccgcac cgcaccgctt gtgtccgatt cagtcatgcc   3720

cgcgacccca tcttcggcaa ccagatcatc cccgacaccg ctatcctcag cgtggtgcca   3780

tttcaccacg gcttcggcat gttcaccacg ctgggctact tgatctgcgg ctttcgggtc   3840

gtgctcatgt accgcttcga ggaggagcta ttcttgcgca gcttgcaaga ctataagatt   3900

caatctgccc tgctggtgcc cacactattt agcttcttcg ctaagagcac tctcatcgac   3960

aagtacgacc taagcaactt gcacgagatc gccagcggcg gggcgccgct cagcaaggag   4020

gtaggtgagg ccgtggccaa acgcttccac ctaccaggca tccgccaggg ctacggcctg   4080

acagaaacaa ccagcgccat tctgatcacc cccgaagggg acgacaagcc tggcgcagta   4140

ggcaaggtgg tgcccttctt cgaggctaag gtggtggact tggacaccgg taagacactg   4200

ggtgtgaacc agcgcggcga gctgtgcgtc cgtggcccca tgatcatgag cggctacgtt   4260

aacaaccccg aggctacaaa cgctctcatc gacaaggacg gctggctgca cagcggcgac   4320

atcgcctact gggacgagga cgagcacttc ttcatcgtgg accggctgaa gagcctgatc   4380

aaatacaagg gctaccaggt agccccagcc gaactggaga gcatcctgct gcaacacccc   4440

aacatcttcg acgccggggt cgccggcctg cccgacgacg atgccggcga gctgcccgcc   4500

gcagtcgtcg tgctggaaca cggtaaaacc atgaccgaga aggagatcgt ggactatgtg   4560

gccagccagg ttacaaccgc caagaagctg cgcggtggtg ttgtgttcgt ggacgaggtg   4620

cctaaaggac tgaccggcaa gttggacgcc cgcaagatcc gcgagattct cattaaggcc   4680

aagaagggcg gcaagatcgc cgtgtaataa ttctagagtc ggggcggccg gccgcttcga   4740

gcagacatga taagatacat tgatgagttt ggacaaacca caactagaat gcagtgaaaa   4800

aaatgcttta tttgtgaaat ttgtgatgct attgctttat ttgtaaccat tataagctgc   4860

aataaacaag ttaacaacaa caattgcatt cattttatgt ttcaggttca gggggaggtg   4920

tgggaggttt tttaaagcgg ccgctcgagt ctagagggcc cgtttaaacc cgctgatcag   4980

cctcgactgt gccttctagt tgccagccat ctgttgtttg cccctccccc gtgccttcct   5040

tgaccctgga aggtgccact cccactgtcc tttcctaata aaatgaggaa attgcatcgc   5100

attgtctgag taggtgtcat tctattctgg ggggtggggt ggggcaggac agcaaggggg   5160

aggattggga agacaatagc aggcatgctg gggatgcggt gggctctatg gcttctgagg   5220

cggaaagaac cagctggggc tctagggggt atccccacgc gccctgtagc ggcgcattaa   5280

gcgcggcggg tgtggtggtt acgcgcagcg tgaccgctac acttgccagc gccctagcgc   5340

ccgctccttt cgctttcttc ccttcctttc tcgccacgtt cgcctaccgt cgaatcaccg   5400

gtaaccttat aagggatttt gccgatttcg gcctattggt taaaaaatga gctgatttaa   5460

caaaaattta acgcgaatta attctgtgga atgtgtgtca gttagggtgt ggaaagtccc   5520

caggctcccc agcaggcaga agtatgcaaa gcatgcatct caattagtca gcaaccaggt   5580

gtggaaagtc cccaggctcc ccagcaggca gaagtatgca aagcatgcat ctcaattagt   5640
```

```
cagcaaccat agtcccgccc ctaactccgc ccatcccgcc cctaactccg cccagttccg   5700
cccattctcc gccccatggc tgactaattt tttttattta tgcagaggcc gaggccgcct   5760
ctgcctctga gctattccag aagtagtgag gaggcttttt tggaggccta ggcttttgca   5820
aaaagctccc gggagcttgt atatccattt tcggatctga tcaagagaca ggatgaggat   5880
cgtttcgcat gattgaacaa gatggattgc acgcaggttc tccggccgct tgggtggaga   5940
ggctattcgg ctatgactgg gcacaacaga caatcggctg ctctgatgcc gccgtgttcc   6000
ggctgtcagc gcaggggcgc ccggttcttt ttgtcaagac cgacctgtcc ggtgccctga   6060
atgaactgca ggacgaggca gcgcggctat cgtggctggc cacgacgggc gttccttgcg   6120
cagctgtgct cgacgttgtc actgaagcgg gaagggactg gctgctattg ggcgaagtgc   6180
cggggcagga tctcctgtca tctcaccttg ctcctgccga gaaagtatcc atcatggctg   6240
atgcaatgcg gcggctgcat acgcttgatc cggctacctg cccattcgac caccaagcga   6300
aacatcgcat cgagcgagca cgtactcgga tggaagccgg tcttgtcgat caggatgatc   6360
tggacgaaga gcatcagggg ctcgcgccag ccgaactgtt cgccaggctc aaggcgcgaa   6420
ttcgagctcg gtacccgggg atcctctaga gtcgacctgc aggcatgcaa gcttggcgta   6480
atcatggtca tagctgtttc ctgtgtgaaa ttgttatccg ctcacaattc cacacaacat   6540
acgagccgga agcataaagt gtaaagcctg gggtgcctaa tgagtgagct aactcacatt   6600
aattgcgttg cgctcactgc ccgctttcca gtcgggaaac ctgtcgtgcc agctgcatta   6660
atgaatcggc caacgcgcgg ggagaggcgg tttgcgtatt gggcgctctt ccgcttcctc   6720
gctcactgac tcgctgcgct cggtcgttcg gctgcggcga gcggtatcag ctcactcaaa   6780
ggcggtaata cggttatcca cagaatcagg ggataacgca ggaaagaaca tgtgagcaaa   6840
aggccagcaa aaggccagga accgtaaaaa ggccgcgttg ctggcgtttt tccataggct   6900
ccgcccccct gacgagcatc acaaaaatcg acgctcaagt cagaggtggc gaaacccgac   6960
aggactataa agataccagg cgtttccccc tggaagctcc ctcgtgcgct ctcctgttcc   7020
gaccctgccg cttaccggat acctgtccgc ctttctccct tcgggaagcg tggcgctttc   7080
tcatagctca cgctgtaggt atctcagttc ggtgtaggtc gttcgctcca agctgggctg   7140
tgtgcacgaa ccccccgttc agcccgaccg ctgcgcctta tccggtaact atcgtcttga   7200
gtccaacccg gtaagacacg acttatcgcc actggcagca gccactggta acaggattag   7260
cagagcgagg tatgtaggcg gtgctacaga gttcttgaag tggtggccta actacggcta   7320
cactagaagg acagtatttg gtatctgcgc tctgctgaag ccagttacct tcggaaaaag   7380
agttggtagc tcttgatccg gcaaacaaac caccgctggt agcggtggtt tttttgtttg   7440
caagcagcag attacgcgca gaaaaaaagg atctcaagaa gatcctttga tcttttctac   7500
ggggtctgac gctcagtgga acgaaaactc acgttaaggg attttggtca tgagattatc   7560
aaaaaggatc ttcacctaga tccttttaaa ttaaaaatga agttttaaat caatctaaag   7620
tatatatgag taaacttggt ctgacagtta ccaatgctta atcagtgagg cacctatctc   7680
agcgatctgt ctatttcgtt catccatagt tgcctgactc cccgtcgtgt agataactac   7740
gatacgggag ggcttaccat ctggccccag tgctgcaatg ataccgcgag acccacgctc   7800
accggctcca gatttatcag caataaacca gccagccgga agggccgagc gcagaagtgg   7860
tcctgcaact ttatccgcct ccatccagtc tattaattgt tgccgggaag ctagagtaag   7920
tagttcgcca gttaatagtt tgcgcaacgt tgttgccatt gctacaggca tcgtggtgtc   7980
acgctcgtcg tttggtatgg cttcattcag ctccggttcc caacgatcaa ggcgagttac   8040
```

```
atgatccccc atgttgtgca aaaaagcggt tagctccttc ggtcctccga tcgttgtcag   8100

aagtaagttg gccgcagtgt tatcactcat ggttatggca gcactgcata attctcttac   8160

tgtcatgcca tccgtaagat gcttttctgt gactggtgag tactcaacca agtcattctg   8220

agaatagtgt atgcggcgac cgagttgctc ttgcccggcg tcaatacggg ataataccgc   8280

gccacatagc agaactttaa aagtgctcat cattggaaaa cgttcttcgg ggcgaaaact   8340

ctcaaggatc ttaccgctgt tgagatccag ttcgatgtaa cccactcgtg cacccaactg   8400

atcttcagca tcttttactt tcaccagcgt ttctgggtga gcaaaaacag gaaggcaaaa   8460

tgccgcaaaa aagggaataa gggcgacacg gaaatgttga atactcatac tcttcctttt   8520

tcaatattat tgaagcattt atcagggtta ttgtctcatg agcggataca tatttgaatg   8580

tatttagaaa aataaacaaa taggggttcc gcgcacattt ccccgaaaag tgccacctga   8640

cgtctaagaa accattatta tcatgacatt aacctataaa aataggcgta tcacgaggcc   8700

ctttcgtc                                                            8708


<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      DPV15b peptide

<400> SEQUENCE: 56

Gly Ala Tyr Asp Leu Arg Arg Arg Glu Arg Gln Ser Arg Leu Arg Arg
1               5                   10                  15

Arg Glu Arg Gln Ser Arg
            20


<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      DPV1047 peptide

<400> SEQUENCE: 57

Val Lys Arg Gly Leu Lys Leu Arg His Val Arg Pro Arg Val Thr Arg
1               5                   10                  15

Met Asp Val


<210> SEQ ID NO 58
<211> LENGTH: 196
<212> TYPE: PRT
<213> ORGANISM: Artificial Sequence
<220> FEATURE:
<223> OTHER INFORMATION: Description of Artificial Sequence: Synthetic
      DPV15b/I-CreI N75/6xHis protein sequence

<400> SEQUENCE: 58

Met Gly Ala Tyr Asp Leu Arg Arg Arg Glu Arg Gln Ser Arg Leu Arg
1               5                   10                  15

Arg Arg Glu Arg Gln Ser Arg Asn Thr Lys Tyr Asn Lys Glu Phe Leu
            20                  25                  30

Leu Tyr Leu Ala Gly Phe Val Asp Gly Asp Gly Ser Ile Ile Ala Gln
        35                  40                  45

Ile Lys Pro Asn Gln Ser Tyr Lys Phe Lys His Gln Leu Ser Leu Thr
    50                  55                  60
```

```
Phe Gln Val Thr Gln Lys Thr Gln Arg Arg Trp Phe Leu Asp Lys Leu
65                  70                  75                  80

Val Asp Glu Ile Gly Val Gly Tyr Val Arg Asp Arg Gly Ser Val Ser
                85                  90                  95

Asn Tyr Ile Leu Ser Glu Ile Lys Pro Leu His Asn Phe Leu Thr Gln
            100                 105                 110

Leu Gln Pro Phe Leu Lys Leu Lys Gln Lys Gln Ala Asn Leu Val Leu
        115                 120                 125

Lys Ile Ile Glu Gln Leu Pro Ser Ala Lys Glu Ser Pro Asp Lys Phe
    130                 135                 140

Leu Glu Val Cys Thr Trp Val Asp Gln Ile Ala Ala Leu Asn Asp Ser
145                 150                 155                 160

Lys Thr Arg Lys Thr Thr Ser Glu Thr Val Arg Ala Val Leu Asp Ser
                165                 170                 175

Leu Ser Glu Lys Lys Lys Ser Ser Pro Ala Ala Ala Leu Glu His His
            180                 185                 190

His His His His
        195


<210> SEQ ID NO 59
<211> LENGTH: 12632
<212> TYPE: DNA
<213> ORGANISM: Artificial Sequence
<220> FEATURE:
<223> OTHER INFORMATION: Description of Artificial Sequence: Synthetic
      cGPS custom lacz integration matrix polynucleotide

<400> SEQUENCE: 59

gaccacaaaa gtgtgatggg tcctctggaa ctggagttgc aggccattgg gagctactgt      60

gtggctggga actggactta gggcctctgc ccaaacagca aatgggctta actctctcca     120

gccccaatat tttctagttt taaagttctt tttcacaaaa agaaaaacac caggaagtcc     180

tactagttat tcagtttgag atataaatag tggtactcca taatgagtcc agcaaatgtt     240

gaaacgaggt tggaagtctg taaatgagat tatgattctg ttggtttgct atacacattt     300

cttttaaaat ttttttataa attttattta aattagaaac aatcttattt tacatatcaa     360

tcccagttca ctctcactcc catcctccca agccccccac caattctccc atccactccc     420

caaggagggc gaggccttcc atgagggatc atcaaaaaat ctgtcacttg gggcagggcc     480

taggccctcc tcccctgtta tacacatttc tttactgtat cactgtatgt aaagtatata     540

tacacatacg agttatgtac tatcatataa tactaaattt ttggactttt taatattagt     600

acatctatag ctatcacatg tttttacctt taaaaatttt tataattgtg tgtgtgtgtg     660

tgtgtgtgtg tgtgtgtgtg tgtgtgtgtg tgtgtatgta tgtgtatgtg tgtgtatgtg     720

tgtaaactgt tttctctttg agataggttc ttactgttta gttcagtctg gcttggaact     780

ttctgtatag cccagactga ccttaactca gtattcctcc cccatctgga gattacaggt     840

atgagccacc atgcccagtc ctgtttttat attgattttg aaaaagggtc tcaaatagtt     900

tagactggct tccaactcac agtgtagctg aggatgacct gaagttctga tgctattgct     960

tctactggtg tgccattatg cccagtttgc acagttatga ggataaaacc taggaccttg    1020

ttcctgtgca tactaggcat agactctacc aattaagcta cattcccagc tcccccaggt    1080

ttactttaaa ggtgataatg ctattctgtt catggatata ccataactga tttaactctg    1140

tactgttggt agacacttaa gatctccatt attttgcact tagcaggagt ttattagagg    1200

aaatatgata tatattggca cttgctcagc tttaggcaag tagaaattct gggtcaagta    1260
```

```
aaagatgttt attgaatatt atcatactgc caaattaacc tctaaaaaat ttcataattt   1320
tatactacca gtggtatgtg agttcatttt tcctcacaat ctcttctaat attttacatt   1380
agagaaatgc aatttaacca aaattcacca gtcttgttag ctttgaacat tgtatctttt   1440
tatttgtatt tttaaatttc atgatgttat agtatacctg ttcttttatt tgagacagaa   1500
tcttattatg tagccctaag tgacctagta cttactctgc tgttgtacag tatgtccctc   1560
aacccatacc cttcctcctg cctcagcctc cagagtgcta gaattatagg catgtaccat   1620
ggtgcctagc atgtacctgg tttttaaagg tagctggaat tataggcatg taccatgatg   1680
cctagcatgt acctggtttt taaagttagt aagttttaat tttggttgag ctgtgtgttg   1740
gtgtgtaagt ataatctcag cacacagagt tcgagacatg ggttatgagt tactatgcag   1800
cctgggctac atagagggat cctgtgtcac cttccccaac cccaaaatc ttccctttgc   1860
catatggaaa acatccccca ctttatttaa tagtttgatt tatgaagcaa gattaccaat   1920
tatggggaca aagaatgtgt cctgtggaag tttaagaagt gtttgttata aaaatataac   1980
tatttggaat cttctattcc tgattttatt tttgtaggac tgaaagactt gcccgagata   2040
aaaagcctga actcaccgcg acgtctgtcg agaagtttct gatcgaaaag ttcgacagcg   2100
tctccgacct gatgcagctc tcggagggcg aagaatctcg tgctttcagc ttcgatgtag   2160
gagggcgtgg atatgtcctg cgggtaaata gctgcgccga tggtttctac aaagatcgtt   2220
atgtttatcg gcactttgca tcggccgcgc tcccgattcc ggaagtgctt gacattgggg   2280
aattcagcga gagcctgacc tattgcatct cccgccgtgc acagggtgtc acgttgcaag   2340
acctgcctga aaccgaactg cccgctgttc tgcagccggt cgcggaggcc atggatgcga   2400
tcgctgcggc cgatcttagc cagacgagcg ggttcggccc attcggaccg caaggaatcg   2460
gtcaatacac tacatggcgt gatttcatat gcgcgattgc tgatccccat gtgtatcact   2520
ggcaaactgt gatggacgac accgtcagtg cgtccgtcgc gcaggctctc gatgagctga   2580
tgctttgggc cgaggactgc cccgaagtcc ggcacctcgt gcacgcggat ttcggctcca   2640
acaatgtcct gacggacaat ggccgcataa cagcggtcat tgactggagc gaggcgatgt   2700
tcggggattc ccaatacgag gtcgccaaca tcttcttctg gaggccgtgg ttggcttgta   2760
tggagcagca gacgcgctac ttcgagcgga ggcatccgga gcttgcagga tcgccgcggc   2820
tccgggcgta tatgctccgc attggtcttg accaactcta tcagagcttg gttgacggca   2880
atttcgatga tgcagcttgg gcgcagggtc gatgcgacgc aatcgtccga tccggagccg   2940
ggactgtcgg gcgtacacaa atcgcccgca gaagcgcggc cgtctggacc gatggctgtg   3000
tagaagtact cgccgatagt ggaaaccgac gccccagcac tcgtccgagg gcaaaggaat   3060
agcacgtgct acgagatttc gattccaccg ccgccttcta tgaaaggttg ggcttcggaa   3120
tcgttttccg ggacgccggc tggatgatcc tccagcgcgg ggatctcatg ctggagttct   3180
tcgcccaccc caacttgttt attgcagctt ataatggtta caaataaagc aatagcatca   3240
caaatttcac aaataaagca tttttttcac tgcattctag ttgtggtttg tccaaactca   3300
tcaatgtatc ttatcatgtc tgtataccgt cgacctctag ctagagcttg gcgtaatcat   3360
ggtcatagct gtttcctgtg tgaaattgtt atccgctcac aattccacac aacatacgag   3420
ccggaagcat aaagaatcga attcccgcgg ccgcacgcta gggataacag ggtaatatag   3480
atcgatgtac gggccagata tacgcgttga cattgattat tgactagtta ttaatagtaa   3540
tcaattacgg ggtcattagt tcatagccca tatatggagt tccgcgttac ataacttacg   3600
gtaaatggcc cgcctggctg accgcccaac gacccccgcc cattgacgtc aataatgacg   3660
```

```
tatgttccca tagtaacgcc aatagggact ttccattgac gtcaatgggt ggactattta   3720
cggtaaactg cccacttggc agtacatcaa gtgtatcata tgccaagtac gccccctatt   3780
gacgtcaatg acggtaaatg gcccgcctgg cattatgccc agtacatgac cttatgggac   3840
tttcctactt ggcagtacat ctacgtatta gtcatcgcta ttaccatggt gatgcggttt   3900
tggcagtaca tcaatgggcg tggatagcgg tttgactcac ggggatttcc aagtctccac   3960
cccattgacg tcaatgggag tttgttttgg caccaaaatc aacgggactt tccaaaatgt   4020
cgtaacaact ccgccccatt gacgcaaatg ggcggtaggc gtgtacggtg ggaggtctat   4080
ataagcagag ctctctggct aactagagaa cccactgctt actggcttat cgaaattaat   4140
acgactcact atagggagac ccaagctggc tagcgtttaa acttaagctt ggtaccgagc   4200
tcggatccac tagtccagtg tggtggaatt ctgcagatcg aaacgatgat agatcccgtc   4260
gttttacaac gtcgtgactg ggaaaaccct ggcgttaccc aacttaatcg ccttgcagca   4320
catccccctt tcgccagctg gcgtaatagc gaagaggccc gcaccgatcg cccttcccaa   4380
cagttgcgca gcctgaatgg cgaatggcgc tttgcctggt ttccggtacc agaagcggtg   4440
ccggaaagct ggctggagtg cgatcttcct gaggccgata ctgtcgtcgt cccctcaaac   4500
tggcagatgc acggttacga tgcgcccatc tacaccaacg taacctatcc cattacggtc   4560
aatccgccgt ttgttcccac ggagaatccg acgggttgtt actcgctcac atttaatgtt   4620
gatgaaagct ggctacagga aggccagacg cgaattattt ttgatggcgt taactcggcg   4680
tttcatctgt ggtgcaacgg gcgctgggtc ggttacggcc aggacagtcg tttgccgtct   4740
gaatttgacc tgagcgcatt tttacgcgcc ggagaaaacc gcctcgcggt gatggtgctg   4800
cgttggagtg acggcagtta tctggaagat caggatatgt ggcggatgag cggcattttc   4860
cgtgacgtct cgttgctgca taaaccgact acacaaatca gcgatttcca tgttgccact   4920
cgctttaatg atgatttcag ccgcgctgta ctggaggctg aagttcagat gtgcggcgag   4980
ttgcgtgact acctacgggt aacagtttct ttatggcagg gtgaaacgca ggtcgccagc   5040
ggcaccgcgc ctttcggcgg tgaaattatc gatgagcgtg gtggttatgc cgatcgcgtc   5100
acactacgtc tgaacgtcga aaacccgaaa ctgtggagcg ccgaaatccc gaatctctat   5160
cgtgcggtgg ttgaactgca caccgccgac ggcacgctga ttgaagcaga agcctgcgat   5220
gtcggtttcc gcgaggtgcg gattgaaaat ggtctgctgc tgctgaacgg caagccgttg   5280
ctgattcgag gcgttaaccg tcacgagcat catcctctgc atggtcaggt catggatgag   5340
cagacgatgg tgcaggatat cctgctgatg aagcagaaca actttaacgc cgtgcgctgt   5400
tcgcattatc cgaaccatcc gctgtggtac acgctgtgcg accgctacgg cctgtatgtg   5460
gtggatgaag ccaatattga aacccacggc atggtgccaa tgaatcgtct gaccgatgat   5520
ccgcgctggc taccggcgat gagcgaacgc gtaacgcgaa tggtgcagcg cgatcgtaat   5580
cacccgagtg tgatcatctg gtcgctgggg aatgaatcag gccacggcgc taatcacgac   5640
gcgctgtatc gctggatcaa atctgtcgat ccttcccgcc cggtgcagta tgaaggcggc   5700
ggagccgaca ccacggccac cgatattatt tgcccgatgt acgcgcgcgt ggatgaagac   5760
cagcccttcc cggctgtgcc gaaatggtcc atcaaaaaat ggctttcgct acctggagag   5820
acgcgcccgc tgatcctttg cgaatacgcc cacgcgatgg gtaacagtct tggcggtttc   5880
gctaaatact ggcaggcgtt tcgtcagtat ccccgtttac agggcggctt cgtctgggac   5940
tgggtggatc agtcgctgat taaatatgat gaaaacggca acccgtggtc ggcttacggc   6000
ggtgattttg gcgatacgcc gaacgatcgc cagttctgta tgaacggtct ggtctttgcc   6060
```

```
gaccgcacgc cgcatccagc gctgacggaa gcaaaacacc agcagcagtt tttccagttc   6120
cgtttatccg ggcaaaccat cgaagtgacc agcgaatacc tgttccgtca tagcgataac   6180
gagctcctgc actggatggt ggcgctggat ggtaagccgc tggcaagcgg tgaagtgcct   6240
ctggatgtcg ctccacaagg taaacagttg attgaactgc ctgaactacc gcagccggag   6300
agcgccgggc aactctggct cacagtacgc gtagtgcaac cgaacgcgac cgcatggtca   6360
gaagccgggc acatcagcgc ctggcagcag tggcgtctgg cggaaaacct cagtgtgacg   6420
ctccccgccg cgtcccacgc catcccgcat ctgaccacca gcgaaatgga tttttgcatc   6480
gagctgggta ataagcgttg gcaatttaac cgccagtcag gctttctttc acagatgtgg   6540
attggcgata aaaaacaact gctgacgccg ctgcgcgatc agttcacccg tgcaccgctg   6600
gataacgaca ttggcgtaag tgaagcgacc cgcattgacc ctaacgcctg ggtcgaacgc   6660
tggaaggcgg cgggccatta ccaggccgaa gcagcgttgt tgcagtgcac ggcagataca   6720
cttgctgatg cggtgctgat tacgaccgct cacgcgtggc agcatcaggg gaaaacctta   6780
tttatcagcc ggaaaaccta ccggattgat ggtagtggtc aaatggcgat taccgttgat   6840
gttgaagtgg cgagcgatac accgcatccg gcgcggattg gcctgaactg ccagctggcg   6900
caggtagcag agcgggtaaa ctggctcgga ttagggccgc aagaaaacta tcccgaccgc   6960
cttactgccg cctgttttga ccgctgggat ctgccattgt cagacatgta taccccgtac   7020
gtcttcccga gcgaaaacgg tctgcgctgc gggacgcgcg aattgaatta tggcccacac   7080
cagtggcgcg gcgacttcca gttcaacatc agccgctaca gtcaacagca actgatggaa   7140
accagccatc gccatctgct gcacgcggaa gaaggcacat ggctgaatat cgacggtttc   7200
catatgggga ttggtggcga cgactcctgg agcccgtcag tatcggcgga attccagctg   7260
agcgccggtc gctaccatta ccagttggtc tggtgtcaaa aagcggccgc tcgagtctag   7320
agggcccgtt taaacccgct gatcagcctc gactgtgcct tctagttgcc agccatctgt   7380
tgtttgcccc tcccccgtgc cttccttgac cctggaaggt gccactccca ctgtcctttc   7440
ctaataaaat gaggaaattg catcgcattg tctgagtagg tgtcattcta ttctgggggg   7500
tggggtgggg caggacagca agggggagga ttgggaagac aatagcaggc atgctgggga   7560
tgcggtgggc tctatggctt ctgaggcgga aagaaccagc tggggctcta gggggtatcc   7620
ccacgcgccc tgtagcggcg cattaagcgc ggcgggtgtg gtggttacgc gcagcgtgac   7680
cgctacactt gccagcgccc tagcgcccgc tcctttcgct ttcttccctt cctttctcgc   7740
cacgttcgcc ggtttaaact cgaggcgcgc cgctagctcg cgaggccgct gggaggccat   7800
cacattgtgg ccctctgtgt gctgaagggg ggctataaat tctttgctga cctgctggat   7860
tacattaaag cactgaatag aaatagtgat agatccattc ccatgactgt agattttatc   7920
agactgaaga gctactgtgt aagtataatt cattcataat ttaaaaaata tggcaatcct   7980
agttttgtat gtatttttgt ttgtttgttt ttactttgaa acagtgtttt tctgggtagc   8040
tttggagcct gtcttggaac tctctgctgt agaccagact gacctacaga gatctacctg   8100
cctctgactc ctgagtgctg agattaaacg agtgcaccac cacctgagcc tcatcaactg   8160
aggcttatcc cagttttttt tagaatttta gtttgagacc ctctctaact tgctcagact   8220
atccttgaac tcattacata ggctgatcta gaaattttag tcatcttgac tcagtttctc   8280
aagtagctgg gattacaggc aggtgctacc acttctggcc ataattgttg ctgttattat   8340
tcactggtac tttacatcac aacactgtag ttcaagacca acatcaaagt gaatattgtt   8400
tgttagtcac ccaagatgga tttgtactta ctttgcatgg tttttctttt gtcttatttt   8460
```

```
gacctggatt ttgacttgtt ttatgatact gctcaggcta gtatcaaact ctgtggttca   8520
aataatcctt ctgtcttagc ctcccaaatt ctgggagtac aagcgtgtat caccatacct   8580
gactgtgttt tgatattttc caaaacaact tttaagaatt actgcagagt acagtgacag   8640
agagagatgg ttcatcagtc acaagcactt gtagagaaga ctggggttta gttactggca   8700
cccaaaagat ggctcacagc tatgtagctc cagttccagg ggacctgatg tcctagcctc   8760
cagataaaat aaaaataagt aagttttaca agaattatgg gactggtgag gtggactcag   8820
tagtcaaagg cactggctgc tctttcagag gacctggttc aattcctagc acccacgtgg   8880
tagttcacag ttgtctttaa ctccagtccc agggatctga tgccatcttc tggcctccaa   8940
gggcaccaga cactaacatg gtacacaaac aaatatgcaa cttgaacacc catacacata   9000
ttttaaaaat aaacaatttc tgttgagact tggtgttttc ctgactgtat atgctggtgg   9060
caaataattt ctctggaact aagttgcttt gagagtaatc ctaaattatt tgaagcaaag   9120
tctcattatt aaggttaaca attatttctc agaaaacaga aaccactttt gacctttggc   9180
cacgttacct ttgtcagagt ctgaagtgat gtagaatatt gacaatatga tgaaacaaaa   9240
tgaatgtaat ctttacatgt aaattccatc attcacaatt ttgattgtgt ggcttatttt   9300
ttttattttc attctctctc ttttttttt gagactctat gtagctctta ctgtcttgga   9360
actcactgta tagaccaggc tggtcttgaa ctcagagacc caactgcctc tacctcctga   9420
gtgctgggat tagaggcatg tgccaccact gcctggctaa aatagatatt tatttttaaa   9480
ataaaactgc aggatattat agagaaactt aagtcaccca tattcttttt gtttttgtt    9540
ttttttttgt ttttggtttt tctagacagg gtttctctgg ctttggaggc tgtcctggaa   9600
ctagctcttg tagaccaggc tggtctcgaa ctcacagcct gcctctgcct cccgagtgct   9660
gggattaaag gcgtgggcca ccaacgcctg gctctctttt tggtttttta agacaggatt   9720
tctctatgta gctttggagc ctatcctggc actcgatctg gagacggatc cccaggaagc   9780
tcctctgtgt cctcataaac cctaacctcc tctacttgag aggacattcc aatcataggc   9840
tgcccatcca ccctctgtgt cctcctgtta attaggtcac ttaacaaaaa ggaaattggg   9900
taggggtttt tcacagaccg ctttctaagg gtaattttaa aatatctggg aagtcccttc   9960
cactgctgtg ttccagaagt gttggtaaac agcccacaaa tgtcaacagc agaaacatac  10020
aagctgtcag ctttgcacaa gggcccaaca ccctgctcat caagaagcac tgtggttgct  10080
gtgttagtaa tgtgcaaaac aggaggcaca ttttccccac ctgtgtaggt tccaaaatat  10140
ctagtgtttt catttttact tggatcagga acccagcact ccactggata agcattatcc  10200
ttatccaaaa cagccttgtg gtcagtgttc atctgctgac tgtcaactgt agcatttttt  10260
ggggttacag tttgagcagg atatttggtc ctgtagtttg ctaacacacc ctgcagctcc  10320
aaaggttccc caccaacagc aaaaaaatga aaatttgacc cttgaatggg ttttccagca  10380
ccattttcat gagtttttg tgtccctgaa tgcaagttta acatagcagt taccccaata   10440
acctcagttt taacagtaac agcttcccac atcaaaatat ttccacaggt taagtcctca  10500
tttaaattag gcaaaggaat tcttgaagac gaaagggcct cgtgatacgc ctatttttat  10560
aggttaatgt catgataata atggtttctt agacgtcagg tggcactttt cggggaaatg  10620
tgcgcggaac ccctatttgt ttatttttct aaatacattc aaatatgtat ccgctcatga  10680
gacaataacc ctgataaatg cttcaataat attgaaaaag gaagagtatg agtattcaac  10740
atttccgtgt cgcccttatt cccttttttg cggcattttg ccttcctgtt tttgctcacc  10800
cagaaacgct ggtgaaagta aaagatgctg aagatcagtt gggtgcacga gtgggttaca  10860
```

```
tcgaactgga tctcaacagc ggtaagatcc ttgagagttt tcgccccgaa gaacgttttc  10920
caatgatgag cacttttaaa gttctgctat gtggcgcggt attatcccgt gttgacgccg  10980
ggcaagagca actcggtcgc cgcatacact attctcagaa tgacttggtt gagtactcac  11040
cagtcacaga aaagcatctt acggatggca tgacagtaag agaattatgc agtgctgcca  11100
taaccatgag tgataacact gcggccaact tacttctgac aacgatcgga ggaccgaagg  11160
agctaaccgc ttttttgcac aacatggggg atcatgtaac tcgccttgat cgttgggaac  11220
cggagctgaa tgaagccata ccaaacgacg agcgtgacac cacgatgcct gcagcaatgg  11280
caacaacgtt gcgcaaacta ttaactggcg aactacttac tctagcttcc cggcaacaat  11340
taatagactg gatggaggcg gataaagttg caggaccact tctgcgctcg gcccttccgg  11400
ctggctggtt tattgctgat aaatctggag ccggtgagcg tgggtctcgc ggtatcattg  11460
cagcactggg gccagatggt aagccctccc gtatcgtagt tatctacacg acggggagtc  11520
aggcaactat ggatgaacga aatagacaga tcgctgagat aggtgcctca ctgattaagc  11580
attggtaact gtcagaccaa gtttactcat atatacttta gattgattta aaacttcatt  11640
tttaatttaa aaggatctag gtgaagatcc tttttgataa tctcatgacc aaaatccctt  11700
aacgtgagtt ttcgttccac tgagcgtcag accccgtaga aaagatcaaa ggatcttctt  11760
gagatccttt ttttctgcgc gtaatctgct gcttgcaaac aaaaaaacca ccgctaccag  11820
cggtggtttg tttgccggat caagagctac caactctttt tccgaaggta actggcttca  11880
gcagagcgca gataccaaat actgtccttc tagtgtagcc gtagttaggc caccacttca  11940
agaactctgt agcaccgcct acatacctcg ctctgctaat cctgttacca gtggctgctg  12000
ccagtggcga taagtcgtgt cttaccgggt tggactcaag acgatagtta ccggataagg  12060
cgcagcggtc gggctgaacg gggggttcgt gcacacagcc cagcttggag cgaacgacct  12120
acaccgaact gagataccta cagcgtgagc tatgagaaag cgccacgctt cccgaaggga  12180
gaaaggcgga caggtatccg gtaagcggca gggtcggaac aggagagcgc acgagggagc  12240
ttccaggggg aaacgcctgg tatctttata gtcctgtcgg gtttcgccac ctctgacttg  12300
agcgtcgatt tttgtgatgc tcgtcagggg ggcggagcct atggaaaaac gccagcaacg  12360
cggccttttt acggttcctg gccttttgct ggccttttgc tcacatgttc tttcctgcgt  12420
tatcccctga ttctgtggat aaccgtatta ccgcctttga gtgagctgat accgctcgcc  12480
gcagccgaac gaccgagcgc agcgagtcag tgagcgagga agcggaagag cgcctgatgc  12540
ggtattttct ccttacgcat ctgtgcggta tttcacaccg catatggtgc actctcagta  12600
caatctgctc tgatgccgca tagttaagcc ag                                12632
```

```
<210> SEQ ID NO 60
<211> LENGTH: 1065
<212> TYPE: DNA
<213> ORGANISM: Artificial Sequence
<220> FEATURE:
<223> OTHER INFORMATION: Description of Artificial Sequence: Synthetic
      Sc MA17-RM2-G19H33 ORF polynucleotide

<400> SEQUENCE: 60
```

```
atggccaata ccaaatataa caaagagttc ctgctgtacc tggccggctt tgtggacggt     60
gacggtagca tcatcgctca gattaaacca aaccagacgc ataagtttaa acatcagcta    120
agcttgacct ttcgtgtgac tcaaaagacc cagcgccgtt ggtttctgga caaactagtg    180
gatgaaattg gcgttggtta cgtatatgat tctggaaccg tttccaatta caatttaagc    240
gaaatcaagc cgctgcacaa cttcctgact caactgcagc cgtttctgaa actgaaacag    300
```

```
aaacaggcaa acctggttct gaaaattatc gaacagctgc cgtctgcaaa agaatccccg    360
gacaaattcc tggaagtttg tacctgggtg gatcagattg cagctctgaa cgattctaag    420
acgcgtaaaa ccacttctga aaccgttcgt gctgtgctgg acagcctgag cgagaagaag    480
aaatcctccc cggcggccgg tggatctgat aagtataatc aggctctgtc taaatacaac    540
caagcactgt ccaagtacaa tcaggccctg tctggtggag gcggttccaa caaagagttc    600
ctgctgtatc ttgctggatt tgtggattct gatggctcca tcattgctca gataaaacca    660
aatcaatctc acaagttcaa acaccagctc tccttggcct ttcaagtcac tcagaagaca    720
caaagaaggt ggttcttgga caaattggtt gatgagattg gtgtgggcta tgtcagagac    780
agaggctctg tgtcagacta catcctgtct gaaattaagc ctcttcataa ctttctcacc    840
caactgcaac ccttcttgaa gctcaaacag aagcaagcaa atctggtttt gaaaatcatc    900
tggagactgc catctgccaa ggagtcccct gacaagtttc ttgaagtgtg tacttgggtg    960
gatcagattg ctgccttgaa tgactccaag accagaaaaa ccacctctga gactgtgagg   1020
gcagttctgg atagcctctc tgagaagaaa aagtcctctc cttag                   1065
```

```
<210> SEQ ID NO 61
<211> LENGTH: 6089
<212> TYPE: DNA
<213> ORGANISM: Artificial Sequence
<220> FEATURE:
<223> OTHER INFORMATION: Description of Artificial Sequence: Synthetic
      Sc HPRT expression vector polynucleotide

<400> SEQUENCE: 61
```

```
atggccaata ccaaatataa caaagagttc ctgctgtacc tggccggctt tgtggacggt     60
gacggtagca tcatcgctca gattaaacca aaccagacgc ataagtttaa acatcagcta    120
agcttgacct ttcgtgtgac tcaaaagacc cagcgccgtt ggtttctgga caaactagtg    180
gatgaaattg gcgttggtta cgtatatgat tctggaaccg tttccaatta caatttaagc    240
gaaatcaagc cgctgcacaa cttcctgact caactgcagc cgtttctgaa actgaaacag    300
aaacaggcaa acctggttct gaaaattatc gaacagctgc cgtctgcaaa agaatccccg    360
gacaaattcc tggaagtttg tacctgggtg gatcagattg cagctctgaa cgattctaag    420
acgcgtaaaa ccacttctga aaccgttcgt gctgtgctgg acagcctgag cgagaagaag    480
aaatcctccc cggcggccgg tggatctgat aagtataatc aggctctgtc taaatacaac    540
caagcactgt ccaagtacaa tcaggccctg tctggtggag gcggttccaa caaagagttc    600
ctgctgtatc ttgctggatt tgtggattct gatggctcca tcattgctca gataaaacca    660
aatcaatctc acaagttcaa acaccagctc tccttggcct ttcaagtcac tcagaagaca    720
caaagaaggt ggttcttgga caaattggtt gatgagattg gtgtgggcta tgtcagagac    780
agaggctctg tgtcagacta catcctgtct gaaattaagc ctcttcataa ctttctcacc    840
caactgcaac ccttcttgaa gctcaaacag aagcaagcaa atctggtttt gaaaatcatc    900
tggagactgc catctgccaa ggagtcccct gacaagtttc ttgaagtgtg tacttgggtg    960
gatcagattg ctgccttgaa tgactccaag accagaaaaa ccacctctga gactgtgagg   1020
gcagttctgg atagcctctc tgagaagaaa aagtcctctc cttagtctag agggcccgcg   1080
gttcgaaggt aagcctatcc ctaaccctct cctcggtctc gattctacgc gtaccggtta   1140
gtaatgagtt taaacggggg aggctaactg aaacacggaa ggagacaata ccggaaggaa   1200
cccgcgctat gacggcaata aaaagacaga ataaaacgca cgggtgttgg gtcgtttgtt   1260
```

```
cataaacgcg gggttcggtc ccagggctgg cactctgtcg ataccccacc gagaccccat   1320

tggggccaat acgcccgcgt ttcttccttt tccccacccc accccccaag ttcgggtgaa   1380

ggcccagggc tcgcagccaa cgtcggggcg gcaggccctg ccatagcaga tctgcgcagc   1440

tggggctcta gggggtatcc ccacgcgccc tgtagcggcg cattaagcgc ggcgggtgtg   1500

gtggttacgc gcagcgtgac cgctacactt gccagcgccc tagcgcccgc tcctttcgct   1560

ttcttccctt cctttctcgc cacgttcgcc ggctttcccc gtcaagctct aaatcggggc   1620

atccctttag ggttccgatt tagtgcttta cggcacctcg accccaaaaa acttgattag   1680

ggtgatggtt cacgtagtgg gccatcgccc tgatagacgg tttttcgccc tttgacgttg   1740

gagtccacgt tctttaatag tggactcttg ttccaaactg gaacaacact caaccctatc   1800

tcggtctatt cttttgattt ataagggatt ttggggattt cggcctattg gttaaaaaat   1860

gagctgattt aacaaaaatt taacgcgaat taattctgtg gaatgtgtgt cagttagggt   1920

gtggaaagtc cccaggctcc ccagcaggca gaagtatgca aagcatgcat ctcaattagt   1980

cagcaaccag gtgtggaaag tccccaggct ccccagcagg cagaagtatg caaagcatgc   2040

atctcaatta gtcagcaacc atagtcccgc ccctaactcc gcccatcccg cccctaactc   2100

cgcccagttc cgcccattct ccgccccatg gctgactaat tttttttatt tatgcagagg   2160

ccgaggccgc ctctgcctct gagctattcc agaagtagtg aggaggcttt tttggaggcc   2220

taggcttttg caaaaagctc ccgggagctt gtatatccat tttcggatct gatcagcacg   2280

tgttgacaat taatcatcgg catagtatat cggcatagta taatacgaca aggtgaggaa   2340

ctaaaccatg gccaagcctt tgtctcaaga agaatccacc ctcattgaaa gagcaacggc   2400

tacaatcaac agcatcccca tctctgaaga ctacagcgtc gccagcgcag ctctctctag   2460

cgacggccgc atcttcactg gtgtcaatgt atatcatttt actgggggac cttgtgcaga   2520

actcgtggtg ctgggcactg ctgctgctgc ggcagctggc aacctgactt gtatcgtcgc   2580

gatcggaaat gagaacaggg gcatcttgag cccctgcgga cggtgccgac aggtgcttct   2640

cgatctgcat cctgggatca aagccatagt gaaggacagt gatggacagc cgacggcagt   2700

tgggattcgt gaattgctgc cctctggtta tgtgtgggag ggctaagcac ttcgtggccg   2760

aggagcagga ctgacacgtg ctacgagatt tcgattccac cgccgccttc tatgaaaggt   2820

tgggcttcgg aatcgttttc cgggacgccg gctggatgat cctccagcgc ggggatctca   2880

tgctggagtt cttcgcccac cccaacttgt ttattgcagc ttataatggt tacaaataaa   2940

gcaatagcat cacaaatttc acaaataaag catttttttc actgcattct agttgtggtt   3000

tgtccaaact catcaatgta tcttatcatg tctgtatacc gtcgacctct agctagagct   3060

tggcgtaatc atggtcatag ctgtttcctg tgtgaaattg ttatccgctc acaattccac   3120

acaacatacg agccggaagc ataaagtgta aagcctgggg tgcctaatga gtgagctaac   3180

tcacattaat tgcgttgcgc tcactgcccg ctttccagtc gggaaacctg tcgtgccagc   3240

tgcattaatg aatcggccaa cgcgcgggga gaggcggttt gcgtattggg cgctcttccg   3300

cttcctcgct cactgactcg ctgcgctcgg tcgttcggct gcggcgagcg gtatcagctc   3360

actcaaaggc ggtaatacgg ttatccacag aatcagggga taacgcagga aagaacatgt   3420

gagcaaaagg ccagcaaaag gccaggaacc gtaaaaaggc cgcgttgctg gcgtttttcc   3480

ataggctccg cccccctgac gagcatcaca aaaatcgacg ctcaagtcag aggtggcgaa   3540

acccgacagg actataaaga taccaggcgt ttccccctgg aagctccctc gtgcgctctc   3600

ctgttccgac cctgccgctt accggatacc tgtccgcctt tctcccttcg ggaagcgtgg   3660
```

-continued

```
cgctttctca tagctcacgc tgtaggtatc tcagttcggt gtaggtcgtt cgctccaagc   3720

tgggctgtgt gcacgaaccc cccgttcagc ccgaccgctg cgccttatcc ggtaactatc   3780

gtcttgagtc caacccggta agacacgact tatcgccact ggcagcagcc actggtaaca   3840

ggattagcag agcgaggtat gtaggcggtg ctacagagtt cttgaagtgg tggcctaact   3900

acggctacac tagaagaaca gtatttggta tctgcgctct gctgaagcca gttaccttcg   3960

gaaaaagagt tggtagctct tgatccggca aacaaaccac cgctggtagc ggtttttttg   4020

tttgcaagca gcagattacg cgcagaaaaa aaggatctca agaagatcct ttgatctttt   4080

ctacggggtc tgacgctcag tggaacgaaa actcacgtta agggattttg gtcatgagat   4140

tatcaaaaag gatcttcacc tagatccttt taaattaaaa atgaagtttt aaatcaatct   4200

aaagtatata tgagtaaact tggtctgaca gttaccaatg cttaatcagt gaggcaccta   4260

tctcagcgat ctgtctattt cgttcatcca tagttgcctg actccccgtc gtgtagataa   4320

ctacgatacg ggagggctta ccatctggcc ccagtgctgc aatgataccg cgagacccac   4380

gctcaccggc tccagattta tcagcaataa accagccagc cggaagggcc gagcgcagaa   4440

gtggtcctgc aactttatcc gcctccatcc agtctattaa ttgttgccgg gaagctagag   4500

taagtagttc gccagttaat agtttgcgca acgttgttgc cattgctaca ggcatcgtgg   4560

tgtcacgctc gtcgtttggt atggcttcat tcagctccgg ttcccaacga tcaaggcgag   4620

ttacatgatc ccccatgttg tgcaaaaaag cggttagctc cttcggtcct ccgatcgttg   4680

tcagaagtaa gttggccgca gtgttatcac tcatggttat ggcagcactg cataattctc   4740

ttactgtcat gccatccgta agatgctttt ctgtgactgg tgagtactca accaagtcat   4800

tctgagaata gtgtatgcgg cgaccgagtt gctcttgccc ggcgtcaata cgggataata   4860

ccgcgccaca tagcagaact ttaaaagtgc tcatcattgg aaaacgttct tcggggcgaa   4920

aactctcaag gatcttaccg ctgttgagat ccagttcgat gtaacccact cgtgcaccca   4980

actgatcttc agcatctttt actttcacca gcgtttctgg gtgagcaaaa acaggaaggc   5040

aaaatgccgc aaaaaaggga ataagggcga cacggaaatg ttgaatactc atactcttcc   5100

tttttcaata ttattgaagc atttatcagg gttattgtct catgagcgga tacatatttg   5160

aatgtattta gaaaaataaa caaatagggg ttccgcgcac atttccccga aaagtgccac   5220

ctgacgtcga cggatcggga gatctcccga tcccctatgg tgcactctca gtacaatctg   5280

ctctgatgcc gcatagttaa gccagtatct gctccctgct tgtgtgttgg aggtcgctga   5340

gtagtgcgcg agcaaaattt aagctacaac aaggcaaggc ttgaccgaca attgcatgaa   5400

gaatctgctt agggttaggc gttttgcgct gcttcgcgat gtacgggcca gatatacgcg   5460

ttgacattga ttattgacta gttattaata gtaatcaatt acggggtcat tagttcatag   5520

cccatatatg gagttccgcg ttacataact tacggtaaat ggcccgcctg gctgaccgcc   5580

caacgacccc cgcccattga cgtcaataat gacgtatgtt cccatagtaa cgccaatagg   5640

gactttccat tgacgtcaat gggtggagta tttacggtaa actgcccact tggcagtaca   5700

tcaagtgtat catatgccaa gtacgccccc tattgacgtc aatgacggta aatggcccgc   5760

ctggcattat gcccagtaca tgaccttatg ggactttcct acttggcagt acatctacgt   5820

attagtcatc gctattacca tggtgatgcg gttttggcag tacatcaatg ggcgtggata   5880

gcggtttgac tcacggggat ttccaagtct ccaccccatt gacgtcaatg ggagtttgtt   5940

ttggcaccaa aatcaacggg actttccaaa atgtcgtaac aactccgccc cattgacgca   6000

aatgggcggt aggcgtgtac ggtgggaggt ctatataagc agagctctct ggctaactag   6060
```

```
agaacccact gcttactggc ttatcgacc                                   6089


<210> SEQ ID NO 62
<211> LENGTH: 5515
<212> TYPE: DNA
<213> ORGANISM: Artificial Sequence
<220> FEATURE:
<223> OTHER INFORMATION: Description of Artificial Sequence: Synthetic
      CD4 KI construct

<400> SEQUENCE: 62

agccccttcg cctcgtgctt gagttgaggc ctggcttggg cgctggggcc gccgcgtgcg     60

aatctggtgg caccttcgcg cctgtctcgc tgctttcgat aagtctctag ccatttaaaa    120

tttttgatga cctgctgcga cgcttttttt ctggcaagat agtcttgtaa atgcgggcca    180

agatcgatct gcacactggt atttcggttt ttggggccgc gggcggcgac ggggcccgtg    240

cgtcccagcg cacatgttcg gcgaggcggg gcctgcgagc gcggccaccg agaatcggac    300

gggggtagtc tcaagctggc cggcctgctc tggtgcctgg cctcgcgccg ccgtgtatcg    360

ccccgccctg ggcggcaagg ctggcccggt cggcaccagt tgcgtgagcg gaaagatggc    420

cgcttcccgg ccctgctgca gggagctcaa aatggaggac gcggcgctcg ggagagcggg    480

cgggtgagtc acccacacaa aggaaaaggg cctttccgtc ctcagccgtc gcttcatgtg    540

actccacgga gtaccgggcg ccgtccaggc acctcgatta gttctcgagc ttttggagta    600

cgtcgtcttt aggttggggg gaggggtttt atgcgatgga gtttccccac actgagtggg    660

tggagactga agttaggcca gcttggcact tgatgtaatt ctccttggaa tttgcccttt    720

ttgagtttgg atcttggttc attctcaagc ctcagacagt ggttcaaagt ttttttcttc    780

catttcaggt gtcgtggaat tggctagagc ttgcatgcct gcaggtcggc cgccacgacc    840

ggtgccgcca ccatcccctg acccacgccc ctgacccctc acaaggagac gaccttccat    900

gaccgagtac aagcccacgg tgcgcctcgc cacccgcgac gacgtccccc gggccgtacg    960

caccctcgcc gccgcgttcg ccgactaccc cgccacgcgc cacaccgtcg acccggaccg   1020

ccacatcgag cgggtcaccg agctgcaaga actcttcctc acgcgcgtcg ggctcgacat   1080

cggcaaggtg tgggtcgcgg acgacggcgc cgcggtggcg gtctggacca cgccggagag   1140

cgtcgaagcg gggggcggtgt tcgccgagat cggcccgcgc atggccgagt tgagcggttc  1200

ccggctggcc gcgcagcaac agatggaagg cctcctggcg ccgcaccggc ccaaggagcc   1260

cgcgtggttc ctggccaccg tcggcgtctc gcccgaccac cagggcaagg gtctgggcag   1320

cgccgtcgtg ctccccggag tggaggcggc cgagcgcgcc ggggtgcccg ccttcctgga   1380

gacctccgcg ccccgcaacc tccccttcta cgagcggctc ggcttcaccg tcaccgccga   1440

cgtcgaggtg cccgaaggac cgcgcacctg gtgcatgacc cgcaagcccg gtgcctgacg   1500

cccgccccac gacccgcagc gcccgaccga aaggagcgca cgaccccatg gctccgaccg   1560

aagccgaccc gggcggcccc gccgaccccg cacccgcccc cgaggcccac cgactctaga   1620

ggatcataat cagccatacc acatttgtag aggttttact tgctttaaaa aacctcccac   1680

acctcccct gaacctgaaa cataaaatga atgcaattgt tgttgttaac ttgtttattg   1740

cagcttataa tggttacaaa taaagcaata gcatcacaaa tttcacaaat aaagcatttt   1800

tttcactgca ttctagttgt ggtttgtcca aactcatcaa tgtatcttat catgtctgga   1860

tcctagcgtt taaacttaag cttggtaccg agctcggatc cactagcgat gtacgggcca   1920

gatatacgcg ttgacattga ttattgacta gttattaata gtaatcaatt acggggtcat   1980

tagttcatag cccatatatg gagttccgcg ttacataact tacggtaaat ggcccgcctg   2040
```

```
gctgaccgcc caacgacccc cgcccattga cgtcaataat gacgtatgtt cccatagtaa   2100
cgccaatagg gactttccat tgacgtcaat gggtggagta tttacggtaa actgcccact   2160
tggcagtaca tcaagtgtat catatgccaa gtacgccccc tattgacgtc aatgacggta   2220
aatggcccgc ctggcattat gcccagtaca tgaccttatg ggactttcct acttggcagt   2280
acatctacgt attagtcatc gctattacca tggtgatgcg gttttggcag tacatcaatg   2340
ggcgtggata gcggtttgac tcacggggat ttccaagtct ccaccccatt gacgtcaatg   2400
ggagtttgtt ttggcaccaa aatcaacggg actttccaaa atgtcgtaac aactccgccc   2460
cattgacgca aatgggcggt aggcgtgtac ggtgggaggt ctatataagc agagctctct   2520
ggctaactag agaacccact gcttactggc ttatcgaaat taatacgact cactataggg   2580
agacccaagc tggctagcgc tgatatggcg tactaccatc accatcacca tcactctaga   2640
tcagaaggag ttcgaaccaa ccggggagtc ccttttaggc acttgcttct ggtgctgcaa   2700
ctggcgctcc tcccagcagc cactcaggga aagaaagtgg tgctgggcaa aaaaggggat   2760
acagtggaac tgacctgtac agcttcccag aagaagagca tacaattcca ctggaaaaac   2820
tccaaccaga taaagattct gggaaatcag ggctccttct taactaaagg tccatccaag   2880
ctgaatgatc gcgctgactc aagaagaagc ctttgggacc aaggaaactt cccccctgatc   2940
atcaagaatc ttaagataga agactcagat acttacatct gtgaagtgga ggaccagaag   3000
gaggaggtgc aattgctagt gttcggattg actgccaact ctgacaccca cctgcttcag   3060
gggcagagcc tgaccctgac cttggagagc ccccctggta gtagcccctc agtgcaatgt   3120
aggagtccaa ggggtaaaaa catacagggg gggaagaccc tctccgtgtc tcagctggag   3180
ctccaggata gtggcacctg gacatgcact gtcttgcaga accagaagaa ggtggagttc   3240
aaaatagaca tcgtggtgct agctttccag aaggcctcca gcatagtcta taagaaagag   3300
ggggaacagg tggagttctc cttcccactc gcctttacag ttgaaaagct gacgggcagt   3360
ggcgagctgt ggtggcaggc ggagagggct tcctcctcca agtcttggat cacctttgac   3420
ctgaagaaca aggaagtgtc tgtaaaacgg gttacccagg accctaagct ccagatgggc   3480
aagaagctcc cgctccacct caccctgccc caggccttgc ctcagtatgc tggctctgga   3540
aacctcaccc tggcccttga agcgaaaaca ggaaagttgc atcaggaagt gaacctggtg   3600
gtgatgagag ccactcagct ccagaaaaat ttgacctgtg aggtgtgggg acccacctcc   3660
cctaagctga tgctgagctt gaaactggag aacaaggagg caaaggtctc gaagcgggag   3720
aaggcggtgt gggtgctgaa ccctgaggcg gggatgtggc agtgtctgct gagtgactcg   3780
ggacaggtcc tgctggaatc caacatcaag gttctgccca catggtccac cccggtgcag   3840
ccaatggccc tgattgtgct gggggggcgtc gccggcctcc tgcttttcat tgggctaggc   3900
atcttcttct gtgtcaggtg ccggcaccga aggcgccaag cagagcggat gtctcagatc   3960
aagagactcc tcagtgagaa gaagacctgc cagtgccctc accggtttca gaagacatgt   4020
agatcgatcg cgagcggccg ctcgagtcta gagggcccgt ttaaacccgc tgatcagcct   4080
cgactgtgcc ttctagttgc cagccatctg ttgtttgccc ctcccccgtg ccttccttga   4140
ccctggaagg tgccactccc actgtccttt cctaataaaa tgaggaaatt gcatcgcatt   4200
gtctgagtag gtgtcattct attctggggg gtggggtggg gcaggacagc aagggggagg   4260
attgggaaga caatagcagg catgctgggg atgcggtggg ctctatggct tctgaggcgg   4320
aaagaaccag ctggggctct agggggtatc cccacgcgcc ctgtagcggc gcattaagcg   4380
cggcgggtgt ggtggttacg cgcagcgtga ccgctacact tgccagcgcc ctagcgcccg   4440
```

```
ctcctttcgc tttcttccct tcctttctcg ccacgttcgc ctaccgtcga atcaccggta   4500

accttataag ggattttgcc gatttcggcc tattggttaa aaaatgagct gatttaacaa   4560

aaatttaacg cgaattaatt ctgtggaatg tgtgtcagtt agggtgtgga aagtccccag   4620

gctccccagc aggcagaagt atgcaaagca tgcatctcaa ttagtcagca accaggtgtg   4680

gaaagtcccc aggctcccca gcaggcagaa gtatgcaaag catgcatctc aattagtcag   4740

caaccatagt cccgccccta actccgccca tcccgcccct aactccgccc agttccgccc   4800

attctccgcc ccatggctga ctaatttttt ttatttatgc agaggccgag gccgcctctg   4860

cctctgagct attccagaag tagtgaggag gcttttttgg aggcctaggc ttttgcaaaa   4920

agctcccggg agcttgtata tccattttcg gatctgatca agagacagga tgaggatcgt   4980

ttcgcatgat tgaacaagat ggattgcacg caggttctcc ggccgcttgg gtggagaggc   5040

tattcggcta tgactgggca caacagacaa tcggctgctc tgatgccgcc gtgttccggc   5100

tgtcagcgca ggggcgcccg gttctttttg tcaagaccga cctgtccggt gccctgaatg   5160

aactgcagga cgaggcagcg cggctatcgt ggctggccac gacgggcgtt ccttgcgcag   5220

ctgtgctcga cgttgtcact gaagcgggaa gggactggct gctattgggc gaagtgccgg   5280

ggcaggatct cctgtcatct caccttgctc ctgccgagaa agtatccatc atggctgatg   5340

caatgcggcg gctgcatacg cttgatccgg ctacctgccc attcgaccac caagcgaaac   5400

atcgcatcga gcgagcacgt actcggatgg aagccggtct tgtcgatcag gatgatctgg   5460

acgaagagca tcaggggctc gcgccagccg aactgttcgc caggctcaag gcgcg        5515
```

<210> SEQ ID NO 63
<211> LENGTH: 5370
<212> TYPE: DNA
<213> ORGANISM: Artificial Sequence
<220> FEATURE:
<223> OTHER INFORMATION: Description of Artificial Sequence: Synthetic SSTR2 KI construct

<400> SEQUENCE: 63

```
agccccttcg cctcgtgctt gagttgaggc ctggcctggg cgctggggcc gccgcgtgcg     60

aatctggtgg caccttcgcg cctgtctcgc tgctttcgat aagtctctag ccatttaaaa    120

tttttgatga cctgctgcga cgcttttttt ctggcaagat agtcttgtaa atgcgggcca    180

agatcgatct gcacactggt atttcggttt ttggggccgc gggcggcgac ggggcccgtg    240

cgtcccagcg cacatgttcg gcgaggcggg gcctgcgagc gcggccaccg agaatcggac    300

gggggtagtc tcaagctggc cggcctgctc tggtgcctgg cctcgcgccg ccgtgtatcg    360

ccccgccctg ggcggcaagg ctggcccggt cggcaccagt tgcgtgagcg gaaagatggc    420

cgcttcccgg ccctgctgca gggagctcaa aatggaggac gcggcgctcg ggagagcggg    480

cgggtgagtc acccacacaa aggaaaaggg cctttccgtc ctcagccgtc gcttcatgtg    540

actccacgga gtaccgggcg ccgtccaggc acctcgatta gttctcgagc ttttggagta    600

cgtcgtcttt aggttggggg gaggggtttt atgcgatgga gtttccccac actgagtggg    660

tggagactga agttaggcca gcttggcact tgatgtaatt ctccttggaa tttgcccttt    720

ttgagtttgg atcttggttc attctcaagc ctcagacagt ggttcaaagt ttttttcttc    780

catttcaggt gtcgtgagga attggctaag cttgcatgcc tgcaggtcgg ccgccacgac    840

cggtgccgcc accatcccct gacccacgcc cctgacccct cacaaggaga cgaccttcca    900

tgaccgagta caagcccacg gtgcgcctcg ccacccgcga cgacgtcccc cgggccgtac    960
```

-continued

```
gcaccctcgc cgccgcgttc gccgactacc ccgccacgcg ccacaccgtc gacccggacc   1020

gccacatcga gcgggtcacc gagctgcaag aactcttcct cacgcgcgtc gggctcgaca   1080

tcggcaaggt gtgggtcgcg gacgacggcg ccgcggtggc ggtctggacc acgccggaga   1140

gcgtcgaagc gggggcggtg ttcgccgaga tcggcccgcg catggccgag ttgagcggtt   1200

cccggctggc cgcgcagcaa cagatggaag gcctcctggc gccgcaccgg cccaaggagc   1260

ccgcgtggtt cctggccacc gtcggcgtct cgcccgacca ccagggcaag ggtctgggca   1320

gcgccgtcgt gctccccgga gtggaggcgg ccgagcgcgc cggggtgccc gccttcctgg   1380

agacctccgc gccccgcaac ctccccttct acgagcggct cggcttcacc gtcaccgccg   1440

acgtcgaggt gcccgaagga ccgcgcacct ggtgcatgac ccgcaagccc ggtgcctgac   1500

gcccgcccca cgacccgcag cgcccgaccg aaaggagcgc acgaccccat ggctccgacc   1560

gaagccaccc ggggcggccc cgccgacccc gcacccgccc ccgaggccca ccgactctag   1620

aggatcataa tcagccatac cacatttgta gaggttttac ttgctttaaa aaacctccca   1680

cacctccccc tgaacctgaa acataaaatg aatgcaattg ttgttgttaa cttgtttatt   1740

gcagcttata atggttacaa ataaagcaat agcatcacaa atttcacaaa taaagcattt   1800

ttttcactgc attctagttg tggtttgtcc aaactcatca atgtatctta tcatgtctgg   1860

atctagcgtt taaacttaag cttggtaccg agctcggatc cactagcgat gtacgggcca   1920

gatatacgcg ttgacattga ttattgacta gttattaata gtaatcaatt acggggtcat   1980

tagttcatag cccatatatg gagttccgcg ttacataact tacggtaaat ggcccgcctg   2040

gctgaccgcc caacgacccc cgcccattga cgtcaataat gacgtatgtt cccatagtaa   2100

cgccaatagg gactttccat tgacgtcaat gggtggagta tttacggtaa actgcccact   2160

tggcagtaca tcaagtgtat catatgccaa gtacgccccc tattgacgtc aatgacggta   2220

aatggcccgc ctggcattat gcccagtaca tgaccttatg ggactttcct acttggcagt   2280

acatctacgt attagtcatc gctattacca tggtgatgcg gttttggcag tacatcaatg   2340

ggcgtggata gcggtttgac tcacggggat ttccaagtct ccaccccatt gacgtcaatg   2400

ggagtttgtt ttggcaccaa aatcaacggg actttccaaa atgtcgtaac aactccgccc   2460

cattgacgca aatgggcggt aggcgtgtac ggtgggaggt ctatataagc agagctctct   2520

ggctaactag agaacccact gcttactggc ttatcgaaat taatacgact cactataggg   2580

agacccaagc tggctagcac catggacatg gcggatgagc cactcaatgg aagccacaca   2640

tggctatcca ttccatttga cctcaatggc tctgtggtgt caaccaacac ctcaaaccag   2700

acagagccgt actatgacct gacaagcaat gcagtcctca cattcatcta ttttgtggtc   2760

tgcatcattg ggttgtgtgg caacacactt gtcatttatg tcatcctccg ctatgccaag   2820

atgaagacca tcaccaacat ttacatcctc aacctggcca tcgcagatga gctcttcatg   2880

ctgggtctgc ctttcttggc tatgcaggtg gctctggtcc actggccctt tggcaaggcc   2940

atttgccggg tggtcatgac tgtggatggc atcaatcagt tcaccagcat cttctgcctg   3000

acagtcatga gcatcgaccg atacctggct gtggtccacc ccatcaagtc ggccaagtgg   3060

aggagacccc ggacggccaa gatgatcacc atggctgtgt ggggagtctc tctgctggtc   3120

atcttgccca tcatgatata tgctgggctc cggagcaacc agtgggggag aagcagctgc   3180

accatcaact ggccaggtga atctggggct tggtacacag ggttcatcat ctacactttc   3240

attctggggt tcctggtacc cctcaccatc atctgtcttt gctacctgtt cattatcatc   3300

aaggtgaagt cctctggaat ccgagtgggc tcctctaaga ggaagaagtc tgagaagaag   3360
```

```
gtcacccgaa tggtgtccat cgtggtggct gtcttcatct tctgctggct tcccttctac   3420

atattcaacg tttcttccgt ctccatggcc atcagcccca ccccagccct taaaggcatg   3480

tttgactttg tggtggtcct cacctatgct aacagctgtg ccaaccctat cctatatgcc   3540

ttcttgtctg acaacttcaa gaagagcttc cagaatgtcc tctgcttggt caaggtgagc   3600

ggcacagatg atggggagcg gagtgacagt aagcaggaca aatcccggct gaatgagacc   3660

acggagaccc agaggaccct cctcaatgga gacctccaaa ccagtatctc aagcttcgaa   3720

ttgggaggtg gcggtagcgg aggtggcggt agcctcgagg attcactggc cgtcgtttta   3780

caacgtcgtg actgggaaaa ccctggcgtt acccaactta atcgccttgc agcacgtccc   3840

cctttcgcca gctggcgtaa tagcgaagag gcccgcaccg atcgctgagc ggccgctcga   3900

gtctagaggg cccgtttaaa cccgctgatc agcctcgact gtgccttcta gttgccagcc   3960

atctgttgtt tgcccctccc ccgtgccttc cttgaccctg gaaggtgcca ctcccactgt   4020

cctttcctaa taaaatgagg aaattgcatc gcattgtctg agtaggtgtc attctattct   4080

ggggggtggg gtggggcagg acagcaaggg ggaggattgg gaagacaata gcaggcatgc   4140

tggggatgcg gtgggctcta tggcttctga ggcggaaaga accagctggg gctctagggg   4200

gtatccccac gcgccctgta gcggcgcatt aagcgcggcg ggtgtggtgg ttacgcgcag   4260

cgtgaccgct acacttgcca gcgccctagc gcccgctcct ttcgctttct tcccttcctt   4320

tctcgccacg ttcgcctacc gtcgaatcac cggtaacctt ataagggatt ttgccgattt   4380

cggcctattg gttaaaaaat gagctgattt aacaaaaatt taacgcgaat taattctgtg   4440

gaatgtgtgt cagttagggt gtggaaagtc cccaggctcc ccagcaggca gaagtatgca   4500

aagcatgcat ctcaattagt cagcaaccag gtgtggaaag tccccaggct ccccagcagg   4560

cagaagtatg caaagcatgc atctcaatta gtcagcaacc atagtcccgc ccctaactcc   4620

gcccatcccg cccctaactc cgcccagttc cgcccattct ccgccccatg gctgactaat   4680

ttttttatt tatgcagagg ccgaggccgc ctctgcctct gagctattcc agaagtagtg   4740

aggaggcttt tttggaggcc taggcttttg caaaaagctc ccgggagctt gtatatccat   4800

tttcggatct gatcaagaga caggatgagg atcgtttcgc atgattgaac aagatggatt   4860

gcacgcaggt tctccggccg cttgggtgga gaggctattc ggctatgact gggcacaaca   4920

gacaatcggc tgctctgatg ccgccgtgtt ccggctgtca gcgcaggggc gcccggttct   4980

ttttgtcaag accgacctgt ccggtgccct gaatgaactg caggacgagg cagcgcggct   5040

atcgtggctg gccacgacgg gcgttccttg cgcagctgtg ctcgacgttg tcactgaagc   5100

gggaagggac tggctgctat tgggcgaagt gccggggcag gatctcctgt catctcacct   5160

tgctcctgcc gagaaagtat ccatcatggc tgatgcaatg cggcggctgc atacgcttga   5220

tccggctacc tgcccattcg accaccaagc gaaacatcgc atcgagcgag cacgtactcg   5280

gatggaagcc ggtcttgtcg atcaggatga tctggacgaa gagcatcagg ggctcgcgcc   5340

agccgaactg ttcgccaggc tcaaggcgcg                                    5370
```

<210> SEQ ID NO 64
<211> LENGTH: 6789
<212> TYPE: DNA
<213> ORGANISM: Artificial Sequence
<220> FEATURE:
<223> OTHER INFORMATION: Description of Artificial Sequence: Synthetic hATX KI construct

<400> SEQUENCE: 64

```
agccccttcg cctcgtgctt gagttgaggc ctggcttggg cgctggggcc gccgcgtgcg     60
```

```
aatctggtgg caccttcgcg cctgtctcgc tgctttcgat aagtctctag ccatttaaaa    120
tttttgatga cctgctgcga cgcttttttt ctggcaagat agtcttgtaa atgcgggcca    180
agatcgatct gcacactggt atttcggttt ttggggccgc gggcggcgac ggggcccgtg    240
cgtcccagcg cacatgttcg gcgaggcggg gcctgcgagc gcggccaccg agaatcggac    300
gggggtagtc tcaagctggc cggcctgctc tggtgcctgg cctcgcgccg ccgtgtatcg    360
ccccgccctg ggcggcaagg ctggcccggt cggcaccagt tgcgtgagcg gaaagatggc    420
cgcttcccgg ccctgctgca gggagctcaa aatggaggac gcggcgctcg ggagagcggg    480
cgggtgagtc acccacacaa aggaaaaggg cctttccgtc ctcagccgtc gcttcatgtg    540
actccacgga gtaccgggcg ccgtccaggc acctcgatta gttctcgagc ttttggagta    600
cgtcgtcttt aggttggggg gaggggtttt atgcgatgga gtttccccac actgagtggg    660
tggagactga agttaggcca gcttggcact tgatgtaatt ctccttggaa tttgcccttt    720
ttgagtttgg atcttggttc attctcaagc ctcagacagt ggttcaaagt ttttttcttc    780
catttcaggt gtcgtggaat tggctagagc ttgcatgcct gcaggtcggc cgccacgacc    840
ggtgccgcca ccatcccctg acccacgccc ctgacccctc acaaggagac gaccttccat    900
gaccgagtac aagcccacgg tgcgcctcgc cacccgcgac gacgtccccc gggccgtacg    960
caccctcgcc gccgcgttcg ccgactaccc cgccacgcgc cacaccgtcg acccggaccg   1020
ccacatcgag cgggtcaccg agctgcaaga actcttcctc acgcgcgtcg ggctcgacat   1080
cggcaaggtg tgggtcgcgg acgacggcgc cgcggtggcg gtctggacca cgccggagag   1140
cgtcgaagcg ggggcggtgt tcgccgagat cggcccgcgc atggccgagt tgagcggttc   1200
ccggctggcc gcgcagcaac agatggaagg cctcctggcg ccgcaccggc ccaaggagcc   1260
cgcgtggttc ctggccaccg tcggcgtctc gcccgaccac cagggcaagg gtctgggcag   1320
cgccgtcgtg ctccccggag tggaggcggc cgagcgcgcc ggggtgcccg ccttcctgga   1380
gacctccgcg ccccgcaacc tccccttcta cgagcggctc ggcttcaccg tcaccgccga   1440
cgtcgaggtg cccgaaggac cgcgcacctg gtgcatgacc cgcaagcccg gtgcctgacg   1500
cccgccccac gacccgcagc gcccgaccga aaggagcgca cgaccccatg gctccgaccg   1560
aagccgaccc gggcggcccc gccgaccccg cacccgcccc cgaggcccac cgactctaga   1620
ggatcataat cagccatacc acatttgtag aggttttact tgctttaaaa aacctcccac   1680
acctcccoct gaacctgaaa cataaaatga atgcaattgt tgttgttaac ttgtttattg   1740
cagcttataa tggttacaaa taaagcaata gcatcacaaa tttcacaaat aaagcatttt   1800
tttcactgca ttctagttgt ggtttgtcca aactcatcaa tgtatcttat catgtctgga   1860
tcctagcgtt taaacttaag cttggtaccg agctcggatc cactagtaat ggttacaaat   1920
aaagcaatag catcacaaat ttcacaaata aagcattttt ttcactgcat tctagttgtg   1980
gtttgtccaa actcatcaat gtatcttatc atgtctgtac gatgtacggg ccagatatac   2040
gcgttgacat tgattattga ctagttatta atagtaatca attacggggt cattagttca   2100
tagcccatat atggagttcc gcgttacata acttacggta aatggcccgc ctggctgacc   2160
gcccaacgac ccccgcccat tgacgtcaat aatgacgtat gttcccatag taacgccaat   2220
agggactttc cattgacgtc aatgggtgga gtatttacgg taaactgccc acttggcagt   2280
acatcaagtg tatcatatgc caagtacgcc ccctattgac gtcaatgacg gtaaatggcc   2340
cgcctggcat tatgcccagt acatgacctt atgggacttt cctacttggc agtacatcta   2400
cgtattagtc atcgctatta ccatggtgat gcggttttgg cagtacatca atgggcgtgg   2460
```

```
atagcggttt gactcacggg gatttccaag tctccacccc attgacgtca atgggagttt   2520
gttttggcac caaaatcaac gggactttcc aaaatgtcgt aacaactccg ccccattgac   2580
gcaaatgggc ggtaggcgtg tacggtggga ggtctatata agcagagctc tctggctaac   2640
tagagaaccc actgcttact ggcttatcga aattaatacg actcactata gggagaccca   2700
agctggctag ccaccatggc aaggaggagc tcgttccagt cgtgtcagat aatatccctg   2760
ttcacttttg ccgttggagt caatatctgc ttaggattca ctgcacatcg aattaagaga   2820
gcagaaggat gggaggaagg tcctcctaca gtgctatcag actccccctg gaccaacatc   2880
tccggatctt gcaagggcag gtgctttgaa cttcaagagg ctggacctcc tgattgtcgc   2940
tgtgacaact tgtgtaagag ctataccagt tgctgccatg actttgatga gctgtgtttg   3000
aagacagccc gtggctggga gtgtactaag gacagatgtg gagaagtcag aaatgaagaa   3060
aatgcctgtc actgctcaga ggactgcttg gccaggggag actgctgtac caattaccaa   3120
gtggtttgca aaggagagtc gcattgggtt gatgatgact gtgaggaaat aaaggccgca   3180
gaatgccctg cagggtttgt tcgccctcca ttaatcatct tctccgtgga tggcttccgt   3240
gcatcataca tgaagaaagg cagcaaagtc atgcctaata ttgaaaaact aaggtcttgt   3300
ggcacacact ctccctacat gaggccggtg tacccaacta aaacctttcc taacttatac   3360
actttggcca ctgggctata tccagaatca catggaattg ttggcaattc aatgtatgat   3420
cctgtatttg atgccacttt tcatctgcga gggcgagaga aatttaatca tagatggtgg   3480
ggaggtcaac cgctatggat tacagccacc aagcaagggg tgaaagctgg aacattcttt   3540
tggtctgttg tcatccctca cgagcggaga atattaacca tattgcagtg gctcaccctg   3600
ccagatcatg agaggccttc ggtctatgcc ttctattctg agcaacctga tttctctgga   3660
cacaaatatg gccctttcgg ccctgagatg acaaatcctc tgagggaaat cgacaaaatt   3720
gtggggcaat taatggatgg actgaaacaa ctaaaactgc atcggtgtgt caacgtcatc   3780
tttgtcggag accatggaat ggaagatgtc acatgtgata gaactgagtt cttgagtaat   3840
tacctaacta atgtggatga tattacttta gtgcctggaa ctctaggaag aattcgatcc   3900
aaatttagca acaatgctaa atatgacccc aaagccatta ttgccaatct cacgtgtaaa   3960
aaaccagatc agcactttaa gccttacttg aaacagcacc ttcccaaacg tttgcactat   4020
gccaacaaca gaagaattga ggatatccat ttattggtgg aacgcagatg gcatgttgca   4080
aggaaacctt tggatgttta taagaaacca tcaggaaaat gcttttttcca gggagaccac   4140
ggatttgata acaaggtcaa cagcatgcag actgtttttg taggttatgg cccaacattt   4200
aagtacaaga ctaaagtgcc tccatttgaa aacattgaac tttacaatgt tatgtgtgat   4260
ctcctgggat tgaagccagc tcctaataat gggacccatg gaagtttgaa tcatctcctg   4320
cgcactaata ccttcaggcc aaccatgcca gaggaagtta ccagacccaa ttatccaggg   4380
attatgtacc ttcagtctga ttttgacctg ggctgcactt gtgatgataa ggtagagcca   4440
aagaacaagt tggatgaact caacaaacgg cttcatacaa aagggtctac agaagagaga   4500
cacctcctct atgggcgacc tgcagtgctt tatcggacta gatatgatat cttatatcac   4560
actgactttg aaagtggtta tagtgaaata ttcctaatgc cactctggac atcatatact   4620
gtttccaaac aggctgaggt ttccagcgtt cctgaccatc tgaccagttg cgtccggcct   4680
gatgtccgtg tttctccgag tttcagtcag aactgtttgg cctacaaaaa tgataagcag   4740
atgtcctacg gattcctctt tcctccttat ctgagctctt caccagaggc taaatatgat   4800
gcattccttg taaccaatat ggttccaatg tatcctgctt tcaaacgggt ctggaattat   4860
```

ttccaaaggg tattggtgaa gaaatatgct tcggaaagaa atggagttaa cgtgataagt 4920
ggaccaatct tcgactatga ctatgatggc ttacatgaca cagaagacaa aataaaacag 4980
tacgtggaag gcagttccat tcctgttcca actcactact acagcatcat caccagctgt 5040
ctggatttca ctcagcctgc cgacaagtgt gacggccctc tctctgtgtc ctccttcatc 5100
ctgcctcacc ggcctgacaa cgaggagagc tgcaatagct cagaggacga atcaaaatgg 5160
gtagaagaac tcatgaagat gcacacagct agggtgcgtg acattgaaca tctcaccagc 5220
ctggacttct tccgaaagac cagccgcagc tacccagaaa tcctgacact caagacatac 5280
ctgcatacat atgagagcga gatttaagcg gccgctcgag tctagagggc ccgtttaaac 5340
ccgctgatca gcctcgactg tgccttctag ttgccagcca tctgttgttt gcccctcccc 5400
cgtgccttcc ttgaccctgg aaggtgccac tcccactgtc ctttcctaat aaaatgagga 5460
aattgcatcg cattgtctga gtaggtgtca ttctattctg gggggtgggg tggggcagga 5520
cagcaagggg gaggattggg aagacaatag caggcatgct ggggatgcgg tgggctctat 5580
ggcttctgag gcggaaagaa ccagctgggg ctctaggggg tatccccacg cgccctgtag 5640
cggcgcatta agcgcggcgg gtgtggtggt tacgcgcagc gtgaccgcta cacttgccag 5700
cgccctagcg cccgctcctt tcgctttctt cccttccttt ctcgccacgt tcgcctaccg 5760
tcgaatcacc ggtaacctta taagggattt tgccgatttc ggcctattgg ttaaaaaatg 5820
agctgattta acaaaaattt aacgcgaatt aattctgtgg aatgtgtgtc agttagggtg 5880
tggaaagtcc ccaggctccc cagcaggcag aagtatgcaa agcatgcatc tcaattagtc 5940
agcaaccagg tgtggaaagt ccccaggctc cccagcaggc agaagtatgc aaagcatgca 6000
tctcaattag tcagcaacca tagtcccgcc cctaactccg cccatcccgc ccctaactcc 6060
gcccagttcc gcccattctc cgccccatgg ctgactaatt ttttttattt atgcagaggc 6120
cgaggccgcc tctgcctctg agctattcca gaagtagtga ggaggctttt ttggaggcct 6180
aggcttttgc aaaaagctcc cgggagcttg tatatccatt ttcggatctg atcaagagac 6240
aggatgagga tcgtttcgca tgattgaaca agatggattg cacgcaggtt ctccggccgc 6300
ttgggtggag aggctattcg gctatgactg ggcacaacag acaatcggct gctctgatgc 6360
cgccgtgttc cggctgtcag cgcaggggcg cccggttctt tttgtcaaga ccgacctgtc 6420
cggtgccctg aatgaactgc aggacgaggc agcgcggcta tcgtggctgg ccacgacggg 6480
cgttccttgc gcagctgtgc tcgacgttgt cactgaagcg ggaagggact ggctgctatt 6540
gggcgaagtg ccggggcagg atctcctgtc atctcacctt gctcctgccg agaaagtatc 6600
catcatggct gatgcaatgc ggcggctgca tacgcttgat ccggctacct gcccattcga 6660
ccaccaagcg aaacatcgca tcgagcgagc acgtactcgg atggaagccg gtcttgtcga 6720
tcaggatgat ctggacgaag agcatcaggg gctcgcgcca gccgaactgt tcgccaggct 6780
caaggcgcg 6789

<210> SEQ ID NO 65
<211> LENGTH: 5250
<212> TYPE: DNA
<213> ORGANISM: Artificial Sequence
<220> FEATURE:
<223> OTHER INFORMATION: Description of Artificial Sequence: Synthetic hMT1 KI construct

<400> SEQUENCE: 65
agccccttcg cctcgtgctt gagttgaggc ctggcttggg cgctggggcc gccgcgtgcg 60

-continued

```
aatctggtgg caccttcgcg cctgtctcgc tgctttcgat aagtctctag ccatttaaaa   120
tttttgatga cctgctgcga cgcttttttt ctggcaagat agtcttgtaa atgcgggcca   180
agatcgatct gcacactggt atttcggttt ttggggccgc gggcggcgac ggggcccgtg   240
cgtcccagcg cacatgttcg gcgaggcggg gcctgcgagc gcggccaccg agaatcggac   300
gggggtagtc tcaagctggc cggcctgctc tggtgcctgg cctcgcgccg ccgtgtatcg   360
ccccgccctg ggcggcaagg ctggcccggt cggcaccagt tgcgtgagcg gaaagatggc   420
cgcttcccgg ccctgctgca gggagctcaa aatggaggac gcggcgctcg ggagagcggg   480
cgggtgagtc acccacacaa aggaaaaggg cctttccgtc ctcagccgtc gcttcatgtg   540
actccacgga gtaccgggcg ccgtccaggc acctcgatta gttctcgagc ttttggagta   600
cgtcgtcttt aggttggggg gaggggtttt atgcgatgga gtttccccac actgagtggg   660
tggagactga agttaggcca gcttggcact tgatgtaatt ctccttggaa tttgcccttt   720
ttgagtttgg atcttggttc attctcaagc ctcagacagt ggttcaaagt ttttttcttc   780
catttcaggt gtcgtggaat tggctagagc ttgcatgcct gcaggtcggc cgccacgacc   840
ggtgccgcca ccatcccctg acccacgccc ctgacccctc acaaggagac gaccttccat   900
gaccgagtac aagcccacgg tgcgcctcgc cacccgcgac gacgtccccc gggccgtacg   960
caccctcgcc gccgcgttcg ccgactaccc cgccacgcgc cacaccgtcg acccggaccg  1020
ccacatcgag cgggtcaccg agctgcaaga actcttcctc acgcgcgtcg ggctcgacat  1080
cggcaaggtg tgggtcgcgg acgacggcgc cgcggtggcg gtctggacca cgccggagag  1140
cgtcgaagcg gggggggtgt tcgccgagat cggcccgcgc atggccgagt tgagcggttc  1200
ccggctggcc gcgcagcaac agatggaagg cctcctggcg ccgcaccggc ccaaggagcc  1260
cgcgtggttc ctggccaccg tcggcgtctc gcccgaccac cagggcaagg gtctgggcag  1320
cgccgtcgtg ctccccggag tggaggcggc cgagcgcgcc ggggtgcccg ccttcctgga  1380
gacctccgcg ccccgcaacc tccccttcta cgagcggctc ggcttcaccg tcaccgccga  1440
cgtcgaggtg cccgaaggac cgcgcacctg gtgcatgacc cgcaagcccg gtgcctgacg  1500
cccgccccac gacccgcagc gcccgaccga aaggagcgca cgaccccatg gctccgaccg  1560
aagccgaccc gggcggcccc gccgaccccg cacccgcccc cgaggcccac cgactctaga  1620
ggatcataat cagccatacc acatttgtag aggttttact tgctttaaaa aacctcccac  1680
acctcccct gaacctgaaa cataaaatga atgcaattgt tgttgttaac ttgtttattg  1740
cagcttataa tggttacaaa taaagcaata gcatcacaaa tttcacaaat aaagcatttt  1800
tttcactgca ttctagttgt ggtttgtcca aactcatcaa tgtatcttat catgtctgga  1860
tcctagcgtt taaacttaag cttggtaccg agctcggatc cactagtaat ggttacaaat  1920
aaagcaatag catcacaaat ttcacaaata aagcattttt ttcactgcat tctagttgtg  1980
gtttgtccaa actcatcaat gtatcttatc atgtctgtac gatgtacggg ccagatatac  2040
gcgttgacat tgattattga ctagttatta atagtaatca attacggggt cattagttca  2100
tagcccatat atggagttcc gcgttacata acttacggta aatggcccgc ctggctgacc  2160
gcccaacgac ccccgcccat tgacgtcaat aatgacgtat gttcccatag taacgccaat  2220
agggactttc cattgacgtc aatgggtgga gtatttacgg taaactgccc acttggcagt  2280
acatcaagtg tatcatatgc caagtacgcc ccctattgac gtcaatgacg gtaaatggcc  2340
cgcctggcat tatgcccagt acatgacctt atgggacttt cctacttggc agtacatcta  2400
cgtattagtc atcgctatta ccatggtgat gcggttttgg cagtacatca atgggcgtgg  2460
```

```
atagcggttt gactcacggg gatttccaag tctccacccc attgacgtca atgggagttt   2520
gttttggcac caaaatcaac gggactttcc aaaatgtcgt aacaactccg ccccattgac   2580
gcaaatgggc ggtaggcgtg tacggtggga ggtctatata agcagagctc tctggctaac   2640
tagagaaccc actgcttact ggcttatcga aattaatacg actcactata gggagaccca   2700
agctggctag ccaccatgca gggcaacggc agcgcgctgc ccaacgcctc ccagcccgtg   2760
ctccgcgggg acggcgcgcg gccctcgtgg ctggcgtccg ccctggcctg cgtcctcatc   2820
ttcaccatcg tggtggacat cctgggcaac ctcctggtca tcctgtcggt gtatcggaac   2880
aagaagctca ggaacgccgg caacatcttt gtggtgagct tagcggtggc agacctggtg   2940
gtggccattt atccgtaccc gttggtgctg atgtcgatat ttaacaacgg gtggaacctg   3000
ggctatctgc actgccaagt cagtgggttc ctgatgggcc tgagcgtcat cggctccata   3060
ttcaacatca ccggcatcgc catcaaccgc tactgctaca tctgccacag tctcaagtac   3120
gacaaactgt acagcagcaa gaactccctc tgctacgtgc tcctcatatg gctcctgacg   3180
ctggcggccg tcctgcccaa cctccgtgca gggactctcc agtacgaccc gaggatctac   3240
tcgtgcacct tcgcccagtc cgtcagctcc gcctacacca tcgccgtggt ggttttccac   3300
ttcctcgtcc ccatgatcat agtcatcttc tgttacctga gaatatggat cctggttctc   3360
caggtcagac agagggtgaa acctgaccgc aaacccaaac tgaaaccaca ggacttcagg   3420
aattttgtca ccatgtttgt ggtttttgtc ctttttgcca tttgctgggc tcctctgaac   3480
ttcattggcc tggccgtggc ctctgacccc gccagcatgg tgcctaggat cccagagtgg   3540
ctgtttgtgg ccagttacta catggcgtat ttcaacagct gcctcaatgc cattatatac   3600
gggctactga accaaaattt caggaaggaa tacaggagaa ttatagtctc gctctgtaca   3660
gccagggtgt tctttgtgga cagctctaac gacgtggccg atagggttaa atggaaaccg   3720
tctccactga tgaccaacaa taatgtagta aaggtggact ccgtttaagc ggccgctcga   3780
gtctagaggg cccgtttaaa cccgctgatc agcctcgact gtgccttcta gttgccagcc   3840
atctgttgtt tgcccctccc ccgtgccttc cttgaccctg gaaggtgcca ctcccactgt   3900
cctttcctaa taaaatgagg aaattgcatc gcattgtctg agtaggtgtc attctattct   3960
ggggggtggg gtggggcagg acagcaaggg ggaggattgg gaagacaata gcaggcatgc   4020
tggggatgcg gtgggctcta tggcttctga ggcggaaaga accagctggg gctctagggg   4080
gtatccccac gcgccctgta gcggcgcatt aagcgcggcg ggtgtggtgg ttacgcgcag   4140
cgtgaccgct acacttgcca gcgccctagc gcccgctcct ttcgctttct tcccttcctt   4200
tctcgccacg ttcgcctacc gtcgaatcac cggtaacctt ataagggatt ttgccgattt   4260
cggcctattg gttaaaaaat gagctgattt aacaaaaatt taacgcgaat taattctgtg   4320
gaatgtgtgt cagttagggt gtggaaagtc cccaggctcc ccagcaggca gaagtatgca   4380
aagcatgcat ctcaattagt cagcaaccag gtgtggaaag tccccaggct ccccagcagg   4440
cagaagtatg caaagcatgc atctcaatta gtcagcaacc atagtcccgc ccctaactcc   4500
gcccatcccg cccctaactc cgcccagttc cgcccattct ccgccccatg gctgactaat   4560
ttttttatt tatgcagagg ccgaggccgc ctctgcctct gagctattcc agaagtagtg   4620
aggaggcttt tttggaggcc taggcttttg caaaaagctc ccgggagctt gtatatccat   4680
tttcggatct gatcaagaga caggatgagg atcgtttcgc atgattgaac aagatggatt   4740
gcacgcaggt tctccggccg cttgggtgga gaggctattc ggctatgact gggcacaaca   4800
gacaatcggc tgctctgatg ccgccgtgtt ccggctgtca gcgcaggggc gcccggttct   4860
```

-continued

```
ttttgtcaag accgacctgt ccggtgccct gaatgaactg caggacgagg cagcgcggct   4920

atcgtggctg gccacgacgg gcgttccttg cgcagctgtg ctcgacgttg tcactgaagc   4980

gggaagggac tggctgctat tgggcgaagt gccggggcag gatctcctgt catctcacct   5040

tgctcctgcc gagaaagtat ccatcatggc tgatgcaatg cggcggctgc atacgcttga   5100

tccggctacc tgcccattcg accaccaagc gaaacatcgc atcgagcgag cacgtactcg   5160

gatggaagcc ggtcttgtcg atcaggatga tctggacgaa gagcatcagg ggctcgcgcc   5220

agccgaactg ttcgccaggc tcaaggcgcg                                  5250
```

<210> SEQ ID NO 66
<211> LENGTH: 5286
<212> TYPE: DNA
<213> ORGANISM: Artificial Sequence
<220> FEATURE:
<223> OTHER INFORMATION: Description of Artificial Sequence: Synthetic hMT2 KI construct

<400> SEQUENCE: 66

```
agccccttcg cctcgtgctt gagttgaggc ctggcttggg cgctggggcc gccgcgtgcg     60

aatctggtgg caccttcgcg cctgtctcgc tgctttcgat aagtctctag ccatttaaaa    120

tttttgatga cctgctgcga cgcttttttt ctggcaagat agtcttgtaa atgcgggcca    180

agatcgatct gcacactggt atttcggttt ttggggccgc gggcggcgac ggggcccgtg    240

cgtcccagcg cacatgttcg gcgaggcggg gcctgcgagc gcggccaccg agaatcggac    300

gggggtagtc tcaagctggc cggcctgctc tggtgcctgg cctcgcgccg ccgtgtatcg    360

ccccgccctg gcggcaaggc ctggcccggt cggcaccagt tgcgtgagcg gaaagatggc    420

cgcttcccgg ccctgctgca gggagctcaa aatggaggac gcggcgctcg ggagagcggg    480

cgggtgagtc acccacacaa aggaaaaggg cctttccgtc ctcagccgtc gcttcatgtg    540

actccacgga gtaccgggcg ccgtccaggc acctcgatta gttctcgagc ttttggagta    600

cgtcgtcttt aggttggggg gaggggtttt atgcgatgga gtttccccac actgagtggg    660

tggagactga agttaggcca gcttggcact tgatgtaatt ctccttggaa tttgcccttt    720

ttgagtttgg atcttggttc attctcaagc ctcagacagt ggttcaaagt ttttttcttc    780

catttcaggt gtcgtggaat tggctagagc ttgcatgcct gcaggtcggc cgccacgacc    840

ggtgccgcca ccatcccctg acccacgccc ctgacccctc acaaggagac gaccttccat    900

gaccgagtac aagcccacgg tgcgcctcgc cacccgcgac gacgtccccc gggccgtacg    960

caccctcgcc gccgcgttcg ccgactaccc cgccacgcgc cacaccgtcg acccggaccg   1020

ccacatcgag cgggtcaccg agctgcaaga actcttcctc acgcgcgtcg ggctcgacat   1080

cggcaaggtg tgggtcgcgg acgacggcgc cgcggtggcg gtctggacca cgccggagag   1140

cgtcgaagcg gggggcggtgt tcgccgagat cggcccgcgc atggccgagt tgagcggttc   1200

ccggctggcc gcgcagcaac agatggaagg cctcctggcg ccgcaccggc ccaaggagcc   1260

cgcgtggttc ctggccaccg tcggcgtctc gcccgaccac cagggcaagg gtctgggcag   1320

cgccgtcgtg ctccccggag tggaggcggc cgagcgcgcc ggggtgcccg ccttcctgga   1380

gacctccgcg ccccgcaacc tccccttcta cgagcggctc ggcttcaccg tcaccgccga   1440

cgtcgaggtg cccgaaggac cgcgcacctg gtgcatgacc cgcaagcccg gtgcctgacg   1500

cccgccccac gacccgcagc gcccgaccga aaggagcgca cgaccccatg gctccgaccg   1560

aagccgaccc gggcggcccc gccgaccccg cacccgcccc cgaggcccac cgactctaga   1620

ggatcataat cagccatacc acatttgtag aggttttact tgctttaaaa aacctcccac   1680
```

-continued

```
acctccccct gaacctgaaa cataaaatga atgcaattgt tgttgttaac ttgtttattg   1740
cagcttataa tggttacaaa taaagcaata gcatcacaaa tttcacaaat aaagcatttt   1800
tttcactgca ttctagttgt ggtttgtcca aactcatcaa tgtatcttat catgtctgga   1860
tcctagcgtt taaacttaag cttggtaccg agctcggatc cactagtaat ggttacaaat   1920
aaagcaatag catcacaaat ttcacaaata aagcattttt ttcactgcat tctagttgtg   1980
gtttgtccaa actcatcaat gtatcttatc atgtctgtac gatgtacggg ccagatatac   2040
gcgttgacat tgattattga ctagttatta atagtaatca attacggggt cattagttca   2100
tagcccatat atggagttcc gcgttacata acttacggta aatggcccgc ctggctgacc   2160
gcccaacgac ccccgcccat tgacgtcaat aatgacgtat gttcccatag taacgccaat   2220
agggactttc cattgacgtc aatgggtgga gtatttacgg taaactgccc acttggcagt   2280
acatcaagtg tatcatatgc caagtacgcc ccctattgac gtcaatgacg gtaaatggcc   2340
cgcctggcat tatgcccagt acatgacctt atgggacttt cctacttggc agtacatcta   2400
cgtattagtc atcgctatta ccatggtgat gcggttttgg cagtacatca atgggcgtgg   2460
atagcggttt gactcacggg gatttccaag tctccacccc attgacgtca atgggagttt   2520
gttttggcac caaaatcaac gggactttcc aaaatgtcgt aacaactccg ccccattgac   2580
gcaaatgggc ggtaggcgtg tacggtggga ggtctatata agcagagctc tctggctaac   2640
tagagaaccc actgcttact ggcttatcga aattaatacg actcactata gggagaccca   2700
agctggctag ccaccatgtc agagaacggc tccttcgcca actgctgcga ggcgggcggg   2760
tgggcagtgc gcccgggctg gtcgggggct ggcagcgcgc ggccctccag gacccctcga   2820
cctccctggg tggctccagc gctgtccgcg gtgctcatcg tcaccaccgc cgtggacgtc   2880
gtgggcaacc tcctggtgat cctctccgtg ctcaggaacc gcaagctccg gaacgcaggt   2940
aatttgttct tggtgagtct ggcattggct gacctggtgg tggccttcta cccctacccg   3000
ctaatcctcg tggccatctt ctatgacggc tgggccctgg gggaggagca ctgcaaggcc   3060
agcgcctttg tgatgggcct gagcgtcatc ggctctgtct tcaatatcac tgccatcgcc   3120
attaaccgct actgctacat ctgccacagc atggcctacc accgaatcta ccggcgctgg   3180
cacacccctc tgcacatctg cctcatctgg ctcctcaccg tggtggcctt gctgcccaac   3240
ttctttgtgg ggtccctgga gtacgaccca cgcatctatt cctgcacctt catccagacc   3300
gccagcaccc agtacacggc ggcagtggtg gtcatccact tcctcctccc tatcgctgtc   3360
gtgtccttct gctacctgcg catctgggtg ctggtgcttc aggcccgcag gaaagccaag   3420
ccagagagca ggctgtgcct gaagcccagc gacttgcgga gctttctaac catgtttgtg   3480
gtgtttgtga tctttgccat ctgctgggct ccacttaact gcatcggcct cgctgtggcc   3540
atcaaccccc aagaaatggc tccccagatc cctgaggggc tatttgtcac tagctactta   3600
ctggcttatt tcaacagctg cctgaatgcc attgtctatg ggctcttgaa ccaaaacttc   3660
cgcagggaat acaagaggat cctcttggcc ctttggaacc cacggcactg cattcaagat   3720
gcttccaagg gcagccacgc ggagggggctg cagagcccag ctccacccat cattggtgtg   3780
cagcaccagg cagatgctct ctaggcggcc gctcgagtct agagggcccg tttaaacccg   3840
ctgatcagcc tcgactgtgc cttctagttg ccagccatct gttgtttgcc cctcccccgt   3900
gccttccttg accctggaag gtgccactcc cactgtcctt tcctaataaa atgaggaaat   3960
tgcatcgcat tgtctgagta ggtgtcattc tattctgggg ggtggggtgg ggcaggacag   4020
caagggggag gattgggaag acaatagcag gcatgctggg gatgcggtgg gctctatggc   4080
```

ttctgaggcg gaaagaacca gctggggctc tagggggtat ccccacgcgc cctgtagcgg 4140
cgcattaagc gcggcgggtg tggtggttac gcgcagcgtg accgctacac ttgccagcgc 4200
cctagcgccc gctcctttcg ctttcttccc ttcctttctc gccacgttcg cctaccgtcg 4260
aatcaccggt aaccttataa gggattttgc cgatttcggc ctattggtta aaaaatgagc 4320
tgatttaaca aaaatttaac gcgaattaat tctgtggaat gtgtgtcagt tagggtgtgg 4380
aaagtcccca ggctccccag caggcagaag tatgcaaagc atgcatctca attagtcagc 4440
aaccaggtgt ggaaagtccc caggctcccc agcaggcaga agtatgcaaa gcatgcatct 4500
caattagtca gcaaccatag tcccgcccct aactccgccc atcccgcccc taactccgcc 4560
cagttccgcc cattctccgc cccatggctg actaattttt tttatttatg cagaggccga 4620
ggccgcctct gcctctgagc tattccagaa gtagtgagga ggcttttttg gaggcctagg 4680
cttttgcaaa aagctcccgg gagcttgtat atccattttc ggatctgatc aagagacagg 4740
atgaggatcg tttcgcatga ttgaacaaga tggattgcac gcaggttctc cggccgcttg 4800
ggtggagagg ctattcggct atgactgggc acaacagaca atcggctgct ctgatgccgc 4860
cgtgttccgg ctgtcagcgc aggggcgccc ggttcttttt gtcaagaccg acctgtccgg 4920
tgccctgaat gaactgcagg acgaggcagc gcggctatcg tggctggcca cgacgggcgt 4980
tccttgcgca gctgtgctcg acgttgtcac tgaagcggga agggactggc tgctattggg 5040
cgaagtgccg gggcaggatc tcctgtcatc tcaccttgct cctgccgaga aagtatccat 5100
catggctgat gcaatgcggc ggctgcatac gcttgatccg gctacctgcc cattcgacca 5160
ccaagcgaaa catcgcatcg agcgagcacg tactcggatg gaagccggtc ttgtcgatca 5220
ggatgatctg gacgaagagc atcaggggct cgcgccagcc gaactgttcg ccaggctcaa 5280
ggcgcg 5286

<210> SEQ ID NO 67
<211> LENGTH: 9944
<212> TYPE: DNA
<213> ORGANISM: Artificial Sequence
<220> FEATURE:
<223> OTHER INFORMATION: Description of Artificial Sequence: Synthetic
5F11 KI construct

<400> SEQUENCE: 67
agccccttcg cctcgtgctt gagttgaggc ctggcttggg cgctggggcc gccgcgtgcg 60
aatctggtgg caccttcgcg cctgtctcgc tgctttcgat aagtctctag ccatttaaaa 120
tttttgatga cctgctgcga cgcttttttt ctggcaagat agtcttgtaa atgcgggcca 180
agatcgatct gcacactggt atttcggttt ttggggccgc gggcggcgac ggggcccgtg 240
cgtcccagcg cacatgttcg gcgaggcggg gcctgcgagc gcggccaccg agaatcggac 300
gggggtagtc tcaagctggc cggcctgctc tggtgcctgg cctcgcgccg ccgtgtatcg 360
ccccgccctg ggcggcaagg ctggcccggt cggcaccagt tgcgtgagcg gaaagatggc 420
cgcttcccgg ccctgctgca gggagctcaa aatggaggac gcggcgctcg ggagagcggg 480
cgggtgagtc acccacacaa aggaaaaggg cctttccgtc ctcagccgtc gcttcatgtg 540
actccacgga gtaccgggcg ccgtccaggc acctcgatta gttctcgagc ttttggagta 600
cgtcgtcttt aggttggggg gaggggtttt atgcgatgga gtttccccac actgagtggg 660
tggagactga agttaggcca gcttggcact tgatgtaatt ctccttggaa tttgcccttt 720
ttgagtttgg atcttggttc attctcaagc ctcagacagt ggttcaaagt ttttttcttc 780

-continued

```
catttcaggt gtcgtggaat tggctagagc ttgcatgcct gcaggtcggc cgccacgacc    840
ggtgccgcca ccatcccctg acccacgccc ctgacccctc acaaggagac gaccttccat    900
gaccgagtac aagcccacgg tgcgcctcgc cacccgcgac gacgtccccc gggccgtacg    960
caccctcgcc gccgcgttcg ccgactaccc cgccacgcgc cacaccgtcg acccggaccg   1020
ccacatcgag cgggtcaccg agctgcaaga actcttcctc acgcgcgtcg ggctcgacat   1080
cggcaaggtg tgggtcgcgg acgacggcgc cgcggtggcg gtctggacca cgccggagag   1140
cgtcgaagcg gggcggtgt tcgccgagat cggcccgcgc atggccgagt tgagcggttc   1200
ccggctggcc gcgcagcaac agatggaagg cctcctggcg ccgcaccggc ccaaggagcc   1260
cgcgtggttc ctggccaccg tcggcgtctc gcccgaccac cagggcaagg gtctgggcag   1320
cgccgtcgtg ctccccggag tggaggcggc cgagcgcgcc ggggtgcccg ccttcctgga   1380
gacctccgcg ccccgcaacc tccccttcta cgagcggctc ggcttcaccg tcaccgccga   1440
cgtcgaggtg cccgaaggac cgcgcacctg gtgcatgacc cgcaagcccg gtgcctgacg   1500
cccgccccac gacccgcagc gcccgaccga aaggagcgca cgaccccatg gctccgaccg   1560
aagccgaccc gggcggcccc gccgaccccg cacccgcccc cgaggcccac cgactctaga   1620
ggatcataat cagccatacc acatttgtag aggttttact tgctttaaaa aacctcccac   1680
acctccccct gaacctgaaa cataaaatga atgcaattgt tgttgttaac ttgtttattg   1740
cagcttataa tggttacaaa taaagcaata gcatcacaaa tttcacaaat aaagcatttt   1800
tttcactgca ttctagttgt ggtttgtcca aactcatcaa tgtatcttat catgtctgga   1860
tcctagcgtt taaacttaag cttggtaccg agctcggatc cactagtaat ggttacaaat   1920
aaagcaatag catcacaaat ttcacaaata aagcattttt ttcactgcat tctagttgtg   1980
gtttgtccaa actcatcaat gtatcttatc atgtctgtac gatgtacggg ccagatatac   2040
gcgcgaggcc tccgcgccgg gttttggcgc ctcccgcggg cgcccccctc ctcacggcga   2100
gcgctgccac gtcagacgaa gggcgcagcg agcgtcctga tccttccgcc cggacgctca   2160
ggacagcggc ccgctgctca taagactcgg ccttagaacc ccagtatcag cagaaggaca   2220
ttttaggacg ggacttgggt gactctaggg cactggtttt ctttccagag agcggaacag   2280
gcgaggaaaa gtagtccctt ctcggcgatt ctgcggaggg atctccgtgg ggcggtgaac   2340
gccgatgatt atataaggac gcgccgggtg tggcacagct agttccgtcg cagccgggat   2400
ttgggtcgcg gttcttgttt gtggatcgct gtgatcgtca cttggtgagt agcgggctgc   2460
tgggctggcc ggggctttcg tggccgccgg gccgctcggt gggacggaag cgtgtggaga   2520
gaccgccaag ggctgtagtc tgggtccgcg agcaaggttg ccctgaactg ggggttgggg   2580
ggagcgcagc aaaatggcgg ctgttcccga gtcttgaatg gaagacgctt gtgaggcggg   2640
ctgtgaggtc gttgaaacaa ggtggggggc atggtgggcg gcaagaaccc aaggtcttga   2700
ggccttcgct aatgcgggaa agctcttatt cgggtgagat gggctggggc accatctggg   2760
gaccctgacg tgaagtttgt cactgactgg agaactcggt ttgtcgtctg ttgcgggggc   2820
ggcagttatg gcggtgccgt tgggcagtgc acccgtacct ttgggagcgc gcgccctcgt   2880
cgtgtcgtga cgtcacccgt tctgttggct tataatgcag ggtggggcca cctgccggta   2940
ggtgtgcggt aggcttttct ccgtcgcagg acgcagggtt cgggcctagg gtaggctctc   3000
ctgaatcgac aggcgccgga cctctggtga ggggagggat aagtgaggcg tcagtttctt   3060
tggtcggttt tatgtaccta tcttcttaag tagctgaagc tccggttttg aactatgcgc   3120
tcggggttgg cgagtgtgtt ttgtgaagtt ttttaggcac cttttgaaat gtaatcattt   3180
```

-continued

```
gggtcaatat gtaattttca gtgttagact agtaaattgt ccgctaaatt ctggccgttt   3240
ttggcttttt tgttagacag atctgtttaa acttaagctt gccgccacca tgggatggag   3300
ctgtatcatc ctgttcctcg tggccacagc aaccggtgtc cacagcgaca tccagatgac   3360
ccagtctcca acctcactgt ctgcatctgt aggagacaga gtcaccatca cttgtcgggc   3420
gagtcagggt attagcagct ggttaacctg gtatcagcag aaaccagaga aagcccctaa   3480
gtccctgatc tatgctgcat ccagtttgca aagtggggtc ccatcaaggt tcagcggcag   3540
tggatctggg acagatttca ctctcaccat cagcagcctg cagcctgaag attttgcaac   3600
ttattactgc caacagtatg atagttaccc tatcaccttc ggccaaggga cacgactgga   3660
gattaaacgt acggtggcgg cgccatctgt cttcatcttc ccgccatctg atgagcagtt   3720
gaaatctgga actgcctctg ttgtgtgcct gctgaataac ttctatccca gagaggccaa   3780
agtacagtgg aaggtggata acgccctcca atcgggtaac tcccaggaga gtgtcacaga   3840
gcaggacagc aaggacagca cctacagcct cagcagcacc ctgacgctga gcaaagcaga   3900
ctacgagaaa cacaaagtct acgcctgcga agtcacccat cagggcctga gctcgcccgt   3960
cacaaagagc ttcaacaggg gagagtgtta gggatccatc tagaagggag aagtgccccc   4020
acctgctcct cagttccagc ctgacccct cccatccttt ggcctctgac ccttttcca     4080
caggggacct accccctattg cggtcctcca gctcatcttt cacctcaccc ccctcctcct   4140
ccttggcttt aattatgcta atgttggagg agaatgaata aataaagtga atctttgcac   4200
ctgtggtttc tctctttcct catttaataa ttattatctg ttgttttacc aactactcaa   4260
tttctcttat aagggactaa atatgtagtc atcctaaggc gcataaccat ttataaaaat   4320
catccttcat tctattttac cctatcatcc tctgcaagac agtcctccct caaacccaca   4380
agccttctgt cctcacagtc ccctgggcca tcggaccgct atcaggacat agcgttggct   4440
acccgtgata ttgctgaaga gcttggcggc gaatgggctg accgcttcct cgtgctttac   4500
ggtatcgccg ctcccgattc gcagcgcatc gccttctatc gccttcttga cgagttcttc   4560
tgagcgggac tctggggttc gaaatgaccg accaagcgac gcccaacctg ccatcacgag   4620
atttcgattc caccgccgcc ttctatgaaa ggttgggctt cggaatcgtt ttccgggacg   4680
ccggctggat gatcctccag cgcggggatc tcatgctgga gttcttcgcc caccccaact   4740
tgtttattgc agcttataat ggttacaaat aaagcaatag catcacaaat ttcacaaata   4800
aagcattttt ttcactgcat tctagttgtg gtttgtccaa actcatcaat gtatcttatc   4860
atgtctgtat accgtcgacc tctagctaga gcttggcgta atcatggtca tagctgtttc   4920
ctgtgtgaaa ttgttatccg ctcacaattc cacacaacat acgagccgga agcataaagt   4980
gtaaagcctg gggtgcctaa tgagtgagct aactcacatt aattgcgttg cgctcactgc   5040
ccgctttcca gtcgggaaac ctgtcgtgcc agctgcatta atgaatcggc caacgcgcgg   5100
ggagaggcgg tttgcgtatt gggcgctctt ccgcttcctc gctcactgac tcgctgcgct   5160
cggtcgttcg gctgcggcga gcggtatcag ctcactcaaa ggcggtaata cggttatcca   5220
cagaatcagg ggataacgca ggaaagaaca tgcgaggcct ccgcgccggg ttttggcgcc   5280
tcccgcgggc gcccccctcc tcacggcgag cgctgccacg tcagacgaag ggcgcagcga   5340
gcgtcctgat ccttccgccc ggacgctcag gacagcggcc cgctgctcat aagactcggc   5400
cttagaaccc cagtatcagc agaaggacat tttaggacgg gacttgggtg actctagggc   5460
actggttttc tttccagaga gcggaacagg cgaggaaaag tagtcccttc tcggcgattc   5520
tgcggaggga tctccgtggg gcggtgaacg ccgatgatta tataaggacg cgccgggtgt   5580
```

```
ggcacagcta gttccgtcgc agccgggatt tgggtcgcgg ttcttgtttg tggatcgctg   5640
tgatcgtcac ttggtgagta gcgggctgct gggctggccg ggctttcgt ggccgccggg   5700
ccgctcggtg ggacggaagc gtgtggagag accgccaagg gctgtagtct gggtccgcga   5760
gcaaggttgc cctgaactgg gggttggggg gagcgcagca aaatggcggc tgttcccgag   5820
tcttgaatgg aagacgcttg tgaggcgggc tgtgaggtcg ttgaaacaag gtgggggca   5880
tggtgggcgg caagaaccca aggtcttgag gccttcgcta atgcgggaaa gctcttattc   5940
gggtgagatg ggctggggca ccatctgggg accctgacgt gaagtttgtc actgactgga   6000
gaactcggtt tgtcgtctgt tgcggggcg gcagttatgg cggtgccgtt gggcagtgca   6060
cccgtacctt tgggagcgcg cgccctcgtc gtgtcgtgac gtcacccgtt ctgttggctt   6120
ataatgcagg gtggggccac ctgccggtag gtgtgcggta ggcttttctc cgtcgcagga   6180
cgcagggttc gggcctaggg taggctctcc tgaatcgaca ggcgccggac ctctggtgag   6240
gggagggata agtgaggcgt cagtttcttt ggtcggtttt atgtacctat cttcttaagt   6300
agctgaagct ccggttttga actatgcgct cggggttggc gagtgtgttt tgtgaagttt   6360
tttaggcacc ttttgaaatg taatcatttg ggtcaatatg taattttcag tgttagacta   6420
gtaaattgtc cgctaaattc tggccgtttt tggctttttt gttagacaga tctgtttaaa   6480
cttaagcttg ccgccaccat gggatggagc tgtatcatcc tgttcctcgt ggccacagca   6540
accggtgtcc acagccaggt gcagctacag cagtggggcg caggactgtt gaagccttcg   6600
gagaccctgt ccctcacctg cgctgtctat ggtgggtcct tcagtgctta ctactggagc   6660
tggatccgcc agcccccagg gaaggggctg gagtggattg gggacatcaa tcatggtgga   6720
ggcaccaact acaacccgtc cctcaagagt cgagtcacca tatcagtaga cacgtccaag   6780
aaccagttct ccctgaagct gaactctgta accgccgcgg acacggctgt gtattactgt   6840
gcgagcctaa ctgcctactg ggccagggga agcctggtca ccgtctcctc agctagcacc   6900
aagggcccat cggtcttccc cctggcaccc tcctccaaga gcacctctgg gggcacagcg   6960
gccctgggct gcctggtcaa ggactacttc cccgaaccgg tgacggtgtc gtggaactca   7020
ggcgccctga ccagcggcgt gcacaccttc ccggccgtcc tacagtcctc aggactctac   7080
tccctcagca gcgtggtgac cgtgccctcc agcagcttgg gcacccagac ctacatctgc   7140
aacgtgaatc acaagcccag caacaccaag gtggacaaga gagttgagcc caaatcttgt   7200
gacaaaactc acacatgccc accgtgccca gcacctgaac tcctgggggg accgtcagtc   7260
ttcctcttcc ccccaaaacc caaggacacc ctcatgatct cccggacccc tgaggtcaca   7320
tgcgtggtgg tggacgtgag ccacgaagac cctgaggtca agttcaactg gtacgtggac   7380
ggcgtggagg tgcataatgc caagacaaag ccgcgggagg agcagtacaa cagcacgtac   7440
cgtgtggtca gcgtcctcac cgtcctgcac caggactggc tgaatggcaa ggagtacaag   7500
tgcaaggtct ccaacaaagc cctcccagcc cccatcgaga aaaccatctc caaagccaaa   7560
gggcagcccc gagaaccaca ggtgtacacc ctgcccccat cccgggatga gctgaccaag   7620
aaccaggtca gcctgacctg cctggtcaaa ggcttctatc ccagcgacat cgccgtggag   7680
tgggagagca atgggcagcc ggagaacaac tacaagacca cgcctcccgt gctggactcc   7740
gacggctcct tcttcctcta cagcaagctc accgtggaca agagcaggtg gcagcagggg   7800
aacgtcttct catgctccgt gatgcatgag gctctgcaca accactacac gcagaagagc   7860
ctctccctgt ctccgggtaa atgagtgcga cggccggcaa gggatccagg ggagagtgtt   7920
agagggagaa gtgcccccac ctgctcctca gttccagcct gacccccctcc catcctttgg   7980
```

```
cctctgaccc tttttccaca ggggacctac ccctattgcg gtcctccagc tcatctttca   8040
cctcaccccc ctcctcctcc ttggctttaa ttatgctaat gttggaggag aatgaataaa   8100
taaagtgaat ctttgcacct gtggtttctc tctttcctca tttaataatt attatctgtt   8160
gttttaccaa ctactcaatt tctcttataa gggactaaat atgtagtcat cctaaggcgc   8220
ataaccattt ataaaaatca tccttcattc tattttaccc tatcatcctc tgcaagacag   8280
tcctccctca aacccacaag ccttctgtcc tcacagtccc ctgggccatg tgagcaaaag   8340
gccagcaaaa ggccaggaac cgtaaaaagg ccgcgttgct ggcgtttttc cataggctcc   8400
gcccccctga cgagcatcac aaaaatcgac gctcaagtca gaggtggcga aacccgatag   8460
ttgcggccgc tcgagtctag agggcccgtt taaacccgct gatcagcctc gactgtgcct   8520
tctagttgcc agccatctgt tgtttgcccc tcccccgtgc cttccttgac cctggaaggt   8580
gccactccca ctgtcctttc ctaataaaat gaggaaattg catcgcattg tctgagtagg   8640
tgtcattcta ttctgggggg tggggtgggg caggacagca agggggagga ttgggaagac   8700
aatagcaggc atgctgggga tgcggtgggc tctatggctt ctgaggcgga aagaaccagc   8760
tggggctcta gggggtatcc ccacgcgccc tgtagcggcg cattaagcgc ggcgggtgtg   8820
gtggttacgc gcagcgtgac cgctacactt gccagcgccc tagcgcccgc tcctttcgct   8880
ttcttccctt cctttctcgc cacgttcgcc taccgtcgaa tcaccggtaa ccttataagg   8940
gattttgccg atttcggcct attggttaaa aaatgagctg atttaacaaa aatttaacgc   9000
gaattaattc tgtggaatgt gtgtcagtta gggtgtggaa agtccccagg ctccccagca   9060
ggcagaagta tgcaaagcat gcatctcaat tagtcagcaa ccaggtgtgg aaagtcccca   9120
ggctccccag caggcagaag tatgcaaagc atgcatctca attagtcagc aaccatagtc   9180
ccgcccctaa ctccgcccat cccgccccta actccgccca gttccgccca ttctccgccc   9240
catggctgac taattttttt tatttatgca gaggccgagg ccgcctctgc ctctgagcta   9300
ttccagaagt agtgaggagg cttttttgga ggcctaggct tttgcaaaaa gctcccggga   9360
gcttgtatat ccattttcgg atctgatcaa gagacaggat gaggatcgtt tcgcatgatt   9420
gaacaagatg gattgcacgc aggttctccg gccgcttggg tggagaggct attcggctat   9480
gactgggcac aacagacaat cggctgctct gatgccgccg tgttccggct gtcagcgcag   9540
gggcgcccgg ttctttttgt caagaccgac ctgtccggtg ccctgaatga actgcaggac   9600
gaggcagcgc ggctatcgtg gctggccacg acgggcgttc cttgcgcagc tgtgctcgac   9660
gttgtcactg aagcgggaag ggactggctg ctattgggcg aagtgccggg gcaggatctc   9720
ctgtcatctc accttgctcc tgccgagaaa gtatccatca tggctgatgc aatgcggcgg   9780
ctgcatacgc ttgatccggc tacctgccca ttcgaccacc aagcgaaaca tcgcatcgag   9840
cgagcacgta ctcggatgga agccggtctt gtcgatcagg atgatctgga cgaagagcat   9900
caggggctcg cgccagccga actgttcgcc aggctcaagg cgcg                     9944
```

<210> SEQ ID NO 68
<211> LENGTH: 6012
<212> TYPE: DNA
<213> ORGANISM: Artificial Sequence
<220> FEATURE:
<223> OTHER INFORMATION: Description of Artificial Sequence: Synthetic Luciferase KI construct

<400> SEQUENCE: 68

```
agccccttcg cctcgtgctt gagttgaggc ctggcttggg cgctggggcc gccgcgtgcg     60
aatctggtgg caccttcgcg cctgtctcgc tgctttcgat aagtctctag ccatttaaaa    120
```

```
tttttgatga cctgctgcga cgcttttttt ctggcaagat agtcttgtaa atgcgggcca    180
agatcgatct gcacactggt atttcggttt ttggggccgc gggcggcgac ggggcccgtg    240
cgtcccagcg cacatgttcg gcgaggcggg gcctgcgagc gcggccaccg agaatcggac    300
gggggtagtc tcaagctggc cggcctgctc tggtgcctgg cctcgcgccg ccgtgtatcg    360
ccccgccctg ggcggcaagg ctggcccggt cggcaccagt tgcgtgagcg gaaagatggc    420
cgcttcccgg ccctgctgca gggagctcaa aatggaggac gcggcgctcg ggagagcggg    480
cgggtgagtc acccacacaa aggaaaaggg cctttccgtc ctcagccgtc gcttcatgtg    540
actccacgga gtaccgggcg ccgtccaggc acctcgatta gttctcgagc ttttggagta    600
cgtcgtcttt aggttggggg gaggggtttt atgcgatgga gtttccccac actgagtggg    660
tggagactga agttaggcca gcttggcact tgatgtaatt ctccttggaa tttgcccttt    720
ttgagtttgg atcttggttc attctcaagc ctcagacagt ggttcaaagt ttttttcttc    780
catttcaggt gtcgtggaat tggctagagc ttgcatgcct gcaggtcggc cgccacgacc    840
ggtgccgcca ccatcccctg acccacgccc ctgacccctc acaaggagac gaccttccat    900
gaccgagtac aagcccacgg tgcgcctcgc cacccgcgac gacgtccccc gggccgtacg    960
caccctcgcc gccgcgttcg ccgactaccc cgccacgcgc cacaccgtcg acccggaccg   1020
ccacatcgag cgggtcaccg agctgcaaga actcttcctc acgcgcgtcg ggctcgacat   1080
cggcaaggtg tgggtcgcgg acgacggcgc cgcggtggcg gtctggacca cgccggagag   1140
cgtcgaagcg gggggcggtgt tcgccgagat cggcccgcgc atggccgagt tgagcggttc   1200
ccggctggcc gcgcagcaac agatggaagg cctcctggcg ccgcaccggc ccaaggagcc   1260
cgcgtggttc ctggccaccg tcggcgtctc gcccgaccac cagggcaagg gtctgggcag   1320
cgccgtcgtg ctccccggag tggaggcggc cgagcgcgcc ggggtgcccg ccttcctgga   1380
gacctccgcg ccccgcaacc tccccttcta cgagcggctc ggcttcaccg tcaccgccga   1440
cgtcgaggtg cccgaaggac cgcgcacctg gtgcatgacc cgcaagcccg gtgcctgacg   1500
cccgccccac gacccgcagc gcccgaccga aaggagcgca cgaccccatg gctccgaccg   1560
aagccgaccc gggcggcccc gccgaccccg cacccgcccc cgaggcccac cgactctaga   1620
ggatcataat cagccatacc acatttgtag aggttttact tgctttaaaa aacctcccac   1680
acctcccctt gaacctgaaa cataaaatga atgcaattgt tgttgttaac ttgtttattg   1740
cagcttataa tggttacaaa taaagcaata gcatcacaaa tttcacaaat aaagcatttt   1800
tttcactgca ttctagttgt ggtttgtcca aactcatcaa tgtatcttat catgtctgga   1860
tcctagcgtt taaacttaag cttggtaccg agctcggatc cactagcgat gtacgggcca   1920
gatatacgcg ttgacattga ttattgacta gttattaata gtaatcaatt acggggtcat   1980
tagttcatag cccatatatg gagttccgcg ttacataact tacggtaaat ggcccgcctg   2040
gctgaccgcc caacgacccc cgcccattga cgtcaataat gacgtatgtt cccatagtaa   2100
cgccaatagg gactttccat tgacgtcaat gggtggagta tttacggtaa actgcccact   2160
tggcagtaca tcaagtgtat catatgccaa gtacgccccc tattgacgtc aatgacggta   2220
aatggcccgc ctggcattat gcccagtaca tgaccttatg ggactttcct acttggcagt   2280
acatctacgt attagtcatc gctattacca tggtgatgcg gttttggcag tacatcaatg   2340
ggcgtggata gcggtttgac tcacggggat ttccaagtct ccaccccatt gacgtcaatg   2400
ggagtttgtt ttggcaccaa aatcaacggg actttccaaa atgtcgtaac aactccgccc   2460
cattgacgca aatgggcggt aggcgtgtac ggtgggaggt ctatataagc agagctctct   2520
```

```
ggctaactag agaacccact gcttactggc ttatcgaaat taatacgact cactataggg   2580
agacccaagc tggctagcgc tgatatcgat cgcgagcggc cgcgaattca ctagtgattg   2640
cagaattcat ggaagatgcc aaaaacatta agaagggccc agcgccattc tacccactcg   2700
aagacgggac cgccggcgag cagctgcaca aagccatgaa gcgctacgcc ctggtgcccg   2760
gcaccatcgc ctttaccgac gcacatatcg aggtggacat tacctacgcc gagtacttcg   2820
agatgagcgt tcggctggca gaagctatga agcgctatgg gctgaataca aaccatcgga   2880
tcgtggtgtg cagcgagaat agcttgcagt tcttcatgcc cgtgttgggt gccctgttca   2940
tcggtgtggc tgtggcccca gctaacgaca tctacaacga gcgcgagctg ctgaacagca   3000
tgggcatcag ccagcccacc gtcgtattcg tgagcaagaa agggctgcaa aagatcctca   3060
acgtgcaaaa gaagctaccg atcatacaaa agatcatcat catggatagc aagaccgact   3120
accagggctt ccaaagcatg tacaccttcg tgacttccca tttgccaccc ggcttcaacg   3180
agtacgactt cgtgcccgag agcttcgacc gggacaaaac catcgccctg atcatgaaca   3240
gtagtggcag taccggattg cccaagggcg tagccctacc gcaccgcacc gcttgtgtcc   3300
gattcagtca tgcccgcgac cccatcttcg gcaaccagat catccccgac accgctatcc   3360
tcagcgtggt gccatttcac cacggcttcg gcatgttcac cacgctgggc tacttgatct   3420
gcggctttcg ggtcgtgctc atgtaccgct tcgaggagga gctattcttg cgcagcttgc   3480
aagactataa gattcaatct gccctgctgg tgcccacact atttagcttc ttcgctaaga   3540
gcactctcat cgacaagtac gacctaagca acttgcacga gatcgccagc ggcggggcgc   3600
cgctcagcaa ggaggtaggt gaggccgtgg ccaaacgctt ccacctacca ggcatccgcc   3660
agggctacgg cctgacagaa acaaccagcg ccattctgat cacccccgaa ggggacgaca   3720
agcctggcgc agtaggcaag gtggtgccct tcttcgaggc taaggtggtg gacttggaca   3780
ccggtaagac actgggtgtg aaccagcgcg gcgagctgtg cgtccgtggc cccatgatca   3840
tgagcggcta cgttaacaac cccgaggcta caaacgctct catcgacaag gacggctggc   3900
tgcacagcgg cgacatcgcc tactgggacg aggacgagca cttcttcatc gtggaccggc   3960
tgaagagcct gatcaaatac aagggctacc aggtagcccc agccgaactg gagagcatcc   4020
tgctgcaaca ccccaacatc ttcgacgccg gggtcgccgg cctgcccgac gacgatgccg   4080
gcgagctgcc cgccgcagtc gtcgtgctgg aacacggtaa aaccatgacc gagaaggaga   4140
tcgtggacta tgtggccagc caggttacaa ccgccaagaa gctgcgcggt ggtgttgtgt   4200
tcgtggacga ggtgcctaaa ggactgaccg gcaagttgga cgcccgcaag atccgcgaga   4260
ttctcattaa ggccaagaag ggcggcaaga tcgccgtgta ataattctag agtcggggcg   4320
gccggccgct tcgagcagac atgataagat acattgatga gtttggacaa accacaacta   4380
gaatgcagtg aaaaaaatgc tttatttgtg aaatttgtga tgctattgct ttatttgtaa   4440
ccattataag ctgcaataaa caagttaaca acaacaattg cattcatttt atgtttcagg   4500
ttcaggggga ggtgtgggag gtttttttaaa gcggccgctc gagtctagag ggcccgttta   4560
aacccgctga tcagcctcga ctgtgccttc tagttgccag ccatctgttg tttgcccctc   4620
ccccgtgcct tccttgaccc tggaaggtgc cactcccact gtcctttcct aataaaatga   4680
ggaaattgca tcgcattgtc tgagtaggtg tcattctatt ctggggggtg gggtggggca   4740
ggacagcaag ggggaggatt gggaagacaa tagcaggcat gctggggatg cggtgggctc   4800
tatggcttct gaggcggaaa gaaccagctg gggctctagg gggtatcccc acgcgccctg   4860
tagcggcgca ttaagcgcgg cgggtgtggt ggttacgcgc agcgtgaccg ctacacttgc   4920
```

```
cagcgcccta gcgcccgctc ctttcgcttt cttcccttcc tttctcgcca cgttcgccta   4980

ccgtcgaatc accggtaacc ttataaggga ttttgccgat ttcggcctat tggttaaaaa   5040

atgagctgat ttaacaaaaa tttaacgcga attaattctg tggaatgtgt gtcagttagg   5100

gtgtggaaag tccccaggct ccccagcagg cagaagtatg caaagcatgc atctcaatta   5160

gtcagcaacc aggtgtggaa agtccccagg ctccccagca ggcagaagta tgcaaagcat   5220

gcatctcaat tagtcagcaa ccatagtccc gcccctaact ccgcccatcc cgcccctaac   5280

tccgcccagt tccgcccatt ctccgcccca tggctgacta attttttta tttatgcaga    5340

ggccgaggcc gcctctgcct ctgagctatt ccagaagtag tgaggaggct tttttggagg   5400

cctaggcttt tgcaaaaagc tcccgggagc ttgtatatcc attttcggat ctgatcaaga   5460

gacaggatga ggatcgtttc gcatgattga acaagatgga ttgcacgcag gttctccggc   5520

cgcttgggtg gagaggctat tcggctatga ctgggcacaa cagacaatcg gctgctctga   5580

tgccgccgtg ttccggctgt cagcgcaggg gcgcccggtt ctttttgtca agaccgacct   5640

gtccggtgcc ctgaatgaac tgcaggacga ggcagcgcgg ctatcgtggc tggccacgac   5700

gggcgttcct tgcgcagctg tgctcgacgt tgtcactgaa gcgggaaggg actggctgct   5760

attgggcgaa gtgccggggc aggatctcct gtcatctcac cttgctcctg ccgagaaagt   5820

atccatcatg gctgatgcaa tgcggcggct gcatacgctt gatccggcta cctgcccatt   5880

cgaccaccaa gcgaaacatc gcatcgagcg agcacgtact cggatggaag ccggtcttgt   5940

cgatcaggat gatctggacg aagagcatca ggggctcgcg ccagccgaac tgttcgccag   6000

gctcaaggcg cg                                                        6012

<210> SEQ ID NO 69
<211> LENGTH: 9
<212> TYPE: PRT
<213> ORGANISM: Unknown
<220> FEATURE:
<223> OTHER INFORMATION: Description of Unknown: "LAGLIDADG" motif

<400> SEQUENCE: 69

Leu Ala Gly Leu Ile Asp Ala Asp Gly
1               5


<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 70

His His His His His His
1               5
```

MEGANUCLEASE RECOMBINATION SYSTEM

The invention relates to a set of genetic constructs which allow the efficient and reproducible introduction of a specific nucleotide sequence at a fixed position in the genome. The present invention also relates to methods using these constructs and to these materials in the form of a kit.

Since the first gene targeting experiments in yeast more than 25 years ago (1, 2), homologous recombination has been used to insert, replace or delete genomic sequences in a variety of cells (3-5). However, targeted events occur at a very low frequency in mammalian cells. The frequency of homologous recombination can be significantly increased by a specific DNA double-strand break (DSB) in the targeted locus (6, 7). Such DSBs can be created using Meganucleases, which are sequence-specific endonucleases that recognize large DNA target sites (>12 bp). These proteins can cleave a unique chromosomal sequence without affecting overall genome integrity. Natural Meganucleases are essentially represented by homing endonucleases, a widespread class of proteins found in eukaryotes, bacteria and archae (8). Early studies of the I-SceI and HO homing endonucleases have illustrated how the cleavage activity of these proteins initiates homologous recombination (HR) events in living cells and demonstrated the recombinogenic properties of chromosomal DSBs (9, 10). Since then, Meganuclease-induced recombination has been successfully used for genome engineering purposes in bacteria (11), mammalian cells (6, 7, 12-14), mice (15) and plants (16, 17).

Gene insertion can be used, for example, to introduce genes of interest in specific loci, for heterologous protein production. Recombinant therapeutic proteins are today mostly produced in mammalian cells such as CHO, mouse SP2/0 and NSO cells, or the human PerC.6 cell line, stably transfected with the gene of interest (18). In the process of selecting highly expressing clones, the level and stability of protein expression are two major criteria. Obtaining reproducible results from one clone to another would be an advantage in terms of improving screening efforts. These principles also apply to the generation of cells for screening of specific drug targets. The same principle can also be applied to the expression of various genes in the same genomic context to comparatively study and analyze the resulting cell lines one to another. Such cell lines can furthermore be subjected to the effect of compounds libraries in screening programs.

At the present time however no means exist to induce a DSB at a locus wherein the insertion/deletion of heterologous sequences can be easily ascertained.

The Inventors have developed a new set of genetic constructs which allow the reproducible integration and expression of a gene of interest (GOI) or a series of genes in otherwise isogenic cell lines.

According to a first aspect of the present invention there is provided a set of genetic constructs comprising:

a) Construct (i) encoded by a nucleic acid molecule, which comprises at least the following components:

A1-A2-A3-A4-A5 (i)

wherein A1 is a first promoter; A2 is a first homologous portion; A3 is a meganuclease cleavage site; A4 is a first marker gene; A5 is a second homologous portion; and wherein construct (i) is configured to be stably integrated into the genome of at least one target cell;

b) Construct (ii) encoded by a nucleic acid molecule, which comprises at least the following components:

A2'-B1-B2-B3-B4-A5' (ii)

wherein A2' comprises a portion of said first homologous portion A2; B1 is a second marker gene different to said first marker gene; B2 is a second promoter; B3 is a multiple cloning site; B4 is a third promoter; A5' comprises a portion of said second homologous portion A5;

c) At least one construct selected from the group comprising, constructs (iii) or (iv) encoded by nucleic acid molecules, which comprise at least the following components:

C1-C2 (iii);

C3 (iv); or

Construct (v) which is an isolated or recombinant protein which comprises at least the following component:

C4 (v);

wherein C1 is a fourth promoter; C2 is the open reading frame (ORF) of a meganuclease; C3 are messenger RNA (mRNA) versions of said meganuclease; C4 is an isolated or recombinant protein of said meganuclease; wherein said meganuclease from constructs (iii), (iv) or (v) recognize and cleave A3; and wherein constructs (iii), (iv) or (v) are configured to be co-transfected with construct (ii) into said at least one target cell.

This system of genetic constructs allows the integration and expression of a GOI in an engineered cell at a specific genomic location. Construct (ii) containing a GOI which can be cloned into portion B3 is integrated into the genome via Meganuclease induced Recombination at a specific site corresponding to the genomic integration position of construct (i). The insertion event occurs at a very high frequency and is very specific.

Each of the genetic constructs consists of the above essential components, A1 to A5, AT and A5', B1 to B4 and C1 to C2, but between these other nucleotide sequences may be present so long as they do not affect the properties of the claimed components as defined herein.

In the present invention, a promoter is a nucleotide sequence which when placed in combination with a second nucleotide sequence encoding an open reading frame causes the transcription of the open reading frame. In addition in the case of a RNA molecule, a promoter can also refer to a non-coding sequence which acts to increase the levels of translation of the RNA molecule.

In the present invention, a homologous portion refers to a nucleotide sequence which shares nucleotide residues in common with another nucleotide sequence so as to lead to a homologous recombination between these sequences, more particularly having at least 95% identity, preferably 97% identity and more preferably 99% identity. The first and second homologous portions of construct (i) and the first and second homologous portions construct (ii) can be 100% identical or less as indicated.

In particular the overlap between the portions A2 and A5 from construct (i) and portions A2' and A5' from construct (ii) is at least 200 by and no more than 6000 bp. Preferably the overlap is between 1000 by and 2000 bp.

In particular therefore components A2' and A5' from construct (ii), comprise at least 200 by and no more than 6000 by of components A2 and A5 from construct (i) respectively.

Most particularly components A2' and A5' from construct (ii), comprise at least 1000 by and no more than 2000 by of components A2 and A5 from construct (i) respectively.

The amounts of overlap necessary to allow efficient levels of homologous recombination are known in the art (49), starting from these known levels the inventors have identified the most efficient ranges of overlap for use with the set of constructs according to the present invention.

In the present invention, a meganuclease cleavage site is intended to mean a 22 to 24 bp double-stranded palindromic, partially palindromic (pseudo-palindromic) or non-palindromic polynucleotide sequence that is recognized and cleaved by a LAGLIDADG homing endonuclease (SEQ ID NO: 69). These terms refer to a distinct DNA location, preferably a genomic location, at which a double stranded break (cleavage) is to be induced by the meganuclease.

The meganuclease cleavage site can be the DNA sequence recognized and cleaved by a wild type meganuclease such as I-CreI or I-DmoI. Alternativley the meganuclease cleavage site can be the DNA sequence recognized and cleaved by altered meganucleases which recognize and cleave different DNA target sequences.

The inventors and others have shown that meganucleases can be engineered so as to recognize different DNA targets. The I-CreI enzyme in particular has been studied extensively and different groups have used a semi-rational approach to locally alter the specificity of I-CreI (26-28).

In addition, hundreds of I-CreI derivatives with locally altered specificity were engineered by combining the semi-rational approach and High Throughput Screening:

Residues Q44, R68 and R70 or Q44, R68, D75 and 177 of I-CreI were mutagenized and a collection of variants with altered specificity at positions ±3 to 5 of the DNA target (5NNN DNA target) were identified by screening (27, 28).

Residues K28, N30 and Q38 or N30, Y33, and Q38 or K28, Y33, Q38 and S40 of I-CreI were mutagenized and a collection of variants with altered specificity at positions ±8 to 10 of the DNA target (10NNN DNA target) were identified by screening (29, 30).

All such variant meganucleases and the variant DNA targets which they recognize and cleave, are included in the present Patent Application and any combination of a particular meganuclease and its target can be used as the meganuclease target sequence represented by feature A3 from construct (i) and the meganuclease encoded variously by constructs (iii), (iv) and (v).

In the present invention a marker gene is a gene product which when expressed allows the differentiation of a cell or population of cells expressing the marker gene versus a cell or population of cells not expressing the marker gene.

In the present invention a multiple cloning site is a short segment of DNA which contains several restriction sites so as to allow the sub-cloning of a fragment of interest into the plasmid comprising the multiple cloning site.

In the present invention a meganuclease is intended to mean an endonuclease having a double-stranded DNA target sequence of 12 to 45 bp. This may be a wild type version of a meganuclease such as I-CreI or I-DmoI or an engineered version of one of these enzymes as described above or fusion proteins comprising portions of one or more meganuclease(s) (31-33).

The inventors have shown that this system can work with a number of diverse model mammalian cell lines for a number of GOIs.

Preferably component A5 comprises a marker gene or a portion thereof.

In accordance with this preferred embodiment of the present invention component A5 must encode a marker gene or a portion thereof such that following the homologous recombination event the detection of altered cells can be detected.

Alternatively a DNA sequence encoding a marker gene can be positioned after component A5, wherein this further portion encodes a marker gene and allows the detection of cells which have undergone homologous recombination.

Preferably component A5' comprises a 3' end deletion of said component A5.

Preferably the components of each of said constructs (i), (ii), (iii), (iv) and (v) are selected from the following groups:

| Component | Group |
|---|---|
| A1 | pEF1α promoter (SEQ ID NO: 1); pSV40 (SEQ ID NO: 20); pCMV (SEQ ID NO: 25); Ubiquitin sub-unit c promoter (SEQ ID NO: 52) |
| A2 | EF1α intron 1 complete sequence, 5' homology (SEQ ID NO: 3) |
| A2' | EF1α intron 1 short sequence, 5' homology (SEQ ID NO: 29) |
| A3* | Meganuclease cleavage site (SEQ ID NO: 8) |
| A4 | Hygromycin resistance gene (SEQ ID NO: 2); Neomycin resistance gene (SEQ ID NO: 7); Puromycin resistance gene (SEQ ID NO: 21) |
| A5 | Neomycin resistance gene (SEQ ID NO: 7) |
| A5' | Inactive neomycin resistance gene deleted of its 3' end, 3' homology (SEQ ID NO: 13) |
| B1 | Hygromycin resistance gene (SEQ ID NO: 2); Neomycin resistance gene (SEQ ID NO: 7); Puromycin resistance gene (SEQ ID NO: 21) |
| B2 | pEF1α promoter (SEQ ID NO: 1); pSV40 (SEQ ID NO: 20); pCMV (SEQ ID NO: 25); Ubiquitin sub-unit c promoter (SEQ ID NO: 52) |
| B3 | Multiple cloning site (SEQ ID NO: 23) |
| B4 | pEF1α promoter (SEQ ID NO: 1); pSV40 (SEQ ID NO: 20); pCMV (SEQ ID NO: 25); Ubiquitin sub-unit c promoter (SEQ ID NO: 52) |
| C1 | pEF1α promoter (SEQ ID NO: 1); pSV40 (SEQ ID NO: 20); pCMV (SEQ ID NO: 25); Ubiquitin sub-unit c promoter (SEQ ID NO: 52) |
| C2* | Meganuclease ORFs (SEQ ID NO: 14); (SEQ ID NO: 15) |
| C3* | Meganuclease ORFs (SEQ ID NO: 14); (SEQ ID NO: 15) and (SEQ ID NO 35) |
| C4* | Meganuclease peptide encoded by (SEQ ID NO: 14); (SEQ ID NO: 15) and (SEQ ID NO: 58) |

*The meganuclease cleavage site used in the set of constructs according to the present invention must be recognized and cleaved by the meganuclease also included in the set of constructs. As pointed out above the meganuclease cleavage site can be a wild type meganuclease target site, such as SEQ ID NO: 8 the wild type cleavage site of the wild type I-CreI meganuclease (provided herein in various forms as SEQ ID NO: 14, 15 and 58). If however component A3 is altered then the meganuclease of component C2, C3 or C4 will also be altered.

The above components are only examples and it is not intended that the present invention be limited to these specific sequences or combinations thereof.

The characteristics of the claimed components are defined herein and the selection of other suitable components, such as resistance genes or promoter sequences is therefore encompassed by the present invention.

Preferred promoting sequences are pCMV promoter (SEQ ID NO: 25), pSV40 promoter (SEQ ID NO: 20), pEF1 (SEQ ID NO: 1) and Ubiquitin sub-unit c promoter (SEQ ID NO: 52).

Preferred marker genes are Neomycin resistance gene (SEQ ID NO: 7); Puromycin resistance gene (SEQ ID NO: 21), Hygromycin resistance gene (SEQ ID NO: 2); blasticidin resistance gene, zeocin resistance gene and phleomycin resistance gene. Many other selectable marker genes exist all these can be used in the present Patent Application Most preferably, the construct (i) comprises SEQ ID NO: 6, which consists of the Inventors preferred construct which was used to create cGPS (cellular Genome Positioning System) cell lines. In this construct, a specific Meganuclease target site has been inserted into the host cell genome at a unique locus. This site is the precise insertion locus of the gene(s) of interest. This site has been inserted at a single copy into the host cell line as part of a larger construct. In the final cGPS cell line, the Meganuclease target site is located near the hygromycin resistance gene and downstream the EF1α promoter. The cGPS cell line is then resistant to hygromycin. Furthermore, the neomycin resistance gene is located just downstream the hygromycin gene but lacks a promoter making the cGPS cell line G418 sensitive (see FIG. 1).

The important features of cGPS locus are listed in table 1 below.

TABLE 1

| Feature | Benefit |
|---|---|
| pEF1α (referred as A1) | Promoter from the human Elongation Factor I alpha gene driving the transcription of the puromycin resistance gene after HR in cGPS cells (SEQ ID NO: 1) |
| EF1α exon 1 | Exon 1 of the human Elongation Factor I alpha gene (SEQ ID NO: 11) |
| EF1α exon 2 | Exon 2 of the human Elongation Factor I alpha gene (SEQ ID NO: 12) |
| EF1α intron 1 (referred as A2, 5' homology) | Intron 1 of the human Elongation Factor I alpha gene, composed of a 1 kb fragment (SEQ ID NO: 10) |
| Meganuclease cleavage site (referred as A3) | Meganuclease cleavage site for targeted insertion of the GOI |
| HygroR (referred as A4) | Hygromycin resistance gene |
| NeoR (referred as A5, 3' homology) | Neomycin resistance gene (inactive because lacking a promoting sequence to drive its transcription) |
| SV40 pA | Polyadenylation signal from SV40 virus (SEQ ID NO: 4, SEQ ID NO: 5), allowing efficient transcription termination and polyadenylation of hygromycin and neomycin resistance genes |

Most preferably, the construct (ii) comprises SEQ ID NO: 22, which consists of pTV-DS-MCS2 which is a 6932 by vector that expresses a GOI under the control of the CMV promoter. It also contains two homology arms for efficient HR and insertion of the GOI at the cGPS locus (see FIG. 2).

The important features of pTV-DS-MCS2 are described in table 2 below. All features have been functionally tested.

TABLE 2

| Feature | Benefit |
|---|---|
| EF1α intron 1 (referred as A2', part of the 5' homology) | 0.8 kb fragment (SEQ ID NO 28) for efficient homologous recombination at the cGPS site composed of the intron 1 of the human Elongation Factor I alpha gene; once reconstituted after HR at the cGPS site, it allows puromycin selection of stable cGPS expressing cell clones |
| NeoR Del3' (referred as A5', part of the 3'homology) | 0.6 kb fragment (SEQ ID NO 26) for efficient homologous recombination at the cGPS site composed of an inactive neomycin resistance gene deleted of its 3' end; once reconstituted after HR at the cGPS site, it allows neomycin selection of stable expressing cell clones |
| PuroR | Puromycin resistance gene (inactive because lacking a promoting sequence to drive its transcription); once reconstituted after HR at the cGPS site, it allows puromycin selection of stable cell clones |
| pCMV | Human cytomegalovirus (CMV, SEQ ID NO: 25) immediate early promoter, driving high-level expression of the GOI |
| MCS2 | Multiple cloning site containing NheI, BmtI, Bsu36I, AscI, BglII, BsrGI, BstBI, EcoRV, PacI, NotI restriction sites for the molecular cloning of GOIs |
| SV40 pA | Polyadenylation signal from SV40 virus (SEQ ID NO: 19), allowing efficient transcription termination and polyadenylation of the puromycin resistance gene |
| BGH pA | Polyadenylation signal from bovine growth hormone gene (SEQ ID NO: 27), allowing efficient transcription termination and polyadenylation of the mRNA of interest |
| pSV40 | SV40 promoter (SEQ ID NO: 20) driving high-level expression of the neomycin resistance gene only after HR |
| pMB1 ORI | Permits high-copy number replication and growth in *E. coli* bla promoter |
| AmpR | Ampicillin (bla) resistance gene (β-lactamase), for selection of transformants in *E. coli* |

Most preferably constructs (iii) comprise SEQ ID NO: 38 and SEQ ID NO: 39, which consist of pCLS1088 (FIG. 33) or pCLS2147 (FIG. 34), respectively. These 5647 by vectors contain two different ORFs of the Meganuclease under the control of the CMV promoter.

The important features of pCLS 1088 and pCLS2147 are described in table 3 below. All features have been functionally tested.

TABLE 3

| Feature | Benefit |
|---|---|
| pCMV | Human cytomegalovirus immediate early promoter; allowing high-level expression of your GOI (Andersson et al., 1989; Boshart et al., 1985; Nelson et al., 1987) |
| Meganuclease(s) | Meganuclease ORFs (SEQ ID NO: 14 or SEQ ID NO: 15), improving HR events at the cGPS locus |
| TK pA | Polyadenylation signal from herpes simplex virus thymidine kinase gene, allowing efficient transcription termination and polyadenylation of the meganuclease mRNA |
| pUC & fl origins | Permits high-copy number replication and growth in *E. coli* |
| AmpR | Ampicillin resistance gene (β-lactamase) for selection of transformants in *E. coli* |

Most preferably constructs (iv) comprise ORFs of the Meganuclease (SEQ ID NO: 14 and SEQ ID NO: 15).

Wherein constructs (iv) consist of Meganuclease polyadenylated mRNAs (SEQ ID NO 34, SEQ ID NO 35), from which the ribosomal scanning is mediated either by 7-methylguanine capped sequence or by internal ribosome entry site (IRES). (see FIG. 3).

Wherein constructs (v) consist of a cell penetrating peptide fused to the N-terminal part of Meganuclease. An example of a meganuclease according to this aspect of the present invention is provided as SEQ ID NO: 58, this sequence encodes an I-CreI monomer with the cell-penetrating peptide DPV15b (SEQ ID NO: 56) fused to the N-terminal of the meganuclease and a 6x hisitidine tag (SEQ ID NO: 70) fused at the C-terminal of the meganuclease. The Inventors have also evaluated another cell-penetrating peptide DPV 1047 (SEQ ID NO: 57).

Cell penetrating peptides were initially developed following the observation that certain proteins, including the HIV-1 protein Tat, could cross the cell membrane (34). The HIV-1 transcriptional activator Tat is a multifunctional protein that, in addition to acting as a powerful inducer of viral gene expression, is transported in and out of the cells (35). This cell penetration property relies on the integrity of a highly basic arginine-rich sequence (amino acids 49-58).

Peptides containing this arginine-rich sequence have been developed, named Tat peptides, that after conjugation to a range of macromolecules can facilitate cellular entry of the conjugate. This method of intracellular delivery has been used successfully in vitro for a range of macromolecules including fluorochromes, enzymes, antibodies and liposomes (41, 42, 43, 45, 47, 48). The Tat peptide has also been shown to facilitate cellular entry of functional proteins such as β-galactosidase in vivo (46).

A number of other proteins and their peptide derivatives have been found to possess similar cell internalization properties including the herpes virus tegument protein VP22 (37), the homoeotic protein of *Drosophila melanogaster* antennapedia (Antp), (the internalizing peptide derived from full length Antp is called penetratin) (36), the protegrin 1 (PG-1) antimicrobial peptide SynB (40) and the basic fibroblast growth factor (39). The carrier peptides derived from these proteins show little sequence homology with each other, but are all highly cationic and arginine- or lysine-rich. Following on from this observation, synthetic polyarginine peptides have been shown to be internalized with a high level of efficiency (38, 44).

All such cell-penetrating peptides which can cause an increase in the rate of internalisation of a meganuclease linked thereto are incorporated in the present patent application.

According to a second aspect of the present invention there is provided a kit to introduce a sequence encoding a GOI into at least one cell, comprising the set of genetic constructs according to the first aspect of the present invention; and instructions for the generation of a transformed cell using said set of genetic constructs.

Preferably the kit, further comprising construct (vi) consisting of SEQ ID NO: 17 (Lac-Z) which consists of pTV-DS-LacZ.

pTV-DS-LacZ is a 9981 by vector that expresses LacZ (as a positive control) in place of the GOI under the control of the CMV promoter as previously described (23). It also contains two homology arms for efficient homologous recombination and insertion of the GOI at the cGPS locus. FIG. 4 summarizes the features of the vector. Features of pTV-DS-LacZ are composed of the very same features as pTV-DS-MCS2 but this plasmid contains the LacZ gene encoding the β-galactosidase protein under the control of the CMV promoter. It can be used as a positive control for HR at the cGPS site.

Preferably, the kit further comprises at least one cell stably transformed with said construct (i).

Most preferably the at least one cell is selected from the group comprising: CHO-K1 cells (Sigma-Aldrich); HEK-293-derived cells (Invitrogen); Caco2 cells (Invitrotech); U2-OS cells (Invitrogen); NIH 3T3 cells (Invitrogen); NSO cells (Sigma-Aldrich); SP2 cells (Sigma-Aldrich); CHO-S cells (Invitrogen); DG44 cells (Invitrogen).

According to a third aspect of the present invention there is provided a method for transforming by HR at least one cell comprising the steps of:

A method for transforming by homologous recombination at least one cell comprising the steps of:

a) stably transforming at least one cell by inserting construct (i) as defined above into the genome of said at least one cell;

b) cloning a sequence coding for a gene of interest into position B3 of construct (ii) as defined above;

c) co-transfecting said cell of step a), with said construct (ii) of step b) and constructs (iii), (iv) or (v) as defined above;

d) following homologous recombination between said construct (ii) and said stably inserted construct (i), selecting at least one cell from step c) based upon: the absence of a first marker gene encoded by component A4 of said construct (i) and the activity of a second marker gene encoded by component B1 and the activity of a third marker gene encoded by component A5.

Most preferably, selection in step d) is carried out sequentially for each of said first marker, said second marker and said third marker.

For a better understanding of the invention and to show how the same may be carried into effect, there will now be shown by way of example only, specific embodiments, methods and processes according to the present invention with reference to the accompanying drawings in which.

Panel A: cGPS NIH3T3 cells are transfected with meganuclease expression plasmid alone (left), lacz integration matrix alone (middle) or both (right). Upon double selection process, resistant clones are stained with X-Gal for lacz expression monitoring.

Panel B: Double resistant clone genomic DNA is digested with RsRII restriction enzyme and analyzed by Southern blotting using a neo probe. Genomic DNA from cGPS NIH3T3 and wt NIH3T3 are analyzed as well.

Figure 10:
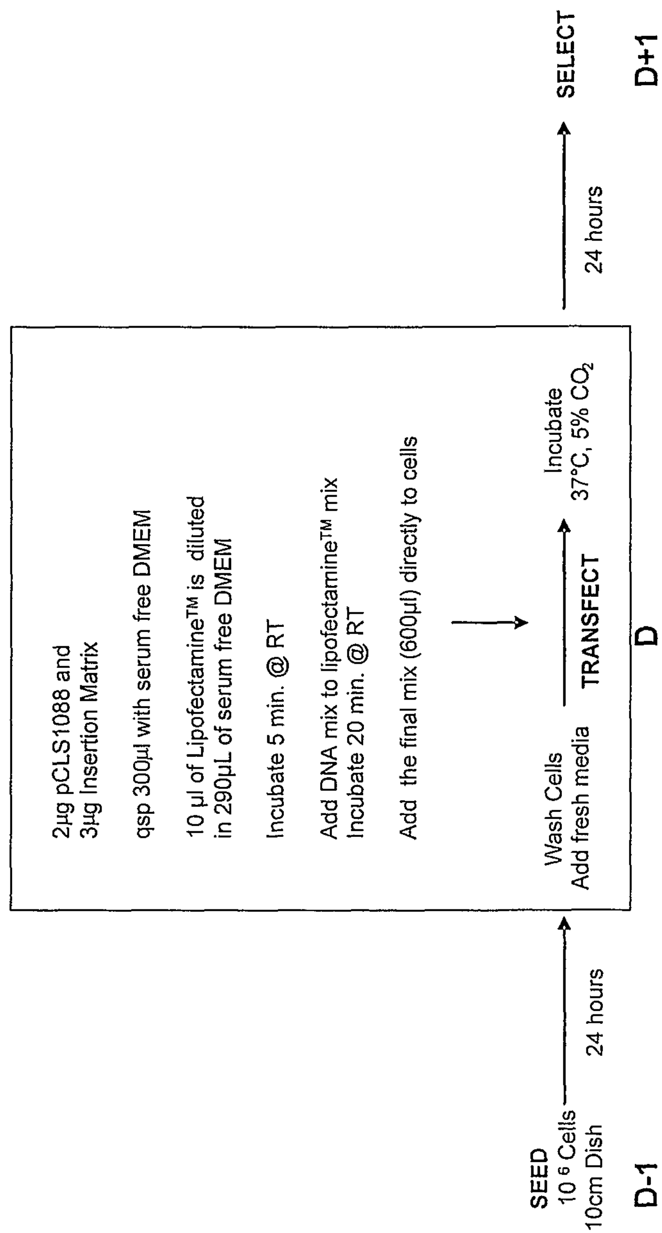

FIG. 10 shows a schematic representation of a transfection protocol for the cGPS HEK 293 cell line according to the present invention.

Figure 11:
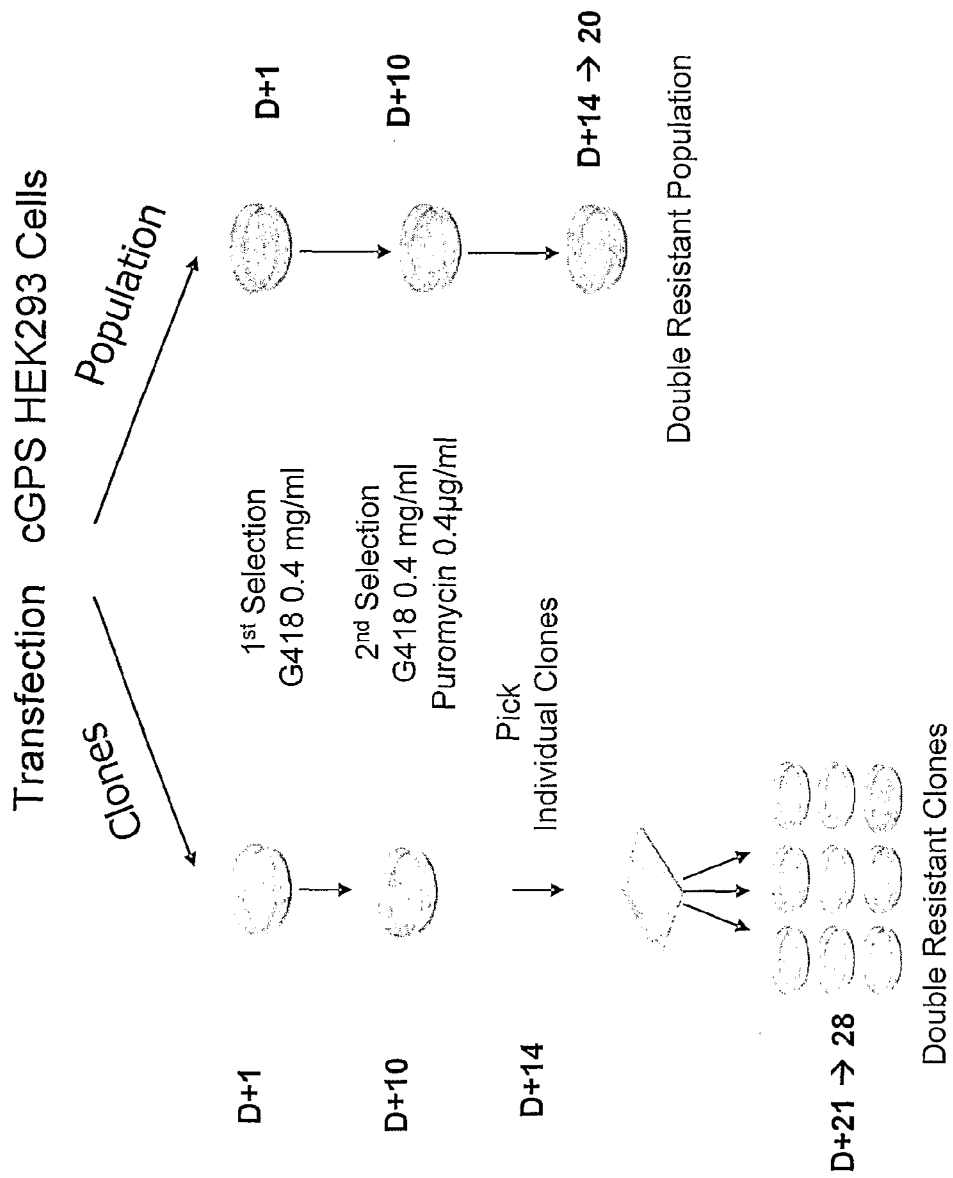

FIG. 11 shows a schematic representation of the clonal selection protocol (left column) and batch selection protocol (right column) for the cGPS HEK 293 cell line.

Figure 12:
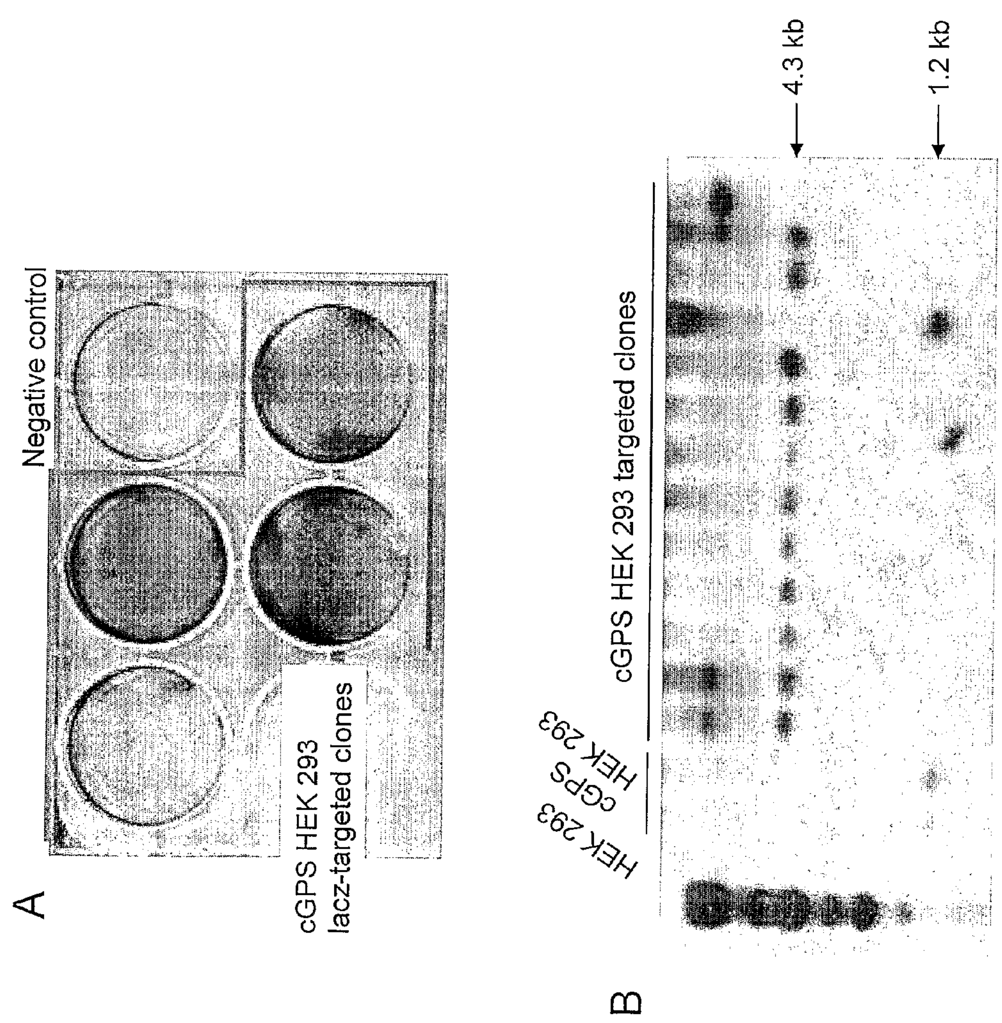

FIG. 12 shows the production of double resistant lacz targeted clones in the cGPS HEK 293 system and their molecular characterization.

Panel A: cGPS HEK293 cells are transfected with meganuclease expression plasmid alone (upper right well), or meganuclease expression plasmid and lacz integration matrix (lower middle well). Upon double selection process, resistant clones are stained with X-Gal for lacz expression monitoring.

Panel B: Double resistant clone genomic DNA is digested with RsRII restriction enzyme and analyzed by Southern blotting using a neo probe. Genomic DNA from cGPS HEK293 and wt HEK293 are analyzed as well.

Figure 13:
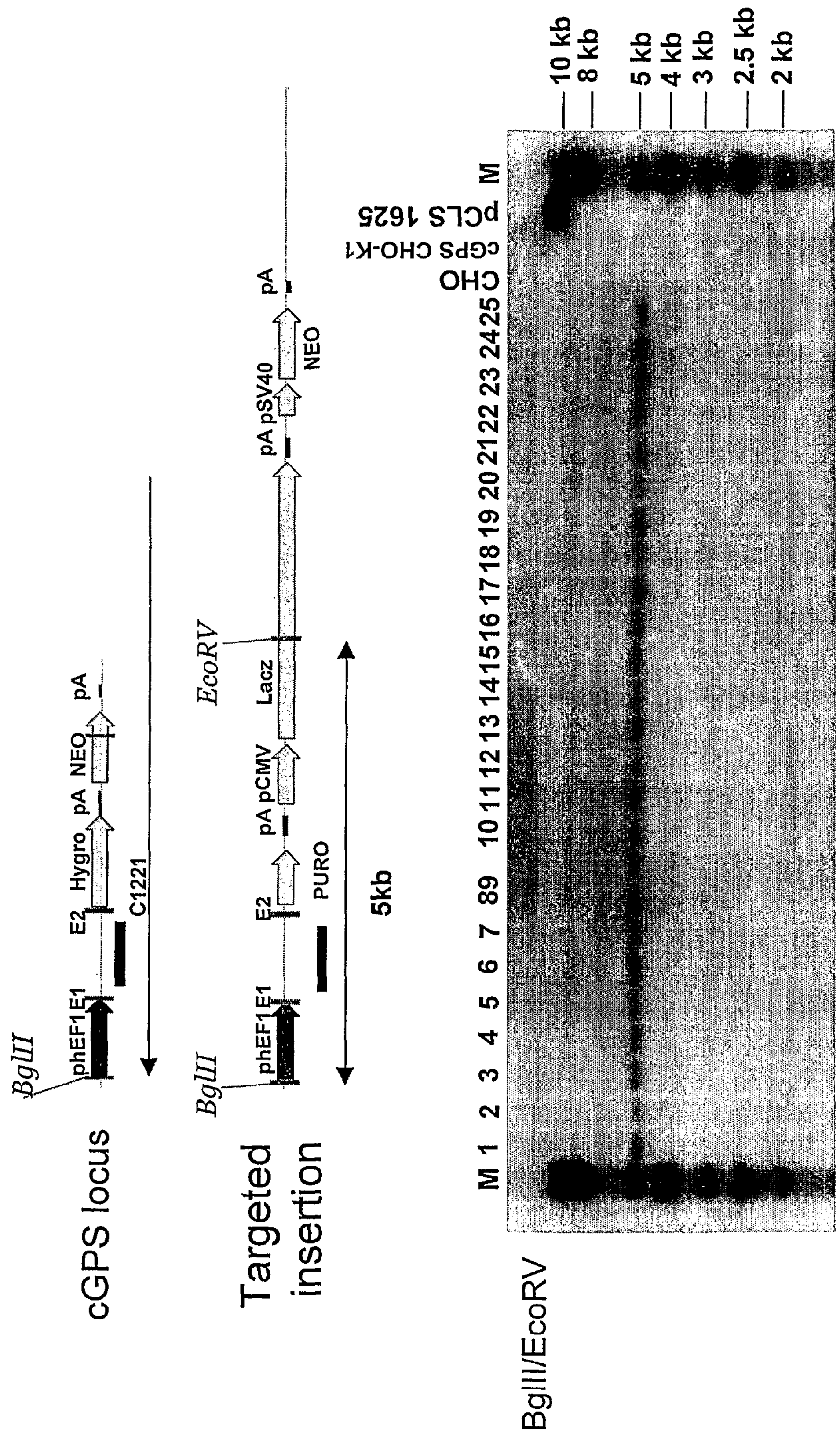

FIG. 13 shows a Southern blot analysis of 25 selected clones targeted with the pTV-DS-LacZ vector.

Figure 14:
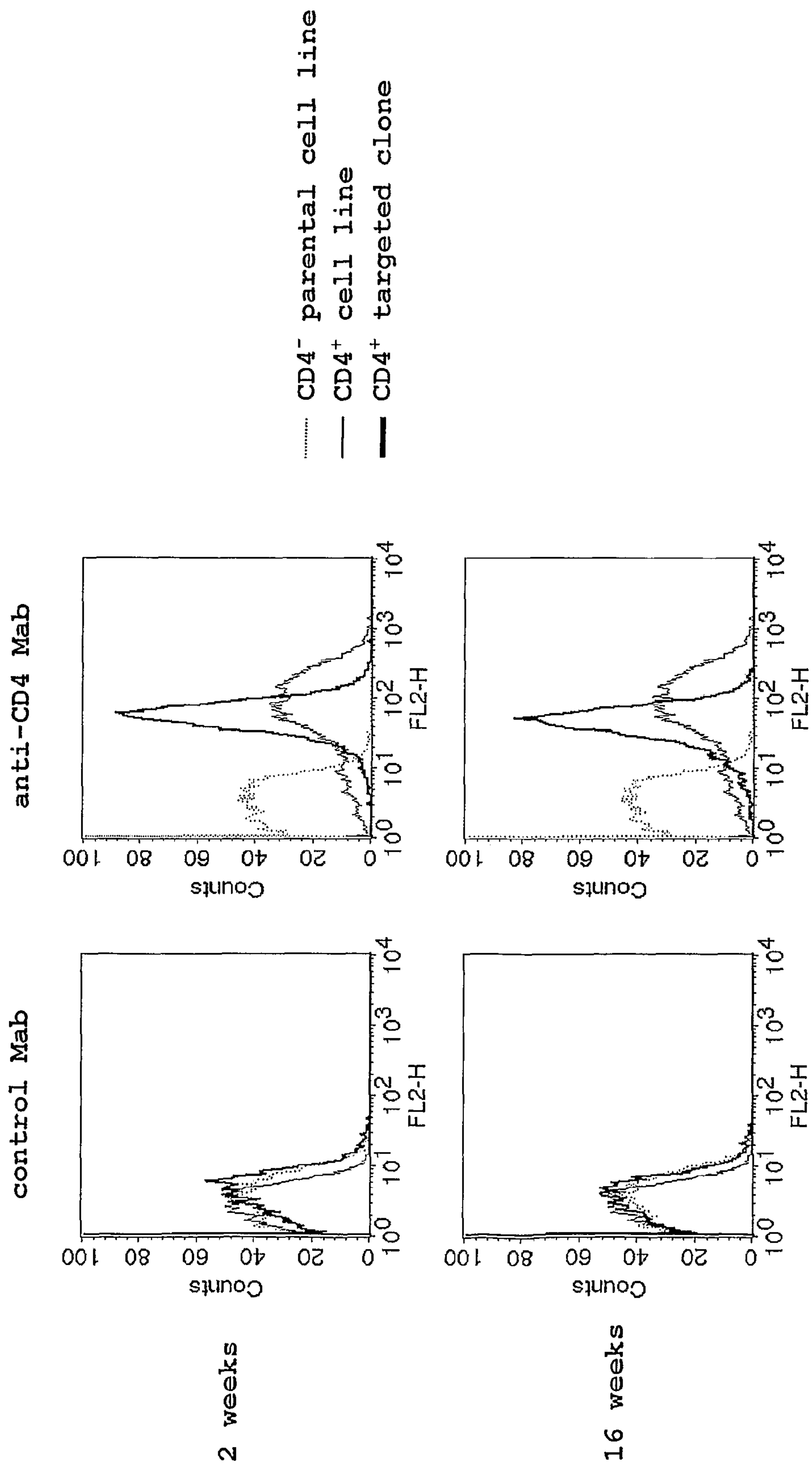

FIG. 14 shows the results of experiments to determine by FACS analysis the stability of human CD4 expression over time.

Figure 15:
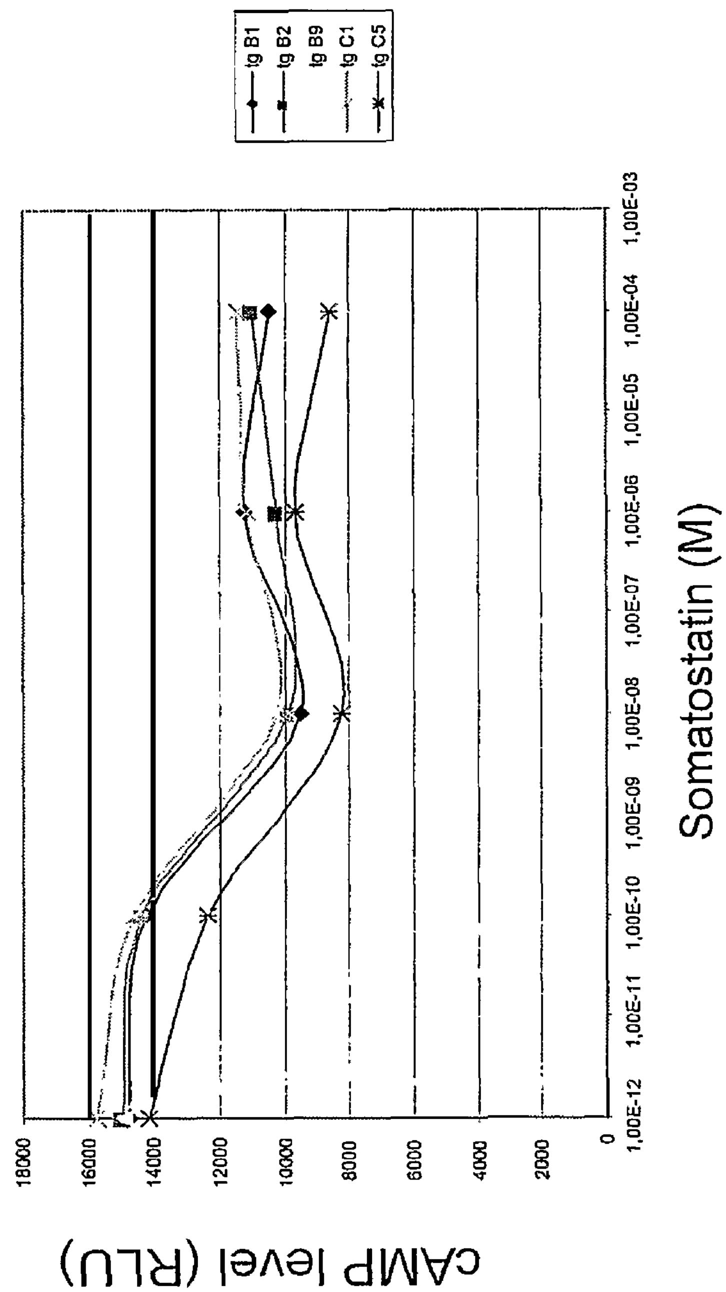

FIG. 15 shows the results of a functional assay for cAMP production inhibition performed upon clones targeted with the somatostatin receptor (GPCR-SSTR2) as GOI.

Figure 16:
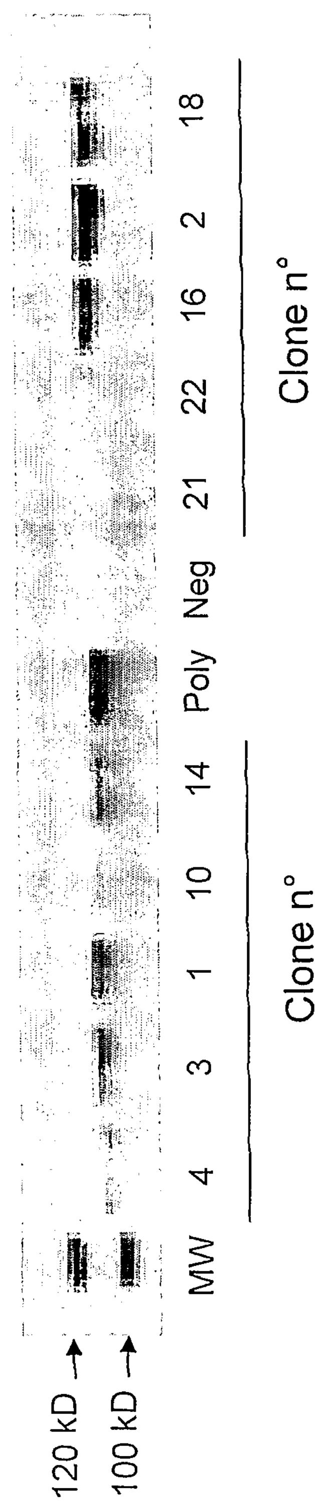

FIG. 16 shows the results of hATX expression from cGPS CHO-K1 hATX.

Figure 17:
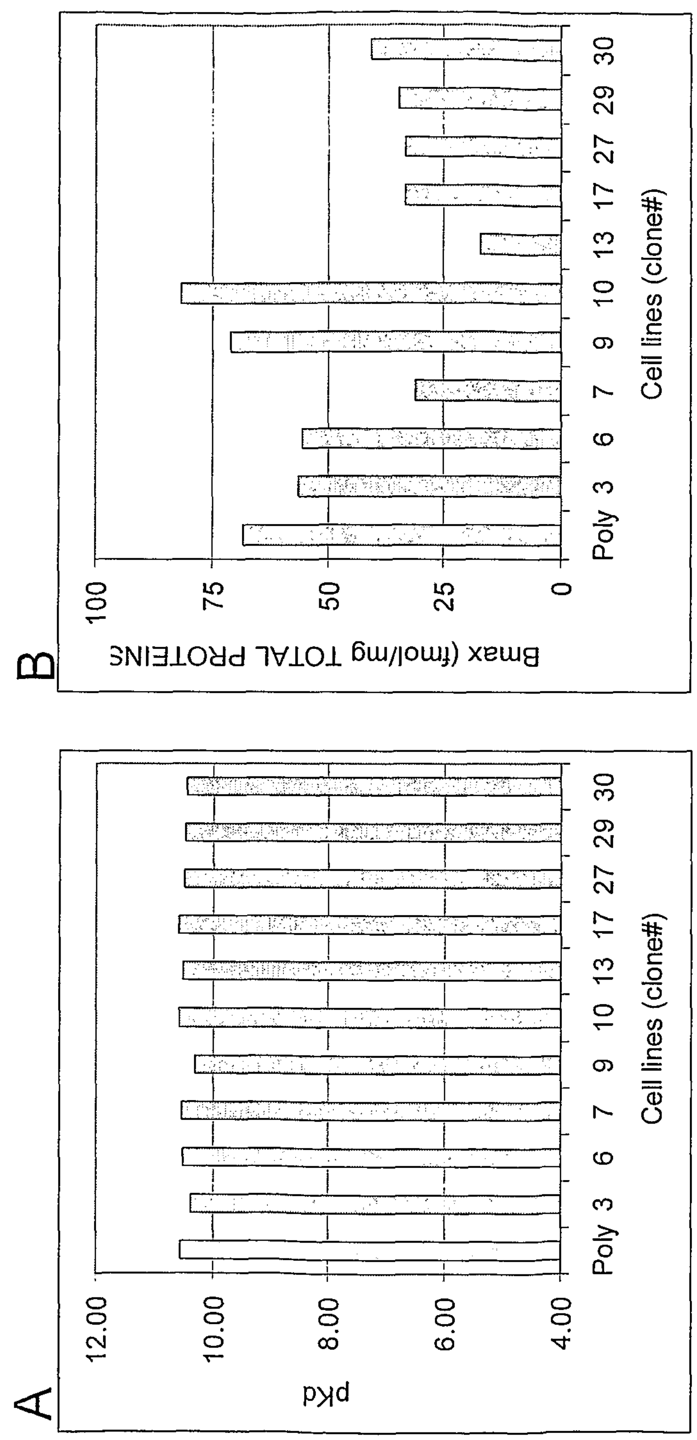

FIG. 17 shows the results of radioligand saturation experiments performed on cGPS CHO-K1 hMT1-targeted clones.

Panel A: The assessment of $hMT_1$ expression in 10 cGPS CHO-K1/$hMT_1$ clones and a cGPS CHO-K1/$hMT_1$ polyclonal cell population was performed by radioligand saturation curves.

Panel B: Figure displays the maximum number of binding sites reported to the total proteins in 10 cGPS CHO-K1/$hMT_1$ clones and a cGPS CHO-K1/$hMT_1$ polyclonal cell population.

Figure 18:
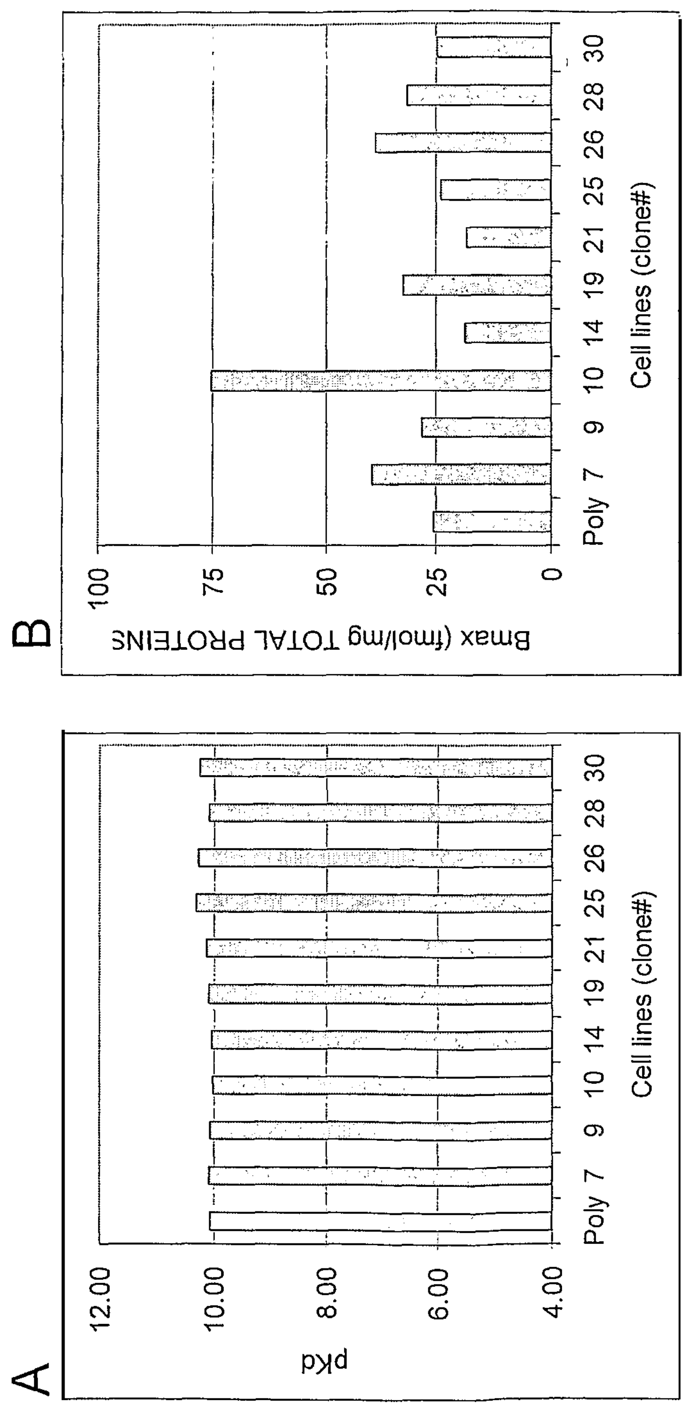

FIG. 18 shows the results of radioligand saturation experiments performed on cGPS CHO-K1 $hMT_2$-targeted clones.

Panel A: The assessment of $hMT_2$ expression in 10 cGPS CHO-K1/$hMT_2$ clones and a cGPS CHO-K1/$hMT_2$ polyclonal cell population was performed by radioligand saturation curves.

Panel B: Figure displays the maximum number of binding sites reported to the total proteins in 10 cGPS CHO-K1/$hMT_2$ clones and a cGPS CHO-K1/$hMT_2$ polyclonal cell population.

Figure 19:
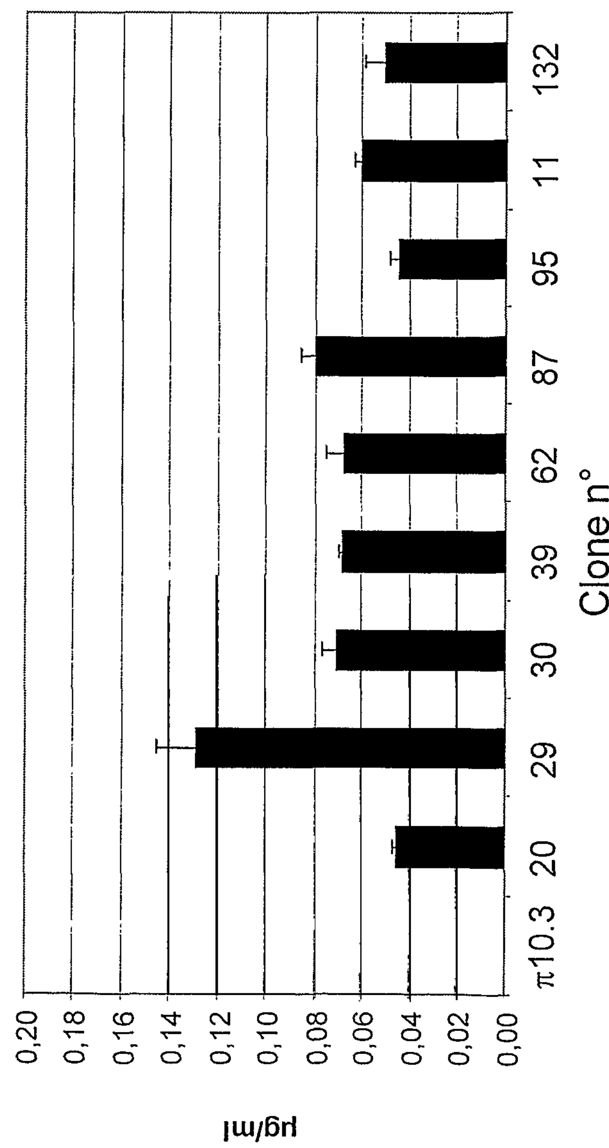

FIG. 19 shows the results of experiments to determine the homogeneity of expression levels of several clones expressing a monoclonal antibody that is controlled by the Ubiquitin sub unit c promoter (pUbc).

Figure 20:
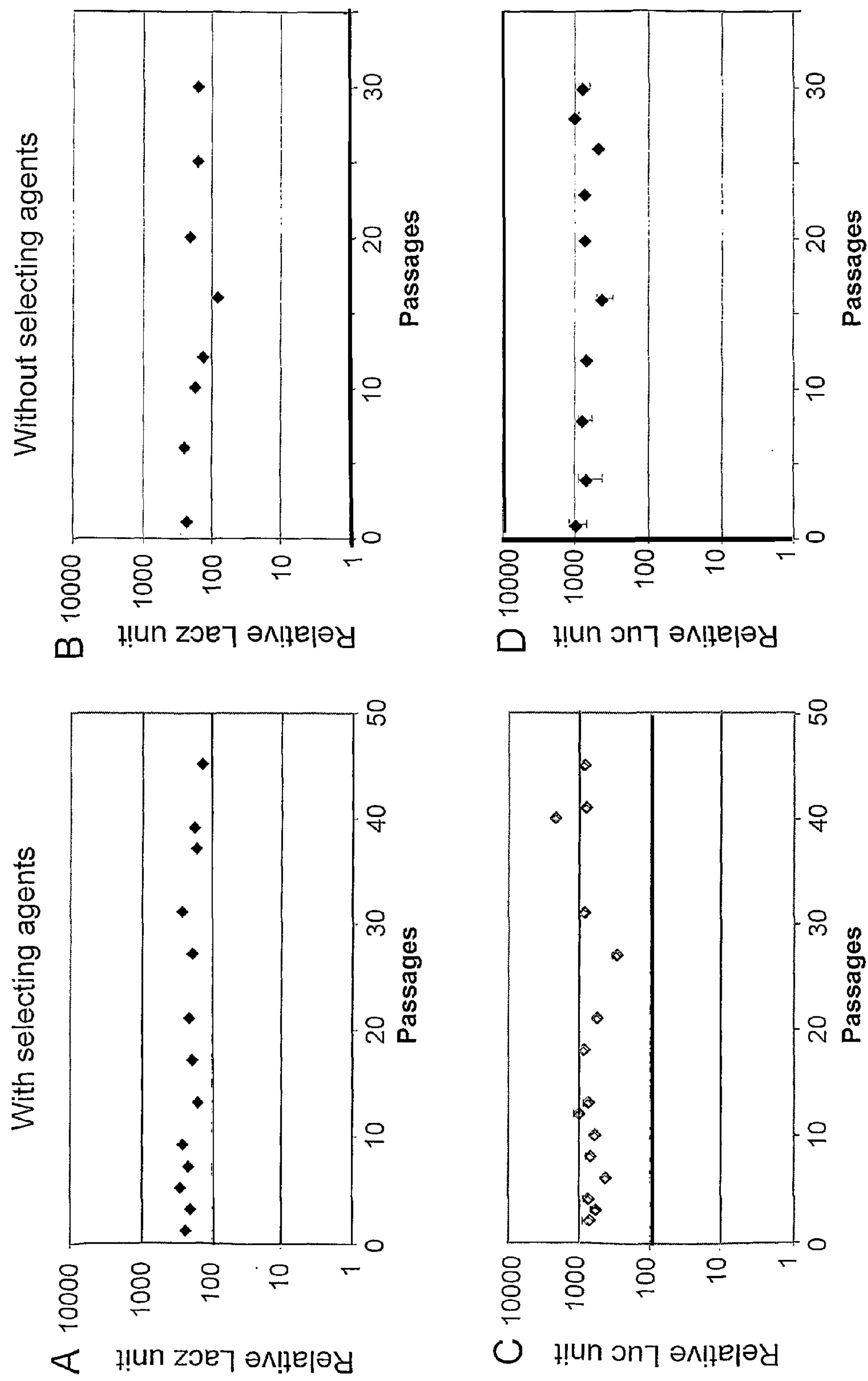

FIG. 20 shows the stability of expression of β-galactosidase (Panel A and B: mean value for 4 cGPS CHO-K1 lacz targeted clones) and luciferase (Panel C and D: mean value for 4 cGPS CHO-K1 luciferase targeted clones) over a period of 23 weeks in the presence (Panel A and C) of the selecting agents and over a period of 15 weeks in the absence (Panel B and D) of selecting agents.

Figure 21:
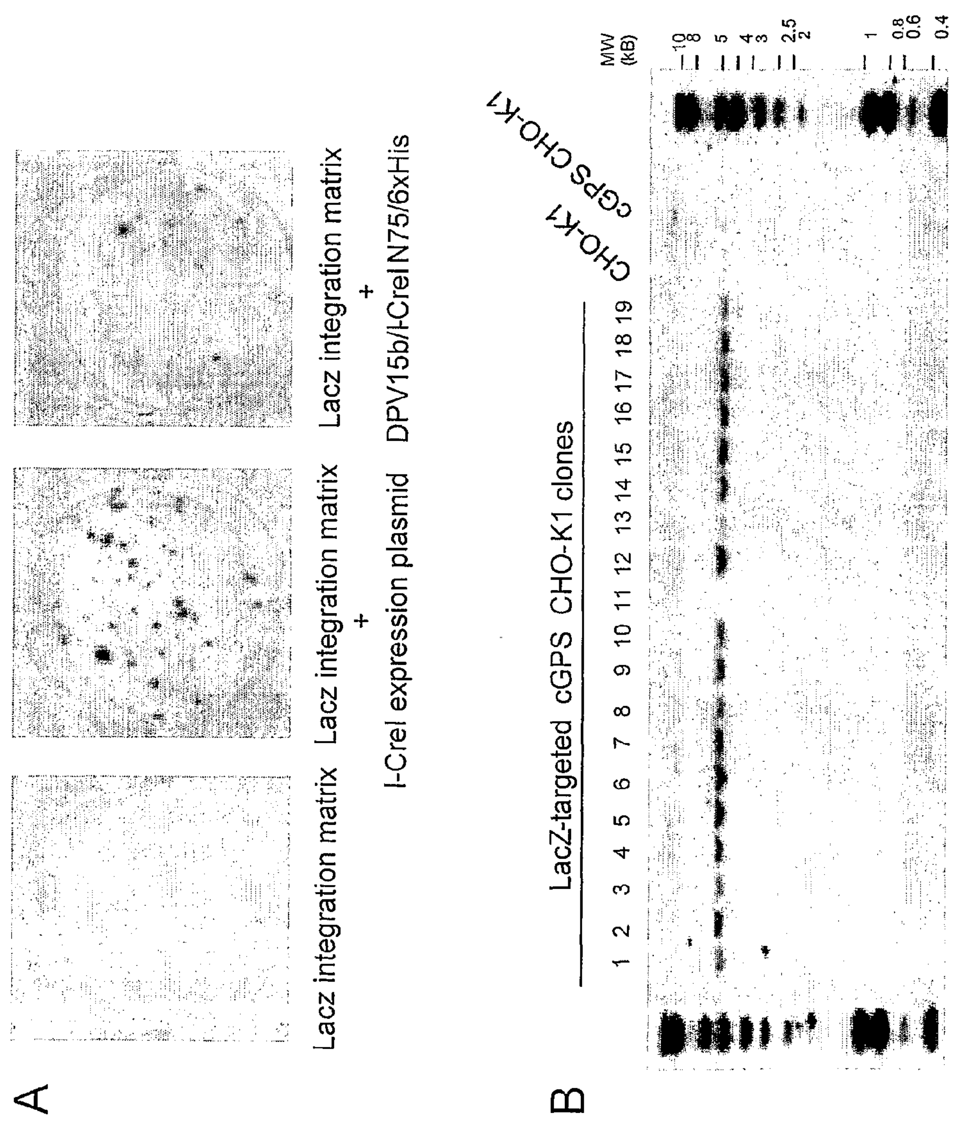

FIG. 21 shows the efficacy of gene targeting through the use of a I-CreI recombinant protein fused to a penetrating peptide (DPV15b/I-CreI N75/6xHis).

Panel A: cGPS CHO-KI cells are transfected with lacz integration matrix alone (negative control, left), lacz integration matrix and meganuclease expression plasmid (positive control, middle) or lacz integration matrix and a I-CreI recombinant protein fused to a penetrating peptide (DPV15b/I-CreI N75/6xHis) (right). Upon double selection process, resistant clones are stained with X-Gal for lacz expression monitoring.

Panel B: Double resistant clone genomic DNA is digested with RsRII restriction enzyme and analyzed by Southern blotting using a neo probe. Genomic DNA from cGPS CHO-K1 and wt CHO-K1 are analyzed as well.

Figure 22:
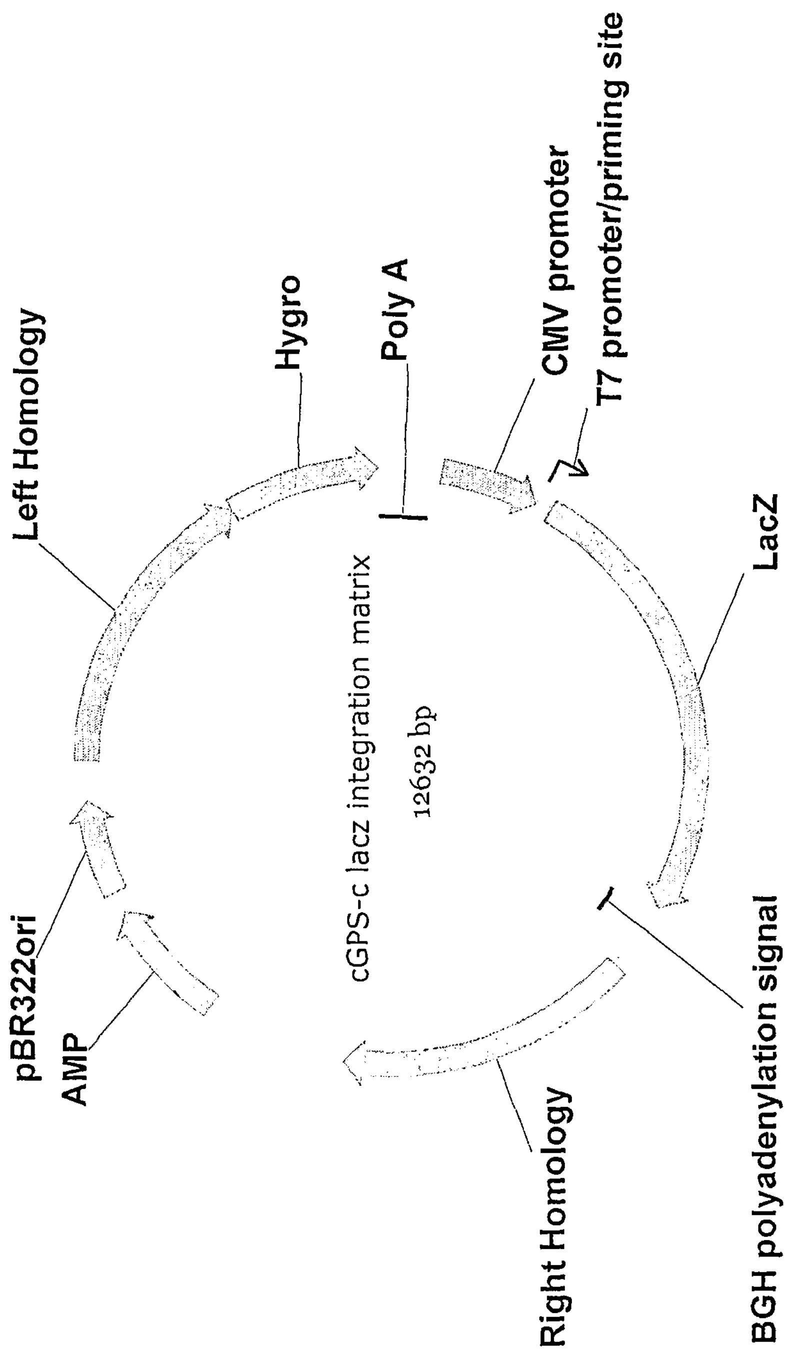

FIG. 22 shows a schematic representation of the cGPS custom CHO-K1 lacz integration matrix vector.

Figure 23:
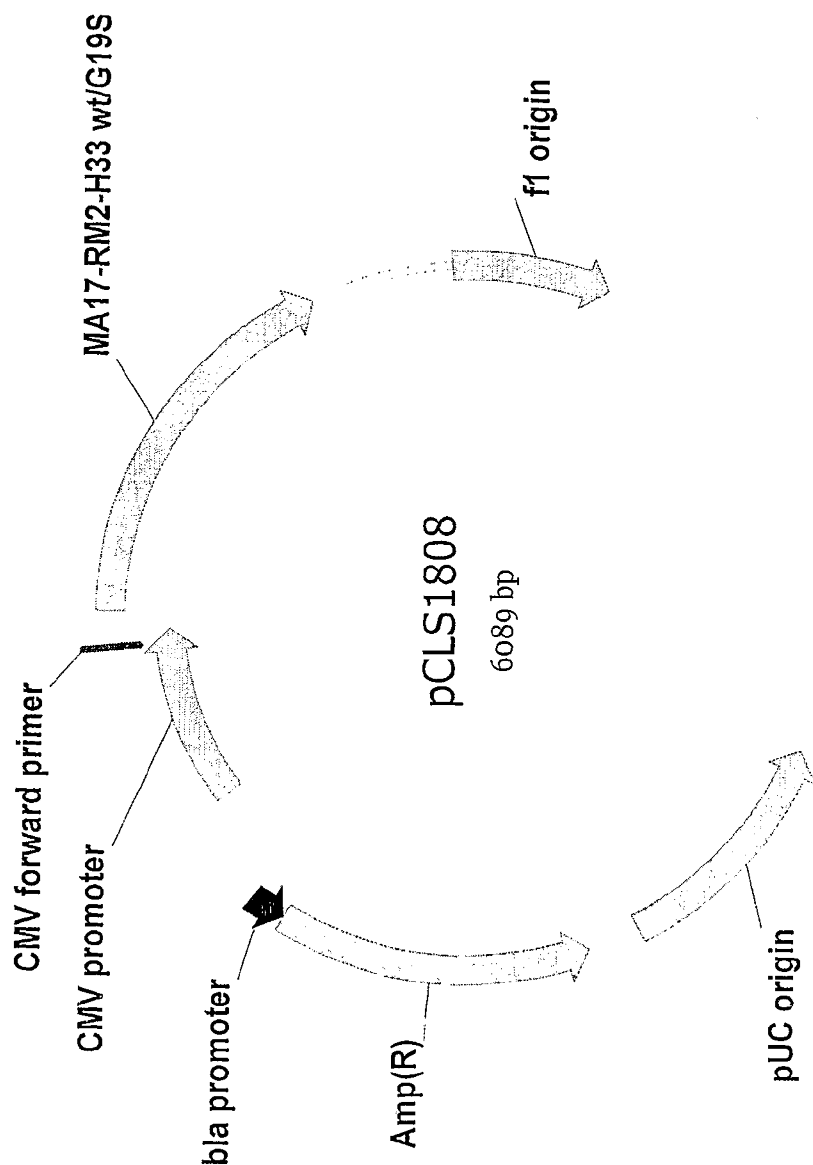

FIG. 23 shows a schematic representation of the Sc MA17-RM2-G19H33 meganuclease expression vector.

Figure 24:
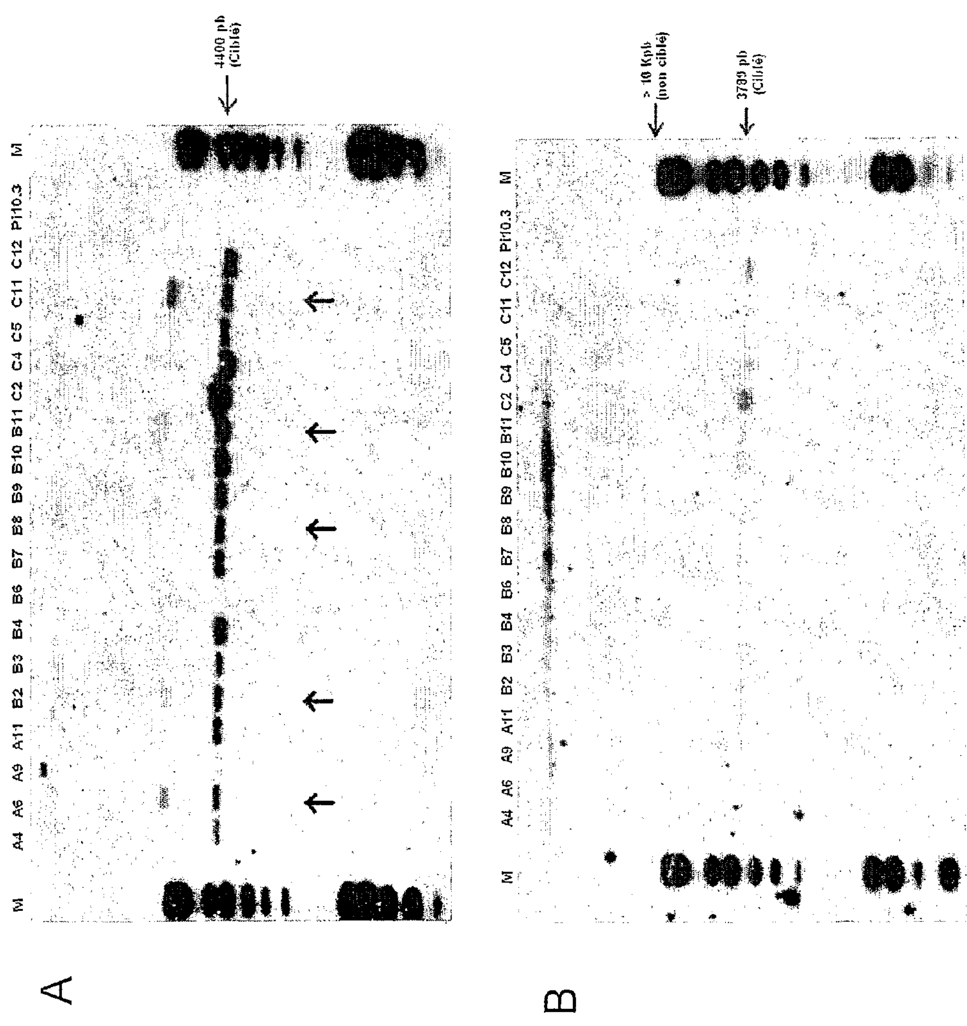

FIG. 24 shows a molecular characterization by southern blot of double targeted clones. Southern blot analysis of 18 double targeted cGPS and cGPS custom CHO-K1 clones expressing both the luciferase gene and the lacz gene reporters using a neo probe (monitoring the cGPS locus, panel A) or a HPRT exon3 probe (monitoring the HPRT locus, panel B).

Figure 25:
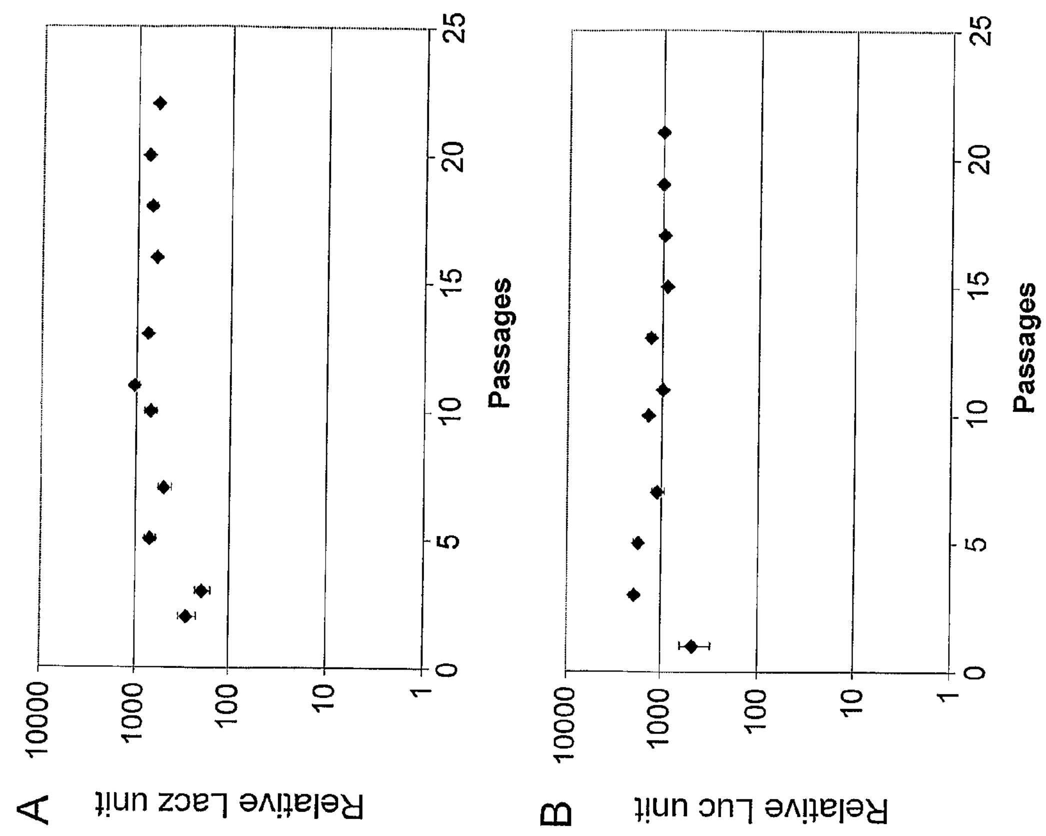

FIG. 25 shows the stability of expression of β-galactosidase (Panel A) and luciferase (Panel B) (mean value for 4 double targeted clones) over a period of 11 weeks.

Figure 26:
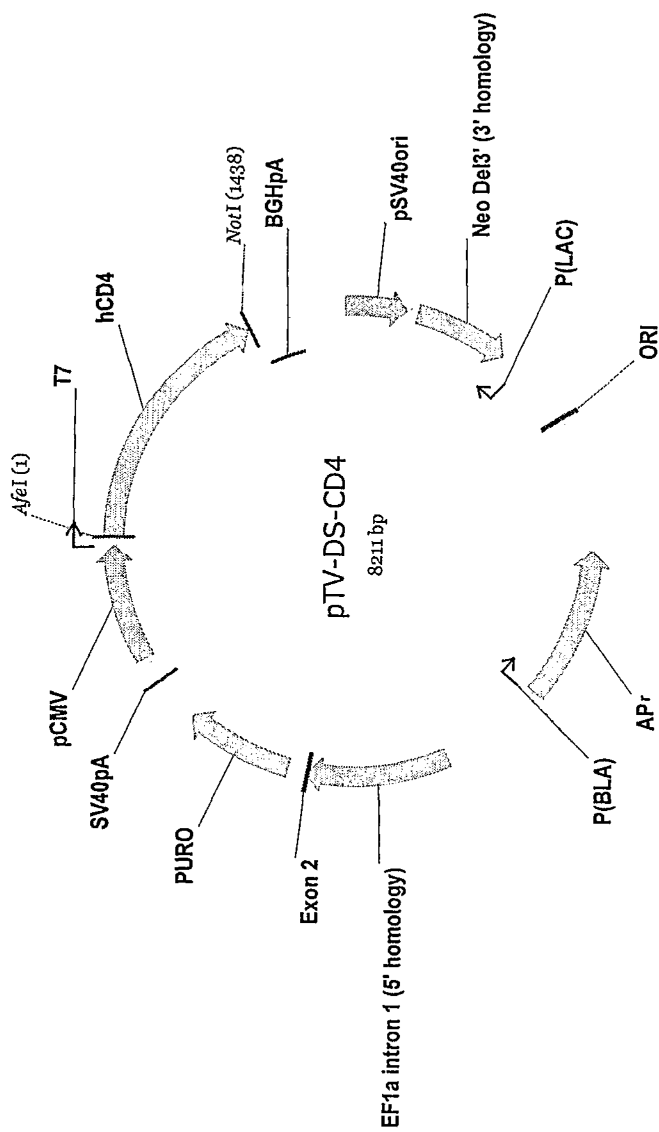

FIG. 26 shows a schematic representation of the pTV-DS-CD4 vector.

Figure 27:
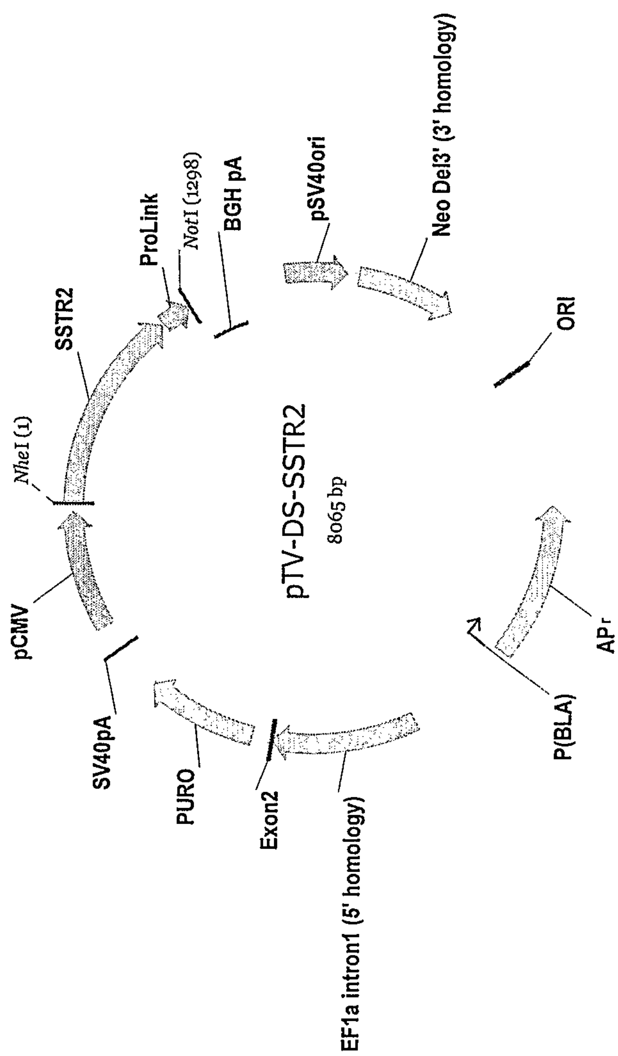

FIG. 27 shows a schematic representation of the pTV-DS-SSTR2 vector.

Figure 28:
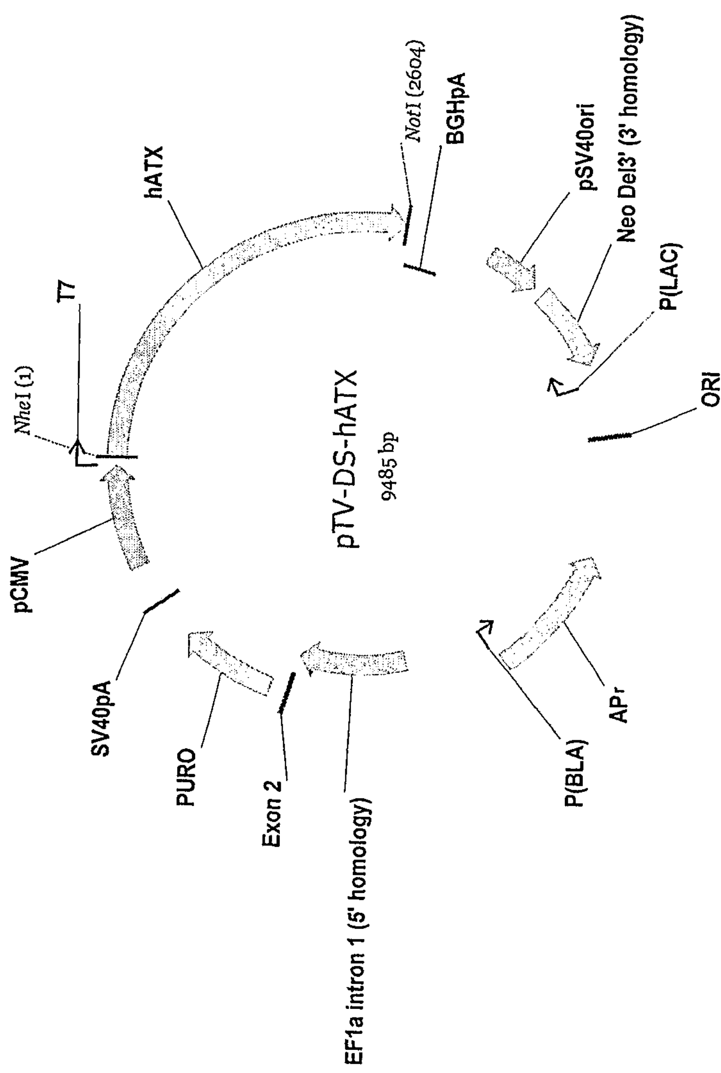

FIG. 28 shows a schematic representation of the pTV-DS-hATX vector.

Figure 29:
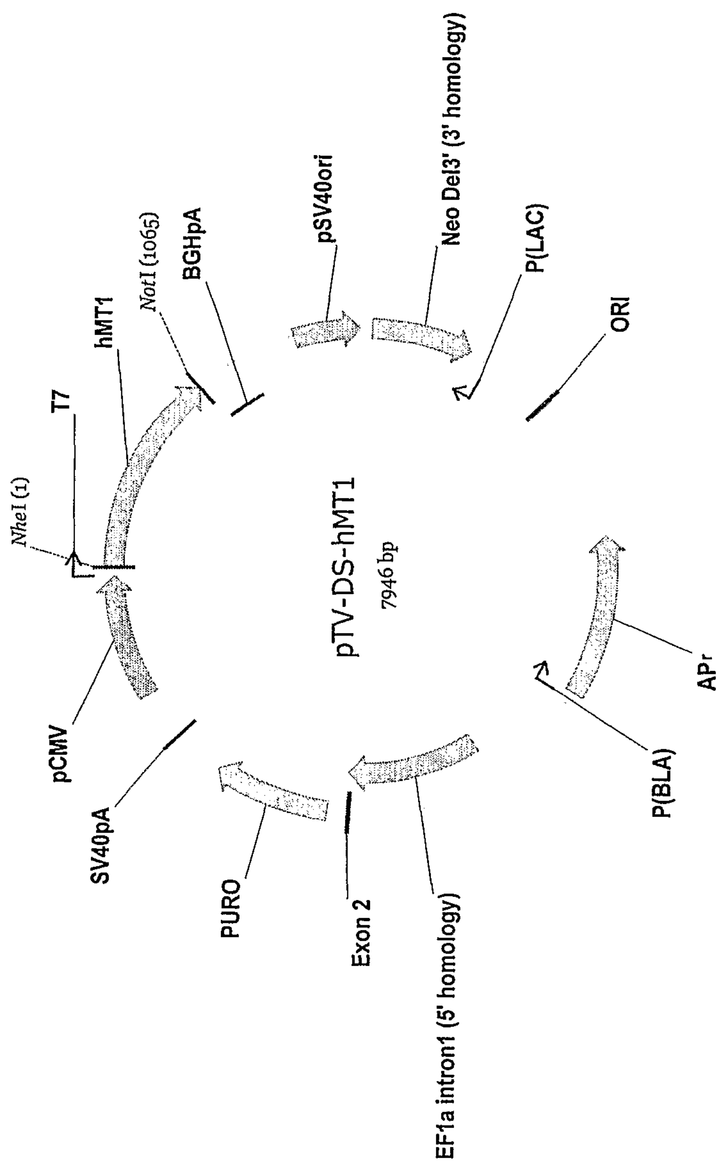

FIG. 29 shows a schematic representation of the pTV-DS-hMT1 vector.

Figure 30:
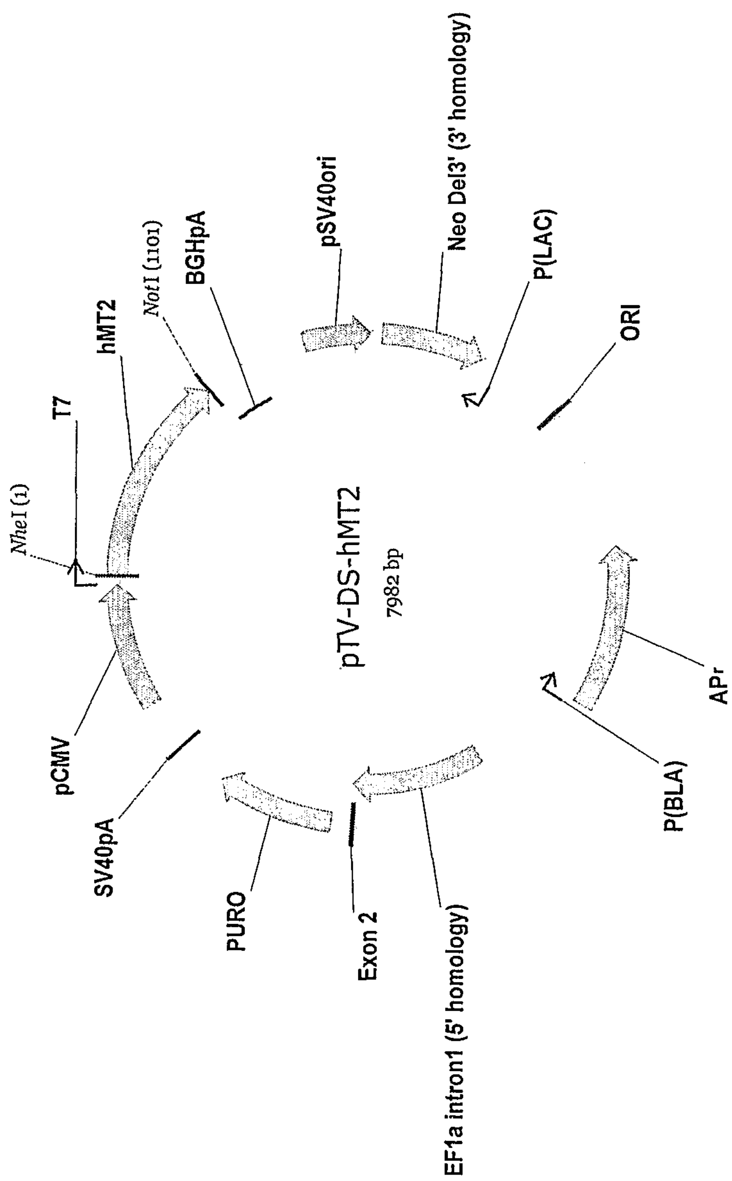

FIG. 30 shows a schematic representation of the pTV-DS-hMT2 vector.

Figure 31:
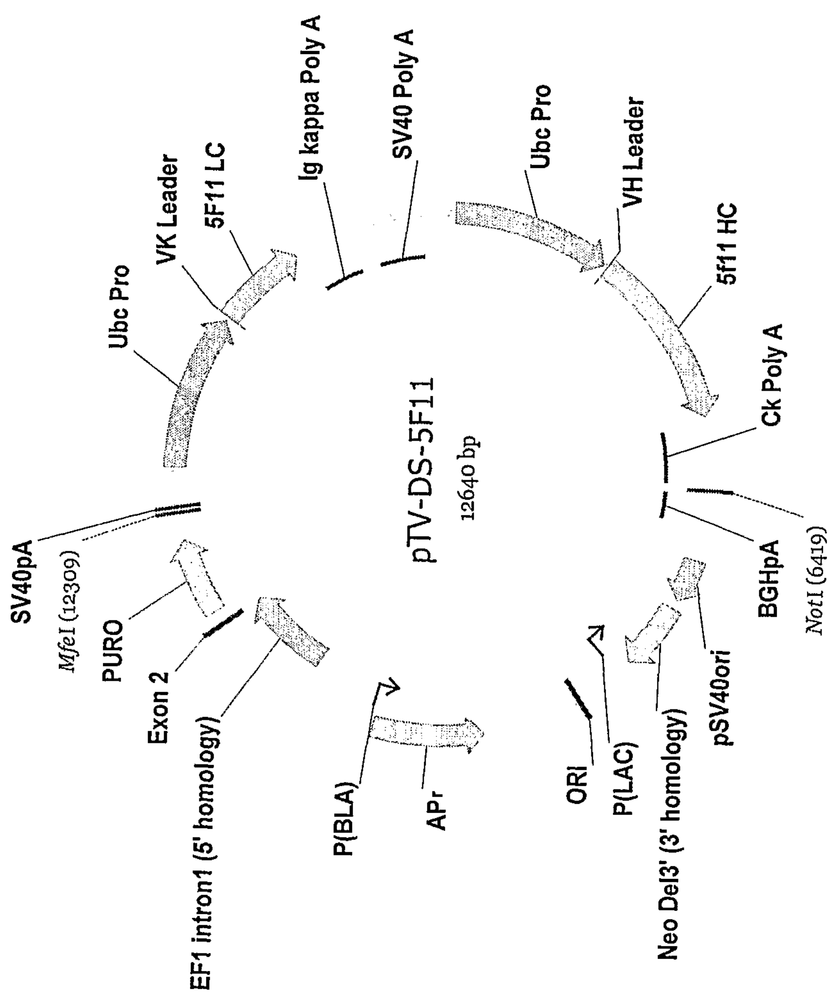

FIG. 31 shows a schematic representation of the pTV-DS-5F11 vector.

Figure 32:
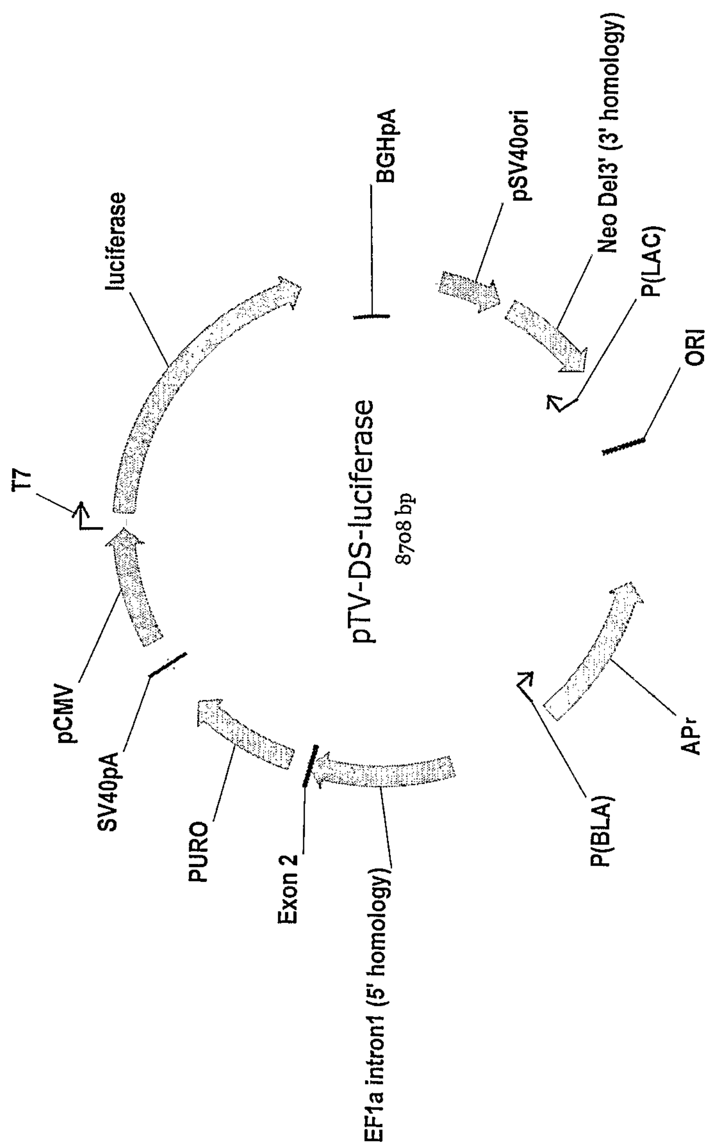

FIG. 32 shows a schematic representation of the pTV-DS-luciferase vector.

Figure 33:
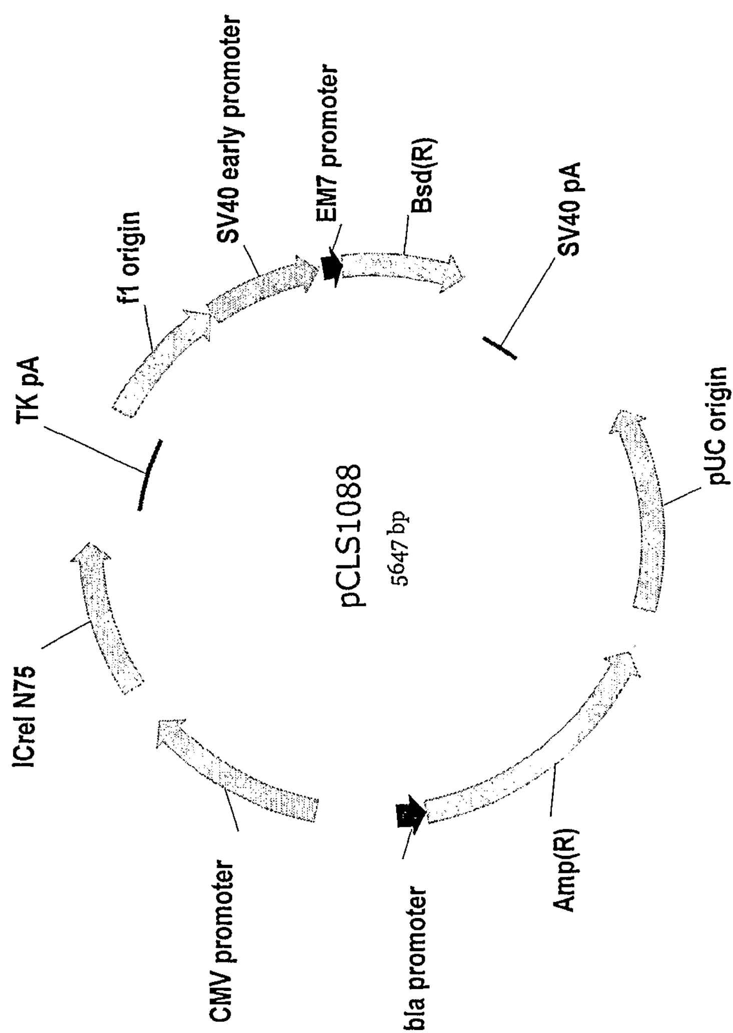

FIG. 33 shows a schematic representation of the I-CreI N75 meganuclease expression vector.

Figure 34:
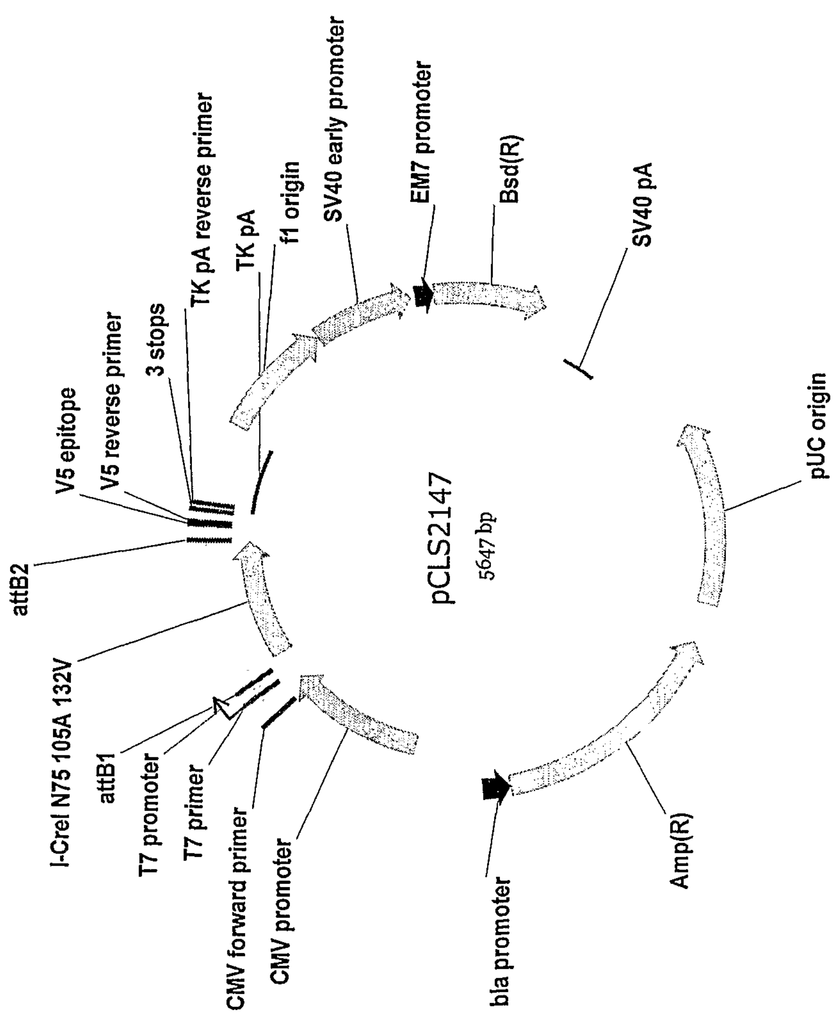

FIG. 34 shows a schematic representation of the I-CreI N75 105A 132V meganuclease expression vector.

There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

Definitions

Amino acid residues in a polypeptide sequence are designated herein according to the one-letter code, in which, for example, Q means Gin or Glutamine residue, R means Arg or Arginine residue and D means Asp or Aspartic acid residue.

hydrophobic amino acid refers to leucine (L), valine (V), isoleucine (I), alanine (A), methionine (M), phenylalanine (F), tryptophane (W) and tyrosine (Y).

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

by "meganuclease" is intended an endonuclease having a double-stranded DNA target sequence of 12 to 45 bp. Examples include I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-May I, PI-Mch I, PI-Mfu I, PI-Mfl I, PI-Mga I, PI-Mgo I, PI-Min I, PI-Mka I, PI-Mle I, PI-Mma 1, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, PI-Tsp I, I-MsoI.

by "parent LAGLIDADG homing endonuclease" (SEQ ID NO: 69) is intended a wild-type LAGLIDADG homing endonuclease (SEQ ID NO: 69) or a functional variant thereof. Said parent LAGLIDADG homing endonuclease (SEQ ID NO: 69) may be a monomer, a dimer (homodimer or heterodimer) comprising two LAGLIDADG homing endonuclease core domains (SEQ ID NO: 69) which are associated in a functional endonuclease able to cleave a double-stranded DNA target of 22 to 24 bp.

- by "homodimeric LAGLIDADG homing endonuclease" (SEQ ID NO: 69) is intended a wild-type homodimeric LAGLIDADG homing endonuclease (SEQ ID NO: 69) having a single LAGLIDADG motif (SEQ ID NO: 69) and cleaving palindromic DNA target sequences, such as I-CreI or I-MsoI or a functional variant thereof.
- by "LAGLIDADG homing endonuclease variant" (SEQ ID NO: 69) or "variant" is intended a protein obtained by replacing at least one amino acid of a LAGLIDADG homing endonuclease sequence(SEQ ID NO: 69), with a different amino acid.
- by "functional variant" is intended a LAGLIDADG homing endonuclease variant (SEQ ID NO: 69) which is able to cleave a DNA target, preferably a new DNA target which is not cleaved by a wild type LAGLIDADG homing endonuclease (SEQ ID NO: 69). For example, such variants have amino acid variation at positions contacting the DNA target sequence or interacting directly or indirectly with said DNA target.
- by "homing endonuclease variant with novel specificity" is intended a variant having a pattern of cleaved targets (cleavage profile) different from that of the parent homing endonuclease. The variants may cleave less targets (restricted profile) or more targets than the parent homing endonuclease. Preferably, the variant is able to cleave at least one target that is not cleaved by the parent homing endonuclease.

The terms "novel specificity", "modified specificity", "novel cleavage specificity", "novel substrate specificity" which are equivalent and used indifferently, refer to the specificity of the variant towards the nucleotides of the DNA target sequence.

- by "I-CreI" is intended the wild-type 1-CreI having the sequence SWISSPROT P05725 or pdb accession code 1g9y (SEQ ID NO: 36).
- by "I-DmoI" is intended the wild-type I-DmoI having the sequence SWISSPROT number P21505 (SEQ ID NO: 37) or the structure PDB code 1b24
- by "domain" or "core domain" is intended the "LAGLIDADG homing endonuclease core domain" (SEQ ID NO: 69) which is the characteristic $\alpha\beta\beta\alpha\beta\beta\alpha$fold of the homing endonucleases of the LAGLIDADG (SEQ ID NO: 69) family, corresponding to a sequence of about one hundred amino acid residues. Said domain comprises four beta-strands folded in an antiparallel beta-sheet which interacts with one half of the DNA target. This domain is able to associate with another LAGLIDADG homing endonuclease core domain (SEQ ID NO: 69) which interacts with the other half of the DNA target to form a functional endonuclease able to cleave said DNA target. For example, in the case of the dimeric homing endonuclease I-CreI (163 amino acids), the LAGLIDADG homing endonuclease core domain (SEQ ID NO: 69) corresponds to the residues 6 to 94. In the case of monomeric homing endonucleases, two such domains are found in the sequence of the endonuclease; for example in I-DmoI (194 amino acids), the first domain (residues 7 to 99) and the second domain (residues 104 to 194) are separated by a short linker (residues 100 to 103).
- by "subdomain" is intended the region of a LAGLIDADG homing endonuclease core domain (SEQ ID NO: 69) which interacts with a distinct part of a homing endonuclease DNA target half-site. Two different subdomains behave independently or partly independently, and the mutation in one subdomain does not alter the binding and cleavage properties of the other subdomain, or does not alter it in a number of cases. Therefore, two subdomains bind distinct part of a homing endonuclease DNA target half-site.
- by "beta-hairpin" is intended two consecutive beta-strands of the antiparallel beta-sheet of a LAGLIDADG homing endonuclease core domain (SEQ ID NO: 69) which are connected by a loop or a turn,
- by "C1221" it is intended to refer to the first half of the I-CreI target site '12' repeated backwards so as to form a palindrome '21'.
- by "cleavage activity" the cleavage activity of the variant of the invention may be measured by a direct repeat recombination assay, in yeast or mammalian cells, using a reporter vector, as described in the PCT Application WO 2004/067736; Epinat et al., Nucleic Acids Res., 2003, 31, 2952-2962; Chames et al., Nucleic Acids Res., 2005, 33, e178, and Arnould et al., J. Mol. Biol., 2006, 355, 443-458. The reporter vector comprises two truncated, non-functional copies of a reporter gene (direct repeats) and a chimeric DNA target sequence within the intervening sequence, cloned in a yeast or a mammalian expression vector. The DNA target sequence is derived from the parent homing endonuclease cleavage site by replacement of at least one nucleotide by a different nucleotide. Preferably a panel of palindromic or non-palindromic DNA targets representing the different combinations of the 4 bases (g, a, c, t) at one or more positions of the DNA cleavage site is tested ($4^n$ palindromic targets for n mutated positions). Expression of the variant results in a functional endonuclease which is able to cleave the DNA target sequence. This cleavage induces homologous recombination between the direct repeats, resulting in a functional reporter gene, whose expression can be monitored by appropriate assay.
- by "DNA target", "DNA target sequence", "target sequence", "target-site", "target", "site"; "recognition site", "recognition sequence", "homing recognition site", "homing site", "cleavage site" is intended a 22 to 24 bp double-stranded palindromic, partially palindromic (pseudo-palindromic) or non-palindromic polynucleotide sequence that is recognized and cleaved by a LAGLIDADG homing endonuclease (SEQ ID NO: 69). These terms refer to a distinct DNA location, preferably a genomic location, at which a double stranded break (cleavage) is to be induced by the endonuclease. The DNA target is defined by the 5' to 3' sequence of one strand of the double-stranded polynucleotide. For example, the palindromic DNA target sequence cleaved by wild type I-CreI is defined by the sequence 5'-$t_{-12}c_{-11}a_{-10}a_{-9}a_{-8}a_{-7}c_{-6}g_{-5}t_{-4}c_{-3}g_{-2}t_{-1}a_{+1}c_{+2}g_{+3}a_{+4}c_{+5}g_{+6}t_{+7}t_{+8}t_{+9}t_{+10}g_{+11}a_{+12}$(SEQ ID NO:8). Cleavage of the DNA target occurs at the nucleotides in positions +2 and −2, respectively for the sense and the antisense strand. Unless otherwise indicated, the position at which cleavage of the DNA target by a meganuclease variant occurs, corresponds to the cleavage site on the sense strand of the DNA target.
- by "DNA target half-site", "half cleavage site" or half-site" is intended the portion of the DNA target which is bound by each LAGLIDADG homing endonuclease core domain (SEQ ID NO: 69).
- by "chimeric DNA target"or "hybrid DNA target" is intended the fusion of a different half of two parent meganuclease target sequences. In addition at least one half of said target may comprise the combination of nucleotides which are bound by separate subdomains (combined DNA target).

by "mutation" is intended the substitution, the deletion, and/or the addition of one or more nucleotides/amino acids in a nucleic acid/amino acid sequence.

by "homologous" is intended a sequence with enough identity to another one to lead to a homologous recombination between sequences, more particularly having at least 95% identity, preferably 97% identity and more preferably 99%.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

"individual" includes mammals, as well as other vertebrates (e.g., birds, fish and reptiles). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and ruminants (e.g., cows, pigs, horses).

"gene of interest" or "GOI" refers to any nucleotide sequence encoding a known or putative gene product.

"genetic disease" refers to any disease, partially or completely, directly or indirectly, due to an abnormality in one or several genes. Said abnormality can be a mutation, an insertion or a deletion. Said mutation can be a punctual mutation. Said abnormality can affect the coding sequence of the gene or its regulatory sequence. Said abnormality can affect the structure of the genomic sequence or the structure or stability of the encoded mRNA. This genetic disease can be recessive or dominant. Such genetic disease could be, but are not limited to, cystic fibrosis, Huntington's chorea, familial hyperchoiesterolemia (LDL receptor defect), hepatoblastoma, Wilson's disease, congenital hepatic porphyrias, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, Duchenne's muscular dystrophy, and Tay-Sachs disease.

"cGPS site" or "cGPS locus" refers to the genomic location at which the essential components of construct (i) have been introduced stably.

"cGPS cell line" refers to at least one cell in which the "cGPS site" or "cGPS locus" is present.

"cell-penetrating peptide" or "CPP" refers to peptides that facilitate cellular uptake of various molecular cargo in particular proteins and large macromolecules which would not normally be able to pass through the cell membrane at a rate sufficient for the cargo to have any effect upon the target cell.

"EF1α" refers to the human gene which encodes an isoform of the alpha subunit of the elongation factor-1 complex, which is responsible for the enzymatic delivery of aminoacyl tRNAs to the ribosome. The sequence of the human EF1α promoter, first and second exon and first intron is provided as SEQ ID NO: 9; the sequence of the human EF1α first intron is provided as SEQ ID NO: 10; the sequence of the human EF1α first exon is provided as SEQ ID NO: 11 and the sequence of the human EF1α second exon is provided as SEQ ID NO: 12.

"vectors": a vector which can be used in the present invention for instance as construct (ii) or (iii) as defined above includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adeno-associated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art.

Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S.*

*cerevisiae;* tetracycline, rifampicin or ampicillin resistance in *E. coli*. These selectable markers can also be used as a part of the constructs (i) and (ii) according to the present invention.

Preferably said vectors are expression vectors, wherein a sequence encoding a polypeptide of the invention is placed under control of appropriate transcriptional and translational control elements to permit production or synthesis of said protein. Therefore, said polynucleotide is comprised in an expression cassette. More particularly, the vector comprises a replication origin, a promoter operatively linked to said encoding polynucleotide, a ribosome site, an RNA-splicing site (when genomic DNA is used), a polyadenylation site and a transcription termination site. It also can comprise enhancer or silencer elements. Selection of the promoter will depend upon the cell in which the polypeptide is expressed.

EXAMPLE 1

Generating Stable Eukaryotic Cell Lines Transfected with Construct (i)

Construct (i) can be stably transfected into cells using known techniques. There are various methods of introducing foreign DNA into a eukaryotic cell and many materials have been used as carriers for transfection, which can be divided into three kinds: (cationic) polymers, liposomes and nanoparticles. Other methods of transfection include nucleofection, electroporation, heat shock, magnetofection and proprietary transfection reagents such as Lipofectamine®, Dojindo Hilymax®, Fugene®, JetPEI®, Effectene®, DreamFect®, PolyFect®, Nucleofector®, Lyovec®, Attractene®, Transfast®, Optifect®.

1.1 CHO-K1

Figure 1:
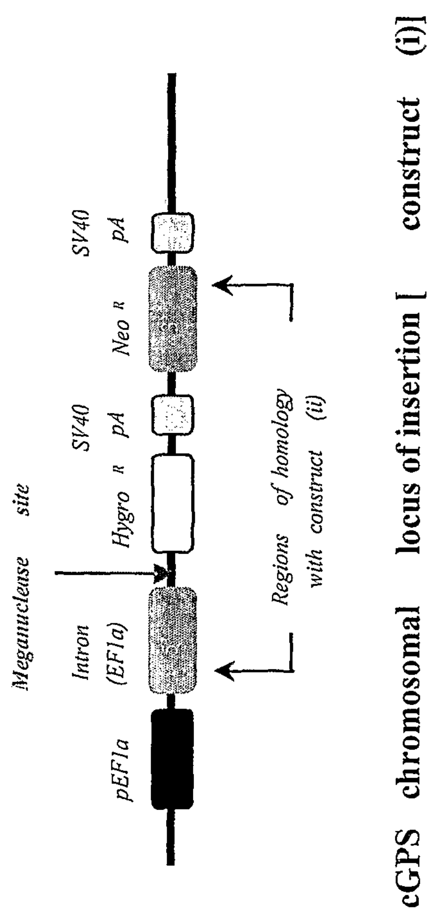
FIG. 1 shows a schematic representation of the cGPS locus.

In the present example construct (i), consists of SEQ ID NO: 6, which comprises a specific Meganuclease target site which has been inserted into the CHO-K1 genome at a unique locus. This site is the precise insertion locus of GOIs. This site has been inserted as a single copy into the CHO-K1 Cell line as part of a larger construct. In the final Cell Line, termed cGPS-CHO-K1, the Meganuclease target site is located near the hygromycin resistance gene and downstream the EF1 alpha promoter. The cGPS-CHO-K1 cell line is then resistant to hygromycin. Furthermore, the neomycin resistance gene is located just downstream the hygromycin gene but lacks a promoter making the cGPS-CHO-K1 cell line G418 sensitive (see FIG. 1).

1.2 NIH 3T3

In the present example construct (i) consists of SEQ ID NO: 6, which comprises a specific Meganuclease target site which has been inserted into the NIH 3T3 genome at a unique locus. This site is the precise insertion locus of GOIs. This site has been inserted as a single copy into the NIH 3T3 Cell line as part of a larger construct. In the final Cell Line, termed cGPSNIH 3T3, the Meganuclease target site is located near the hygromycin resistance gene and downstream the EF1 alpha promoter. The cGPSNIH 3T3 cell line is then resistant to hygromycin. Furthermore, the neomycin resistance gene is located just downstream the hygromycin gene but lacks a promoter making the cGPSNIH 3T3 cell line G418 sensitive (see FIG. 1).

1.3 HEK 293

In the present example construct (i), consists of SEQ ID NO: 6, which comprises a specific Meganuclease target site which has been inserted into the human HEK 293 genome at a unique locus. This site is the precise insertion locus of GOIs. This site has been inserted as a single copy into the HEK 293 Cell line as part of a larger construct. In the final Cell Line, termed cGPSHEK 293, the Meganuclease target site is located near the hygromycin resistance gene and downstream the EF1 alpha promoter. The cGPSHEK 293 cell line is then resistant to hygromycin. Furthermore, the neomycin resistance gene is located just downstream the hygromycin gene but lacks a promoter making the cGPSHEK 293 cell line G418 sensitive (see FIG. 1).

EXAMPLE 2

Highly Efficient Targeted Insertion of Gene of Interest (GOI) in cGPS Cell Line 2.1 Cloning of GOI into Construct (ii)

Figure 2:
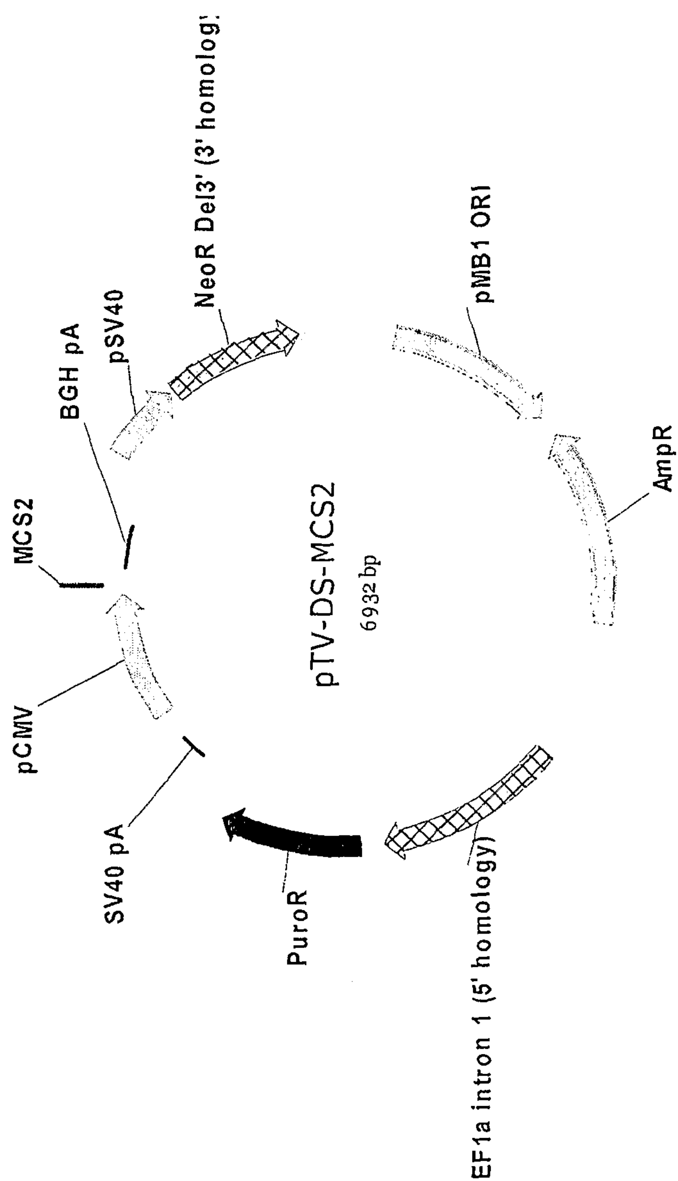
FIG. 2 shows a schematic representation of the pTV-DS-MCS2 vector.
Figure 3:
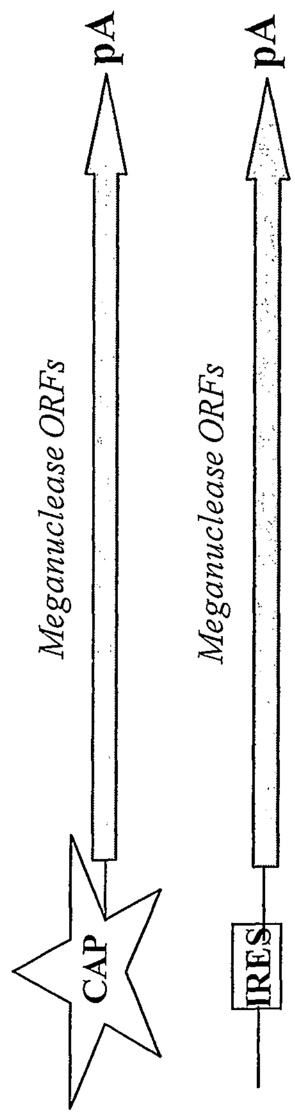
FIG. 3 shows a schematic representation of a Meganuclease capped polyadenylated mRNA.

The first step for generating a cell line expressing a GOI is to sub-clone the GOI into the pTV-DS-MCS2 vector (SEQ ID NO: 22; see FIG. 2). For this purpose a multiple cloning site has been introduced therein.

The expression of the gene of interest will be controlled by a CMV promoter and the bovine growth hormone (BGH) polyadenylation signal. The pTV-DS-MCS2 plasmid contains all the characteristics to favor a highly efficient HR event at the cGPS locus (SEQ ID NO: 6). A left homology arm (corresponding to portion A2 of construct (i) and A2' of construct (ii)) is composed of a 0.8 kb fragment homologous to the genomic 1 kb upstream the Meganuclease target site in the cGPS Cell Line. A right homology arm (corresponding to A5 of construct (i) and to A5' of construct (ii)) is composed of a 0.6 kb fragment homologous to the genomic 0.8 kb downstream the Meganuclease target site in the cGPS Cell Line.

Both homology arms are separated by (i) the puromycin resistance gene (which lacks a promoter on the plasmid), (ii) a CMV promoter for the expression of the GOI, (iii) a multiple cloning site for the insertion of the GOI, (iv) a polyadenylation signal controlling the stability of the mRNA for the GOI, and (v) a modified neomycin resistance gene. By itself, the pTV-DS-MCS2 plasmid cannot induce a puromycin and neomycin resistance phenotype.

Figure 4:
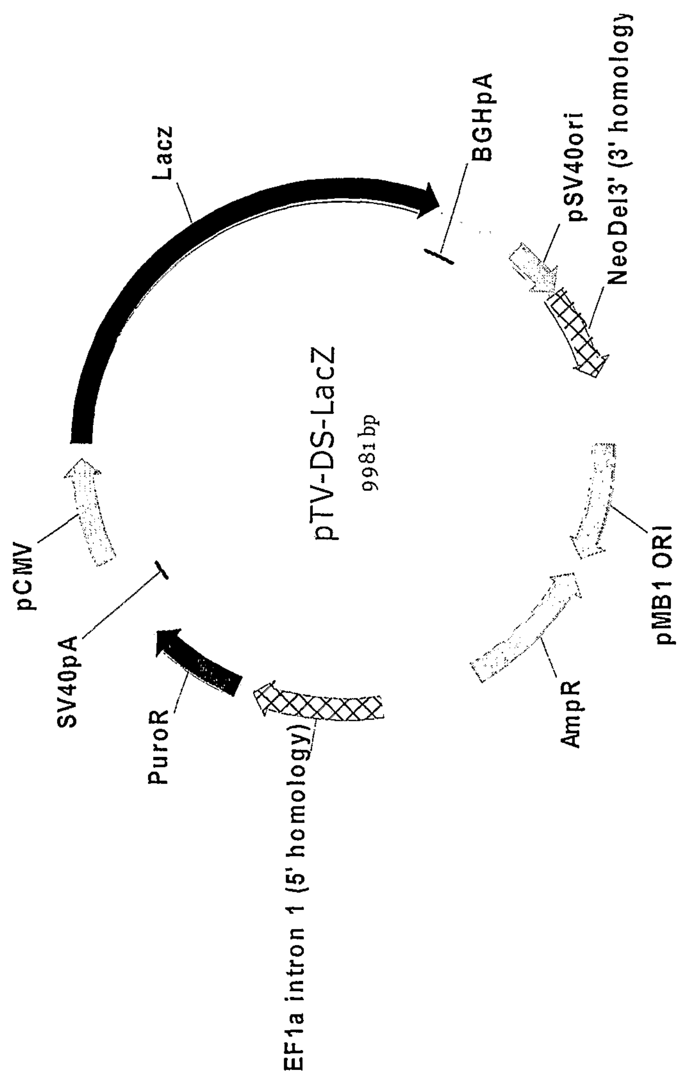
FIG. 4 shows a schematic representation of the pTV-DS-LacZ vector.

For example, the pTV-DS-LacZ plasmid (SEQ ID NO: 17; see FIG. 4) has been obtained by cloning the lacZ gene into the multiple cloning site of the pTV-DS-MCS2. The pTV-DS-LacZ plasmid (SEQ ID NO: 17) can be used as a positive control vector for mammalian cell transfection. It may be used to assay for expression levels in the cGPS cell lines. The sequence of the cGPS site following insertion of the lacZ gene is provided as SEQ ID NO: 18, the sequence of the cGPS site prior to insertion of the lacZ gene is provided as SEQ ID NO: 24.

Insertion of LacZ at the cGPS locus can be monitored as if it was the GOI.

2.2 cGPS CHO-K1 Cell Line 2.2.1 cGPSCHO-K1 Culture Conditions and Transfection cGPSCHO-K1 cells are sub-cultured in F-12K complete medium supplemented with 0.6 mg/ml of hygromycin. cGPSCHO-K1 cells are passed twice a week at 1:10-1:40 ratio.

Media and Supplements

- Complete medium: F-12K medium (Invitrogen-Life Science) is supplemented with 2 mM L-glutamine, penicilline (100 UI/ml), streptomycine (100 μg/ml), amphotericine B (Fongizone) (0.25 μg/ml) and 10% FBS.
- PBS
- Hygrornycin B solution (Sigma).
- Puromycin dichloride (Sigma).
- G418 sulfate (Invitrogen-Life Science).
- Trypsin-EDTA solution (Invitrogen-Life Science).
- Freezing medium: F12K complete medium supplemented with 10% DMSO.

Transfection.

One day prior to transfection, the cGPSCHO-K1 cells are seeded in 10 cm tissue culture dishes ($2\times10^5$ cells per dish) in complete F-12K medium.

On D day, 2 μg of pTV plasmid versions (pTV-DS-MCS2 containing any GOI or pTV-DS-LacZ) and 1 μg of meganuclease constructs (pCLS 1088 or pCLS2147 plasmid DNAs, or meganuclease-encoding mRNAs) are diluted in EC-R buffer. 6 μl of Enhancer Reagent is added (ratio nucleic acid (μg):enhancer (μl) should be 1:2).

Total volume DNA: enhancer EC-R buffer should be 100 μl. Vortex 10" and incubate 5' at room temperature.

Add 24 μl of TransMessenger™ (Qiagen) reagent (ratio nucleic acid (μg):TransMessenger™ (μl) should be 1:8) to the mix. Vortex 10" and incubate 10' at room temperature.

Meantime, replace culture medium with 9 ml of fresh medium.

Add 900 μl of serum- and antibiotic-free medium of the transfection mix and dispense over plated cells.

Incubate dish in a 37° C., 5% $CO_2$ humidified incubator.

Figure 5:
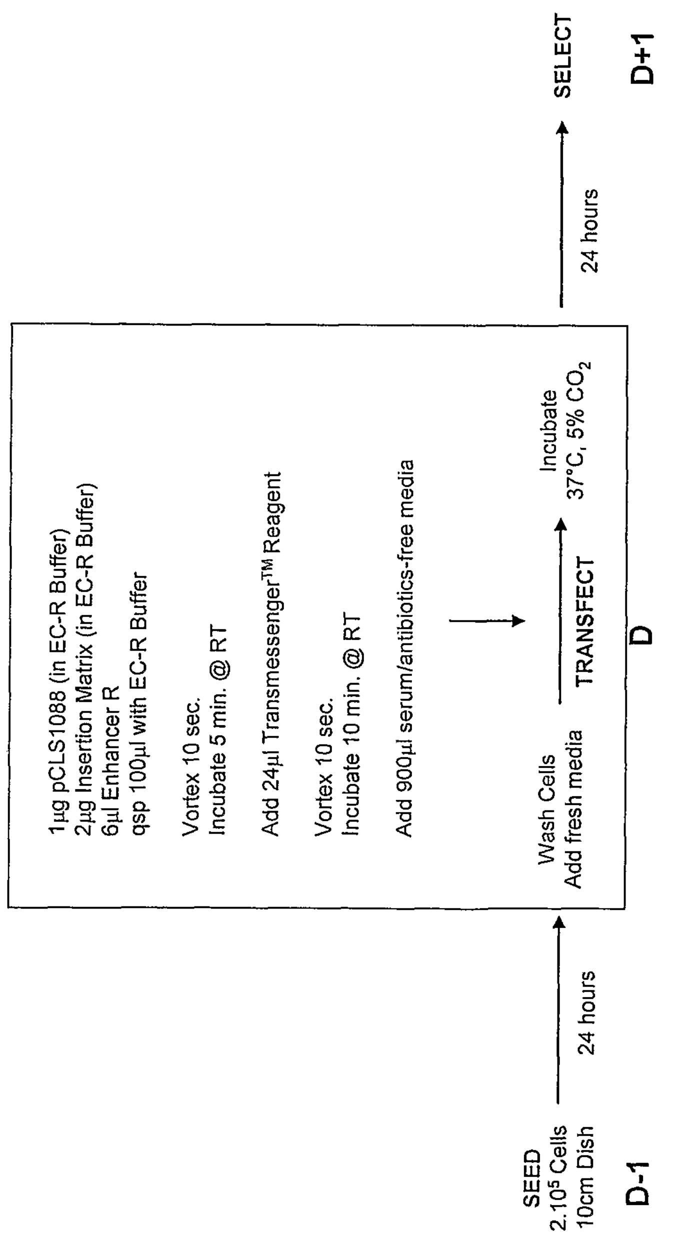
FIG. 5 shows a schematic representation of a transfection protocol for the cGPS CHO-K1 cell line according to the present invention.

A schematic representation of the transfection protocol is shown in FIG. 5.

Figure 6:
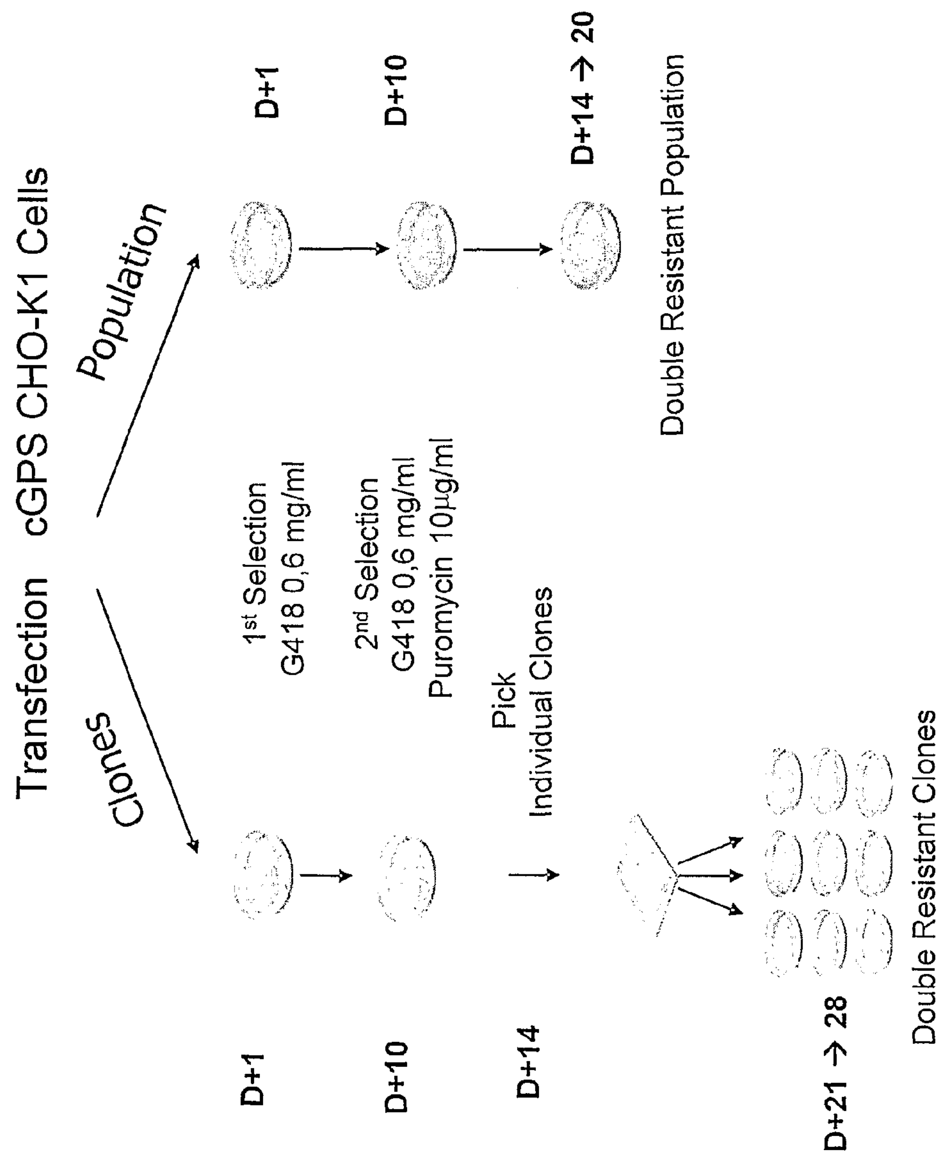
FIG. 6 shows a schematic representation of the clonal selection protocol (left column) and batch selection protocol (right column) for the cGPS CHO-K1 cell line.

2.2.2 cGPS CHO-K1 Targeted Clones Selection 2.2.2.1 cGPS CHO-K1 Clonal Selection Clonal selection is a longer but better protocol to select the proper cell line expressing the GOI. FIG. 6 shows a schematic representation of the clonal selection protocol (left column).

cGPS CHO-K1 cells are transfected with the protocol described above (2.2.1). 24 hours after transfection, the cells are washed and fresh medium supplemented with 0.6 mg/ml of G418 is added.

After 10 days of G418 selection, the culture medium is replaced with complete medium supplemented with G418 at 0.6 mg/ml and puromycin at 10 μg/ml.

3 to 4 days later, double resistant clones are picked up and seeded in a 96 well plate. Double resistant clones are amplified to reach confluence of a 10 cm culture dish 7 to 10 days later, double resistant clones can be characterized by analytical PCR and Southern blotting experiments. Positive control clones can be assayed for β-galactosidase activity, if pTV-DS-LacZ has been used as a positive control.

2.2.2.2 cGPS CHO-K1 Population Selection

In addition to the clonal selection described above, a population selection procedure can be used to retrieve the insertion clones. This procedure is faster and much easier to handle; however, the inventors believe that the clonal procedure is better to obtain pure single insertion clones.

For example, cGPS CHO-K1 cells are transfected with the protocol described above (2.2.1).

24 hours after transfection, wash the cells and add fresh medium supplemented with 0.6 mg/ml of G418.

10 days after G418 selection, wash the cells and add fresh medium supplemented with G418 at 0.6 mg/ml and puromycin at 10 μg/ml.

4 to 10 days later, double resistant population can be amplified in complete medium supplemented with the two selective agents.

FIG. 6 shows a schematic representation of the population selection protocol (right column).

Targeted insertion for different GOIs in the cGPS CHO-K.1 are presented in examples 3, 4, 5, 6 and 7.

2.3 cGPS NIH 3T3 Cell Line 2.3.1 cGPS NIH 3T3 Culture Conditions and Transfection cGPS NIH 3T3 cells are sub-cultured in DMEM complete medium supplemented with 0.6 mg/ml of hygromycin. cGPS NIH 3T3 cells are passed twice a week at 1:3-1:10 ratio.

Media and Supplements

- Complete medium: DMEM medium (Invitrogen-Life Science) is supplemented with 2 mM L-glutamine, penicilline (100 UI/ml), streptomycine (100 μg/ml), amphotericine B (Fongizone) (0.25 μg/ml) and 10% FBS.
- PBS
- Hygromycin B solution (Sigma).
- Puromycin dichloride (Sigma).
- G418 sulfate (Invitrogen-Life Science).
- Trypsin-EDTA solution (Invitrogen-Life Science).
- Freezing medium: DMEM complete medium supplemented with 10% DMSO.

Transfection.

One day prior to transfection, the cGPS NIH 3T3 cells are seeded in 10 cm tissue culture dishes ($2.5\times10^5$ cells per dish) in complete medium.

On D day, 1 μg of pTV plasmid versions (pTV-DS-MCS2 containing any GOI or pTV-DS-LacZ) and 1 μg of meganuclease constructs (pCLS1088 or pCLS2147 plasmid DNAs, or meganuclease-encoding mRNAs) are diluted in 300 μl of EC buffer. 16 μl of Enhancer Reagent is added (ratio nucleic acid (μg):enhancer (μl) should be 1:8).

Total volume DNA: EC buffer should be 300 μl. Vortex lightly and incubate 5' at room temperature.

Add 40 μl of Effectene™ (Qiagen) reagent (ratio nucleic acid (μg):Effectene™ (μl) should be 1:20) to the mix. Vortex 10" and incubate 10' at room temperature.

Meantime, replace culture medium with 9 ml of fresh medium.

Add 1 ml of complete medium of the transfection mix and dispense over plated cells.

Incubate dish in a 37° C., 5% $CO_2$ humidified incubator.

Figure 7:
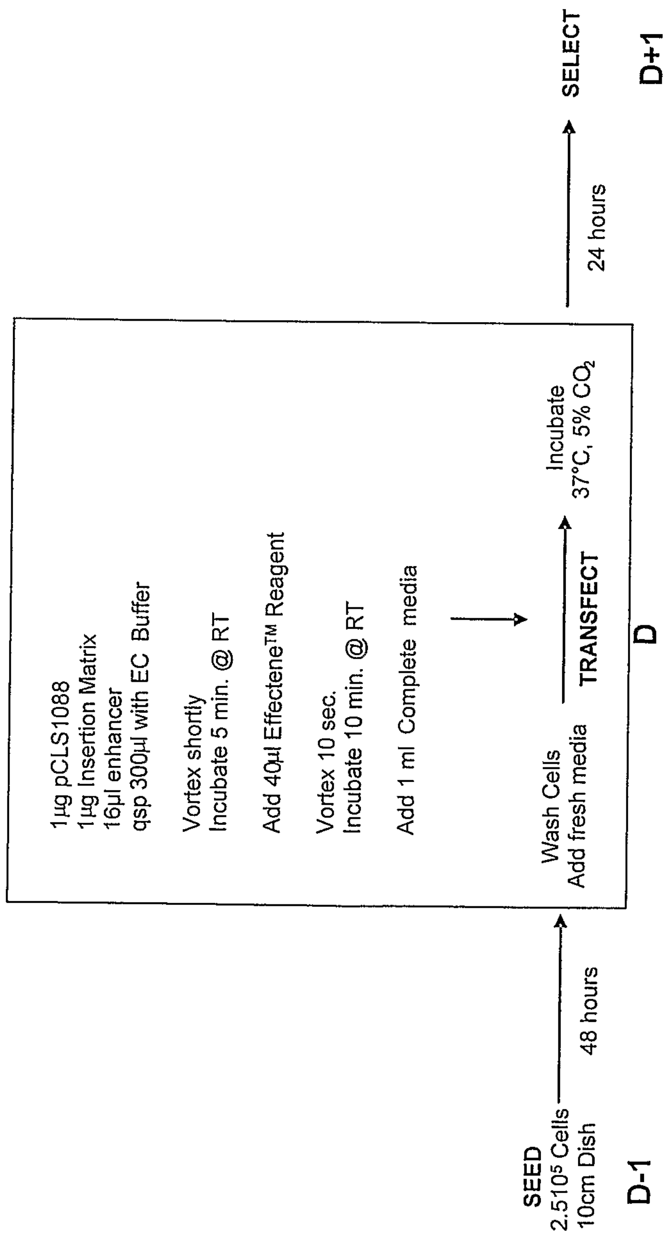
FIG. 7 shows a schematic representation of a transfection protocol for the cGPS NIH 3T3 cell line according to the present invention.

A schematic representation of the transfection protocol is shown in FIG. 7.

2.3.2 cGPS NIH 3T3 Targeted Clones Selection

Figure 8:
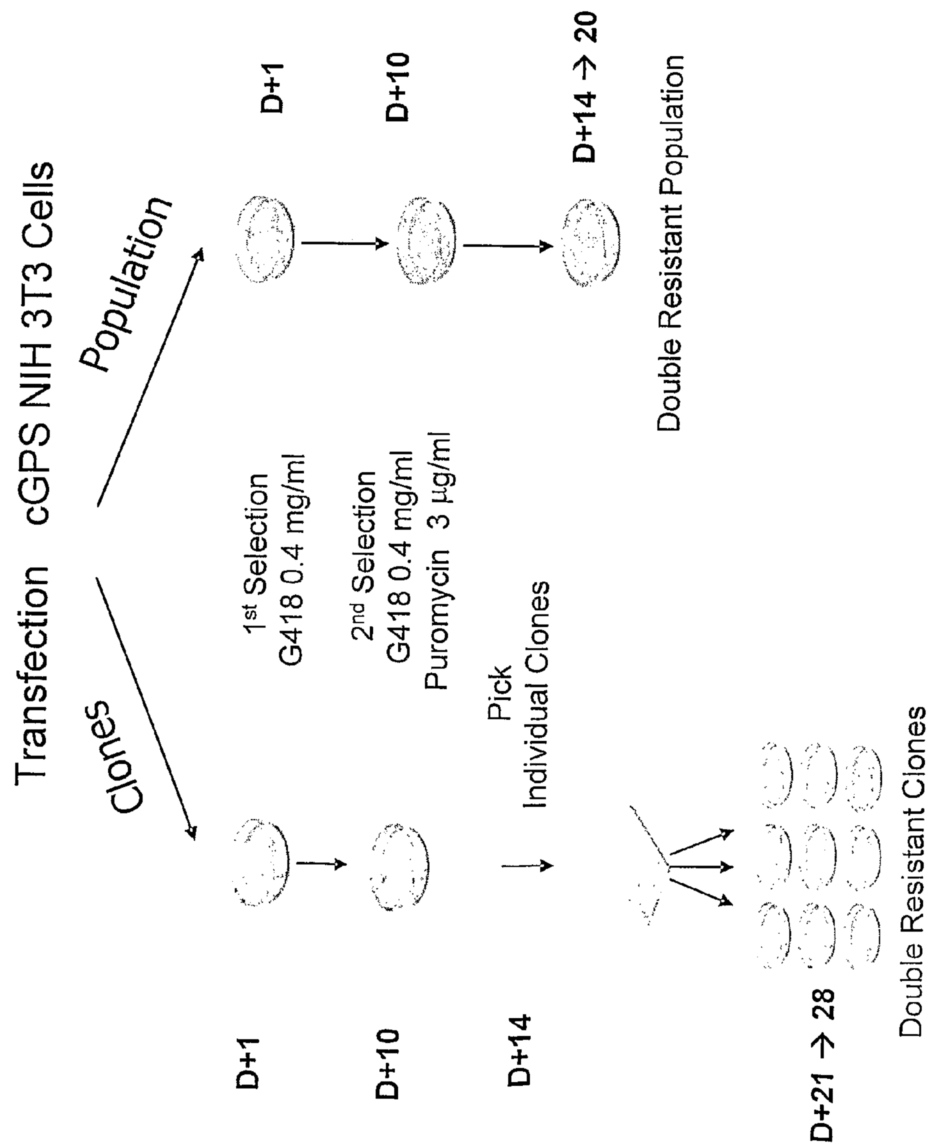
FIG. 8 shows a schematic representation of the clonal selection protocol (left column) and batch selection protocol (right column) for the cGPS NIH 3T3 cell line.

Clonal selection is a longer but better protocol to select the proper cell line expressing the GUI. FIG. 8 shows a schematic representation of the clonal selection protocol (left column).

cGPS NIH 3T3 cells are transfected with the protocol described above (2.3.1). 24 hours after transfection, the cells are washed and fresh medium supplemented with 0.4 mg/ml of G418 is added.

10 days after G418 selection, single colony clones are picked up and seeded in 96 well plates in complete medium supplemented with G418 at 0.4 mg/ml and puromycin at 3 μg/ml.

6 to 7 days later, double resistant clones can be amplified in complete medium supplemented with the two selective agents.

7 to 10 days later, double resistant clones can be characterized by analytical PCR and Southern blotting experiments. Positive control clones can be assayed for β-galactosidase activity, if pTV-DS-LacZ has been used as a positive control.

Figure 9:
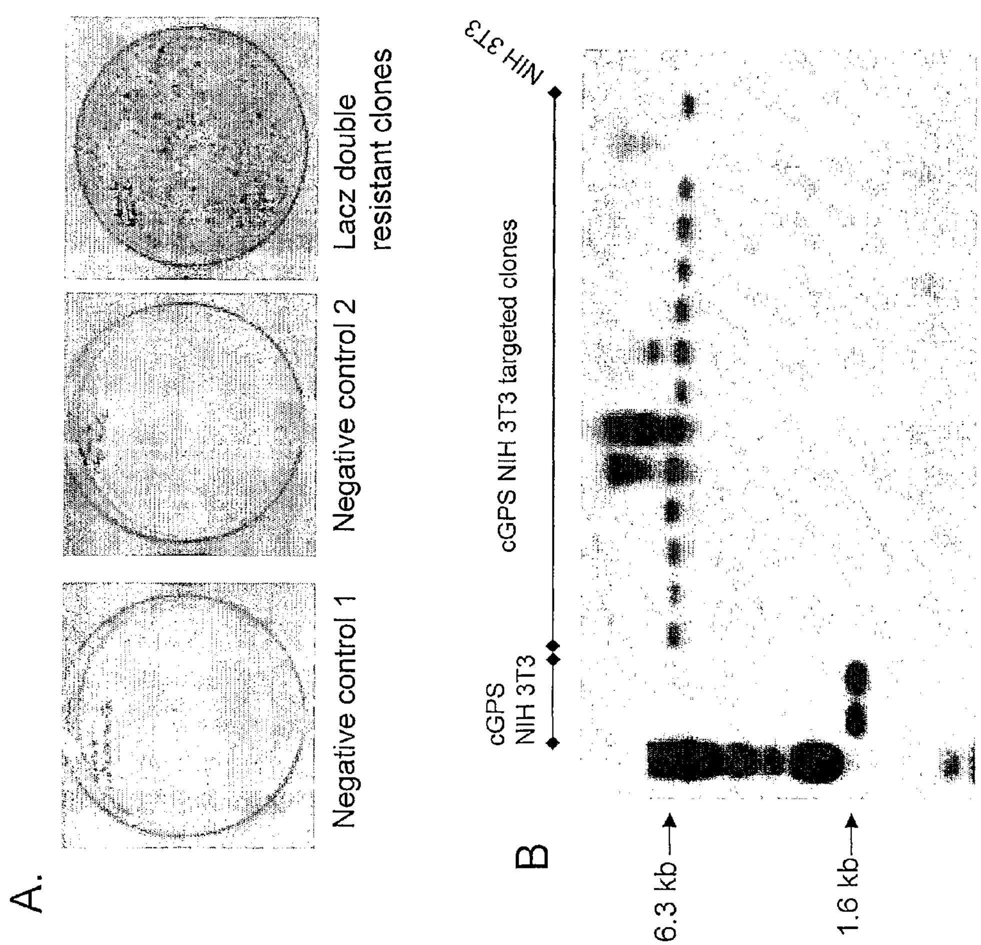
FIG. 9 shows the production of double resistant lacZ targeted clones in the cGPS NIH 3T3 system and their molecular characterization.

As shown on FIG. 9 panel A, double resistant clones are only present upon co-transfection with meganuclease expression vector and pTV-DS-Lacz. No double resistant clone is obtained in the controls (i.e. meganuclease expression vector transfected cells (negative control 1) or pTV-DS-lacZ (negative control 2) transfected cells). Furthermore, near all double resistant clones expressed the lacz gene as revealed by X-gal staining (see example 6 for materials and methods). Several double resistant clones are picked at random and amplified for molecular characterization by Southern blotting (see section 2.5). As shown on FIG. 9 panel B, genomic DNA from 14 double resistant clones is digested with the RsrII restriction enzyme, immobilized on nitrocellulose membrane and hybridized with a $^{32}P$-neomycine probe. A correct targeted insertion is characterized by the identification of a band at 6.3 kb. Such band is identified for all double resistant clones analyzed, while a band at 1.6 kb is shown for the parental cGPS NIH 3T3. In addition to the 6.3 kb band, others bands are present for 4/14 clones and is probably due to an additional random insertion. Hence, these results demonstrate that cGPS NIH 3T3 double resistant clones, obtained with the method described above, expressed the reported gene, present on the integration matrix, that is correctly targeted in the cGPS locus.

2.4 cGPS HEK 293 Cell Line 2.4.1 cGPS HEK 293 Culture Conditions and Transfection cGPS HEK 293 cells are sub-cultured in DMEM complete medium supplemented with 0.1 mg/ml of hygromycin. cGPS HEK 293 cells are passed twice a week at 1:3-1:10 ratio.

Media and Supplements

Complete medium: DMEM medium Glutamax (Invitrogen-Life Science) is supplemented with penicilline (100 UI/ml), streptomycin (100 μg/ml), amphotericine B (Fongizone) (0.25 μg/ml) and 10% FBS.

PBS

Hygromycin B solution (Sigma).

Puromycin dichloride (Sigma).

G418 sulfate (Invitrogen-Life Science).

Trypsin-EDTA solution (Invitrogen-Life Science).

Freezing medium: DMEM complete medium supplemented with 10% DMSO.

Transfection.

One day prior to transfection, the stable cGPSHEK 293 cells are seeded in 10 cm tissue culture dishes ($10^6$ cells per dish) in complete medium.

On D day, 3 μg of pTV plasmid versions (pTV-DS-MCS2 containing any GOI or pTV-DS-LacZ) and 2 μg of meganuclease constructs (pCLS1088 or pCLS2147 plasmid DNAs, or meganuclease-encoding mRNAs) are diluted in 300 μl of DMEM without serum. On the other hand, 10 μl of Lipofectamine 2000 (Invitrogen) are mixed with 290 μl of DMEM without serum.

The two mixes are incubated 5 min at room temperature. Then the DNA mix is added to the lipofectamine mix and incubated for 20 min. at room temperature.

Meantime, replace culture medium with 9 ml of fresh medium.

After the incubation period, add the total transfection mix (600 μl) over plated cells.

Incubate dish in a 37° C., 5% $CO_2$ humidified incubator.

Change medium 6 hours after transfection (optional)

A schematic representation of the transfection protocol is shown in FIG. 10.

2.4.2 cGPS HEK 293 Targeted Clones Selection

Clonal selection is a longer but better protocol to select the proper cell line expressing the GOI. FIG. 11 shows a schematic representation of the clonal selection protocol (left column).

cGPS HEK 293 cells are transfected with the protocol described above (2.4.1). 24 hours after transfection, culture medium is replaced with fresh medium supplemented with 0.4 mg/ml of G418.

After 12 days of G418 selection, the second selective agent (puromycin) is added at the concentration of 0.4 μg/ml.

After 7-9 days of double selection, single colony clones are picked up and seeded in 96 well plates in complete medium supplemented with G418 at 0.4 mg/ml and puromycin at 0.4 μg/ml.

10 days later, double resistant clones can be characterized by analytical PCR and Southern blotting experiments. Positive control clones can be assayed for β-galactosidase activity, if pTV-DS-LacZ has been used as a positive control.

As shown on FIG. 12 panel A, double resistant clones are obtained upon cotransfection with meganuclease expression vector and pTV-DS-lacZ. These double resistant clones expressed the lacz gene as revealed by X-gal staining (see example 6 for materials and methods). Several double resistant clones are picked at random and amplified for molecular characterization by Southern blotting (see section 2.5). As shown on FIG. 12 panel B, gDNA from 13 double resistant clones is digested with the RsrII restriction enzyme, immobilized on nitrocellulose membrane and hybridized with a $^{32}$P-neo probe. A correct targeted insertion is characterized by the identification of a band at 4.3 kb. Such band is identified for 11 double resistant clones out of 13 clones analyzed, while a band at 1.6 kb is shown for the parental cGPS HEK 293. In addition to the 4.3 kb band, a second band is present for 3 out of 11 clones and is probably due to an additional random insertion. Hence, these results demonstrate that cGPS HEK 293 double resistant clones, obtained with the method described above, expressed the reported gene, present on the integration matrix, that is correctly targeted in the cGPS locus.

2.5 Molecular Characterisation of Insertion Clones

A correct targeted insertion in double resistant clones can be easily identified at the molecular level by Southern blot analysis (FIG. 13). Alternatively PCR primers can also be designed for a quicker characterization of targeted clones.

Materials and Methods

Genomic DNA (gDNA) from targeted clones was purified from $10^7$ cells (about a nearly confluent 10 cm dish) using the Blood and Cell culture DNA midi kit (Qiagen, 5 to 10 μg of gDNA are digested with a 10-fold excess of restriction enzyme by overnight incubation).

Digested gDNA was separated on a 0.8% agarose gel and transfer on nylon membrane.

Nylon membranes were then probed with a $^{32}$P DNA probe specific for the EF1α intron.

After appropriate washes, the specific hybridization of the probe is revealed by autoradiography.

To Check the Left Region of the Targeted Insertion:

```
Forward oligo (in the cGPS locus) F1_Prom:
CCCCGACCGGAGCTGAGAGTAATT          (SEQ ID NO: 30)

Reverse oligo (in the pTV-DS-MCS2 vector) B1_Pur:
CAGGAGGCCTTCCATCTGTTG             (SEQ ID NO: 31)
```

The amplification product is 1794 base pairs (bp) long.

For Checking the Right Region of the Targeted Insertion:

```
Forward oligo (in the pTV-DS-MCS2 vector) SV40s:
CTGTGGAATGTGTGTCAGT               (SEQ ID NO: 32)

Reverse oligo (in the cGPS locus) NEOr:
CAACGCTATGTCCTGATAGCGGTC          (SEQ ID NO: 33)
```

The amplification product is 1073 by long.

Results

For example (FIG. 13), the targeted insertion of LacZ is checked in the 5' side with a double digest BglII (1 site upstream of pEF1α promoter) and EcoRV (a unique site in the LacZ gene). The probe is located within the EF1α intron. Thus, the native locus when digested within BglII/EcoRV, gives a band higher than 10 kb. On the contrary, a targeted insertion will bring the EcoRV site from LacZ in the vicinity of the BglII site. Upon double digest, a 5 kb DNA fragment is generated that is identified with the intron probe. The same approach can be used for the 3' side of the insertion.

EXAMPLE 3

Expressing Gene of Interest in cGPS CHO-K1 Cell Line 3.1 CD4 Expression

The human CD4 ORF (SEQ ID NO: 40) has been cloned in the pTV-DS-MCS2. The resulting vector (pTV-DS-CD4, FIG. 26, SEQ ID NO: 41) has been transfected in cGPS CHO-K1 cells according to the protocol described in 2.2.1. The sequence of the cGPS site following insertion of the CD4 gene is provided as SEQ ID NO: 62. Targeted clones surviving the selection process (2.2.2) are isolated and the expression of the transmembrane CD4 protein is evaluated.

Materials and Methods

Cells from targeted clones are washed twice in PBS and incubated with 2 ml of Versene solution. After 5 min. incubation at 37° C., cells are collected in a 15 ml conical tube. The cells are counted.

$10^6$ cells are transferred in 5 ml tube (Falcon, 2058) and centrifuge at 300 g for 5 min. at 4° C. Cells are washed once with FACS buffer. Cell pellets are re-suspended in 20 μl of Biotin conjugated anti-CD4 or Biotin-conjugated isotype control antibody. After 30 min. of incubation on ice, cells are washed once in FACS buffer. Cell pellets are then incubated with 20 μl of Streptavidin-conjugated PE for 30 min. on ice and protected from light. The cells are washed once in FACS buffer and finally re-suspended in 0.5 ml of FACS buffer.

Results

The cells sample are analyzed on a FACS vantage II (BD Bioscience) using a 488 nm Ion-Argon laser. The emitted fluorescence (emission wave length at approximately 580 nm) is collected in the fluorescence 2 channel (FIG. 14).

These experiments showed that the CD4 gene product could be reliably inserted into the cGPS locus and then be stably expressed over a prolonged period of time.

3.2 Somatostatin Receptor (GPCR SSTR2) Expression

The human GPCR SSTR2 ORF (SEQ ID NO: 42) has been cloned in the pTV-DS-MCS2. The resulting vector (pTV-DS-SSTR2, FIG. 27, SEQ ID NO: 43) has been transfected in cGPS CHO-K1 cells according to the protocol described in 2.2.1. The sequence of the cGPS site following insertion of the SSTR2 gene is provided as SEQ ID NO: 63. Targeted clones surviving the selection process (2.2.2) are isolated and the expression of the SSTR2 protein is evaluated.

Materials and Methods

GPCR SSTR2 activity is accomplished by measuring the inhibition of cAMP production after proper agonist stimulation of the SSTR2 receptor. The inventors used the protocol and reagents provided by the HitHunter™ cAMP XS+ assay kit (DiscoverX). Briefly, cells from targeted clones are seeded in white 96 well plates at the density of $10^4$ cells per well. After co stimulation of cells with Forskolin (100 μM) and increasing concentrations of Somatostatin (from $10^{-12}$ M to $10^{-4}$ M), cells are lysed and cAMP level is measured using a microplate luminometer (Victor, Perkin Elmer) (FIG. 15).

Results

In these experiments individual clones were seen to show essentially the same cAMP production inhibition profile in response to different levels of somatostatin.

3.3 Human AUTOTAXIN (hATX).

The human AUTOTAXIN ORF (SEQ ID NO: 44) has been cloned in the pTV-DS-MCS2. The resulting vector (pTV-DS-hATX, FIG. 28 SEQ ID NO: 45) has been transfected in cGPS CHO-K1 cells according to the protocol described in 2.2.1. The sequence of the cGPS site following insertion of the hATX gene is provided as SEQ ID NO: 64. Targeted clones surviving the selection process (2.2.2) are isolated and the expression of the hATX protein is evaluated by western blotting.

Materials and Methods

Preparation of ATX Conditioned Media cGPS CHO-K1 hATX targeted clones were washed twice with PBS first, 3 times with serum-free FK12 medium supplemented with 1% glutamin in order to remove serum (2 ml per well and per wash for a 6 wells plate), and then incubated with the same medium (1 ml per well) 6 hours at 37° C. in a humidified atmosphere containing 7% CO2. After incubation, conditioned-medium (CM) was separated from the cells, centrifuged to eliminate cell debris and then dialyzed overnight against 10 liters of 20 mM HEPES, pH 7.4, 6 mM D(+)-glucose, 1 mM $CaCl_2$, and 1.2 mM $MgSO_4$ using Spectra-Por 1.7 ml/cm tubing (Pierce Chemicals, Interchim, Montluçon, France). After dialysis CM are concentrated (about 15 fold) using an Amicon Ultra 10,000 (Millipore). Concentrated conditioned media (CCM) were aliquoted and stored at −20° C. before use.

SDS-PAGE Separation and Western Blotting

SDS-PAGE 4-12% was performed according to Laemmli (25) followed by Sypro Ruby staining and Western Blotting detection. After addition of sample buffer (Novex, Invitrogen) concentrated fractions of CM were boiled at 100° C. for 5 min. Electrophoretic separation of proteins was carried out on a 1 mm-thick 18×10-cm gel 4-12% acrylamide. An equivalent amount of total protein in sample buffer was loaded into a 4-mm well of the gel and separated at 40 mA. A total of 30 μg of standards (Mark12, or Magic Mark, Invitrogen) migrated in a neighboring lane. One of the gel was stained with Sypro Ruby and the other was transferred to nitrocellulose membranes and stained with chicken anti-autotaxin antibody followed by an HRP-conjugated anti-chicken antibody (Sigma Aldrich) before chemiluminescence detection of the immuno-complexes.

Results

The detection of hATX in the supernatants of cGPS CHO-K1 hATX targeted clones is performed by western blot. FIG. 16 shows the identification of a band over 100 kD using a specific antibody for the human ATX, in conditioned media from 10 cGPS CHO-K1 hATX targeted clones supernatants or from a cGPS CHO-K1 hATX targeted cell population (poly). No band is detected in the supernatant from the negative control. These results indicate that this rather large secreted protein is expressed by all cGPS CHO-K1 hATX targeted clones.

3.4 Human Melatonin 1 Receptor (hMT1) and Human Melatonin 2 Receptor (hMT2)

The human GPCR MT1 ORF (SEQ ID NO: 46) has been cloned in the pTV-DS-MCS2. The resulting vector (pTV-DS-hMT1, FIG. 29, SEQ ID NO: 47) has been transfected in cGPS CHO-K1 cells according to the protocol described in 2.2.1. The sequence of the cGPS site following insertion of the hMT1 gene is provided as SEQ ID NO: 65. Targeted clones surviving the selection process (2.2.2) are isolated and the expression of the MT1 protein is evaluated.

The human GPCR MT2 ORF (SEQ ID NO: 48) has been cloned in the pTV-DS-MCS2. The resulting vector (pTV-DS-hMT2, FIG. 30, SEQ ID NO: 49) has been transfected in cGPS CHO-K1 cells according to the protocol described in 2.2.1. The sequence of the cGPS site following insertion of the hMT2 gene is provided as SEQ ID NO: 66. Targeted clones surviving the selection process (2.2.2) are isolated and the expression of the hMT2 protein is evaluated.

Materials and Methods

Radio-Ligand Saturations with Intact Cells cGPS CHO-K1 hMT1 targeted clones and cGPS CHO-K1 hMT2 targeted clones were resuspended in Tris/HCl 50 mM pH 7.4, EDTA 1 mM and MgCl2 5 mM and dispensed in 96-well polypropylene plates at 13,000 cells/well. [$^{125}$I]-2-Iodomelatonine 5 pM to 1.5 nM was added to determine the total binding signal, while control wells contained an additional 1 μM melatonin to determine non specific binding. The incubation was performed at 37° C. for 2 hrs in a total volume of 250 μL. Cells were then transferred to unifilter GF/B plates (Perkin Elmer) with a FilterMate cell harvester (Perkin Elmer) and washed 3 times with 1 ml of ice-cold Tris 50 mM. Microscint 20 (40 μl/well, Perkin Elmer) was added before sealing plates. The radioligand associated with filter plates was evaluated by scintillation counting using a TopCount (Perkin Elmer). Experiments were conducted in triplicates, and data are expressed as fmol radioligand specific binding sites (total minus non specific) per mg of total protein. Graphic representations and data analysis were generated using PRISM 4.03 (GraphPad).

Results

Ten cGPS CHO-K1 hMT1 targeted clones and 10 cGPS CHO-K1 hMT2 targeted clones were picked at random and functionally tested for radioligand saturations experiments using [$^{125}$I]-iodomelatonin. Results obtained for the hMT1 are presented on FIG. 17 and those for hMT2, on FIG. 18. From saturations curves, pKd values are obtained by Scatchard analysis (FIG. 17, panel A and FIG. 18, panel A). From the saturations curves, the quantity (fmol) of specific binding sites per mg of total protein (Bmax, FIG. 17 panel B and FIG. 18, panel A) is measured. Similar results are obtained with both receptors. The data indicate that pKd values from each clones are very closed to each other and to polyclonal cGPS CHO-K1 hMT1- or hMT2-targeted cell population. However, some variations of hMT1 and hMT2 receptors expression is observed from clones to clones. pKd and Bmax values for both receptors are consistent with previous published observations.

EXAMPLE 4

Expressing GOI Under the Control of Different Promoters

In this example, the heavy chain (SEQ ID NO: 50) and the light chain (SEQ ID NO: 51) of the 5F11 monoclonal antibody (Medarex Inc.) have been cloned in the pTV-DS-MCS2. Both chains are under the control of the Ubiquitin sub-unit c promoter (pUbc SEQ ID NO: 52). The resulting vector (pTV-DS-5F11, FIG. 31, SEQ ID NO: 53) has been transfected in cGPS CHO-K1 cells according to the protocol described in 2.2.1. The sequence of the cGPS site following insertion of the 5F11 gene is provided as SEQ ID NO: 67. Targeted clones surviving the selection process (2.2.2) are isolated and the expression of the 5F11 monoclonal antibody protein is evaluated.

Materials and Methods

Cells from targeted clones are seeded in 96 well plates (Costar) at the density of $10^4$ cells per well. After 48 h of culture in complete medium, supernatants are collected and assayed for monoclonal antibody expression by ELISA. Briefly, 96 well plates are coated with a Goat-anti-Human kappa light chain (Southern Biotechnology Associates) in PBS overnight at 4° C. All washing steps are done in PBS, 0.1% Tween 20. After washing, plates are blocked in PBS, 1% BSA (PBA) for 90 min at 37° C. under shaking. After washing, 50 μl of diluted supernatant from samples are added and incubated for 90 min at 37° C. under shaking. After washing, a goat-anti-human IgG Fc coupled to Alkaline Phosphatase (Jackson ImmunoResearch) in PBA is added. After washing, the Developing buffer (Pierce) containing 1 mg/ml PNPP (Pierce) is added. Optical density (OD) is read at 405 nm using a microplate Reader (Model 550, BioRad) (FIG. 19).

Results

This study showed that the measured level of antibody expression was greater than 0.04 μg/ml in 48 hours for each of the generated clones and that expression levels were generally homogenous, although clone 29 showed higher expression levels in comparison to the other studied clones.

EXAMPLE 5

Long-Lasting Expression of GOI in the Presence or Absence of Selecting Drugs

In this example, the inventors monitored the level of expression of four cGPS CHO-K1 targeted clones expressing the lacZ gene and of four cGPS CHO-K1 targeted clones expressing the luciferase gene. The lacZ ORF (SEQ ID NO: 16) has been cloned in the pTV-DS-MCS2. The resulting vector (pTV-DS-lacz, FIG. 4, SEQ ID NO: 17) has been transfected in cGPS CHO-K1 cells according to the protocol described in 2.2.1. Targeted clones surviving the selection process (2.2.2) are isolated and characterized according to section 2.5. The luciferase ORF (SEQ ID NO: 54) has been cloned in the pTV-DS-MCS2. The resulting vector (pTV-DS-luciferase, FIG. 32, SEQ ID NO: 55) has been transfected in cGPS CHO-K1 cells according to the protocol described in 2.2.1. The sequence of the cGPS site following insertion of the luciferase gene is provided as SEQ ID NO: 68. Targeted clones surviving the selection process (2.2.2) are isolated and characterized according to section 2.5.

The 4 cGPS CHO-K1 lacz targeted clones and the 4 cGPS CHO-K1 luciferase targeted clones were maintained in culture over a period of 45 passages (two passages per week). Each clone was cultured in the presence of selecting drugs (Puro; 10 μg/ml and G418: 0.6 mg/ml). Furthermore, the inventors evaluated the expression of the two reporter gene for the same clones but without selecting drugs (i.e. in complete F12K medium) over a period of time corresponding to 30 passages.

Materials and Methods

Lacz expression: Cells from targeted clones are washed twice in PBS then incubated with 5 ml of trypsin-EDTA solution. After 5 min. incubation at 37° C., cells are collected in a 15 ml conical tube and counted.

Cells are then resuspended in complete F-12K medium at the density of 50000 cells/ml. 100 μl (5000 cells) are aliquoted in triplicate in a white 96 well plate (Perkin-Elmer). 100 μl of beta-Glo reagent (Promega) is added per well and after a 30 min. incubation period, the plate can be read on a luminometer (Viktor, Perkin-Elmer).

Luciferase expression: Cells from targeted clones are washed twice in PBS then incubated with 5 ml of trypsin-EDTA solution. After 5 min. incubation at 37° C., cells are collected in a 15 ml conical tube and counted.

Cells are then resuspended in complete F-12K medium at the density of 50000 cells/ml. 100 μl (5000 cells) are aliquoted in triplicate in a white 96 well plate (Perkin-Elmer). 100 μl of One-Glo reagent (Promega) is added per well and after a short incubation the plate can be read on a microplate luminometer (Viktor, Perkin-Elmer).

Results

The data are presented on FIG. 20. On panels A and B, the mean level of lacz expression for 4 cGPS CHO-K1 lacz targeted clones is measured as a function of time in the presence or absence of selecting agents, respectively. On panels C and D, the mean level of luciferase expression for 4 cGPS CHO-K1 luciferase targeted clones is shown as a function of time in the presence or absence of selecting agents, respectively. These data indicates that the expression of both reporters is remarkably stable even after a long period of culture. Furthermore the presence of the selecting agents is not necessary to ensure a long lasting expression of transgene since the stability of reporter expression is equivalent when the targeted clones are cultivated without selecting agents.

EXAMPLE 6

Generating Targeted Clones Using I-CreI Recombinant Protein

In this example, the inventors addressed the possibility to use I-CreI as a recombinant protein instead of I-CreI expression vector plasmid or mRNA to achieve efficient gene targeting in cGPS CHO-K1 system. Two different cell-penetrating peptides, also termed DPVs have been demonstrated to transport reporter proteins to the nucleus in a variety of mammalian cell lines including epithelial (HeLa, HCT116), myeloid (HL-60), erythroid (K562), lymphoid (Molt4), fibroblast (NIH-3T3) cells, as well as primary hepatocyte cultures (24). They have been shown to efficiently mediate the internalization of molecules as little as a few Daltons, and up to 200 kDa. These peptidic sequences, DPV15b (SEQ ID NO: 56) and DPV1047 (SEQ ID NO: 57) have been fused to the N-terminal part of the I-CreI N75 meganuclease protein (SEQ ID NO: 14) and resulting recombinant protein has been produced in *E. coli* and purified. In this example, the inventors used the purified recombinant protein termed DPV15b/I-CreI N75/6× His (SEQ ID NO: 58).

Materials and Methods

Transfection: On D day, 0.5 μg of the pTV-DS-lacz (SEQ ID NO: 17) is transfected in cGPS CHO-K1 cells by using the PolyFect® reagent from Qiagen. One day after the transfection of the integration matrix (D+1), 1000 μg of the purified DPV15b/I-CreI N75/6× His (SEQ ID NO: 58) meganuclease protein is directly added into transfected cGPS CHO-K1 cells.

Selection: cGPS CHO-K1 cells are transfected with the protocol described above. 24 hours after transfection, the cells are washed and fresh medium supplemented with 0.6 mg/ml of G418 is added. After 10 days of G418 selection, the culture medium is replaced with complete medium supplemented with G418 at 0.6 mg/ml and puromycin at 10 μg/ml. 3 to 4 days later, double resistant clones are visualized through an inverted microscope. At this step, double resistant clones are either stained for lacz expression monitoring or picked up for amplification and molecular characterization. (see section 2.5)

X-gal staining: Culture medium is removed and LacZ-targeted double resistant cGPS CHO-K1 adherent cells are washed once with PBS. 5 ml of fixing buffer (100 mM phosphate buffer, 1 mM $MgCl_2$, 0.5% (v/v) glutaraldehyde (Prolabo, 25% solution)) is added. After 10 min. of incubation on ice, fixing is replaced by 5 ml of washing buffer (100 mM phosphate buffer, 1 mM $MgCl_2$, 0.02% (v/v) NP40). Then, 5 ml of staining buffer (10 mM phosphate buffer, 1 mM $MgCl_2$, 33 mM KFerri [Potassium hexacyanoferrate (III)], 33 mM KFerro [Potassium hexacyanoferrate (II)], 0.1% (v/v) X-Gal) is added for incubation at 37° C. Blue cells should appear within 24 hours.

Results

As shown in FIG. 21 panel A, double resistant ($Neo^R$/$Puro^R$) cGPS CHO-K1 cell colonies are generated after the KI assay, from the moment that the I-CreI N75 meganuclease is expressed (pCLS 1088) or added by fusion with a DPV cell penetrating peptide (DPV15b/I-CreI N75/6xHis (SEQ ID NO: 58)) in association with the transfection of a LacZ-encoding integration matrix (pCLS1625). By contrast, the sole transfection of the integration matrix does not generate any cell colony, highlighting the importance of I-CreI N75 meganuclease to mediate homologous recombination in the cGPS CHO-K1 KI model.

Although a fewer number of cell colonies have been generated by the delivery of DPV15b/I-CreI N75/6× His (SEQ ID NO: 58) recombinant proteins (around 30, leading to a selection frequency of $3\times10^{-4}$) over those depicted from the transfection of I-CreI N75-encoding DNA plasmid (around 50, with a selection frequency of $5\times10^{-4}$), these results clearly indicates that the DPV15b/I-CreI N75/6× His (SEQ ID NO: 58) recombinant protein triggers targeted integration of the lacz gene. Moreover, all these cGPS CHO-K1 lacZ targeted clones are blue after X-Gal staining for both DNA and protein conditions, probably suggesting that all cell clones have been positively targeted.

However, since the expression of the reporter LacZ gene could arise from a random chromosomal integration, a Southern blot analysis has been settled in order to check the correct cGPS genetic pattern of integration for different double resistant cGPS CHO-K1 cell clones. Genomic DNAs extracted from nineteen individual cGPS CHO-K1 lacz targeted clones, as well as from CHO-K1 and untargeted cGPS CHO-K1 cells have been submitted to the hybridization with a probe is specific to the cGPS chromosomal locus (i.e. the EF1α intron sequence).

As shown in FIG. 21 panel B, a vast majority of LacZ-targeted cGPS CHO-K1 cell clones (18 out of 19) contain the expected cGPS modified locus, with a band around 5 kb which demonstrates the targeted insertion of the LacZ gene. By contrast, the hybridization of genomic DNA extracts originating from the original untargeted cGPS CHO-K1 cell line reveals the presence of a higher band (10 kb), and no band is detected in the negative control, i.e. the CHO-K1 cell lineage that does not contain the EF1α intron sequence. The targeting at the cGPS locus is highly specific since no additional band is detected from LacZ-targeted cGPS CHO-K1 cell clones, therefore revealing the absence of any random integration elsewhere in the genome.

EXAMPLE 7

Generating Doubled Targeted Cell Line by Combining the cGPS CHO-K1 System with a Custom Meganuclease Gene Targeting System In this example, the inventors addressed the possibility to use the cGPS CHO-K1 system in combination with a custom meganuclease cGPS system, leading to the targeting of two genes of interest into two distinct loci of the CHO-K1 genome. The insertion of the two GOI is sequential. The first GOI is inserted in the cGPS locus as described in section 2.2. Once a cGPS CHO-K1 targeted clone is identified as described in section 2.5, a second GOI is inserted in the cGPS CHO-K1 targeted clone through a custom meganuclease, named Sc MA17-RM2-G19H33 (SEQ ID NO: 60), that has been engineered to cleave in the 3rd exon of the CHO-K1 HPRT gene (WO2008/059382). The cGPS Custom CHO-K1 Integration Matrix containing the lacZ gene (FIG. 22; SEQ ID NO: 59), and Meganuclease Expression Vector (FIG. 23; SEQ ID NO: 61) are co-transfected into the cGPS CHO-K1 targeted clone. Upon co-transfection, the engineered meganuclease is expressed, recognizes its HPRT recognition site and induces a DNA double-strand break at this precise site. Homologous recombination occurs at the meganuclease recognition site. The gene of interest, cloned in the Integration Matrix in between the homology regions, is integrated at the meganuclease recognition site during this recombination event. Following meganuclease-induced homologous recombination, the hygromycin resistant gene is transcribed via the endogenous HPRT promoter and expressed as a fusion protein with the first exons of HPRT (exons 1, 2 and part of exon 3). In addition to the newly acquired hygromycin-resistance phenotype, targeting the mono-allelic HPRT gene locus leads to its inactivation, therefore allowing resistance to 6-thioguanine (6-TG) nucleotides. Thus, stable cGPS CHO-K1 targeted clone can be selected for the double hygromycin/6-TG resistance and expression of the recombinant protein of interest.

In the following example, the luciferase gene is chosen as the first GOI, to be inserted in the cGPS CHO-K1 locus, while the lacz gene is the second GOI, to be inserted in the HPRT locus. After selection of double targeted clones, the expression of the two reporter genes is monitored over 20 passages (40 weeks) in order to evaluate their stability.

Materials and Methods

Transfection

One day prior to transfection, cGPS CHO-K1 targeted clone cells are seeded in a 10 cm tissue culture dish ($2\times10^5$ cells per dish). On transfection day, 1 μg of the Meganuclease Expression Vector and 2 μg of the Integration Matrix, containing the lacZ gene, are diluted in 275 μl of medium without serum. 25 μl of the PolyFect™ reagent is added to the diluted DNA and the transfection mix is vortexed for 10" and incubated 10' at room temperature.

In the meantime culture medium is replaced with 9 ml of fresh medium. Then 700 μl of complete medium is added to the transfection mix and the total volume is dispensed over plated cells.

Transfected cells are incubated in a 37° C., 5% $CO_2$ humidified incubator.

Selection 3 days after transfection, cells are washed and fresh medium, supplemented with 0.6 mg/ml of hygromycin B, is added.

After 7 days of hygromycin selection (Day+10), fresh medium, supplemented with 0.6 mg/ml of hygromycin B and 5 μg/ml of 6-thioguanine (Hybrimax, Sigma), is added.

After 5 or 8 days of double selection (Day+15 to Day+18), single colony clones are picked and seeded in 96 well plates in complete medium supplemented with 0.6 mg/ml of hygromycin B at and 5 μg/ml of 6-thioguanine.

Double resistant clones are amplified in complete medium supplemented with the two selective agents. For downstream experiments (i.e. molecular characterization, lacZ expression, etc . . . ) the inventors strongly recommend to maintain both selective agents to maintain homogeneous expression.

Southern Blot

Genomic DNA (gDNA) is purified from $10^7$ cells (about a nearly confluent 10 cm dish). 5 to 10 μg of gDNA are digested with a 10-fold excess of EcoRV restriction enzyme by overnight incubation. Digested DNA is transferred on a nitrocellulose membrane and hybridization is performed with a $^{32}$P-labeled-lacz probe (see section 2.5 for details).

Results

The inventors have previously produced cGPS CHO-K1 targeted clones expressing the luciferase reporter gene (see example 4 and FIG. 20 panel C and D). One of these cGPS CHO-K1 luciferase targeted clone has been used to perform a second targeted insertion of the lacz gene into the Hprt locus. cGPS CHO-K1 luciferase targeted cells are co-transfected with the integration matrix containing the lacz gene and the meganuclease expression vector specific for the hamster Hprt gene. Upon selection, as described in the materials and methods section, hygromycin and 6-TG resistant clones are analyzed for correct insertion of the lacz gene in the Hprt gene. As shown on FIG. 24 panel A, 18 clones out of 18 are correctly targeted. 5 clones out of 18 present additional bands corresponding probably to the random insertion of the integration matrix. These data are in accordance with the data obtained when the experiment is done in CHO-K1. Furthermore, the inventors verified by southern blot that the cGPS CHO-K1 locus, site of the first targeted insertion is still modified. As shown on FIG. 24 panel B, the 18 analyzed clones present a hybridization pattern compatible with a modified cGPS CHO-K1 locus. All together, these data demonstrate that the first targeted insertion in the cGPS CHO-K1 locus has no impact on the efficiency of the second insertion, and the second targeted insertion is not prejudicial to the first, at least at the genomic level.

To verify whether the double insertion has an impact on the expression of the two reporter genes, four doubled targeted clones were maintained in culture over a period of 11 weeks (21 passages) and regularly checked for lacz and luciferase expression. As shown on FIG. 25 panel A, the expression of the lacz gene is stable allover the study period. Similarly, the luciferase expression is stable (FIG. 25 panel B) and comparable to those observed for single cGPS CHO-K1 targeted clones (FIG. 20 panel C and D).

References

1. Hinnen, A., Hicks, J. B., and Fink, G. R. (1978) Transformation of yeast. *Proc Natl Acad Sci USA* 75, 1929-33.
2. Rothstein, R. J. (1983) One-step gene disruption in yeast. *Methods Enzymol* 101, 202-11.
3. Thomas, K. R., and Capecchi, M. R. (1987) Site-directed mutagenesis by gene targeting in mouse embryo-derived stem cells. *Cell* 51, 503-12.
4. Capecchi, M. R. (2001) Generating mice with targeted mutations. *Nat Med* 7, 1086-90.
5. Smithies, O. (2001) Forty years with homologous recombination. *Nat Med* 7, 1083-6.
6. Rouet, P., Smih, F., and Jasin, M. (1994) Introduction of double-strand breaks into the genome of mouse cells by expression of a rare-cutting endonuclease. *Mol Cell Biol* 14, 8096-106.
7. Choulika, A., Perrin, A., Dujon, B., and Nicolas, J. F. (1995) Induction of homologous recombination in mammalian chromosomes by using the I-SceI system of *Saccharomyces cerevisiae*. *Mol Cell Biol* 15, 1968-73.
8. Chevalier, B. S., and Stoddard, B. L. (2001) Homing endonucleases: structural and functional insight into the catalysts of intron/intein mobility. *Nucleic Acids Res* 29, 3757-74.
9. Dujon, B., Colleaux, L., Jacquier, A., Michel, F., and Monteilhet, C. (1986) Mitochondrial introns as mobile genetic elements: the role of intron-encoded proteins. *Basic Life Sci* 40, 5-27.

10. Haber, J. E. (1995) In vivo biochemistry: physical monitoring of recombination induced by site-specific endonucleases. *Bioessays* 17, 609-20.

11. Posfai, G., Kolisnychenko, V., Bereczki, Z., and Blattner, F. R. (1999) Markerless gene replacement in *Escherichia coli* stimulated by a double-strand break in the chromosome. *Nucleic Acids Res* 27, 4409-15.

12. Sargent, R. G., Brenneman, M. A., and Wilson, J. H. (1997) Repair of site-specific double-strand breaks in a mammalian chromosome by homologous and illegitimate recombination. *Mol Cell Biol* 17, 267-77.

13. Donoho, G., Jasin, M., and Berg, P. (1998) Analysis of gene targeting and intrachromosomal homologous recombination stimulated by genomic double-strand breaks in mouse embryonic stem cells. *Mol Cell Biol* 18, 4070-8.

14. Cohen-Tannoudji, M., Robine, S., Choulika, A., Pnto, D., El Marjou, F., Babinet, C., Louvard, D., and Jaisser, F. (1998) I-SceI-induced gene replacement at a natural locus in embryonic stem cells. *Mol Cell Biol* 18, 1444-8.

15. Gouble, A., Smith, J., Bruneau, S., Perez, C., Guyot, V., Cabaniols, J. P., Leduc, S., Fiette, L., Ave, P., Micheau, B., Duchateau, P., and Paques, F. (2006) Efficient in toto targeted recombination in mouse liver by meganuclease-induced double-strand break. *J Gene Med* 8, 616-22.

16. Siebert, R., and Puchta, H. (2002) Efficient Repair of Genomic Double-Strand Breaks by Homologous Recombination between Directly Repeated Sequences in the Plant Genome. *Plant Cell* 14, 1121-31.

17. Puchta, H., Dujon, B., and Hohn, B. (1996) Two different but related mechanisms are used in plants for the repair of genomic double-strand breaks by homologous recombination. *Proc Natl Acad Sci USA* 93, 5055-60.

18. Wurm, F. M. (2004) Production of recombinant protein therapeutics in cultivated mammalian cells. *Nat Biotechnol* 22, 1393-8.

19. Craig, N L. (1988) The mechanism of conservative site-specific recombination. *Annu Rev Genet* 22, 77-105.

20. Sauer, B. (1994) Site-specific recombination: developments and applications. *Curr Opin Biotechnol* 5, 521-7.

21. Sambrook, J., Fritsch, E. F., and Maniatis, T. (1989). Molecular Cloning: A Laboratory Manual, Second Edition (Plainview, New York: Cold Spring Harbor Laboratory Press).

22. Ausubel, F. M., Brent, R., Kingston, R. E., Moore, D. D., Seidman, J. G., Smith, J. A., and Struhl, K. (1994). Current Protocols in Molecular Biology (New York: Greene Publishing Associates and Wiley-Interscience).

23. O'Gorman, S., Fox, D. T., and Wahl, G. M. (1991). Recombinase-Mediated Gene Activation and Site-Specific Integration in Mammalian Cells. *Science* 251, 1351-5.

24. de Coupade, C., Fittipaldi, A., Chagnas, V., Michel, M., Carlier, S., Tasciotti, E., Darmon, A., Ravel, D., Kearsley, J., Giacca, J. and Cailler, F. (2005) Novel human-derived cell-penetrating peptides for specific subcellular delivery of therapeutic biomolecules. *Biochem. J.* 390, 407-418.

25 Laemmli, U. (1970) Cleavage of structural proteins during the assembly of the head of bacteriophage T4. *Nature* 227, 680-685.

26. Seligman et al., Genetics, 1997, 147, 1653-1664; Sussman et al., J. Mol. Biol., 2004, 342, 31-41.

27. International PCT Applications WO 2006/097784 and WO 2006/097853.

28. Arnould et al., J. Mol. Biol., 2006, 355, 443-458; Rosen et al., Nucleic Acids Res., 2006, 34, 4791-4800 ; Smith et al., Nucleic Acids Res., 2006, 34, e149.

29. Smith et al., Nucleic Acids Res., 2006, 34, e149;

30. International PCT Applications WO 2007/060495 and WO 2007/049156

31. Chevalier et al., Mol. Cell., 2002, 10, 895-905.

32. Epinat et al., Nucleic Acids Res, 2003, 31, 2952-62.

33. International PCT Applications WO 03/078619 and WO 2004/031346.

34. Ruben, S., Perkins, A., Purcell, R., Joung, K., Sia, R., Burghoff, R., Haseltine, W. A. and Rosen, C. A. (1989) Structural and functional characterization of human immunodeficiency virus tat protein. J. Virol. 63, 1-8

35. Tyagi, M., Rusnati, M., Presta, M. and Giacca, M. (2001) Internalization of HIV-1 tat requires cell surface heparan sulfate proteoglycans. J. Biol. Chem. 276, 3254-3261

36. Derossi, D., Calvet, S., Trembleau, A., Brunissen, A., Chassaing, G. and Prochiantz, A. (1996) Cell internalization of the third helix of the Antennapedia homeodomain is receptor-independent. J. Biol. Chem. 271, 18188-18193 *Res,* 566, 131-67.

37. Elliott, G. and O'Hare, P. (1997) Intercellular trafficking and protein delivery by a herpesvirus structural protein. Cell (Cambridge, Mass.) 88, 223-233

38. Futaki, S., Goto, S. and Sugiura, Y. (2003) Membrane permeability commonly shared among arginine-rich peptides. J. Mol. Recognit. 16, 260-264

39. Jans, D. A. (1994) Nuclear signaling pathways for polypeptide ligands and their membrane receptors FASEB J. 8, 841-847

40. Kokryakov, V. N., Harwig, S. S., Panyutich, E. A., Shevchenko, A. A., Aleshina, G. M., Shamova, O. V., Korneva, H. A. and Lehrer, R. I. (1993) Protegrins: leukocyte antimicrobial peptides that combine features of corticostatic defensins and tachyplesins. FEBS Lett. 327, 231-236

41. Mie, M., Takahashi, F., Funabashi, H., Yanagida, Y., Aizawa, M. and Kobatake, E. (2003) Intracellular delivery of antibodies using TAT fusion protein A. Biochem. Biophys. Res. Commun. 310, 730-734

42. Silhol, M., Tyagi, M., Giacca, M., Lebleu, B. and Vives, E. (2002) Different mechanisms for cellular internalization of the HIV-1 Tat-derived cell penetrating peptide and recombinant proteins fused to Tat. Eur. J. Biochem. 269, 494-501

43. Stein, S., Weiss, A., Adermann, K., Lazarovici, P., Hochman, J. and Wellhoner, H. (1999) A disulfide conjugate between anti-tetanus antibodies and HIV (37-72)Tat neutralizes tetanus toxin inside chromaffin cells. FEBS Lett. 458, 383-386

44. Suzuki, T., Futaki, S., Niwa, M., Tanaka, S., Ueda, K. and Sugiura, Y. (2001) Possible existence of common internalization mechanisms among arginine-rich peptides. J. Biol. Chem. 277, 2437-2443

45. Torchilin, V. P., Rammohan, R., Weissig, V. and Levchenko, T. S. (2001) TAT peptide on the surface of liposomes affords their efficient intracellular delivery even at low temperature and in the presence of metabolic inhibitors. Proc. Natl. Acad. Sci. U.S.A. 98, 8786-8791

46. Schwarze, S. R., Ho, A., Vocero-Akbani, A. and Dowdy, S. F. (1999) In vivo protein transduction: delivery of a biologically active protein into the mouse. Science 285, 1569-1572

47. Tasciotti, E., Zoppe, M. and Giacca, M. (2003) Transcellular transfer of active HSV-1 thymidine kinase mediated by an 11-amino-acid peptide from HIV-1 Tat. Cancer Gene Ther. 10, 64-74

48. Vives, E., Brodin, P. and Lebleu, B. (1997) A truncated HIV-1 Tat protein basic domain rapidly translocates through the plasma membrane and accumulates in the cell nucleus. J. Biol. Chem. 272, 16010-16017

49. PEREZ C, GUYOT V, CABANIOLS J, GOUBLE A, MICHEAUX B, SMITH J, LEDUC S, PAQUES F, DUCHATEAU P, (2005) BioTechniques vol. 39, n° 1, pp. 109-115

The invention claimed is:

1. A set of genetic constructs, comprising:

a) construct (i) comprising SEQ ID NO: 6, wherein construct (i) is configured to be stably integrated into the genome of at least one target cell;

b) construct (ii) comprising SEQ ID NO: 22; and c) at least one construct selected from the group consisting of construct (iii), construct (iv), and construct (v), which respectively comprise components:

C1-C2 (iii),

C3 (iv), and

C4 (v), wherein constructs (iii) and (iv) are nucleic acid molecules and construct (v) is an isolated or recombinant protein, wherein C1 is a promoter, C2 is an open reading frame (ORF) of a meganuclease, C3 is messenger RNA (mRNA) encoding of said meganuclease, and C4 is an isolated or recombinant protein of said meganuclease, wherein said meganuclease from constructs (iii), (iv), or (v) recognizes and cleaves a meganuclease cleavage site in construct (i), and wherein constructs (iii), (iv), or (v) are configured to be co-transfected with construct (ii) into said at least one target cell.

2. The set of claim 1, wherein said components of each of said constructs (iii), (iv), and (v) are selected from the following groups:

for C1, SEQ ID NO: 1, SEQ ID NO: 20, SEQ ID NO: 25, and SEQ ID NO: 52;

for C2, SEQ ID NO: 14 and SEQ ID NO: 15;

for C3, an mRNA equivalent of SEQ ID NO: 14, SEQ ID NO: 5, and SEQ ID NO: 35; and for C4, Meganuclease peptide encoded by SEQ ID NO: 14 and SEQ ID NO: 15 or the meganuclease peptide of SEQ ID NO: 58.

3. The set of claim 1, wherein construct (iii) comprises SEQ ID NO: 38 or SEQ ID NO: 39.

4. The set of claim 1, wherein construct (iv) comprises an mRNA equivalent of SEQ ID NO: 14, SEQ ID NO: 15, or SEQ ID NO: 35.

5. The set of claim 1, wherein construct (v) further comprises a cell penetrating peptide at the C or N terminus of said meganuclease.

6. The set of claim 5, wherein the cell-penetrating peptide is selected from the group consisting of SEQ ID NO: 56 and SEQ ID NO: 57.

7. A kit suitable for introducing a sequence encoding a Gene of Interest (GOI) into at least one cell, comprising:

the set of claim 1; and an instruction for generating a transformed cell with said set.

8. The kit of claim 7, further comprising:

construct (vi) consisting of SEQ ID NO: 17 or SEQ ID NO: 54.

9. The kit of claim 7, further comprising: at least one isolated cell stably transformed with said construct (i).

10. The kit of claim 9, wherein said at least one isolated cell is selected from the group consisting of a CHO-K1 cell, and HEK293 cell, a Caco2 cell, a U2-OS cell, an NIH 3T3 cell, an NSO cell, an SP2 cell, a CHO-S cell, and a DG44 cell.

11. A method for transforming by homologous recombination at least one isolated cell, comprising:

(a) stably transforming at least one isolated cell by inserting construct (i) comprising SEQ ID NO: 6, into the genome of said at least one isolated cell;

(b) cloning a sequence coding for a gene of interest into a multiple cloning site of construct (ii) comprising SEQ ID NO: 22;

(c) co-transfecting said cell of step (a) with said construct (ii) of step (b) and construct (iii), (iv), or (v), which respectively comprise components:

C1-C2 (iii),

C3 iv), and

C4 (v), wherein constructs (iii) and (iv) are nucleic acid molecules and construct (v) is an isolated or recombinant protein, wherein C1 is a, C2 is an open reading frame (ORF) of a meganuclease, C3 is a messenger RNA (mRNA) encoding said meganuclease, and C4 is an isolated or recombinant protein of said meganuclease, wherein a meganuclease from constructs (iii), (iv), or (v) recognizes and cleaves a meganuclease cleavage site in construct (i); and (d) following homologous recombination between said construct (ii) and said stably inserted construct (i), selecting at least one cell from step (c) based upon: absence of hygromycin resistance, presence of puromycin resistance, and presence of neomycin resistance.

12. The method of claim 11, wherein the selecting in step (d) is carried out sequentially for each of said hygromycin resistance, said puromycin resistance, and said neomycin resistance.

* * * * *